United States Patent
Ong et al.

(10) Patent No.: US 11,142,561 B2
(45) Date of Patent: Oct. 12, 2021

(54) B1SP FUSION PROTEIN THERAPEUTICS, METHODS, AND USES

(71) Applicant: THE UNIVERSITY OF BRITISH COLUMBIA, Vancouver (CA)

(72) Inventors: Christopher J. Ong, Vancouver (CA); James William Peacock, Vancouver (CA); Martin E. Gleave, Vancouver (CA)

(73) Assignee: The University of British Columbia, Vancouver (CA)

( * ) Notice: Subject to any disclaimer, the term of this patent is extended or adjusted under 35 U.S.C. 154(b) by 2 days.

(21) Appl. No.: 15/737,605

(22) PCT Filed: Jun. 29, 2016

(86) PCT No.: PCT/CA2016/000182
§ 371 (c)(1),
(2) Date: Dec. 18, 2017

(87) PCT Pub. No.: WO2017/000059
PCT Pub. Date: Jan. 5, 2017

(65) Prior Publication Data
US 2018/0162923 A1    Jun. 14, 2018

Related U.S. Application Data

(60) Provisional application No. 62/185,772, filed on Jun. 29, 2015.

(51) Int. Cl.
| | | |
|---|---|---|
| C07K 14/705 | (2006.01) | |
| A61P 35/00 | (2006.01) | |
| A61K 45/06 | (2006.01) | |

(52) U.S. Cl.
CPC ........ *C07K 14/70546* (2013.01); *A61K 45/06* (2013.01); *A61P 35/00* (2018.01); *C07K 2319/03* (2013.01); *C07K 2319/30* (2013.01); *C07K 2319/31* (2013.01)

(58) Field of Classification Search
CPC .. C07K 2319/30; C07K 2319/31; A61P 35/00
See application file for complete search history.

(56) References Cited

U.S. PATENT DOCUMENTS

| | | | |
|---|---|---|---|
| 7,994,286 B2 | 9/2011 | Watts et al. | |
| 9,198,966 B2 | 12/2015 | Offermanns et al. | |
| 2007/0275888 A1* | 11/2007 | Sunahara | C07K 14/47 514/19.3 |
| 2010/0189713 A1* | 7/2010 | Chedotal | A01K 67/0276 424/130.1 |
| 2014/0044741 A1* | 2/2014 | Offermanns | A61P 43/00 424/174.1 |
| 2016/0075752 A1 | 3/2016 | Offermanns et al. | |
| 2016/0311873 A1* | 10/2016 | Neufeld | C07K 14/4702 |

FOREIGN PATENT DOCUMENTS

| | | |
|---|---|---|
| WO | WO 2001014420 | 3/2001 |
| WO | 2010108154 | 9/2010 |
| WO | WO 2011138449 | 11/2011 |
| WO | WO 2012107531 | 8/2012 |
| WO | 2016/135130 | 9/2016 |
| WO | WO 2017000059 | 1/2017 |

OTHER PUBLICATIONS

Accession No. NP_001337049, Sep. 12, 2020.*
Altschul et al. (1990) "Basic local alignment search tool"; *J Mol. Biol.* 215; pp. 403-410.
Altschul et al. (1997) "Gapped BLAST and PSI-BLAST: a new generation of protein database search programs"; *Nucleic Acids Res.* 25(17); pp. 3389-3402.
Ballard et al (1998) "Anthrax toxin-mediated delivery in vivo and in vitro of a cytotoxic T-lymphocyte epitope from ovalbumin"; *Infect. Immun* 66(2); pp. 615-619.
Blanke et al(1996) "Fused polycationic peptide mediates delivery of diphtheria toxin A chain to the cytosol in the presence of anthrax protective antigen"; *Proc Natl Acad Sci U S A.* 93(16); pp.
Cadima-Couto, et al (2009) "Ubiquitin-fusion as a strategy to modulate protein half-life: A3G antiviral activity revisited"; *Virology* 393(2); pp. :286-294.
Demarchi et al (1996) "Activation of transcription factor NF-kappaB by the Tat protein of human immunodeficiency virus type 1"; *J Virol* 70(7); pp. 4427-4437.
Dietz et al (2004) "Delivery of bioactive molecules into the cell: the Trojan horse approach"; *Mol Cell. Neurosci* 27 (2); pp. 85-131.
Dilber et al (1999) "Intercellular delivery of thymidine kinase prodrug activating enzyme by the herpes simplex virus protein, VP22"; *Gene Ther.* 6(1); pp. 12-21.
Flanagan, JG. and Leder, P. (1990) "The kit ligand: a cell surface molecule altered in steel mutant fibroblasts"; *Cell* vol. 63(1); pp. 185-194.
Fujihara et al (1999) "Intranuclear targeted delivery of functional NF-kappaB by 70 kDa heat shock protein"; *EMBO J* 18(2); pp. 411-419.

(Continued)

*Primary Examiner* — Hong Sang
(74) *Attorney, Agent, or Firm* — Bozicevic, Field & Francis LLP; Shweta Chandra

(57) ABSTRACT

Provided are methods, uses and pharmaceutical compositions for treatment of cancer with a B1SP fusion protein in a biologically effective amount sufficient to cause cell death of a prostate cancer cell or to inhibit proliferation of the prostate cancer cells. The cancer may be prostate cancer, breast cancer, ovarian cancer, bladder cancer, kidney cancer, glioblastoma or endometrial cancer. The prostate cancer may be an androgen receptor (AR) positive prostate cancer and the B1SP fusion protein may include a sema domain, a structural stabilization domain; and a half life extending moiety.

36 Claims, 33 Drawing Sheets
Specification includes a Sequence Listing.

(56) References Cited

OTHER PUBLICATIONS

Gherardi, et al (2004) "The sema domain"; *Curr Opin Struct Biol.* 14(6); pp. 669-678.
Giordano, S. et al. (2002). "The semaphorin 4D receptor controls invasive growth by coupling with Met"; *Nat Cell Biol.* 4(9); pp. 720-724.
Goldenberg, S. L., N. Bruchovsky, et al. (1988) "The combination of cyproterone acetate and low dose diethylstilbestrol in the treatment of advanced prostatic carcinoma";*J Urol.* 140(6); 1460-1465.
Hariton-Gazal et al (2002) "Targeting of nonkaryophilic cell-permeable peptides into the nuclei of intact cells by covalently attached nuclear localization signals"; *Biochemistry* 41(29); pp. 9208-9214.
Heinlein, C. A. and Chang C. (2004), "Androgen Receptor in Prostate Cancer"; *Endocrine Reviews* 25(2); pp. 276-308.
Herman, J. G. and Meadows G. G. (2007). "Increased class 3 semaphorin expression modulates the invasive and adhesive properties of prostate cancer cells"; *Int J Oncol* 30(5); pp. 1231-1238.
Huggins, C. and Hodges C. (1941). "Studies on prostatic cancer. I. the effect of castration, of estrogen and of androgen injection on serum phosphatases in metastatic carcinoma of the prostate"; *Cancer Res* 1; pp. 293-297.
Hutt, et al (2012) "Plasma half-life extension of small recombinant antibodies by fusion to immunoglobulin-binding domains"; J Biol Chem. 287(7); pp. 4462-4469.
Kolodkin, et al. (1993). "The semaphorin genes encode a family of transmembrane and secreted growth cone guidance molecules"; *Cell* 75(7); pp. 1389-1399.
Kruger, et al. (2005). "Semaphorins command cells to move"; *Nat Rev Mol Cell Biol.* 6(10); pp. 789-800.
Kyte & Doolittle (1982) "A simple method for displaying the hydropathic character of a protein"; . *J Mol Biol* 157; pp. 105-132.
Morris et al (2001) "A peptide carrier for the delivery of biologically active proteins into mammalian cells"; *Nature Biotechnol* 19(12); pp. 1173-1176.
Nair et.al (2003) "Mimicry of native peptide antigens by the corresponding retro-inverso analogs is dependent on their intrinsic structure and interaction propensities";*J. Immunol.*170(3); pp. 1362-1373.
Negishi, et al (2005) "Plexins: axon guidance and signal transduction"; *Cell Mol Life Sci* 62; pp. 1363-1371.
Perez et al (1992) "Antennapedia homeobox as a signal for the cellular internalization and nuclear addressing of a small exogenous peptide"; *J. Cell Sci* 102; pp. 717-722.
Petrylak, D.P. et al. (2004). "Docetaxel and estramustine compared with mitoxantrone and prednisone for advanced refractory prostate cancer"; *N. Engl J Med* 351(15); pp. 1513-1520.
Pooga et al (1998) "Cell penetration by transportan"; *FASEB J* 12; pp. 67-77.
Prior et al (1992) "Translocation mediated by domain II of Pseudomonas exotoxin A: transport of barnase into the cytosol"; *Biochemistry* 31; pp. 3555-3559.
Rattan et al. (1992), "Protein synthesis, posttranslational modifications, and aging"; *Ann N Y Acad Sci.* 663; pp. 48-62.
Ryser et al (1980) "Conjugation of methotrexate to poly (L-lysine) as a potential way to overcome drug resistance"; *Cancer* 45: pp. 1207-1211.
Seifter et al. (1990) "Analysis for protein modifications and non-protein co factors"; *Methods Enzymol.* 182; pp. 626-646.
Shen et al (1978) "Conjugation of poly-L-lysine to albumin and horseradish peroxidase: a novel method of enhancing the cellular uptake of proteins"; *Proc Natl Acad Sci U S A.* 7(4); pp. 1872-1876.
Stenmark et al (1991) "Peptides fused to the amino-terminal end of diphtheria toxin are translocated to the cytosol"; *J Cell Biol.* 113; pp. 1025-1032.
Swiercz, et al. (2004). "Plexin-B1/RhoGEF-mediated RhoA activation involves the receptor tyrosine kinase ErbB-2"; *J Cell Bioll* 65(6); pp. 869-680.
Swiercz, et al. (2008) "ErbB-2 and met reciprocally regulate cellular signaling via plexin-B1"; *J Biol Chem.* 283(4); pp. 1893-1901.
Tamagnone. and Comoglio (2000). "Signalling by semaphorin receptors: cell guidance and beyond"; *Trends Cell Biol.* 10(9); pp. 377-383.
Tannock, et al (2004) "Docetaxel plus prednisone or mitoxantrone plus prednisone for advanced prostate cancer"; *N Engl J Med.* 351(15); pp. 1502-1512.
Verras, et al. (2007) "The androgen receptor negatively regulates the expression of c-Met: implications for a novel mechanism of prostate cancer progression"; *Cancer Res* 67(3); pp. 967-975.
Wiedlocha et al (1994) "Dual mode of signal transduction by externally added acidic fibroblast growth factor"; *Cell* 76; pp. 1039-1051.
Wolfert et al (1996) "Atomic force microscopic analysis of the influence of the molecular weight of poly(L)lysine on the size of polyelectrolyte complexes formed with DNA"; *Gene Ther.* 3; pp. 269-273.
Worzfeld, T. and Offermanns S. (2014) "Semaphorins and plexins as therapeutic targets"; *Nat Rev Drug Discov.* 13(8); pp. 603-621.
Christensen et al., (2005) "Proteolytic Processing Converts the Repelling Signal Sema3E into an Inducer of Invasive Growth and Lung Metastasis", Cancer Research, 65(14):6167-6177.
Conrotto et al., (2005) "Sema4D induces angiogenesis through Met recruitment by Plexin B 1", Blood, 105(11):4321-4329.
Jian et al., (2015) "SEMA4B inhibits growth of non-small cell lung cancer in vitro and in vivo", Cellualr Signalling, 27:1208-1213.
Klostermann et al., (1998) "The Chemorepulsive Activity of the Axonal Guidance Signal Semaphorin D Requires Dimerization", Journal of Biological Chemistry, 273(13):7326-7331.
Koppel, Adam and Raper, Jonathan A. (1998) "Collapsin-1 Covalently Dimerizes, and Dimerization Is Necessary for Collapsing Activity", Journal of Biological Chemistry, 273(25):15708-15713.
Worzfeld et al., (2012) "ErbB-2 signals through Plexin-B1 to promote breast cancer metastasis", J Clin Invest, 122(4):1296-1305.

\* cited by examiner

FIG. 1A

| | | | | | | | |
|---|---|---|---|---|---|---|---|
| SM3A_CHICK/57- | YHTFLLD---- | EERSRLYVGA | KDHIFSFNLV | N-IKEYQ---- | -KIVWPVSH | SRRDECKW-- | -AGKDI---- | --LRECANFI |
| SM3E_HUMAN/58- | LHTMLLD---- | EYQERLFVGG | RDLVYSLSLE | R-ISDGY---- | -KEIHWPSTA | LKMEECIM-- | -KGKDA---- | ----GECANYV |
| SM3C_MOUSE/54- | YRILLMD---- | EDQDRIYVGS | KDHILSLNIN | N-ISQEP---- | -LSVFWPAST | IKVEECKM-- | -AGKDP---- | --THGCGNFV |
| Q9NS98/58-503 | LQAMYLD---- | EYRDRLFLGG | LDALYSLRLD | Q-AWPDP---- | -REVLWPPQP | GQREECVR-- | -KGRDP---- | --LTECANFV |
| SM3D_CHICK/58- | FRTLLLD---- | EERGRLLVGA | KDHIFLLNLV | D-LNKNV---- | -KKIYWPAAK | EKMELCKL-- | -AGKDA---- | --HTDCANFI |
| SMZ2_BRARE/74- | FQTVLLD---- | EERSRLLLGA | KDHVYLLDPD | N-INKHP---- | -KKLSWPASR | DRVEMCIL-- | -AGKNP---- | --LTECANFI |
| 2800035/56-498 | YQALLVD---- | EERGRLFVGA | ENHVASLNLD | N-ISKRA---- | -KKLAWPAPV | EWREECNW-- | -AGKDI---- | --GTECMNFV |
| SZ1A_BRARE/57- | YDTFLMD---- | GERGRLLVGA | EDHVFSFDLV | N-INRDV---- | -KQIAWPATP | SKRDECKW-- | -AGKDL---- | --RKDCSNFV |
| 1000207/57-529 | YRILLKD---- | EDHDRMYVGS | KDYVLSLDLH | D-INREP---- | -LIIHWAASP | QRIEECVL-- | -SGKDV---- | --NGECGNFV |
| 12405803/53-48 | FLTLTIT---- | EPTGLLYVGA | REALFAFSME | A-LELQG---- | -AISWEAPV | EKKTECIQ-- | -KGKNN---- | --QTECFNFI |
| SM4F_MOUSE/71- | YSALLVD---- | PASHTLYVGA | RDSIFALTLP | F-SGEKP---- | -RRIDWMVPE | THRQNCRK-- | -KGKK----- | --EDECHNFI |
| SM4D_MOUSE/50- | YSALLMS---- | EDKDTLYVGA | REAVFAVNAL | N-ISEKQ---- | -HEVYWKVSE | DKKSKCAE-- | -KGKSK---- | --QTECLNYI |
| SMZ7_BRARE/53- | YTTMLLR---- | DDLNLLLGA | REAIFALDLD | D-ITIKK---- | -AMLKWEVTR | DQQNDCSN-- | -KGKDA---- | --TNDCKNYI |
| Q9HCF3/82-515 | YSTLLLE---- | EASARLLVGA | RGALFSLSAN | D-IGDGAH--- | -KEIHWEASP | EMQSKCHQ-- | -KGKNN---- | --QTECFNHV |
| YTALLLS---- | RDGRTLYVGA | REALFALSSN | L-SFLPGGEY | -QELLWGADA | EKKQQCSF-- | -KGKDP---- | --QRDCQNYI |
| BAB21836/126-5 | FDTLLIS---- | DDGNTLYVGA | RETVLALNIQ | N-PGIPRLK-- | -NMIPWPASE | RKKTECAF-- | -KKKSN---- | --ETQCFNFI |
| SM4A_MOUSE/64- | IQNVVLY---- | --KHHVYIGA | VNKIYVLNET | -LQNISV---- | -YKTGPILES | PGCAPCEDCK | DKANLSNSV- | --WKDNVNMA |
| Q90975/52-496 | IQNVILH---- | --EHHIFLGA | TNYIYVLNEE | DLQKVAE---- | -YKTGPVLEH | PDCFPCQDCS | SKANLSGGV- | --WKDNINMA |
| 307196/52-496 | IQSIIMF---- | --KGYVYVGA | VNKIYVLNEN | -LTKISE---- | -YKTGPLLKH | SDCLPCKNCT | DNLLSPNGT- | --WKDSVNMA |
| Q9W650/48-490 | IQNVVTL---- | --DGIIYVGA | TNRIYALAPS | -LTKLSE---- | -YRTGPLLAN | QTCGQKVANA | SSGGG----- | --RKDNLNVA |
| Q08757/51-503 | VQNIAVF---- | PDPPTVFVAV | RNRILVVDPE | -LRLRSV---- | -LVTGPTGS- | APCEICRLCP | AAVD-AP--- | --GPEDVDNVL |
| Q9GN0/50-493 | IQNIVNN---- | SFYQEVYVAS | QNVIEAVNQS | -LEKVWE---- | -LRTGPVGS- | PECKICDLCN | TDKD-PS(1) | --LEDTNNEV |
| Q9GM5/50-490 | VQNIAVN--WD | SQQKEIYIGC | QNAIKAVSGT | -LEEMWE---- | -VKTGPVGS- | PDCETCKLCD | VEAD-PE--- | --DPVDTDSEV |
| RON_HUMAN/55-5 | VQAMVTYEGD | RNESAVFVAI | RNRLHVLGPD | -LKSVQS---- | -LATGPAGD- | PGCQTCAACG | PGPHG----- | --PPGDTDTKV |
| Q62190/57-510 | VQATAAY-ED | STNSAVFVAT | RNHLHVLGPD | -LQFIEN---- | -LTTGPIGN- | PGCQTCASCG | PGPH---GP- | --PKDTDTLV |
| P79950/50-488 | IQNLVSQ---- | --EDLLFLTI | TNHLYVLTGN | ELHMLQN---- | -LTTGPTNS- | -QCTLCSKCQ | MGNALPS--- | --QPEDTESQV |
| P91823/44-487 | LTHLVVH---- | NKTGEVYVGA | INRIYKLSNN | -LTLLRT---- | -HVTGPVEDN | EKCYPPP-SV | QSCP-HGLI- | --TTNNVNKL |
| P70208/34-473 | LTHLAVH---- | RVTGEVFVGA | VNRVFKLAPN | -LTELRA---- | -HVTGPIEDN | ARCYPPP-SM | RVCS-HRLV- | --PVDNVNKL |
| P70206/49-494 | LTHLVVH---- | EQTGEVYVGA | VNRIYKLSGN | -LTLLRA---- | -HVTGPVEDN | EKCYPPP-SV | QSCP-HGLG- | --STDNVNKL |
| O75051/119-561 | FNHLTVH---- | QGTGAVYVGA | INRVYKLTGN | -LTIQVA---- | -HKTGPEEDN | KSCYPPL-IV | QPCS-EVLT- | --LTNNVNKL |
| O96681/75-504 | LNHLLVD---- | TITGRVFVGG | VNRLYQLSPD | -LELSET---- | -VKTGPQNDS | VECSILD-CP | LNAV-RS--- | --PTDNYNKV |
| O96682/87-517 | FTHMSFD---- | FMHNVLFAGA | TNKILKLNEN | -LRVLAE---- | -AVTGPLHDS | PQCHAGG-CP | EDIETS---- | --LVNNFNKI |
| LQHLARD---- | PTSGTLYLGA | TNFLFQLSPG | -LQLEAT---- | -VSTGPVLDS | RDCLPPV-MP | DECP-QA--- | --QPTNNPNQL |
| O15031/37-453 | LNHLAVD---- | EASGVVYLGA | VNALYQLDAK | -LQLEQQ---- | -VATGPALDN | KKCTPPI-EA | SQCH-EA--- | --EMTDNVNQL |
| FNHLVLA---- | PDQGKLYVGA | VNHLFQLSPE | -LKMESV---- | -AVTGPVIDS | PDCVPFR-DL | AECP-QA--- | --QLTDNANQL |
| Q9N375/43-495 | FEKMAID---- | PSTTRVFVGA | VNSLYDLTSA | DLTVRRH---- | -VQTGPQDDS | PLCRGKWNKK | NSLKKLY(16) | SRTNSHTKA |
| Q9Y4D7/119-589 | TNNFALD---- | GAAGTVYLAA | VNRLYQLSGA | NLSLEAE---- | -AAVGPVPDS | PLCHAPQLPQ | ASCEHPR--- | --RLTDNYNKI |
| O45657/66-471 | IDDFIVS---- | RDQQTIYVAS | LNRLTSLSIS | NFSIQHE---- | -VSLGPVQDS | PWCSADGKSC | L--KLVN(16) | FPTDVRTKI |

```
Q90975/52-496    LLLETY-Y---DDQLISCGS -VSGGVCHRH IIPPDNP--- AD---IESEV H--CMYSPQV DGEADNCPDC VVSTLGTKVL
307196/52-496    LVVDTY-Y---DDQLISCGS -VNRGTCQRH VFPHNHT--- ADIQSEVH-- ----CIFSPQ- IEEPSQCPDC VVSALGAKVL
Q9W650/48-490    LFVQDF-Y---DDQLISCGN -IRKGECQRH TLHSDKP--- WD--IASDV H--CLYSSQM VEDKDSCPDC IVSTAGSKIL
Q9YGM7/50-505    LVVENI-Y---DKGLFSCGS -ADNGVCRRH VLEDDV---S LDEEG(4)VD E(4)FTDLKQ DKGQPRDSDV VVSPSGSQVL
Q08757/51-503    -LLLDP-V---EPWLYSCGT -ARRGLCYLH QLDVRG---S EVTIA---ST R--CLYSAA- ANSPVNCPDC VASPLGSTAI
Q9YGN0/50-493    -LLLDT-L---FMYLYTCGS -SQYGVCYFH QLNSTGE--- PPSL----S K--CLYRKK- SNSAAYCPDC VASSLGTKVT
Q9YGM5/50-490    -LVLDP-AGI LLPYLYVCGS -TQHGICYFI DIESPE---- -------HAP Q--CLYKKQ- RNSPTRCPDC LASPLGTKVS
RON_HUMAN/55-5   -LVLDP-A---LPALVSCGS -SLQGRCFLH DLEPQGT--- AV--HLAAP A--CLFSAH- HNRPDDCPDC VASPLGTRVT
Q62190/57-510    -LVMEP-G---LPALVSCGS -TLQGRCFLH ELEPRGK--- ALHL---AAP A--CLFSAN- NNKPEACTDC VASPLGTRVT
P79950/50-488    -LVADP-E---ESVIYSCGS -SLHGLCFMH VIASSK---I VDS------- -KCLFN-QN RNNASSCPDC IASPLGTLLI
Q91823/44-487    -LLIDY-S---DNRLIACGS -ASQGICQFL RLDDLF---- -KLG(4)RK EHYL-SSVN ESGTM----- --SGVIIEV
P70208/34-473    -LLIDY-A---ARRLVACGS -IWQGICQFL RLDDLF---- -KLG(4)RK EHYL-SGAQ EPDSM----- --AGVIVEQ
P70206/49-494    -LLLDY-A---ANRLLACGS -ASQGICQFL RLDDLF---- -KLG(4)RK EHYL-SSVR EAGSM----- --AGVLIAG
O75051/119-561   -LIIDY-S---ENRLLACGS -LYQGVCKLL RLDDLF---- -ILV(4)KK EH-YLSSVN KTGTMY---- --GVIVRS
O96681/75-504    -LLIDRAT---SRLIACGS -LFQGTCTVR NLQNVSIIEH EV-------- ---------- -PD------- ---AVV
Q96682/87-517    LVVSYAH----DGILIACGS -IRQGACEIY SLPRFPATPQ FFAV------ ---------- ---------- ---PLA
O43157/35-463    LLVS-PG----ALVVCGS -VHQGVCEQR RLGQLEQLLL RPERP----- ---------- ---------- ---GDTQY
O15031/37-453    -LLLD-PP---RKRLVECGS -LFKGICALR ALSNISL--- RLFYE----- ---------- ---------- ---SFVA
Q9QY40/34-435    -LLVS-SR---TQELVACGQ -VKQGVCEKR RLGDVTQ--- --VLY----- ---------Q AEDPGD---- ---GQFVA
Q9N375/43-495    -LSVYD-K---SSKLIECSN -LYQGRCRLR NLHNISEVIS EAIEP----- ---------- DGSGEK---- ---RVS
Q9Y4D7/119-589   -LQLDP-G---QGLVVVCGS -IYQGFCQLR RRGNISAVAV RFPPA(4)EP V---TVFPSM LNVAANHPNA STVGLVLPPA
O45657/66-471    -L-QILP----TNQILQCGS -VKLGSCSTF NSKLSLITES TIAV------ ---------- -AANSPDA-- ---STVS
VA39_VACCV/42-   V--EDAD----KDTLVCGTN NGNPKCWKID GSDDPKHR-- ---------- ---------- ---------- ---------- G
Q9TYS4/68-465    RTYFELTN---DTLILCGT HALQPTCAEF RKGNAK---- ---------- ---------- ---------- ----------
O75326/75-477    TLLER-RS---EGLLACGT NARHPSCWNL VNGTVV---- ---------- ---------- ---------- ----------
Q64906/97-496    TLLHN-QT---DGLLACGT NSQKPSCWLI NNLTTQ---- ---------- ---------- ---------- ----------
Q9J5F6/46-415    TFIGG-YD---DKILVCGT NSSSPTCWYI NGTIKEPT-- ---------- ---------- ---------- ----------
Q9N138/36-461    RFLAFTNN---LDSIYVCSS VGMRPEIRVL DSLSLR---- ---------- ---------- ---------- ----------
Q9P2H9/58-489    KVLLKKND---DALFVCGT NAFNPSCRNY KMDTLE---- ---------- ---------- ---------- ----------
SM6B_HUMAN/65    KVLLLRDE---STLFVCGS NAFNPVCANY SIDTLQ---- ---------- ---------- ---------- ----------
SM6C_HUMAN/61    RVLVPWDS---QTLLACGT NSFSPVCRSY GITSLQ---- ---------- ---------- ---------- ----------
SM2A_SCHGR/39-   RVIQPMGD---GSRLYICGT NAHSPKDWVV YSNLT----- ---------- ---------- ---------- ----------
C49423/68-506    RVIQSMDQ---GDRLYVCGT NAHNPKDYVI YANLTH---- ---------- ---------- ---------- ----------
SM1A_SCHAM/50-   RVLAKIDD---DRVLICGT NAYKPLCRHY ALKDGD---- ---------- ---------- ---------- ----------
SM1A_TRICF/48-   RILYSSEP---GKLVICGT NSYKPLCRTY AFKEGK---- ---------- ---------- ---------- ----------
SM1A_DROME/47-   RIMVVPSP---GRLFVCGT NSFRPMCNTY IISDSN---- ---------- ---------- ---------- ----------
O44253/61-492    RVYALRPN---GEVLLCGT NSYKPRCRHY TAVEVSSEEA GSA------- ---------- ---------- ----------
SM1A_CAEEL/54-   RVLARKSA---GVSLVCGT HAFSPKCREY TVTEFG---- ---------- ---------- ---------- ----------
```

```
O43157/35-463     VAANDPAVST VGL--VAQGL AGEPL----- ---------- ---------- ---------- ----LFVG RGYTSR-GVG GGI-PPITTR ALWPPDPQ-
O15031/37-453     SNDEGVATVG ---------- LVSST G--P----G GDRV------ ---------- ---------- ----LFVG KGN----GPH DN-GIVSTR LLDRTDSREA
Q9QY40/34-435     ANTLGVTTV- ---------- ---GL -VVPL-PGRD L--------- ---------- ---------- ----LLVA RG-LA--GKL SAGVPPLTVR QLAGPQP---
Q9N375/43-495     NDTSSSVVIF V--------- ---GS G--PAN--LS SEPV------ ---------- ---------- ----LYVG ATIGSG-DHD RMSVSSLFLR PQKAFEVVFP
Q9Y4D7/119-589    AGAGGSRLLV GA-------- TYTGY GSS-FFPRNR SLE------- ---------- DHRFEN T-------P EIAIRSLDTR --GDLAKLFT
O45657/66-471     KIIDNRLIVA ASA------- TKESP YRDPF-PAVA IRNL------ ---------- ---------- PGLNVE NAG-DLEGEA AVFLRAAYKN --------
VA39_VACCV/42-    ---------- ---------- --GRG YAPY--QNSK VTIIS----- ---------- ---------- HNG CVLSDINISK EGIKR--WR RFDGP----
Q9TYS4/68-465     ---------- ----PQ R--- -LISAV GMSPIDADST APFIRS-NE- ---------- ---------- NIITV NVA-ELSSSE PLLVRRNVIK MWKGIEN--
O75326/75-477     ---------- ----PLGEMR GYAPFSPDEN SLVLFEGRA- ---------- ---------- GDEVYST IRKQEYNGKI RRFRRIRG ---------
Q64906/97-496     ---------- -----FLGPKL GLAPFSPSSG NLVLFD-QN- ---------- ---------- DTYST INLYKSLSGS HKFRRIAG ---------
Q9J5F6/46-415     ---------- ----PYGR GLSPESYDMT GLVLI--DG- ---------- ---------- KEIYS -TIKKYSHLS TGFSRIVGK ---------
Q9NI38/36-461     ---------- ----DQQ EP--- -RTEI GICVVDPTFN FTAVVV-DS( 4)DATSVYSG IRT-GMGGEN HLIYRPPLTK NGKQ-----
Q9P2H9/58-489     ---------- ----P-FG DEF--- -SGM ARCPYDAKHA NVALFA-DG- ---------- ---------- KLYSA TVT-DFLAID AVIYRSLG ---------
SM6B_HUMAN/65-    ---------- ----PVG DNI--- -SGM ARCPYDPKHA NVALFS-DG- ---------- ---------- MLFTA TVT-DFLAID AVIYRSLG ---------
SM6C_HUMAN/61-    ---------- ----QE-G EE--- -LSGQ ARCPFDATQS NVAIFA-EG- ---------- ---------- SLYSA TAA-DFQASD AVVYRSLG ---------
SM2A_SCHGR/39-    ---------- HLQRH EYVPGIGVGI AKCPFDPEDS STAVWV-EN( 4)DLPGLYSG TNA-EFTKAD TVIFRTDLYN LTTGR----
C49423/68-506     ---------- LPRS EYVIGVGLGI AKCPYDPLDN STAIYV-EN( 4)GLPGLYSG TNA-EFTKAD TVIFRTDLYN TSAKR----
SM1A_SCHAM/50-    ---------- ----YVVE KEY--- -EGR GLCPFDPDHN STAIYS-EG- ---------- ---------- QLYSA TVA-DFSGTD PLIYRGP ---------
SM1A_TRICF/48-    ---------- ----YLVE KEV--- -EGI GLCPYNPEHN STSVSY-NG- ---------- ---------- QLFSA TVA-DFSGGD PLIYREP ---------
SM1A_DROME/47-    ---------- ----YTLE ATK--- -NGQ AVCPYDPRHN STSVLA-DN- ---------- ---------- ELYSG TVA-DFSGSD PIIYREP ---------
O44253/61-492     HAHAMRYEVS RDV--- -EAQ GLCPYSPAHN STYAFA-DG- ---------- ---------- HLYSA TVA-DFSGGD PLIYREN ---------
SM1A_CAEEL/54-    ---------- IRNT RQF--- -DGQ GISPYDPKHN SSALYV-PG- ---------- ---------- TNQLFVA TVT-DFVGND ALIYRKTIDE TPSSK----
Q9P283/177-588    ---------- R-TT EKI--- -NGV ARCPYDPRHN STAVISSQG- ---------- ---------- ELYAA TVI-DFSGRD PAIYRSLG ---------
SM5A_MOUSE/58-    ---------- EIH DQI--- -SGM ARCPYSPQHN STALLTASG- ---------- ---------- ELYAA TAM-DFPGRD PAIYRSL ---------
Q9VTT0/63-469     ---------- ---------- ---VDSGV VKCPFHPQAN STSLLQSNG- ---------- ---------- QLFVG TAT-DFSGSD VAILRTGVES ---------
Q9QZC2/46-435     ---------- ---------- ---LRNGT EVVSCHPQGS TAGVVYRAS- ---------- ---------- GTDLWYLA VAATYVLPEP ETANRCNPAA SDRDTAIALK
Consensus/60%     .......... .......pG. tbsPbps... ..sl...... ---------- ---------- .bLYst *s..-b.tps shbhRsht.p ..........
SM3A_CHICK/57-    ---------- ---------- -PIRTE QHDSRWLN-- ---DPRFI SAHLIPESD- ---------- NPEDDKIY FFFRENAIDG --EH-TGKA THARIGQICK
SM3E_HUMAN/58-    ---------- ---------- -HIRTE HDDERLLK-- ---EPKFV GSYMIPDNE- ---------- DRDDNKVY FFFTEKALEA --EN-NAHA IYTRVGRLCV
SM3C_MOUSE/54-    ---------- ---------- -QLRTD QHNSKWLS-- ---EPMFV DAHVIPDGT- ---------- DPNDAKVY FFFKERLTDN --NR-STKQ IHSMIARICP
Q9NS98/58-503     ---------- ---------- -ALRSD S-DQSLLH-- ---DPRFV MAARIPENS- ---------- DQDNDKVY FFFSETVPSP --DGGSNHV TVSRVGRVCV
SM3D_CHICK/58-    ---------- ---------- -DHHYIRTD ISEHYWLT-- ---GAKFI ATFPIDTY-- ---------- NPDDDKIY FFFREISQDS ---ST-SDKT ILSRVGRVCK
SMZ2_BRARE/74-    ---------- ---------- -HQQYIRTD ISEDYWIN-- ---EGKFI SAHPISDTY- ---------- NPDDDKIY FFFREASRDG ---ST-TDKS VLSRVARICR
2880035/56-498    ---------- ---------- -SLRTE PHDSRWLN-- ---EPKFV KVFWIPESE- ---------- NPDDDKIY FFFRETAVEA --APALGRL SVSRVGQICR
SZ1A_BRARE/57-    ---------- ---------- -PIRTE QHDSRWLN-- ---EPRFL GIHLIPESD- ---------- NPEDDKIF LFFKENAMDG --EH-TGKA TISRIGQLCK
1000207/57-529    ---------- ---------- -AMRTD QYNSRWLN-- ---DPSFI HAELIPDSA- ---------- ERNDDKLY FFFRERSAEA ---PQ--SPA VYARIGRICL
12405803/53-48    ---------- ---------- -PHHSMKTE -YLAFWLN-- ---EPHFV GSAYVPESVG SFTGDDDKVY FFFRERAVES ---DC-YAEQ VVARVARVCK
SM4F_MOUSE/71-    ---------- ---------- -AEDWIRTE -TLSSWLN-- ---APAFV AAMVLSPAEW GDEDGDDEIF FFFTETSRVL --DS-YERI KVPRVARVCA
```

FIG. 1F

| | | | | | | |
|---|---|---|---|---|---|---|
| SM4D_MOUSE/50- | ---HSPLRTE | -YAIPWLN----- | ---EPSFV | FADVIQKSPD | GPEGEDDKVY | FFFTEVSVEY ---EF-VFKL MIPRVARVCK |
| SMZ7_BRARE/53- | ---ESIRTE | -FTSTWLS----- | ---EPNFI | HMAHIPEGQS | NPDGDDDKIY | LFFFSETAVEY ---ES-YTKV DVSRVARVCK |
| Q9HCF3/82-515 | ----SLRTE | ETPMHWLN----- | ---DAEFV | FSVLVRESKA | SAVGDDDKVY | YFFFTERATEE (6)QS-RSSH RVARVARVCK |
| BAB21836/126-5 | ---PT-KTE | -SSINWLQ----- | ---DPAFV | ASAYIPESLG | SLQGDDDKIY | FFFFSETGQEF ---EF-FENT IVSRIARICK |
| SM4A_MOUSE/64- | ---SHPVLKTD | IF-LRWLH----- | ---ADASFV | AAIP------ | ---STQVVY | FFFEETASEF ---DF-FEEL YISRVAQVCK |
| Q90975/52-496 | FLTDQSYIDI | LPQF--------- | -RDSYPIKYV | HAFE------ | ---HDHFVY | FLTVQRESL----DSQT FHTRIIRFCT |
| Q90975/52-496 | FLTDQSYIDI | LPEF--------- | -RDSYPIKYV | HAFE------ | ---SNNFIY | FLTVQRETL----DAQT FHTRIIRFCS |
| 3071196/52-496 | YLTDQSYIDV | LPHL--------- | -RDIYPIRYI | YTFE------ | ---SNNFVY | FLTVQRESL----DSQA YHTRIVRICS |
| Q9W650/48-490 | FFSNRSYMDL | IPPL--------- | -RGSYLRYV | YSFH------ | ---SGPFTY | FLTVQQVSK----DSQT YHTRIVRMCS |
| Q9YGM7/50-505 | ---DPFHSLTV | LPHY--------- | -QDVYPIHYV | HSFT------ | ---DGDHVY | LVTVQPEFP----GSST FHTRLVRLSA |
| Q08757/51-503 | ---SDVRGLTV | LPSL--------- | -RNTYHIEYV | YSFF------ | ---TQEFVF | FLSVQRESPD ---Q-ESSP FQTRLGRLPR |
| Q9YGN0/50-493 | ---MVTDGLTV | LPSL--------- | -RSTYKIDYI | HSFA------ | ---TKEYVY | FLSLQRENPS ---N-SNSP LQTRLGRLPI |
| Q9YGM5/50-490 | ---PGFVALSV | LPKH--------- | -LVSYSIEYV | HSFH------ | ---TGAFVY | FLTVQPASVT ---D-DPSA LHTRLARLSA |
| RON_HUMAN/55-5 | ---PGFPSLSV | LPKY--------- | -LASYLIKYV | YSFH------ | ---SGDFVY | FLTVQPISVI ---S-PPSA LHTRLVRLNA |
| Q62190/57-510 | ---GGFHSLTV | LETF--------- | -RDSYPIHYV | HTFT------ | ---SGSYVY | FLTVQPEHPL ----SST YHSRVVRLYK |
| P79950/50-488 | FGFVYQDEFV | SSQLKIPS(5) | FPTFDIYYV | YSFS------ | ---SEQFVY | YLTLQLDTQL (4)ST-GEQF FTSKIVRLCV |
| Q91823/44-487 | FSLVYQDEFV | SSQIKIPS(5) | YPAFDIYYI | YGFV------ | ---SASFVY | FLTLQLDTQQ (4)TA-GEKF FTSKIVRMCA |
| P70208/34-473 | FGFVYQDEFV | SSQLKIPS(5) | FPAFDIYYV | YSFR------ | ---SEQFVY | YLTLQLDTQL (4)AA-GEHF FTSKIVRLCV |
| P70206/49-494 | LDYELHSDFV | SSLIKIPS(5) | VSHFDIFYI | YGFA------ | ---SGGFVY | FLTVQPETPE (5)SA-GDLF YTSRIVRLCK |
| 075051/119-561 | ASSAVTTGTR | TFINSYAR---- | -ETYFVNYV | YGFS------ | ---SERFSY | FLTTQLKHSH ---HS-SPKE YITKLVRICQ |
| O96681/75-504 | FSIQQSIINI | DVKY--------- | -RDHFLVDYI | YGFN------ | ---SSEYAY | FIVQKKSH ---LA-DEAG YVTRLARICI |
| O96682/87-517 | -AAFSYEETA | KLAVGRLS----- | -EYSHHFV | SAFA------ | ---RGASAY | FLFLRRDLQA ---QSRA FRAYVSRVCL |
| 043157/35-463 | FEAYTDHATY | KAGY--LS----- | -TNTQQFV | AAFE------ | ---DGPYVF | FVFNQQDKH ----PAR NRTLLARMCR |
| 015031/37-453 | FSSEGLGRLV | VGDFS-------- | -DYNNSYV | GAFS------ | ---DAHSAY | FVFRRRGARA ----QTE YRSYVARVCL |
| Q9QY40/34-435 | GLYGGTHVSL | DYRSRGY------ | -YKYQIDYI | NGFE------ | ---SGDYAY | FVTRQRVNIA ---DDSS IQSRLVRVCT |
| Q9N375/43-495 | FDLNPSDDNI | LKIKQGAK----- | -EQHKLGFV | SAFLHPSDP- | -PPGAQSYAY | LALNSEARA ---GD-KESQ ARSLLARICL |
| Q9Y4D7/119-589 | ---------- | -------------- | --AFKFL | YTFT------ | ---HQHFVF | VVAMVTPR-----E-SRLP MTTRLIRFCR |
| 045657/66-471 | ---CGYDLYTA | DNVIPK------- | -DGLRGAFV | DK-------- | ---DGTYDKVY | ILFTDTIGS ----KRIV KIPYIAQMCL |
| VA39_VACCV/42- | ---DVILRTP | R-GLSSFE----- | -QANFL | SMHKVKKV-- | ---RGVEEVL | FFFSESPMET ---EG-CGLH KVARVGRVCE |
| Q9TYS4/68-465 | ---ESELYT- | ---SDTVMQ----- | -NPQFI | KATIVHQD-- | -QAYDDDKIY | YFFREDNPDK ---NP-EAPL NVSRVAQLCR |
| 075326/75-477 | ---QVELYT- | ---SDTAMH----- | -RPQFV | QATAVHKN-- | -ESYDDDKIY | FFFQENSHSD ---FK-QFPH TVPRVGQVCS |
| Q64906/97-496 | ---PVLYT- | ---SSSTMK----- | -NPKFV | HLVSLQET-- | -NSINDTIY | IFFQEEG------- -MAKVSRVCK |
| Q9J5F6/46-415 | LHASIRTI | YSDNKWLN----- | -EPQFV | GSFD------ | ---VGQHVF | FFFREIAHDN ---SF-GERI VHSRVARVCK |
| Q9N138/36-461 | ESPTLRTV | KHDSKWLK----- | -EPYFV | QAVD------ | ---YGDYIY | FFFREIAVEY ---NT-MGKV VFPRVAQVCK |
| Q9P2H9/58-489 | DRPTLRTV | KHDSKWFK----- | -EPYFV | HAVE------ | ---WGSHVY | FFFREIAMEF ---NY-LEKV VVSRVARVCK |
| SM6B_HUMAN/65- | PQPPLRSA | KYDSKWLR----- | -EPHFV | QALE------ | ---HGDHVY | FFFREVSVED ---AR-LGKV QFSRVARVCK |
| SM6C_HUMAN/61- | REYSFKRTL | KYDSKWLD----- | -NPNFV | GSFD------ | ---VGEYVL | FFFRETAVEY ---IN-CGKS VYSRVARVCK |
| SM2A_SCHGR/39- | LEYKFKRTL | KYDSKWLD----- | -KPNFV | GSFD------ | ---IGEYVY | FFFRETAVEY ---IN-CGKA VYSRIARVCK |
| C49423/68-506 | | | | | | |

FIG. 1G

```
SM1A_SCHAM/50-     ------LRTE RSDLKQLN-- ---------- ----APNFV NTME------ ------YNDFIF FFFFRETAVEY ---IN-CGKA IYSRVARVCK
SM1A_TRICF/48-     ------QRTE LSDLKQLN-- ---------- ----APNFV NSVA------ ------YGDYIF FFYRETAVEY ---MN-CGKV IYSRVARVCK
SM1A_DROME/47-     ------LQTE QYDSLSLN-- ---------- ----APNFV SSFT------ ------QGDFVY FFFRETAVEF ---IN-CGKA IYSRVARVCK
O44253/61-492      ------LRTE QYDLKQLN-- ---------- ----QPDFV GAIE------ ------RNGYVL FFFRELSMEV ---MN-FGKA VYSRVARVCK
SM1A_CAEEL/54-     ---SAANIRTQ SYDARVLN-- ---------- ----APNFV ATFA------ ------YKEHVY FWFREIASEA IDNN-EEPQ IYARVARVCK
Q9P283/177-588     ---SGPPLRTA QYNSKWLN-- ---------- ----EPNFV AAYD------ ------IGLFAY FFLRENAVEH ----D-CGRT VYSRVARVCK
SM5A_MOUSE/58-     ---GTLPPLRTA QYNSKWLN-- ---------- ----EPNFV SSYD------ ------IGNFTY FFFFRENAVEH ----D-CGKT VFSRPARVCK
Q9VTT0/63-469      ---NKRFLRTK QYNNNWLS-- ---------- ----GAQFV GSFE------ ------AGHFVY FLLRESAAEH ---MS-CGKV IYSRVARVCK
Q9QZC2/46-435      NTEGRSLATQ ELGRLKLRG- ---------- --SAGSLHFV DAFL------ ------WNGSVY FPYYPNYTS GAATGWP SMARIAQ--S
Consensus/60%      ......bcT. b.s.pbbp.. .......... ..pspFV hta....... .....sscbly FbFp-pssp. ......ssps bb*RltRlcp SM3A_CHICK/57-     NDFGGHR-SL V-NKWTTFLK ARLICSVP-- ----GPNGIDT HFDELQDVFL MNSK------ ---------- DP-KN PIVYGVFT-
SM3E_HUMAN/58-     NDVGGQR-IL V-NKWSTFLK ARLVCSVP-- ----GMNGIDT YFDELEDVFL LPTR------ ---------- DH-KN PVIFGLFN-
SM3C_MOUSE/54-     NDTGGQR-SL V-NKWTTFLK ARLVCSVT-- ----DEDGPET HFDELEDVFL LETD------ ---------- NP-RT TLVYGIFT-
Q9NS98/58-503      NDAGGQR-VL V-NKWSTFLK ARLVCSVP-- ----GPGAET HFDQLEDVFL LWPK------ ---------- AG-KS LEVYALFS-
SM3D_CHICK/58-     NDMGGQR-SL I-NKWTTFLK ARLVCSIP-- ----GPEGADT HFDELQDIFL LSTR------ ---------- DE-RN PLVYGVFT-
SMZ2_BRARE/74-     NDVGGLR-SL T-NKWTTFLK ARLVCSIP-- ----GPDGVDT HFDELQDIFL LPSR------ ---------- DE-KN PMVYGVFT-
2880035/56-498     NDVGGQR-SL V-NKWTTFLK ARLVCSVP-- ----GVE-GDT HFDQLQDVFL LSSR------ ---------- DH-RT PLLYAVFS-
SZ1A_BRARE/57-     NDMGGHR-SL V-NKWTTFLK AKLTCSVP-- ----GLNGIDT HFDELQDVFL MSAK------ ---------- DP-KN PVIYAVFT-
1000207/57-529     NDDGGHC-CL V-NKWSTFLK ARLVCSVP-- ----GEDGIET HFDELQDVDFV QQTQ------ ---------- DV-RN PVIYAVFT-
12405803/53-48     GDMGGAR-TL Q-RKWTTFLK ARLACSAP-- ----NW--QL YFNQLQAMHT LQDT------ ---------- SW-HN TTFFGVFQ-
SM4F_MOUSE/71-     GDLGGRK-TL Q-QRWTTFLK ADLLCPGP-- ----EH--GR ASGVLQDMTE LRPQ------ ---------- PGAGT PLFYGIFS-
SM4D_MOUSE/50-     GDQGGLR-TL Q-KKWTSFLK ARLICSKP-- ----DS--GL VFNILQDVFV LRAP------ ---------- GL-KE PVFYAVFT-
SMZ7_BRARE/53-     GDLGGQR-TL Q-KKWTSFLK ARLDCQVP-- ----NTN-LPL ---LVQDVFH LCPD------ ---------- DW-TT CVFYAVFT-
Q9HCF3/82-515      GDLGGKK-IL Q-KKWTSFLK ARLICHIP-- ---------- LYETLRGVCS LDAE------ ---------- TS-SR THFYAAFTLS
BAB21836/126-5     GDEGGER-VL Q-QRWTSFLK AQLLCSRP-- ----DD--GF PFNVLQDVFT LSPSP----- ---------- QDW-RD TLFYGVFT-
SM4A_MOUSE/64-     NDVGGEK-LL Q-KKWTTFLK AQLLCAQP-- ----GQ--L PFNIIRHAVL LPAD------ ---------- SP-SV SRIYAVFT-
Q90975/52-496      LD-------- -SEMRSYME MPLECIFTE( 6)--I--RKE VFNILQAAYV SKPGA-ALA HEMGLG-LID DILYGVFA-
307196/52-496      IN-------- -SGLHSYME MPLECILTE( 6)--T--KKE VFNILQAAYV SKPGA-QLA RQIGAS-LND DILFGVFA-
Q9W650/48-490      SD-------- -SELRSYIE MPLECIFTEK RRK-RSTASA VFNIVQAAYL GRAGE-DLA EEMGVK-PDD DILYGVFA-
Q9YGM7/50-505      SD-------- -HDIRRYVE MPLECISTD( 5)--SMEDVK VFNILQAATV TKVGSDVELQ RQLRLE-EGD DVLFAAFA-
Q08757/51-503      HE-------- -PELRRYRE IVLDCRYES( 10)EETERDV AYNVLQAAHA ARPGA-RLA RDLGID-GTE TVLFGAFA-
Q9YGN0/50-493      NE-------- -WEMKRYRE VILECRFEP( 7)GSEPYKDV VYNVVQAAHF AKAGR-ELA EELGAE-EED DILYGVFA-
Q9YGM5/50-490      SI-------- -REVWMYRE VVLECHFNP( 5)-GDF-RGI VYNGLQAAHF GRAGK-DLA EELRVD-EQE DILYGVFA-
RON_HUMAN/55-5     TE-------- -PELGDYRE LVLDCRFAP( 5)-GAPEGGQ PYPVLQVAHS APVGA-QLA TEISIA-EGQ EVLFGVFV-
Q62190/57-510      VE-------- -PEIGDYRE LVLDCHFAP( 6)APE--GTQ PYPVLQAAHS APVDA-KLA VELSIS-EGQ EVLFGVFV-
P79950/50-488      KE-------- -EEMRSYRE LILECRLEP( 5)-RRRAEPR IFNVLQAAHV ATVGS-TLA GELDIS-ETD PVLFAVFA-
Q91823/44-487      DD-------- -PKFYSYVE FPIGCMKDG- --------V EYRLIQDAYL SKPGK-RLA KELGIS-ERE DILFTVFS-
```

FIG. 1H

```
P70208/34-473     GD----------SEFYSYVE FPIGCSWRG-------------V EYRLVQSAHL AKPGL--LLA QALGVP-ADE DVLFTIFS
P70206/49-494     ND----------PKFYSYVE FPIGCEQAG-------------V EYRLVQDAYL SRPGQ--ALA KQLGLA-EDE EVLFTVFA
O75051/119-561    DD----------PKFHSYVS LPFGCTRAG-------------V EYRLLQAAYL AKPGD--SLA QAFNIT-SQD DVLFAIFS
O96681/75-504     ED----------SNYYSYTE IPVECISD---------AQ--GGT KFNLIVQAGFL GKPSS--NLA QSLGIS-IQN DVLFAVFS
O96682/87-517     TD----------PNYDSYTE ITVQCTATE---------NNV DYNIVRDAKV TPASH--KLA QKMGIK-KDD HVLVTVFS
O43157/35-463     RD----------QHYYSYVE LPLACEG----------GR--------YGLIQAAAV ATSR-------EVAHG EVLFAAFS
O15031/37-453     ED----------PNYYSYLE MDLQCRDPD------------------IHAAAF-------GT-CLA ASVAAP-GSG RVLYAVFS
Q9QY40/34-435     RD----------VNLYSYVE MPLTCHGQ---------------------GLIQAAFL TP---------------DTLLGAFS
Q9N375/43-495     GD----------KNFHSYTE VPLECTQN-------------GV EFNLVQDVYV TRAGY--ELA KSLDIS-VSD PVLYGVFW
Q9Y4D7/119-589    PHGAGGD---A K-KLTESYIQ LGLQCAGG---------------------------AGRGD--LYS RLVSVF-PAR ERLFAVFE
O45657/66-471     ND----------TKFESYSE IELQCRGED--------GRS---YRQI--IHS RT------------------QSY DKLIASFS
VA39_VACCV/42-    NDEGGPS--SL SSHRWSTFLK VELECDID---------ETDTDTF YFNQFAGVA---------------IKTDND TILYVFFD
Q9TYS4/68-465     DDPGGRL--SY N-KEWSSYEK ARIECSIE---------ATNK NFNRLQDVFL LPDP-------------ESP TSFYGAFR
Q75326/75-477     GDQGGES--SL SVSKWNTFLK AMLVCSDA---------DTGR IYNELQDIFI WQAP-----------SGQ-WRD TRVYGVFS
Q64906/97-496     SDQGES---SL SVYKWTTFLK ARLACVDY---------DLNV RFNYLKDVVV IKG------------ENS-WEE TLIYGLFL
Q9J5F6/46-415     HDQGSG---SL SGSKWSTFLK SIMICE-----------AN--FPF YFDHIQSVKR VDK--------------KS-PNE TIIYGLFF
Q9N138/36-461     KDIGGRN--VL R-QVWTSFVK ARLNCSVS---------GD--SHF YFNILQAVTD VIR---------------HGE TYFYATFS
Q9P2H9/58-489     NDMGGSQRVL E-KQWTSFLK ARLNCSVP---------GD--SHF YFNVLQAVTG VVS--------------INGR DVVLATFS
SM6B_HUMAN/65-    NDVGGSPRVL E-KQWTSFLK ARLNCSVP---------GD--STF YFDVLQALTG PV---------------LGGR PVVLAVFS
SM6C_HUMAN/61-    RDMGGSPRAL D-RHWTSFLK LRLNCSIP---------GE--FPF YFNEIQGVYK MPN--------------NLHGR SALFGVFS
SM2A_SCHGR/39-    KDVGGKN--IL S-QNWATFLK ARLNCSIP---------GE--FPF YFNEIQSVYQ LPS----------------T DKFFGVFS
C49423/68-506     KDVGGKN--LL A-HNWATYLK ARLNCSIS---------GD--YPF YFNEIQSTSD IIEGN------------DK SRFFATFT
SM1A_SCHAM/50-    HDKGGPH--QF G-DRWTSFLK SRLNCSVP---------GE--YPF YFDEIQSTSD IVEGR----------YGGQ-VE KLIYGVFT
SM1A_TRICF/48-    DDKGGPH--QS R-DRWTSFLK ARLNCSIP---------GD--YPF YFNEIQSASN LVEG-----------YNSDDSK KIIYGILT
SM1A_DROME/47-    WDKGGPH--RF R-NRWTSFLK SRLNCSIP---------GE--YPF YFDEIQAISP IVE------------QYGS-MSS KLIYGVFN
O44253/61-492     NDRGGPY--SH G-KSWTSFLK ARLNCSVP---------GD--FPF YFNELKAVSD PID------------SGSK SLIYAVFT
SM1A_CAEEL/54-    NDKGGAR--PA N-ERWTSYLK ARLNCSLP---------SGS--SPF YFNELKAVSD PID-------------AG-NNN HVVYTVFS
Q9P283/177-588    NDVGGRF--LL E-DTWTTFMK ARLNCSRP---------GE--VPF YYNELQSAFH LP--------------EQ DLIYGVFT
SM5A_MOUSE/58-    NDIGGRF--LL E-DTWTTFMK ARLNCSRP---------GE--VPF YYNELQGTFF LP--------------EL DLIYGIFT
Q9VTT0/63-469     NDVGGGQLL  R-DNWTSFLK ARLNCSLP---------GE--YPY YFDEIQGMTY AE--------------SE SILYATFR
Q9ZC2/46-435      TEV-------L ------FQG-Q AALDCDHGH-----------------------------PEGR-RLL LSSSLV-EAV DIWAGVFS
Consensus/60%     sD.GG....h .pcWs*alK spLsCshs........s....sh bFsblQssah h.s.........s..pp sllatVF*..

SM3A_CHICK/57-    TS--------- S NIFKGSAVCM YSMTDVRRVF L-GPYAHRDG P---NYQWVP -Y-QGRVPYP RPGTCPSKTF GG------FDST
SM3E_HUMAN/58-    TI--------- S NIFRGHAICV YHMSSIRAAF N-GPYAHKEG P---EYHWSV -Y-EGKVPYP RPGSCASKVN GGR-----YGTT
SM3C_MOUSE/54-    TS--------- S SVFKGSAVCV YHLSDIQTVF N-GPFAHKEG P---NHQLIS -Y-QGRIPYP RPGTCPGGAF TPN-----MRTT
Q9NS98/58-503     TV--------- S AVFKQGFAVCV YHMADIWEVE N-GPFAHRDG P---QHQWGP -Y-GGKVPFP RPGVCPSKMT AQPGRPFGST
SM3D_CHICK/58-    TT--------- S SVFKGSAVCV YSMADIRAVF N-GPYAHKES A---DHRWVQ -Y-EGRIPYP RPGTCPSKTY DPL-----IKST
```

FIG. 1I

```
SMZ2_BRARE/74-          TT------ S  SIFKGSAVCV YTMEDIRAAF N-GPYAHKEG P---DHRWVE -Y-EGRIPYP RPGTCPSRTY DPH----IKTT
2880035/56-498          TS------ S  SIFQGSAVCV YSMNDVRRAF L-GPFAHKEG P---MHQWVS -Y-QGRVPYP RPGMCPSKTF GT-----FSST
SZ1A_BRARE/57-          TS------ S  NIFRGSAICM YSMADIRRVF L-GPYAHRDG P---NYQWVP -F-QGRVPYP RPGTCPSKTF GG-----FDST
1000207/57-529          SS------ G  SVFRGSAVCV YSMADIRMVF N-GPFAHKEG P---NYQWMP -F-SGKMPYP RPGTCPGGTF TPS----MKST
12405803/53-48          AQ------ W  GDMYLSAICE YQLEEIQRVF E-GPYKEYHE E---AQKWDR -Y-TDPVPSP RPGSCINNWH RRHG---YTSS
SM4F_MOUSE/71-          SQ------ W  EGAAISAVCA FRPQDIRAVL N-GPFRELKH D---CNRGLP -Y-VMDNEVPQP RPGECITNNM KFQQ---FGSS
SM4D_MOUSE/50-          PQ------ L  NNVGLSAVCA YTLATVEAVF SRGKYMQSAT VEQSHTKWVR -Y-NGPVPTP RPGACIDSEA RAAN---YTSS
SMZ7_BRARE/53-          PQ------ S  DSSQYSAVCS YKIEDIKTVF SKGKFKAPFN VETSFVKWVM -Y-SGELPDP RPGACIDNHA REKG---ITKS
Q9HCF3/82-515           TQ------ W  KTLEASAICR YDLAEIQAVF A-GPYMEYQD G---SRRWGR -Y-EGVPEP RPGSCITDSL RSQG---YNSS
BAB21836/126-5          SQW----- HR GTTEGSAVCV FTMKDVQRVF S-GLYKEVNR E---TQQWYT -V-THPVPTP RPGACITNSA RERK---INSS
SM4A_MOUSE/64-          SQW----- QV GGTRSSAVCA FSLTDIERVF K-GKYKELNK E---TSRWTT -Y-RGSEVSP RPGSCSM--- --------
Q90975/52-496           QTNQI--- PQ EPTNRSAVCA VSVRTINEFF NK-IVDKQNM K---CLQHFY -GKD------ -SKYCLNRAF SR-----NAS
3071196/52-496          QSKPD--- SA EPMDRSAMCA FPIKYVNDFF NK-IVNKNNV R---CLQHFY -GPN------ -HEHCFNRTL LR-----NSS
Q9W650/48-490           QSKPD--- SP EPNNRSAVCA VSVKTINEFF NS-AADKQNT K---CLEHFY -GKD------ -NRLCINNKR FLR(4)----
Q9YGM7/50-505           RGKPN--- ST EATPNSAICV MSLKLINSMF KM-YMQKCNT V---DLYHFT ---------GS DKKSCYNVS- -------SSD
Q08757/51-503           ESHPE--- SR APQHNSAVCA FPLRLLNQAI RE-GMDKCCG T---GTQT-- LKRGLAFFQ PQQYCPHSV- ----------N
Q9YGN0/50-493           VTDDN--- G- VTEHDSALCA FPVDNVNKAI AD-GVDDCCQ S---GPEQ-- LSRGLCHFQ PCESCPHESM ENN-------
Q9YGM5/50-490           VVNEL--- G- ETQRNSALCA FPLSKVNHAI DE-GVEACCR S---GTEQ-- LSRGLGHFQ PLESCPHESS E---------
RON_HUMAN/55-5          TGKDG--- GP GVGPNSVVCA FPIDLLDTLI DE-GVERCCE S---PVHPG- LRRGLDFFQ SPSFCPNPPG LEA-LS----
Q62190/57-510           TVKDG--- GS GMGPNSVVCA FPIYHLNLLI EE-GVEYCCH S---SNSSSL LSRGLDFFQ TPSFCPNPPG G---(4)----
P79950/50-488           QSEPM--- SA QPRKYSAVCA FPISLIDLSI ED-GMNACCS N---TNSVR- LTRGLNFFQ PEMECPQN- ----------
Q91823/44-487           QGQKN--- RI KPPKESVLCL FTLKKIKDKI KE-RIQSCYR G---DGKLSL -----PWLLN KELGCINSPL QI--------
P70208/34-473           QGQKN--- RA NPPRQTILCL FTLSSINAHI RR-RIQSCYR G---EGTLAL -----PWLLN KELPCINTPL Q-----INGN
P70206/49-494           QGQKN--- RV KPPKESALCI FTLRAIKEKI KE-RIQSCYR G---EGKLSL -----PWLLN KELGCINSPL QI--------
O75051/119-561          KGQKQ--- YH HPPDDSALCA FPIRAINLQI KG-RLQSCYQ G---EGNLEL -----NWLLG KDVQCTKAP- ----------
O96681/75-504           KGEG---- N  TPTNNSALCI YSLKSIRRKF MQ-NIKSCFN G---SGMRGL NFISPSMP-- -CVLTKL QTIG------
O96682/87-517           PSREI--- SN QPESKSAMCI YSIKDIEDMF IE-NIHLCFN G---TTKDRN -LGYISGTI NDGRCPIVGS LG--------
SAAPP(8)AA              SAAPP(8)AA GASGASALCA FPLDEVDRLA NR-TRDACYT R---EGRAED GTEVAYIEYD VNSDCAQLPV DTLDAY----
O15031/37-453           RDSR---- S  SGGPGAGLCL FPLDKVHAKM EA-NRNACYT G---TREARD IFYK--PFH GDIQCGGHAP -------GSS
Q9QY40/34-435           AG------ TSQAQAALCA FPLADLDRSM EQ-ARRLCYT T---GGQGPS -Y-GMEEATVEYG VTSRCVTLPP -------DSP
Q9N375/43-495           EGDKNSYRSQ EPTGKSAICM FTMREIETSF KQ-NIMKCYK G---TSGLKK NLPW---FS SNDDCRFTT- ----------
Q9Y4D7/119-589          RPQGS--- PA ARAAPAALCA FRFADVRAAI RA-ARTACFV E---PAPDVV AVLDSVVQGT GP-ACERKL- -------NI
O45657/66-471           TS------ -- STSPKSSICV FSMQKVKLTF WY-NVDRCRS G-------TD SIRLPHI--G RDTKC---- --------K
VA39_VACCV/42-          SP------ -- -YSKSALCT YSMNTIKQSF ST-------- --SKLEG--- -Y-TKQLPSP ASGICLP--- -------AG
Q9TYS4/68-465           SQ------ L  AGIGASAICK YSKKVISGSF A-SGYKEST- ---------- -----PDTCSR ---------- --------A
O75326/75-477           NP------ -- -WNYSAVCV YSLGDIDKVF RT-------- --SSLKG--- -Y-HSSLPNP RPGKCL---- -------PDQ
Q64906/97-496           SP------ -- -WNFSAVCV FTVKDIDHVF KT-------- --SKLKN--- -Y-HHKLPTP RPGQCM---- -------KNH
Q9J5F6/46-415           NE------ -- -WNYSAVCM FKFDKIQNNF NT-------- --SPLKG--- -YSGGKVLSV RPGTCLNT--
```

FIG. 1J

```
Q9NI38/36-461     TS--------E TAFTSSAICM FQLSSINHLL D-TGLLMEET A---NGQFSV  T-ADEIPAH RPGTCSQ----------NS
Q9P2H9/58-489     TP--------Y NSIPGSAVCA YDMLDIASVF T-GRFKEQKS P---DSTWTP -VPDERVPKP RPGCCAGSSS LER---YATS
SM6B_HUMAN/65-    TP--------S NSIPGSAVCA FDLTQVAAVF E-GRFREQKS P---ESIWTP -VPEDQVPRP RPGCCAAPGM Q----YNAS
SM6C_HUMAN/61-    TQ--------T NSIPGSAVCA FYLDEIERGF E-GKFKEQRS L---DGAWTP -VSEDRVPSP RPGSCAGVGG AAL---FSSS
SM2A_SCHGR/39-    TS--------V TGLTGSAICS FTLKDIQEVF S-GKFKEQAT S---SSAWLP -VLPSRVPDP RPGECV---------NDT
C49423/68-506     TS--------T NGLIGSAVCS FHINEIQAAF N-GKFKEQSS S---NSAWLP -VLNSRVPEP RPGTCV---------NDT
SM1A_SCHAM/50-    TP--------V NSIGGSAVCA FSMKSILESF D-GPFKEQET M---NSNWLA -VPSLKVPEP RPGQCVN---------DS
SM1A_TRICF/48-    TP--------V NAIGGSAICA YQMADILRVF E-GSFKHQET I---NSNWLP -VPQNLVPEP RPGQCVR---------DS
SM1A_DROME/47-    TP--------S NSIPGSAVCA FALQDIADTF E-GQFKEQTG I---NSNWLP -VNNAKVPDP RPGSCHN---------DS
O44253/61-492     TS--------V NAIPGSAVCA FNVDDILAAF D-GEFKSQKD S---QSHWLP -VEREQVPKP RPGQCVE---------DS
SM1A_CAEEL/54-    TP--------D SDVRMSAVCK FSMKKIREEF DNGTFKHQNN A---QSMWMA -FNRNEVPKP RPGSCSP---------DS
Q9P283/177-588    TN--------V NSIAASAVCA FNLSAISQAF N-GPFRYQEN P---RAAWLP -IAN-PIPNF QCGTLPET---------GPN
SM5A_MOUSE/58-    TN--------V NSIASSAVCV FNLSAISQAF N-GPFKYQEN S---RSAWLP -YPN-PNPNF QCGTMDQGLY
Q9VTT0/63-469     TS--------G SSIFGSAVCA YNLSSINAAF D-GPFKQQEH S---DAAWKT -VNTNQ---R SQFQCGTSSI GHW
Q9ZC2/46-435      AATGE-GQER RSPATTALCL FRMSEIQAHA R---------- SCSWDF---- ----QA TEHNCKEG--------
Consensus/60%     ss........s ssb.sSAlCs aslpcIppsF p..sbppps s...sspbhs .h.psbhs.s +stsCss.. .........ss SM3A_CHICK/57-    KDLPDEVIT- -FARSHPAMY NPVFPINSR- PIMIKTDVDY QFTQIVVDR- VDA---EDG- ----QYDVMFI GTDIGTVLKV
SM3E_HUMAN/58-    KDYPDDAIR- -FARSHPLMY QAIKPAHKK- PILVKTDGKY NLKQIAVDR- VEA---EDG- ----QYDVLFI GTDNGIVLKV
SM3C_MOUSE/54-    KDFPDDVVT- -FIRNHPLMY NSISPIHRR- PLIVRIGTDY KYTKIAVDR- VNA---ADG- ----RYHVLFL GTDRGTVQKV
Q9NS98/58-503     KDYPDEVLQ- -FARAHPLMF WPVRPRHGR- PVLVKTHLAQ QLHQIVVDR- VEA---EDG- ----TYDVIFL GTDSGSVLKV
SM3D_CHICK/58-    RDFPDEVIS- -FIKRHPLMY KSVYPLTGG- PVFTRINVDY RLTQIVVDH- VMA---EDG- ----QYDIFL GTDIGTVLKA
SM22_BRARE/74-    KDFPDEVIS- -FIRLHPLMY QSVHPMTGR- PIFTRINTEY RLTQIIVDR- VAA---EDG- ----QYAVMFL GTDMGSVLKV
2880035/56-498    KDFPDDVIQ- -FARNHPLMY NSVLPTGGR- PLFLQVGANY TFTQIAADR- VAA---ADG- ----HYDVLFI GTDVGTVLKV
SZ1A_BRARE/57-    KDLPDDVIT- -FARLHPAMY NPVQPMGGK- PIVVRTNVEY QFTQLVVDR- VEA---EDG- ----QYDVMFI GTDLGTVLKV
1000207/57-529    KDYPDEVIN- -FMRSHPLMY QAVYPLQRR- PLVVRTGAPY RLTTIAVDQ- VDA---GDG- ----RYEVLFL GTDRGTVQKV
12405803/53-48    LELPDNILN- -FVKKHPLME EQVGPRWSR- PLLVKKGTNF --THLVADR- VTG---LDG- ----ATYTVLFI GTGDGWLLKA
SM4F_MOUSE/71-    LSLPDRVLT- -FIRDHPLMD RPVFPADGR- PLLVTTDTAY --LRVVAHR- VTS---LSG- ----KEYDVLYL GTEDGHLHRA
SM4D_MOUSE/50-    LNLPDKTLQ- -FVKDHPLMD DSVTPIDNR- PKLIKKDVNY --TQIVVDR- TQA---LDG- ----TFYDVMFI STDRGALHKA
SMZ7_BRARE/53-    LELPDKTLQ- -FVKDKPLMD QAVTA---EQ PLLVKRGAAF --TRIVVTT- ATA---LNG- ----TSHQVMFI GTKSGSVLKA
Q9HCF3/82-515     QDLPSLVLD- -FVKLHPLMA RPVVPTRGR- PLLLKRNIRY --THLTGTP- VTT---PAG- ----PTYDLLFL GTADGWIHKA
BAB21836/126-5    LQLPDRVLN- -FLKDHFLMD GQVR----SR MLLLQPQARY --QRVAVHR- VPG---LH-- ----HTYDVLFL GTGDGRLHKA
SM4A_MOUSE/64-    GPSSDKALT- -FMKDHFLMD EHVV----GT PLLVKSGVEY --TRLAVES- ARG---VDG- ----SSHVVMYL GTSTGPLHKA
Q90975/52-496     ---------YC RAQD-DEYRL EVTTPLQRV- DLFMGQFNNI LLTSIS---- ---------- ------VFT KGNLTIANL GTSEGRFMQI
307196/52-496     ---------GC EARR-DEYRT EFTTALQRV- DLFMGQFSEV LLTSIS---- ---------- ------TFI KGDLTIANL GTSEGRFMQV
Q9W650/48-490     ----------C STPI-DEYRV EVTTVLRRL- DLFMDQFRNV LLTSIS---- ---------- ------VFT QGRLTIANL GTSEGRFMQV
Q9YGM7/50-505     DCDPHEGIH- -EGKEGKYRL QVTQFVQRL- EYWQKVLTNT LVTSIT---- ---------- ------VVT VHGRAVGYL GTADGRHIQV
Q08757/51-503     LSAP-----VT NTSC-WDQPT LVPAASHKV- DLFNGRLSGT LLTSIF---- ---------- ------VTV LQNVTVAHL GTAQGRVLQM
```

```
SM3A_CHICK/57-    VSIPKETW------HELEEVLLE EMTVFRE--P TVIS-AMKIS TKQ   (SEQ ID NO:11)
SM3E_HUMAN/58-    ITIYNQEM------ESMEEVILE ELQIFKD--P VPII-SMEIS SKR   (SEQ ID NO:12)
SM3C_MOUSE/54-    VVLPTNSSA-----SGELILE ELEVFKN--H VPIT-TMEIS SKK      (SEQ ID NO:13)
Q9NS98/58-503     IALQAGSA------EPEEVVLE ELQVFKV--P TPIT-EMEIS VKR     (SEQ ID NO:14)
SM3D_CHICK/58-    VSITKEKW------TKEEVVLE ELQIFKH--P SFIS-TMEIS QKQ     (SEQ ID NO:15)
SMZ2_BRARE/74-    VSITQENW------SSEEIILE ELQVFKN--P SPIL-NMEVS SKQ     (SEQ ID NO:16)
2880035/56-498    ISVPKGSR------PSAEGLLLE ELHVFED--S AAVT-SMQIS SKR     (SEQ ID NO:17)
SZ1A_BRARE/57-    VTIPRESW------HDLEEVVLE EMTVFRE--P TPIT-AMELS TKQ     (SEQ ID NO:18)
1000207/57-529    IVLPKDDQ------EMEELMLE EVEVFKD--P APVK-TMTIS SKR      (SEQ ID NO:19)
12405803/53-48    VSLGP---------WVHLIE ELQLFD---Q EPMR-SLVLS QSK        (SEQ ID NO:20)
SM4F_MOUSE/71-    VRIGA---------QLSVLE DLALFPE--P QPVE-SMKLY HDW        (SEQ ID NO:21)
SM4D_MOUSE/50-    VILTK---------EVHVIE ETQLFRD--F EPVL-TLLLS SKK        (SEQ ID NO:22)
SMZ7_BRARE/53-    VNYNG---------EMVIME EIQLFDP--S EPIK-ILRLS SSK        (SEQ ID NO:23)
Q9HCF3/82-515     VVLGS---------GMHIIE ETQVFRE--S QSVE-NLVIS LLQ        (SEQ ID NO:24)
BAB21836/126-5    VSVGP---------RVHIIE ELQIFSS--G QPVQ-NLLLD THR        (SEQ ID NO:25)
SM4A_MOUSE/64-    VV--PQD-------SSAYLVE EIQLSPD--S EPVR-NLQLA PAQ       (SEQ ID NO:26)
Q90975/52-496     VVSRSEPTA-----PH------V SFQL---DS HAVSPQVVVE QSA      (SEQ ID NO:27)
307196/52-496     VVSRSGPST-----PH------V NFLL---DS HPVSPEVIVE HTL      (SEQ ID NO:28)
Q9W650/48-490     IISRTGQPK-----PH------V NFLL---EA RPISPEIVIN TAS      (SEQ ID NO:29)
Q9YGM7/50-505     VFSRFASP------HV------ NIRL---DS RPVSGSVVLP GQD       (SEQ ID NO:30)
Q08757/51-503     VLQRSSSYV-----VALT NFSLGE--P GLVQHATGLQ GHS           (SEQ ID NO:31)
Q9YGN0/50-493     VLTRSSPII-----F-------A NYSLVE--N QRVSSIAAVY SSE      (SEQ ID NO:32)
Q9YGM5/50-490     ILSLYRPIV-----FA NYSLGD--G E-VSRTAAVY SED             (SEQ ID NO:33)
RON_HUMAN/55-5    ELVRSLNYL-----LY------VS NFSLGD--SG QPVQRDVSRL GDH   (SEQ ID NO:34)
Q62190/57-510     EIARSLNYL-----L-------YVS NFSLGS--SG QPVHRDVSRL GND  (SEQ ID NO:35)
P79950/50-488     VLQRNSKPR-----TLS NFSIS---DT HPVSREVTRI RDS           (SEQ ID NO:36)
Q91823/44-487     LVDLSASSS-----HLVQQYE NVVVH---EG NAILRDLVLS PDR       (SEQ ID NO:37)
P70208/34-473     RVDGSQDAQ-----LYE TVSVV---QG SPILRDLLFS PDH           (SEQ ID NO:38)
P70206/49-494     LVDLANPSG-----RPALAYE SVVAQ---EG NPILRDLVLS PNR       (SEQ ID NO:39)
O75051/119-561    RADGPPHGG-----VQYEMV SV-LK---DG SPILRDMAFS IDQ        (SEQ ID NO:40)
O96681/75-504     VIESSSIAN-----EYA SFAVD---LG SEINRDMQFD NQN           (SEQ ID NO:41)
O96682/87-517     LLSGQSPGE-----YE EIVVD---AG NRILPNTMMS PKK            (SEQ ID NO:42)
O43157/35-463     YLGPGSDGH-----PYS TQSIQ---QG SAVSRDLTFD GTF           (SEQ ID NO:43)
O15031/37-453     YLTPDGTSS-----EYD SILVE---IN KRVKRDLVLS GDL           (SEQ ID NO:44)
Q9QY40/34-435     FLNSSHGQV-----YHS QQVGP---PG SAISPDLLVD SNG           (SEQ ID NO:45)
Q9N375/43-495     LIESKRSAE-----KYA TEMLI---DN EPILSDMEFG GDG           (SEQ ID NO:46)
Q9Y4D7/119-589    NLNESMQVV-----SRR VVTVA---YG EPVHHVMQFD PAD           (SEQ ID NO:47)
O45657/66-471     KWDEHHSN------QLEEYG RKEVGDGRTG SEVSKMVKFG DFV        (SEQ ID NO:48)
```

FIG. 1M

```
VA39_VACCV/42-   DTKSKQTRS-   --SQVDARLF SVMVTSK--P LFIA-DIGIG VGM  (SEQ ID NO:49)
Q9TYS4/68-465    VVPSTDKTG-   -----RHAV TLKVLPT--N SKIV-DMSLY SKN  (SEQ ID NO:50)
O75326/75-477    VEPGEQEH--   ---SFAFNIM EIQPFRR--A AAIQ-TMSLD AER  (SEQ ID NO:51)
Q64906/97-496    VRYEDSN---   ---STTALNIL EINPFQK--P APIQ-NILLD NTN  (SEQ ID NO:52)
Q9J5F6/46-415    VVYEDGV---   -----INVI ELTLKQY--P SPVL-ALVSD ERS  (SEQ ID NO:53)
Q9NI38/36-461    ISHWKEGN--   ---EWKSNLIE EKSLKIA--A SRIN-DVALL PAE  (SEQ ID NO:54)
Q9P2H9/58-489    LARIGNSG--   --FLNDSLFLE EMSVYNS--E K-CSYDGVED KRI  (SEQ ID NO:55)
SM6B_HUMAN/65-   LVRPNASTS-   GTSGLSVFLE EFETYRP--D RCGR-PGGGE TGQ  (SEQ ID NO:56)
SM6C_HUMAN/61-   LTPGGRSGG-   ---PEPILLE EIDAYSP--A RCSG-KRTAQ TAR  (SEQ ID NO:57)
SM2A_SCHGR/39-   VQWYDSGG--   ---LPQSLLVD IFDVTP---P EPVQ-ALHLS KEY  (SEQ ID NO:58)
C49423/68-506    VQYRNGES--   ---LSKLLD IFEVAP---N EAIQ-VMEIS QTR  (SEQ ID NO:59)
SM1A_SCHAM/50-   LNSASFDSS-   -DTVDSVVIE ELQVLPP--G VPVK-NLYVV RMD  (SEQ ID NO:60)
SM1A_TRICF/48-   VNIPKRHAK-   ---ALLYRKY RTSVHPH--G APVK-QLKIA PGY  (SEQ ID NO:61)
SM1A_DROME/47-   VNAESADSA-   -DKVTSVVIE EIDVLTK--S EPIR-NLEIV RTM  (SEQ ID NO:62)
O44253/61-492    INILSTHPN(   4)RLKTVVIS EMQVLPL--G TPIR-ELVIS TSK  (SEQ ID NO:63)
SM1A_CAEEL/54-   VEVDG-----   ---NATVIQ SATVFQR--G VPIV-NLLTT KES  (SEQ ID NO:64)
Q9P283/177-588   LSTASRSL--   ---HGCYLE ELHVLPPGRR EPLR-SLRIL HSA  (SEQ ID NO:65)
SM5A_MOUSE/58-   RAPLSQSS--   ---GSCLLE EIELFPERRS EPIR-SLQIL HSQ  (SEQ ID NO:66)
Q9VTT0/63-469    SVKYDGDGV-   ----QTCLV ELWQADDTGT SSLL-NMAYL KVS  (SEQ ID NO:67)
Q9QZC2/46-435    VLGENLTSN-   ----CPEVIY EIK-----EE TPVFYKLVPH PMK  (SEQ ID NO:68)
Consensus/60%    lh.s.s....   .........hlp pbplb.....s pslp.sb.ls spp
```

FIG. 2A

| | | | | | | | |
|---|---|---|---|---|---|---|---|
| 86\|O60486/1-54 | NCNKH---- | K SCSECLTATD PH | CHS----LQRC | TFQ------- | -GDCVHSEN- | -LENWLDIS- | -SGAKKCP (SEQ ID NO:69) |
| AD28103\|AAD281 | RCDVYG---- | K ACAECCLARD PY | CAW D------GSQC | SRY------- | -FPTAKRRT- | RRQDIRNG-- | -DPLTQCS (SEQ ID NO:70) |
| AAD09425b/1-53 | DCSDY----- | K TCGDCLGARD PY | CGW CSL----ENKC | SPR------- | -SNCQDDAN- | DPFYWVSY-- | -KTGKCT (SEQ ID NO:71) |
| 36\|O42236/1-53 | RCRIYG---- | T ACADCCLARD PY | CAW D------GNSC | SRF------- | -YPTGKRRS- | RRQDVRHG-- | -NPLTQCR (SEQ ID NO:72) |
| AA21714\|CAA217 | NCAQQ----- | T SCSKCVQLQD PH | CAW DSS----IARC | VHG------- | -GSWTGDQF- | -IQNMVFG-- | -QSEQCP (SEQ ID NO:73) |
| AC83081\|AAC830 | RCDTYG---- | K ACADCCLARD PY | CAW D------GNAC | SRY------- | -APTSKRRA- | RRQDVKYG-- | -DPITQCW (SEQ ID NO:74) |
| AA75629\|BAA756 | NCGRL----- | Q SCSECIAQD PV | CAW SFR----LDAC | VA-------- | -HAGEHRG- | MVQDIESA-- | -DVSSLCP (SEQ ID NO:75) |
| AAD09426a/1-53 | HCSVY----- | T NCSACLESRD PF | CGW CSL----EKRC | TVR------- | -STCQRDTS- | -ASRWLSL-- | -GSGQQCI (SEQ ID NO:76) |
| 51\|O75051/1-51 | SCEQY----- | T TCGECLSSGD PH | CGW CAL----HNMC | SRR------- | -DKCQ----- | -QAWEPNRF | AASISQCV (SEQ ID NO:77) |
| 54\|Q92854/1-53 | FCGKH----- | G TCEDCVLARD PY | CAW SPP----TATC | VALH------ | -QTESPSRG- | LIQEMSG--- | -DASVCP (SEQ ID NO:78) |
| 77\|Q62177/1-53 | RCTALG---- | R ACAECCLARD PY | CAW D------GSAC | TRF------- | -QPTAKRRF- | RRQDIRNG-- | -DPSTLCS (SEQ ID NO:79) |
| AD21310\|AAD213 | RCQIYG---- | Q GCAECCLARD PY | CAW D------GTQC | SRY------- | -IPASKRRA- | RRQDIKHG-- | -DPSSHCW (SEQ ID NO:80) |
| 78\|Q62178/1-52 | NCSVY----- | E SCVDCVLARD PH | CAW DPE----SRLC | SLLS------ | -GSTKP---- | WKQDMERG-- | -NPEWVCT (SEQ ID NO:81) |
| 26\|Q75326/1-51 | LCEVYG---- | G GCHGCLMSRD PY | CGW D------QGRC | IS-------- | -IYSSERS-- | VLQSINPA-- | -EPHKECP (SEQ ID NO:82) |
| 57\|O43157/1-54 | SCAQH----- | L DCASCLAHRD PY | CGW CVL----LGRC | SRR------- | -SECSRGQG- | PEQWLWSF-- | -QPELGCL (SEQ ID NO:83) |
| 26\|O09126/1-53 | FCEKH----- | G SCEDCVLARD PY | CAW SPA----IKAC | VTLH------ | -QEEASSRG- | WIQDMSG--- | -DTSSCL (SEQ ID NO:84) |
| 72\|Q13372/1-53 | RCQAYG---- | A ACADCCLARD PY | CAW D------GQAC | SRY------- | -TASSKRRS- | RRQDVRHG-- | -NPIRQCR (SEQ ID NO:85) |
| 3\|A49423/1-53 | HCASK----- | T RCKDCVELQD PH | CAW DAK----QNLC | VSI------- | -DTVTSYRF- | LIQDVVRG-- | -DDNKCW (SEQ ID NO:86) |
| ECGRY\|AAC72345 | ECGRY----- | Q TCLDCVLARD PH | CGW DLD----TEHC | ATIN------ | SIHRTRSST- | VIQSLNDG-- | -DASQCP (SEQ ID NO:87) |
| SEX_HUMAN/1-51 | TCEQY----- | Q SCAACLGSGD PH | CGW CVL----RHRC | CRE------- | -GACLGASA- | PHGFAEE--- | -LSKCV (SEQ ID NO:88) |
| 31\|O15031/1-52 | ECLSY----- | P TCTQCRDSQD PY | CGW CVV----EGRC | TRK------- | -AECPRAEEA | SHWLWSR--- | -SKSCV (SEQ ID NO:89) |
| 91\|Q13591/1-48 | RCQFY----- | R TRSTCIGAQD PY | CGW DVV----MKKC | TSL------- | -EESLSMTQ- | WEQSIS---- | ---ACP (SEQ ID NO:90) |
| 23\|Q91823/1-51 | SCEQY----- | E SDTCLGSRD PH | CGW CVL----HNMC | SRK------- | -DKCERADE- | -LHRFTS--- | -DQRQCV (SEQ ID NO:91) |
| AC72346\|AAC723 | QCDLYG---- | Q ACAECCLARD PY | CTW D------GHSC | SQF------- | -MPTGRRRN- | IRQVNDDG-- | -NPLNQCV (SEQ ID NO:92) |
| 37\|O42237/1-56 | QCDMYG---- | T ACADCCLARD PY | CAW D------GISC | SRYYP----- | TGMQAKRRF- | RRQDVRHG-- | -NAAQQCF (SEQ ID NO:93) |
| 06\|P70206/1-51 | SCVQY----- | T SCEICLGSRD PH | CGW CVL----HSIC | SRQ------- | -DACERAEE- | -PQRFAS--- | -DLLQCV (SEQ ID NO:94) |
| SEX_HUMAN_1/1- | NCSVL----- | Q SCMSCVGSPY P-- | CHW CKY----RHTC | TSRP------ | -HECSFQEG- | RVHSPE---- | ----GCP (SEQ ID NO:95) |
| BAA31595a/1-54 | ACNVH----- | S TCGDCVGAAD AY | CGW CAL----ETRC | TLQ------- | -QDCTNSSQ- | -QHFWTSAS- | -EGPSRCP (SEQ ID NO:96) |
| 3\|B49423/1-57 | RCHNDKI--- | T SCSECVALQD PY | CAW DKI----AGKC | RSHG------ | APRWLEENY- | FYQNVATG-- | -QHAACP (SEQ ID NO:97) |
| 79\|P97579/1-44 | GCGHF----- | Q SCSQCLSAPY FIQ | CGW C-------HNRC | VHS------- | -NECPS---- | ----GTWTQ- | ---EICL (SEQ ID NO:98) |
| 23\|Q91823_1/1- | KCSALR---- | E SCGLCLKSDR RFE | CGW CVS----EKKC | TLR------- | -QNCPT---- | LENPWMHAS- | -TANSRCT (SEQ ID NO:99) |
| SEX_HUMAN_2/1- | KCWAQR---- | P SCGLCLKADP RFN | CGW CIS----EHRC | QLR------- | -THCPA---- | PKTNWMHLS- | -QKGTRCS (SEQ ID NO:100) |
| 06\|P70206_1/1- | KCPALR---- | Q SCGLCLKADP RFE | CGW CVA----ERRC | SLR------- | -HHCPADSP- | -ASWMHAH-- | -HGSSRCT (SEQ ID NO:101) |
| ITB2_BOVIN/1-5 | ECTNYKV--- | S TCRDCIESGP G-- | CAW CQ-----KLNF | TGQGEP---D | SIRCD----- | TRAELLS--- | --KGCP (SEQ ID NO:102) |
| ITB8_RABIT/1-5 | RCASSHA--- | V SCSECLALGP D-- | CGW CV-----HEDF | ISGGP----R | SERCD----- | IVSNLIS--- | --KGCP (SEQ ID NO:103) |
| MET_HUMAN/1-44 | GCRHF----- | Q SCSQCLSAPP FVQ | CGW C-------HDKC | VRS------- | -EECLS---- | ----GTWTQ- | ---QICL (SEQ ID NO:104) |
| 79\|Q62179/1-71 | NCSLY----- | P TCGDCLLARD PY | CAW T------GSAC | RLASL(18)V | KELCKN---- | SSYKARFL-- | -VPGKPCK (SEQ ID NO:105) |
| 23\|Q91823_2/1- | NCSVH----- | Q SCLSCVNGSF P-- | CHW CKY----RHVC | THNA------ | -ADCSFQEG- | -RVNMSE--- | ---DCP (SEQ ID NO:106) |

FIG. 2B

| ID | Seq | | | | | | | SEQ ID NO |
|---|---|---|---|---|---|---|---|---|
| 83\|O60283/1-71 | NCSGL----R | TCGQCLEQPG | ------ | CGW | CND(5)RGHC | IEGSS(16)D | TNLCPKEKN- | ---YEWSFI--- | ---QCP (SEQ ID NO:107) |
| 56\|ITB1_HUMAN/ | RCLKANA--K | SCGECIQAGP | N--- | CGW | CT--NSTF | LQEGMP---T | SARCD----- | DLEALKK----- | --KGCP (SEQ ID NO:108) |
| 75\|Q90975/1-44 | GCHHF----Q | SCSQCLLAPA | FMR-- | CGW | C---GQQC | LRA------- | -PECNG---- | ---GTWTQ---- | -ETCL (SEQ ID NO:109) |
| AAD09425a/1-54 | RCREMA---D | SCGICLALSE | KYN-- | CGW | CSS--TNTC | EVE------- | -EQCNKNKE- | GKTDWLN----- | -RSEICP (SEQ ID NO:110) |
| AA08917\|CAA089 | GCDHL----T | TCTSCLVSSR | VTE-- | CGW | C---EGRC | TRA------- | -NQCPP---- | ---SVWTQ---- | --EYCT (SEQ ID NO:111) |
| 07\|P70207_1/1- | KCAAQR---E | SCGLCLKADH | KFE-- | CGW | CSG--ERRC | TLH------- | -QHCPS---- | TSSPWLDWS-- | SHNVKCS (SEQ ID NO:112) |
| 57\|O45657/1-43 | TCSHH----S | SCTECLVSVD | PL--- | CQW | CHP--TQSC | TTS------- | -ARCT----- | ---SPVTS---- | ---QCP (SEQ ID NO:113) |
| 57\|Q08757/1-43 | GCRHF----- | TCDRCLRAER | FMG-- | CGW | C---GNGC | TRH------- | -HECA----- | ---GPWVQ---- | --DSCP (SEQ ID NO:114) |
| AA09100\|CAA091 | GCAHF----R | TCSMCLMAPR | FMN-- | CGW | C---SGVC | SRQ------- | -HQCD----- | ---MQWEK---- | --DSCA (SEQ ID NO:115) |
| AAD25372a/1-46 | RCDQH----T | DCYSCTANTN | D---- | CHW | C---NDHC | VPVN------ | -HSCTEGQI- | SIAKYE------ | ---SCP (SEQ ID NO:116) |
| 51\|O75051_2/1- | NCSAH----Q | LCLSCVNSAF | R---- | CHW | CKY--RNLC | THDP------ | -TTCSFQEG- | -RINISE----- | ---DCP (SEQ ID NO:117) |
| RON_HUMAN/1-43 | GCRHF----L | TCGRCLRAWH | FMG-- | CGW | C---GNMC | GQQ------- | -KECP----- | ---GSWQQ---- | --DHCP (SEQ ID NO:118) |
| 95\|O60295/1-76 | NCSGY----C | TCSHCLEQPG | ------ | CGW | CTD(5)KGKC | IEGSY(21)N | SSMCLED--- | SRYNWSFI---- | ---HCP (SEQ ID NO:119) |
| AAD09426b/1-48 | DCSHH----G | NCQECLQSSW | G---- | CNW | CIF--DNKC | VHKS------ | -LQCR----- | NIENAVS----- | TVGHCP (SEQ ID NO:120) |
| 86\|O60486_1/1- | NCSSL----K | ECPACVETG- | ------ | CAW | CKS--ARRC | IHPF------ | -TACDP---- | ---SDYER---- | NQEQCP (SEQ ID NO:121) |
| 57\|O45657_1/1- | DCSGY----G | TCSSCMSSEY | N---- | CAW | CSG--LHKC | SN-------- | -----SCG-- | ---ALEK------ | SKACV (SEQ ID NO:122) |
| 73\|Q26473/1-58 | RCGSDKI--T | NCRECVSLQD | PY--- | CAW | DNV--ELKC | TAVGS----P | DWSAGKRRF- | -IQNISLG---- | EHKACG (SEQ ID NO:123) |
| 19\|Q60519/1-48 | RCSAY----H | SQGACLGARD | PY--- | CGW | DGK--RQLC | STL------- | -EDSSNMSL- | WIQNIT------ | ---TCP (SEQ ID NO:124) |
| 70\|Q92070/1-51 | ECPKIKV--G | TCKNCIQSGP | G---- | CAW | CK--KLSF | TKAGEP---D | SNRCD----- | TIEQLQQ----- | --RGCP (SEQ ID NO:125) |
| 8\|JC5148/1-43 | TCGHL----K | SCSHCLSSPS | VN--- | CGW | S----KNHC | STK------- | -QECLN---- | --EEWIQ----- | --ETCP (SEQ ID NO:126) |
| ITB7_HUMAN/1-4 | SCQPA----P | SCQKCIISHP | S---- | CAW | CK--QLNF | TASGEA---E | ARRCA----- | RREELLA----- | --RGCP (SEQ ID NO:127) |
| AD20947\|AAD209 | PCALR----T | ACGECTSSSS | E---- | CMW | CSN--MKQC | VDSNA(4)FP | FGQC------ | --MEWYT----- | -MSSCP (SEQ ID NO:128) |
| 47\|O88347/1-50 | ICTSGSA--T | SCEECLLIHP | K---- | CAW | CS--KEYF | GNPRS----I | TSRCD----- | LKANLIR----- | --NGCE (SEQ ID NO:129) |
| 51\|Q64151/1-54 | DCTKY----R | FCVDCVLARD | PY--- | CAW | NVN--TSRC | VATT------ | SGRSGS---F | LVQHVANL---- | DTSKMCN (SEQ ID NO:130) |
| \|HSCSABR_1/1-5 | ECTKFKV--S | SCRECIESGP | G---- | CTW | CQ--KLNF | TGPGDP---D | SIRCD----- | TRPQLLM----- | --RGCA (SEQ ID NO:131) |
| AAD03057a/1-48 | QCDAH----R | SEAACLAAGP | GIR-- | CVW | NTG--SSQC | ISWA------ | -LATDE---- | QEEKLKS----- | ---ECF (SEQ ID NO:132) |
| AD25372\|AAD253 | QCDAH----R | SEAACVAAGP | GIR-- | CLW | DTQ--SSRC | TSW------- | -ELATEEQA- | --EKLKS----- | ---ECF (SEQ ID NO:133) |
| NCSFGR---S | DCSLCRAANP | DYR-- | CAW | CGG--QSRC | VYE------- | -----ALC-- | ---NTTS---- | --ESCP (SEQ ID NO:134) | | | | |
| 31\|O15031_1/1- | ICQQL----R | ECDSCLSREG | ----- | CIW | CTE--ERQTC | QEGNARDGAF | FNSCDI---- | ----WVS----- | -GSECP (SEQ ID NO:135) |
| 41\|P90641/1-50 | DCSVGH---G | DCSRCQTAMP | QYG-- | CVW | CEG--ERPRC | VTR------- | -EACGE---- | ---AEAVA---- | --TQCP (SEQ ID NO:136) |
| 57\|O43157_1/1- | TCEEQ----T | DCVSCASKSG | ----- | CGW | CSS--GEQC | LPNE------ | -QECVDGPG- | MLTSWE------ | ---KCP (SEQ ID NO:137) |
| YC81_CAEEL/1-4 | ACSDA----K | TCGECISLDS | S---- | CGW | CT--LLNY | TDDIG----- | NPQCD----- | LASSLSQ----- | -RGCS (SEQ ID NO:138) |
| 63\|P92163/1-47 | GCAQA----T | QCALCLRRPH | ----- | CGW | CAW(5)GGRC | MEGGLSGPRD | GLTCGR---- | PGASWAFL---- | ---SCP (SEQ ID NO:139) |
| 97\|O75097/1-58 | KCDVLG(5)P | DCSLCVTRDP | KYK-- | CAW | CSN(4)NETC | IAD------- | --KNSISSG- | SKSAIEN----- | ---ECP (SEQ ID NO:140) |
| AD09426\|AAD094 | PCSLR----T | SCSNCTSNGM | E---- | CMW | CSS--TKRC | VDSNA(4)FP | YGQCL----- | ---EWQTA---- | ---TCS (SEQ ID NO:141) |
| 83\|O60283_1/1- | SCIQA----R | TCGDCIITDP | S---- | CAW | CA--QPDF | QDAEN----- | YPRCDS---- | ---PDTLR---- | -ERGCM (SEQ ID NO:142) |
| 77\|O61677_1/1- | VCEEH----K | TCGECQRDPG | ----- | CGW | LAD(5)LGLC | IRGTS----T | GPLEPKPEN- | --STWYFI---- | ---DCP (SEQ ID NO:143) |
| YC81_CAEEL_1/1 | DCSRTA(5)T | ACTSCLSAQW | P---- | CFW | CSQ--QHSC | VSNQ------ | -SRCEA---- | SPNPTSP----- | --QDCP (SEQ ID NO:144) |
| BAA31595b/1-53 | | | | | | | | | |

FIG. 2C

```
83|P97483/1-47      ICTARGV--N  SCQQCLAVSP  V-------  CAW  CS----DETL  SQGS--------  -PRCN------  LKENLLK-----  ----DNCA (SEQ ID NO:145)
ITB6_HUMAN/1-4      LCLGGA---E  TCEDCLLIGP  Q-------  CAW  CA----QENF  THPSG------V  GERCD------  TPANLLA-----  ----KGCQ (SEQ ID NO:146)
83|O60283_2/1-      RCYRY----A  DCASCTANTN  G-------  CQW  CD----DKKC  ISAN--------  -SNCSM-----  SVKNYT------  ----KCH  (SEQ ID NO:147)
YC81_CAEEL_2/1      PCAQR----N  NCSDCTDLEQ  --------  CMW  CPS---TNRC  INL---------  -EAYT------  LSFAYG------  ----QCH  (SEQ ID NO:148)
AD17212|AAD172      GCAWGGA--E  SCSDCLLIGP  -H------  CAW  CS----QENF  THLSG------A  GERCD------  TPANLLA-----  ----KGCQ (SEQ ID NO:149)
57|O45657_2/1-      SCTNLA---S  DCSSCLALSP  SLS-----  CGW  C-----NRQC  SH----------  -ECHE------  --SKATA-----  ----VCD  (SEQ ID NO:150)
12|Q07012/1-47      ICATRGV--S  SCQKCLSVSP  Q-------  CAW  CS----QEVF  GKGA--------  -PRCD------  LKSELLS-----  ----NGCE (SEQ ID NO:151)
94|O17494/1-42      ACTRL----T  KCNQCIGEAN  --------  CAW  CS----DKDF  GSS---------  -RCDS------  --QKILE-----  ----LNGCS(SEQ ID NO:152)
AD09425|AAD094      DCSTH----S  SCTRCVSSEF  P-------  CDW  CVE---AHRC  TH----------  -DTAE------  ------------  ----NCR  (SEQ ID NO:153)
C211_HUMAN/1-5      ACSQNTN--K  TCEECLKNVS  --------  CLW  CNT---NKAC  LDYPV(4)PP   ASLCKL-----  SSARWG------  ----VCW  (SEQ ID NO:154)
83|O60283_3/1-      ICNKL----T  SCKSCSLNLN  --------  CQW  DQR---QQEC  QALP--------  AHLCG------  --EGWSHI----  ----GDACL(SEQ ID NO:155)
AC78492|AAC784      TCHLA----S  NCAECLAHGD  PH------  CAW  AD----GVDC  IDI---------  -RTD-------  QRKSASQ-----  ----DSGTCD(SEQ ID NO:156)
AA09086|CAA090      GCQHF----L  TCAVCLTAPK  FVG-----  CGW  C-----SGVC  SWE---------  -SDCD------  --HHWRN-----  ----DSCP (SEQ ID NO:157)
13|Q22913/1-53      YCRIGSNDLN  TCETCVGKGS  N-------  CFW  CGG---KTKRC MPFDW------Y  YPDCNI-----  KHVKYN------  ----VCW  (SEQ ID NO:158)
AD03057|AAD030      YCNKK----T  SCRSCALDQN  --------  CQW  EPR---NQEC  IALP--------  ENICG------  IGWHLVG-----  ----NSCL (SEQ ID NO:159)
97|O75097_1/1-      ECRRL----R  TCSECLARHP  RTL(11) CKW CTNC--PEGAC  IGRN--------  -GSCTS-----  ------------  ----ENDCR(SEQ ID NO:160)
97|O75097_2/1-      PCHLL----P  NCTSCLDSKG  ADGGWQHCVW  SSS---LQQC  LSPSY(4)CM   AGGCGR-----  ------------  --LLRG------  ----PESCS(SEQ ID NO:161)
97|O75097_3/1-      PCRIL----S  SPEACNQSGA  --------  CTW  C-----HGAC  LSGDQA-----H  RLGCG------  ------------  ----GSPCS(SEQ ID NO:162)
57|O43157_2/1-      DCVAVT(5)A  QCQACVSSRW  G-------  CNW  CVW---QHLC  THK---------  -ASCDA-----  GPMVASH-----  ----QSP  (SEQ ID NO:163)
AA31595|BAA315      NCAMGS---P  DCSQCLGRED  LGHL----  CMW  SD----------           ---  -GCRLRG----  PLQPMAG-----  ----TCP  (SEQ ID NO:164)
31|O15031_2/1-      DCRQAM(5)L  PCISCVSNRW  T-------  CQW  DLR---YHEC  REA---------  -SPNPEDGI--  VRAHMED-----  ----SCP  (SEQ ID NO:165)
megfb/1-50          ECRRL----R  TCSECLARHP  RTL(11) CKW CT----NC    PEG---------  -ACIGR-----  ------------  ----NGSCT(SEQ ID NO:166)
ITB4_HUMAN/1-4      RCKKAPV--K  SCTECVRVDK  D-------  CAY  CT----DEMF  RD----------  -RRCN------  TQAELLA-----  ----AGCQ (SEQ ID NO:167)
Consensus/60%       pCs.b....p  *CspCl.tps  s-------  CtW  C.....pppC  sp..........  ..pCs......  ...sb.p.....  ....ppCs
```

B1SP FUSION PROTEIN THERAPEUTICS, METHODS, AND USES

FIELD OF THE INVENTION

The present invention relates to compositions and methods for the treatment of cancer. The invention more specifically relates to potential therapeutics for treatment of prostate, lung and breast cancer.

CROSS REFERENCE TO RELATED APPLICATIONS

This application is a 35 U.S.C. § 371 national stage entry of International Application No. PCT/CA2016/000182, filed 29 Jun. 2016, which application claims the benefit of U.S. Provisional Patent Application Ser. No. 62/185,772 filed on 29 Jun. 2015, entitled "B1SP FUSION PROTEIN THERAPEUTICS, METHODS, AND USES", which applications are incorporated herein by reference in their entireties.

BACKGROUND

Among American men, advanced prostate cancer (CaP) is presently the most frequently diagnosed cancer and is the second leading causes of cancer-related deaths. In 2009, an estimated 192,280 American men will be diagnosed with CaP and 27,360 will die of the disease. While early stage disease is frequently curable with surgery or radiation therapy, approximately ⅓ of patients clinically present with locally advanced or metastatic disease that is associated with a poor prognosis. Therapeutic androgen suppression through surgical or medical castration still remains the most effective therapy for advanced CaP since its inception in 1941 by Charles Huggins (Huggins and Hodges 1941). Androgen suppression consistently induces tumour regression in over 80% of patients with advanced disease due to the exquisite dependence of CaP cells on the androgen signaling axis for their growth and survival (Isaacs et al. 1997). Furthermore, Androgen Receptor (AR) expression is maintained throughout prostate cancer progression, and the majority of androgen independent or hormone refractory prostate cancers express AR (Heinlein and Chang 2004). However, despite initial success in achieving significant and tangible clinical responses, the duration of progression-free survival remains transient (~1-3 years) and progression to lethal castration-resistant disease (also frequently referred to as androgen independent or hormone refractory disease) is essentially universal (Bruchovsky et al. 1988; Goldenberg et al. 1988; Bruchovsky et al. 1989). Thus, the current standard of care for patients with Castration-Resistant Prostate Cancer (CRPC) remains only palliative, with chemotherapy—eg. docetaxel (Petrylak et al. 2004; Tannock et al. 2004) inducing only marginal survival benefits at a cost of, at times, significant morbidity.

Semaphorins are a large family of highly conserved secreted or cell surface signaling proteins that were originally identified as mediators of cell migration and axon guidance in the developing nervous system (Tamagnone and Comoglio 2000; Kruger et al. 2005). While semaphorins have been best characterized in the nervous system, they are known to be expressed in other tissues. Semaphorins have been implicated in a variety of dynamic physiological processes including angiogenesis, tissue morphogenesis, and immunity (Kolodkin et al. 1993; Kruger et al. 2005). Semaphorins regulate numerous biological responses including cell proliferation, adhesion, migration and apoptosis through interaction of semaphorins with their cognate receptors, plexins. Plexins are single pass transmembrane receptors that have highly conserved intracellular domains that have intrinsic GAP (GTPase-activating protein) activity towards R-Ras12 (Negishi et al. 2005). Nine vertebrate plexins have been identified, grouped into four subfamilies (Plexin A to D) based on computational phylogenetic analyses. Semaphorins and plexins both express a conserved 500 amino acid extracellular motif called the SEMA domain that is thought to be involved in protein-protein interactions. Membrane-associated semaphorins bind directly to plexins whereas secreted semaphorins, often have an additional binding component (either neuropilins 1 or 2 (Npn-1 or Npn-2)) as co-receptors. Plexins are thought to regulate the actin cytoskeleton by controlling the activity of the small GTPases, Rnd1, R-Ras, Rac and Rho12. When plexins bind to semaphorin they are thought to also interact with and activate the receptor tyrosine kinases, Her2/neu (ErbB2), and hepatocyte growth factor/scatter factor receptor (c-Met) (Giordano et al. 2002; Swiercz et al. 2004; Swiercz et al. 2008).

SEMA3C is a member of the class 3 semaphorins, which are a subfamily of secreted semaphorins (Tamagnone and Comoglio 2000; Verras et al. 2007). SEMA3C has been shown to bind to receptor complexes comprised of Plexin A1, A2, or B1 in association with either Npn-1 or Npn-210. Plexins can actively influence their binding affinity (and possibly selectivity) for the different subsets of secreted semaphorins. For example, the binding of SEMA3C to neuropilins seems to be inhibited by the co-expression of plexin A1, whereas it is increased in the presence of plexin A2 or B1. Herman and Meadows (2007) suggest an association between SEMA3C expression and increased invasion and adhesion in PC-3 AR negative cancer cells. However, AR negative prostate cancers represent a small minority of late stage androgen independent prostate cancers (Heinlein and Chang 2004). A number of B-type Plexin polypeptides have been suggested as inhibiting the binding of Plexin-B1 and Erb-B2 (U.S. Pat. No. 9,198,966).

SUMMARY

The present invention is based, in part, on the surprising discovery that B1SP fusion proteins inhibit semaphorin-mediated signaling pathways. The present invention is based, in part, on the surprising discovery that B1SP fusion proteins bind to neuropilins and plexins in a dose dependent manner. The present invention is based, in part, on the surprising discovery that B1SP fusion proteins have a potent effect on semaphorin signaling. The present invention is based, in part, on the surprising discovery that B1SP fusion proteins are potent inhibitors of EGFR phosphorylation in prostate cancer cells. The present invention is based, in part, on the surprising discovery that B1SP fusion proteins are inhibitors of R1881-induced proliferation of prostate cancer cells in a dose dependent manner. The present invention is based, in part, on the surprising discovery that B1SP fusion proteins inhibit the association of SEMA3C with NRP1 and PLEXIN B1. The present invention is based, in part, on the surprising discovery that B1SP enhances the interaction of PLEXIN B1 with HER2/ErbB2 in DU145 cells. Furthermore, the present invention is based, in part, on the surprising discovery that B1SP fusion proteins are useful for cancer treatment.

In accordance with a first embodiment, there is provided a method for treating cancer, the method including administering a biologically effective amount of a B1SP fusion protein to cancer cells, wherein the B1SP fusion protein includes: (a) a sema domain; (b) a structural stabilization domain; and (c) a half life extending moiety.

In accordance with another embodiment, there is provided a method for killing or inhibiting the proliferation of androgen receptor (AR) positive prostate cancer including contacting the prostate cancer with a biologically effective amount of a composition including a B1SP fusion protein, wherein the B1SP fusion protein includes: (a) a sema domain; (b) a structural stabilization domain; and (c) a half life extending moiety.

In accordance with another embodiment, there is provided a method of inhibiting growth of an androgen dependent prostate cancer comprising administering androgen deprivation therapy and a B1SP fusion protein, wherein the B1SP fusion protein comprises: (a) a sema domain; (b) a structural stabilization domain; and (c) a half life extending moiety.

In accordance with another embodiment, there is provided a use of a B1SP fusion protein for the manufacture of a medicament to treat cancer, wherein the B1SP fusion protein includes: (a) a sema domain; (b) a structural stabilization domain; and (c) a half life extending moiety.

In accordance with another embodiment, there is provided a use of a B1SP fusion protein to treat cancer, wherein the B1SP fusion protein includes: (a) a sema domain; (b) a structural stabilization domain; and (c) a half life extending moiety.

In accordance with another embodiment, there is provided a B1SP fusion protein for the treatment of cancer, wherein the B1SP fusion protein includes: (a) a sema domain; (b) a structural stabilization domain; and (c) a half life extending moiety.

In accordance with another embodiment, there is provided a pharmaceutical composition comprising a B1SP fusion protein in combination with a physiologically acceptable carrier, wherein the B1SP fusion protein includes: (a) a sema domain; (b) a structural stabilization domain; and (c) a half life extending moiety.

In accordance with another embodiment, there is provided a commercial package including a B1SP fusion protein and instructions for its use in the treatment of prostate cancer, wherein the B1SP fusion protein includes: (a) a sema domain; (b) a structural stabilization domain; and (c) a half life extending moiety.

The B1SP fusion protein may further include one or more of a linker and a hinge between the structural stabilization domain and the half life extending domain. The structural stabilization domain may be a Plexins-Semaphorins-Integrins domain (PSI domain). The structural stabilization domain may be a PSI domain from either Plexin B1 or Plexin B2 or Plexin B3. The structural stabilization domain may be SCAQHLDCASCLAHRDPYCG WCVLLGRCSRRSECSRGQGPEQ (SEQ ID NO: 1). The biologically effective amount is an amount sufficient to cause cell death of a cancer cell or to inhibit proliferation of the cancer cell. The cancer cell may be a prostate cancer, breast cancer, ovarian cancer, bladder cancer, kidney cancer, glioblastoma or endometrial cancer cell. The cancer cell may be prostate cancer cell. The prostate cancer cell may be an androgen receptor (AR) positive prostate cancer cell. The cancer may be a prostate cancer, breast cancer, ovarian cancer, bladder cancer, kidney cancer, glioblastoma or endometrial cancer. The cancer cell may be prostate cancer. The prostate cancer may be an androgen receptor (AR) positive prostate cancer.

The half life extending moiety may be selected from: a fragment crystallizable region (Fc region); immunoglobulin-binding domaindomain B (IgBD); Novozymes Albufuse Albumin; serum albumin; ubiquitin; polyethylene glycol (PEG) moiety (PEGylation); Amunix XTEN; an unstructured polymer having a polypeptide backbone; poly-glycine; elastin-like polypeptide; polysialic acid; PASylation (Pro, Ala and Ser (PAS)); glycosylation; HESylation (coupling to hydroxyethyl starch); and Heptune (heparosan conjugation). The half life extending moiety may be selected from: a fragment crystallizable region (Fc region); immunoglobulin-binding domaindomain B (IgBD); Novozymes Albufuse Albumin; serum albumin; and biquitin. The half life extending moiety may be selected from: polyethylene glycol (PEG) moiety (PEGylation); Amunix XTEN; an unstructured polymer having a polypeptide backbone; poly-glycine; elastin-like polypeptide; polysialic acid; PASylation (Pro, Ala and Ser (PAS)); glycosylation; HESylation (coupling to hydroxyethyl starch); and Heptune (heparosan conjugation). The half life extending moiety may be selected from: an Fc region and albumin. The half life extending moiety may be IgBD. The B1SP fusion protein may further include one or more of a linker and a hinge between the structural stabilization domain and the half life extending domain.

The androgen deprivation therapy and the B1SP fusion protein may be initiated at about the same time. The B1SP fusion protein may be initiated after androgen deprivation therapy and before the androgen dependent cancer becomes androgen independent. The androgen deprivation therapy may include administering a luteinizing hormone-releasing hormone (LHRH) analog. The androgen deprivation therapy may include administering anti-androgen treatment. The androgen deprivation therapy may include administering an adrenal androgen inhibitor. The androgen deprivation therapy may be surgical. The androgen deprivation therapy and the SEMA3C inhibitor may be administered with one or more further therapeutic regimen(s). The therapeutic regimen may be a chemotherapeutic regimen. The therapeutic regimen may be a radiotherapeutic regimen.

The B1SP fusion protein may have an amino acid sequence comprising SEQ ID NO:2. The B1SP fusion protein may have an amino acid sequence consisting of SEQ ID NO:2. The B1SP fusion protein may have only one structural stabilization domain. The B1SP fusion protein may have only one PSI domain. The PSI domain may be SCAQHLDCASCLAHRDPYCG WCVLLGRCSRRSECSRGQGPEQ (SEQ ID NO: 1).

BRIEF DESCRIPTION OF THE DRAWINGS

FIGS. 1A-1M show a chromo alignment of sema domains with consensus sequences.

FIGS. 2A-2C show a chromo alignment of structural stabilization domains with consensus sequences.

In FIG. 3E, B1SP $EC_{50}$ (8.436 nM) were determined using a PE-labelled B1SP (B1SP-PE) which was serially diluted and added to DU145 cells for 1 hour. Cells were washed with DPBS before measurement of PE-Fluorescence intensity (FI). In FIGS. 3F-3H, bar graphs show the Mean and SEM Interactions/cell (FIG. 3F) B1SP binding to PLEXINB1 in DU145 cells, (FIG. 3G) B1SP inhibits the interaction between SEMA3C and NRP1 in DU145 cells and (FIG. 3H) B1SP inhibits the interaction between SEMA3C and PLEXIN B1 in DU145 cells based on photomicrographs of in-situ proximity ligation assay (PLA) results.

FIGS. 5B and 5C show that B1SP inhibits phosphorylation of Shc isoforms downstream of the EGFR.

FIG. 6B shows a Quantitative densitometric analysis of the blot in A and demonstrates that B1SP can inhibit Sema3C-mediated EGFR phosphorylation. Similarly, FIG. 6C shows the inhibition of EGFR phosphorylation in LNCaP, where the LNCaP cells were serum starved, media was then changed and the cells were treated with either truncated Semaphorin Fusion proteins (2.0 µM) (ALB SRGLI and Δ13) and Plexin B1 Fusion protein (B1SP) (2.0 µM) for 60 minutes. Cells were then stimulated with EGF (10 ng/ml) for 10 min and the cells were harvested and evaluated for the expression of EGFR phosphorylation (pEGFR), and EGFR levels. Blots (not shown) were reprobed for Vinculin as loading control and the densitometry analysis EGFR phosphorylation levels was performed.

In FIG. 7B, the 22RV1 PC cells were serum starved, and a B1SP conditioned medium (CM) was added to the cells for the indicated time-points followed by stimulation with 5.0 ng/ml EGF for 10 minutes, then the cells were harvested and evaluated for the expression of pEGFR, and EGFR as compared to the vinculin loading control and control EGFR phosphorylation evaluated in untreated cells at the termination of the time course. Both FIG. 7A and FIG. 7B show plots of a quantitative densitometric analysis. Similarly, the inhibition of EGFR phosphorylation was tested in 22RV1 PC cells (C), MCF10A normal human mammary cells (FIG. 7D), MR49F PC cells (FIG. 7E) and V16A castration-resistant prostate cancer (CRPC) stem cells (FIG. 7F), with increasing concentrations of B1SP (i.e. 0.5, 1, 2 and 4.0 µM).

(FIG. 8C) shows the inhibitory effect of B1SP on growth expressed as percentage of maximum androgen (R1881) sensitive growth. FIG. 8D shows a plot of B1SP fusion protein dose response on a log scale.

DETAILED DESCRIPTION

Definitions

Figure 1B:
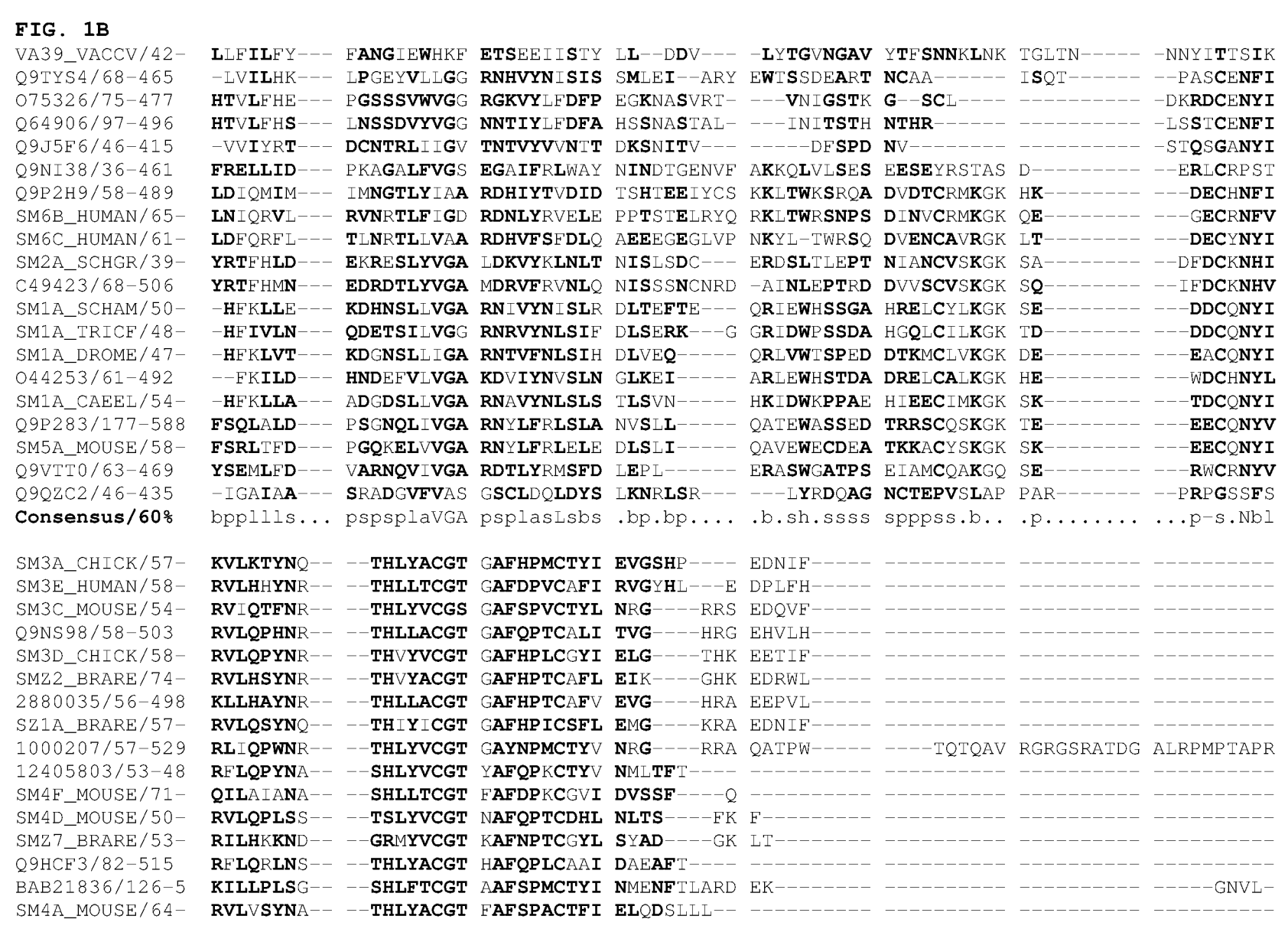
Figure 1D:
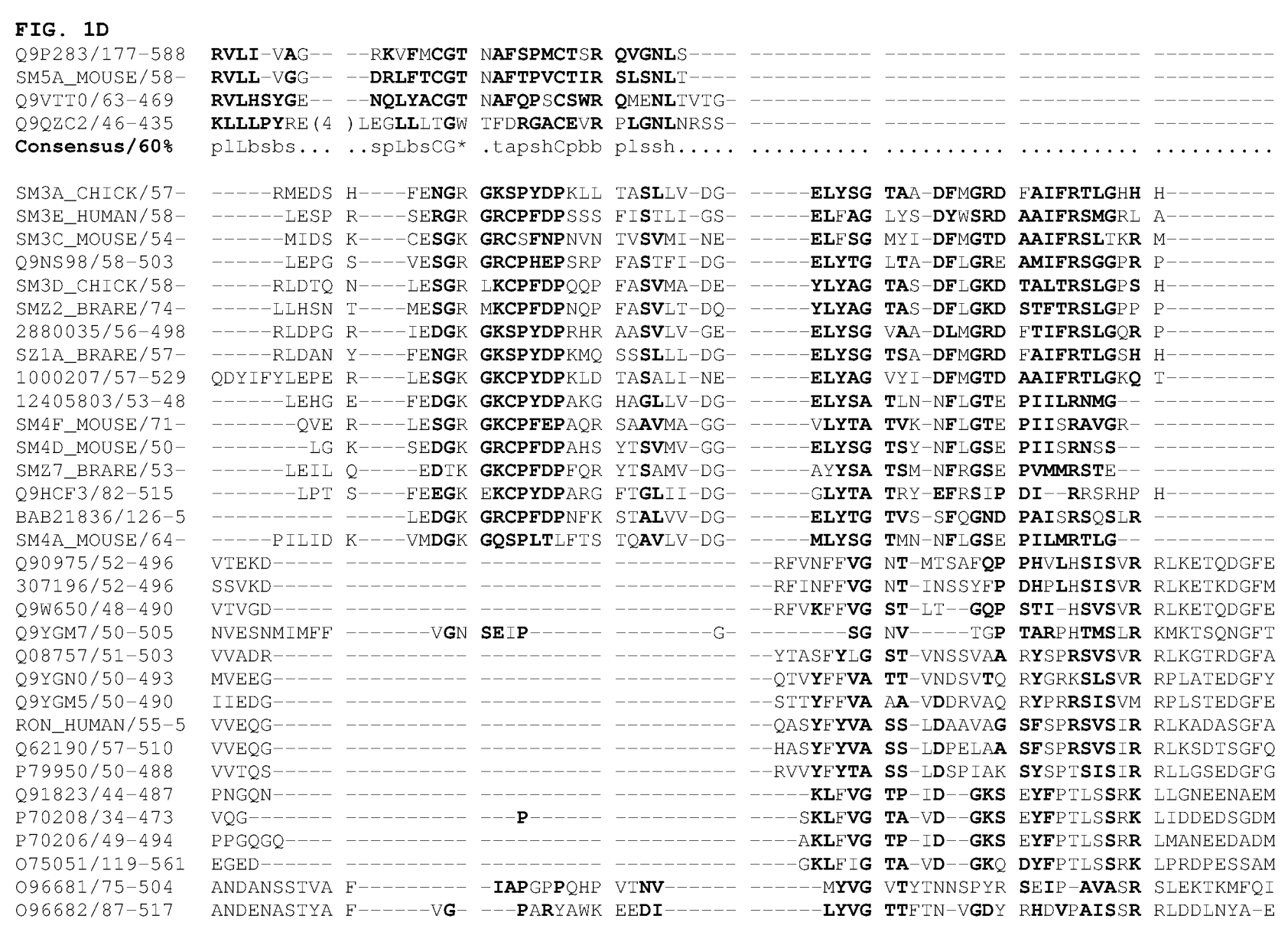
Figure 1K:
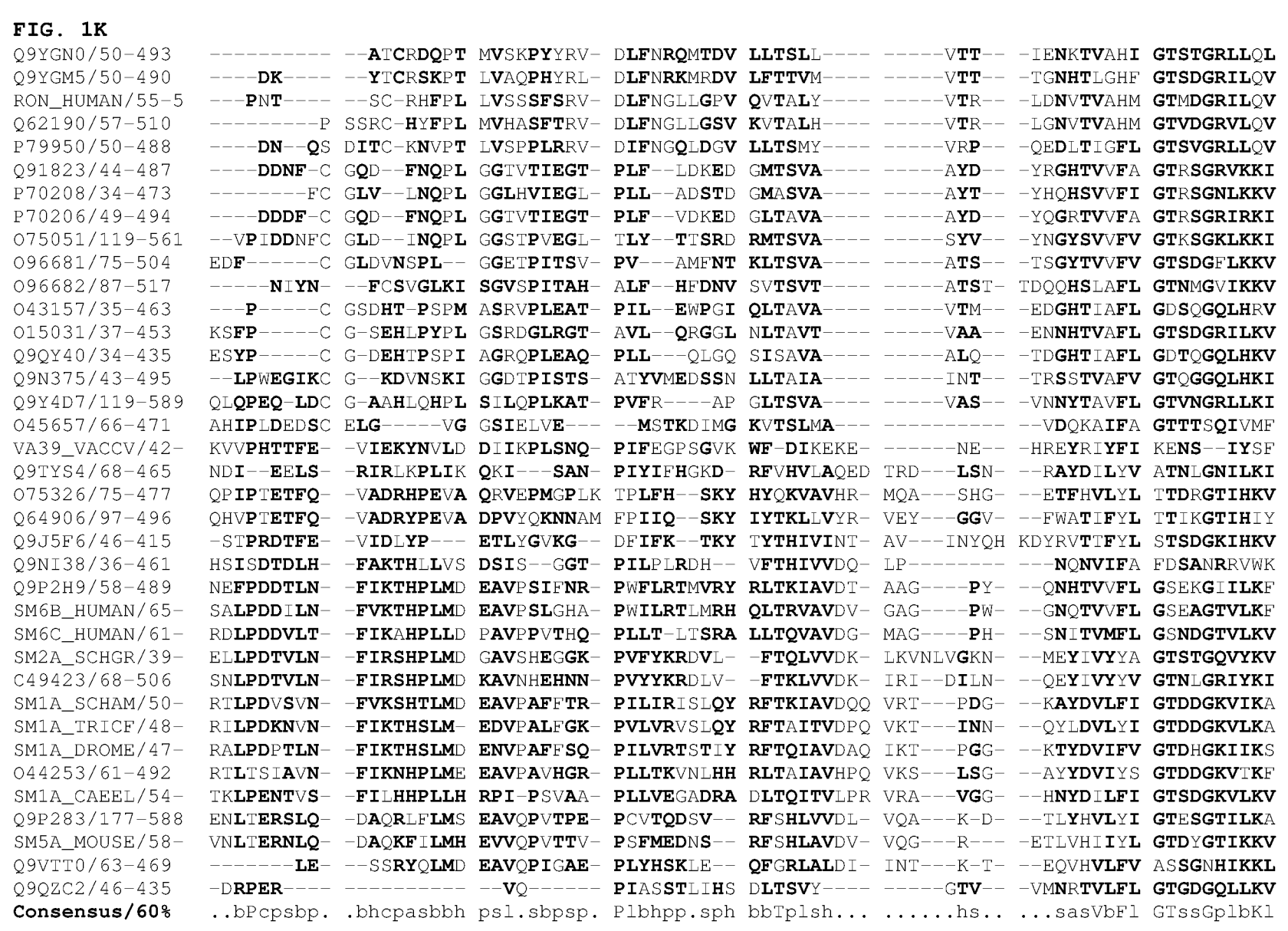
Figure 3A:
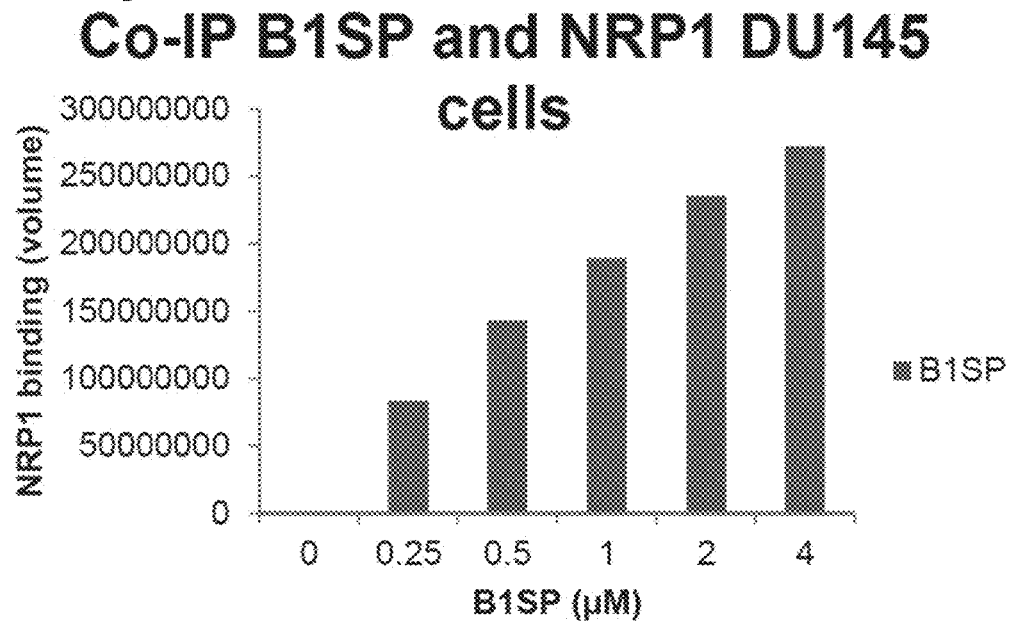
FIGS. 3A-3H shows that a B1SP fusion protein binds to (FIG. 3A) NRP 1 and (FIG. 3B) Plexin B1 and NRP1 in a dose-dependent manner in DU145 cells in a co-immunoprecipitation assays and in experiments of dose-responses to B1SP treatment the relative amount of B1SP in complex with either (FIG. 3C) NRP1 or (FIG. 3D) Plexin B1 also showed dose-dependent relationships.

A "sema domain" as used herein refers to a distinctive protein domain of approximately 500 amino acids having a 7 blade β propeller, wherein the sema domain may also include one or more long loops and/or insertions, such as an extrusion (Gherardi E. et al. 2004). The sema domain may be from any one of the 1-7 classes of animal semaphorins, viral semaphorin, plexins or from the MET and RON receptor tyrosine kinases (RTKs) as are known in the art. Alternatively, the sema domain may be formed by a combination of σ3 propeller blades from one or more different sema domains (see FIG. 1—SEMA DOMAIN CHROMO ALIGNMENT). The Sema domain is characterised by a conserved set of cysteine residues, which form four disulfide bonds to stabilise the structure. The sema domain fold is a variation of the beta propeller topology, with seven blades radially arranged around a central axis. Each blade contains a four-stranded (strands A to D) antiparallel beta sheet. The inner strand of each blade (A) lines the channel at the centre of the propeller, with strands B and C of the same repeat radiating outward, and strand D of the next repeat forming the outer edge of the blade. The large size of the sema domain is not due to a single inserted domain, but results from the presence of additional secondary structure elements inserted in most of the blades. The sema domain uses a 'loop and hook' system to close the circle between the first and the last blades. The blades are constructed sequentially with an N-terminal beta-strand closing the circle by providing the outermost strand (D) of the seventh (C-terminal) blade. The beta-propeller is further stabilized by an extension of the N-terminus, providing an additional, fifth beta-strand on the outer edge of blade 6. As used herein an inhibitory sema domain is meant to encompass any sema domain that is capable of inhibiting (1) EGFR phosphorylation, (2) c-Met phosphorylation or (3) VEGFR phosphorylation in cancer cells or inhibiting R1881-induced proliferation, adhesion or cell migration of cancer cells.

A "structural stabilization domain" as used herein refers to a Cystine Rich Domain (CRD) or a Plexins-Semaphorins-Integrins domain (PSI domain). For example, the $1^{st}$ PSI domain of Plexin B1 having the sequence, SCAQHLD-CASCLAHRDPYCGWCVLLGRCSRRSECSRGQGPEQ (SEQ ID NO:1). Alternative structural stabilization domains are known in the art or may be engineered based on a consensus sequence (see FIG. 2). Alternatively, the structural stabilization domain may be a PSI domain from either Plexin B2 or Plexin B3. Furthermore, the structural stabilization domain should be compatible with the SEMA domain being stabilized. PSI domains or CRDs are cysteine rich domains found in extracellular parts of over 500 signaling proteins. The core structure of a structural stabilization domain consists of a three stranded antiparallel beta-sheet and two alpha-helices.

The source (i.e. animal origin) of the SEMA domain and/or the structural stabilization domain may have implications for the development of human therapeutic proteins. For example, the differences in amino acid sequence between the source and the human sequence may lead to increased risk of immunogenicity of the therapeutic protein.

A "half life extending moiety" as used herein refers to any moiety that prolongs the half life of the fusion protein within a subject (Hutt M. et al. The Journal of Biological Chemistry (2012) 287(7):4462-4469). For example, a fragment crystallizable region (Fc region); immunoglobulin-binding domain (IgBD) B; Novozymes™ Albufuse™ Albumin; serum albumin; ubiquitin; chemical attachment of a polyethylene glycol (PEG) moiety or PEGylation; Amunix™ XTEN™ product which comprises a long, hydrophilic, and unstructured polymer having a polypeptide backbone. Furthermore, half-life may be extended by conjugation to poly-glycine, elastin-like polypeptide, and polysialic acid. PASylation is another strategy for extending half life of proteins by addition of conformationally disordered polypeptide chains with expanded hydrodynamic volume comprising the small residues Pro, Ala and Ser (PAS). Alteration of glycosylation, HESylation (coupling to hydroxyethyl starch) and Heptune (heparosan conjugation) are other methods for half life extension. The half life extending domain may be suitable for use with both monomers (for example, albumin) or dimers (for example, fc region)).

The fragment crystallizable region (Fc region) as used herein is the tail region of an antibody that interacts with cell surface receptors called Fc receptors and some proteins of the complement system. This property allows antibodies to activate the immune system. In IgG, IgA and IgD antibody isotypes, the Fc region is composed of two identical protein fragments, derived from the second and third constant domains of the antibody's two heavy chains; IgM and IgE Fc regions contain three heavy chain constant domains (CH domains 2-4) in each polypeptide chain.

A "Linker" as used herein refers to short peptide sequences that occur between protein domains. Linkers are often composed of flexible residues like glycine and serine so that the adjacent protein domains are free to move relative to one another. Longer linkers are used when it is necessary to ensure that two adjacent domains do not sterically interfere with one another. When two different proteins or peptides are linked, linkers are often also added, to make it more likely that the proteins fold independently and behave as expected.

Alternatively, linkers may enable protein purification or linkers in protein or peptide fusions are sometimes engineered with cleavage sites for proteases or chemical agents that enable the liberation of the two separate proteins.

A "Hinge" as used herein refers to the hinge fragment, which acts as a pivot in native immunoglobulins. The hinge is a flexible amino acid stretch in the central part of the heavy chains of the IgG and IgA immunoglobulin classes, which links these 2 chains by disulfide bonds. The hinge is particularly rich in cysteine and proline amino acids, may be extremely variable in amino acid sequence, and does not resemble other immunoglobulin regions. A portion of the IgM heavy chain has similar properties to the gamma hinge. The three-dimensional structure of the hinge region (225-232/225'-232') in synthetic peptide vaccines is identical to that of the fragment in the native protein, so the subdomain character of the IgG fragment is retained even upon N- and C-terminal elongation with peptide sequences unrelated to IgG.

"Systemic delivery," as used herein, may refer to delivery of lipid particles or other carriers that leads to a broad biodistribution of a B1SP fusion protein within an organism. Some techniques of administration can lead to the systemic delivery of certain agents, but not others. Systemic delivery means that a useful, preferably therapeutic, amount of an agent is exposed to most parts of the body. To obtain broad biodistribution generally requires a blood lifetime such that the agent is not rapidly degraded or cleared (such as by first pass organs (liver, lung, etc.) or by rapid, nonspecific cell binding) before reaching a disease site distal to the site of administration. Systemic delivery of a B1SP fusion protein can be by any means known in the art including, for example, intravenous, subcutaneous, and intraperitoneal. In an embodiment, systemic delivery of a B1SP fusion protein is by intravenous delivery.

"Local delivery," as used herein, refers to delivery of a B1SP fusion protein directly to a target site within an organism. For example, a B1SP fusion protein can be locally delivered by direct injection into a disease site, other target site, or a target organ such as the prostate.

As used herein, an "inhibitor" refers to an agent that restrains, retards, or otherwise causes inhibition of a physiological, chemical or enzymatic action or function. An inhibitor may cause at least 5% decrease in enzyme activity. An inhibitor may also refer to a drug, compound or agent that prevents or reduces the expression, transcription or translation of a gene or protein. An inhibitor may reduce or prevent the function of a protein, for instance by binding to and/or activating/inactivating another protein or receptor. An inhibitor may reduce or prevent the interaction of an enzyme or protein with another enzyme or protein. An inhibitor may cause degradation or clearance of a protein from a cell or from the body of a subject. For instance, an inhibitor may bind to the protein and such binding may target the protein for cellular degradation or for clearance from the body. Binding of an inhibitor may prevent it from binding its cognate receptor, could prevent other important molecular interactions, or could alter the conformation of the protein. Binding of an inhibitor to the receptor of the protein may also prevent interaction of the protein with the receptor, and would thus also inhibit the cellular function of the protein in question. Such an inhibitor may be a B1SP fusion protein as described herein. All such embodiments are considered within the definition of an inhibitor and are considered to be within the scope of the present invention.

The terms "peptide", "polypeptide" and "protein" may be used interchangeably, and refer to a compound comprised of at least two amino acid residues covalently linked by peptide bonds or modified peptide bonds, for example peptide isosteres (modified peptide bonds) that may provide additional desired properties to the peptide, such as increased half-life. A peptide may comprise at least two amino acids. The amino acids comprising a peptide or protein described herein may also be modified either by natural processes, such as posttranslational processing, or by chemical modification techniques which are well known in the art.

Modifications can occur anywhere in a peptide, including the peptide backbone, the amino acid side-chains and the amino or carboxyl termini. It is understood that the same type of modification may be present in the same or varying degrees at several sites in a given peptide.

Examples of modifications to peptides may include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, *Proteins-Structure and Molecular Properties*, $2^{nd}$ ed., T. E. Creighton, W. H. Freeman and Company, New York, 1993 and Wold F, *Posttranslational Protein Modifications: Perspectives and Prospects*, pgs. 1-12 in *Posttranslational Covalent Modification of Proteins*, B. C. Johnson, ed., Academic Press, New York, 1983; Seifter et al., *Analysis for protein modifications and nonprotein cofactors, Meth. Enzymol.* (1990) 182: 626-646 and Rattan et al. (1992), *Protein Synthesis: Posttranslational Modifications and Aging,"* Ann NY Acad Sci 663: 48-62.

A "substantially similar sequence" refers to an amino acid sequence that differs from a reference sequence only by one or more substitutions, but which may, for example, be functionally homologous to another substantially similar sequence. It will be appreciated by a person of skill in the art the aspects of the individual amino acids in a peptide of the invention that may be substituted.

Amino acid sequence similarity or identity may be computed by using the BLASTP and TBLASTN programs which employ the BLAST (basic local alignment search tool) 2.0 algorithm. Techniques for computing amino acid sequence similarity or identity are well known to those skilled in the art, and the use of the BLAST algorithm is described in ALTSCHUL et al. 1990, *J Mol. Biol.* 215: 403-410 and ALTSCHUL et al. (1997), *Nucleic Acids Res.* 25: 3389-3402.

Amino acids may be described as, for example, polar, non-polar, acidic, basic, aromatic or neutral. A polar amino acid is an amino acid that may interact with water by hydrogen bonding at biological or near-neutral pH. The polarity of an amino acid is an indicator of the degree of hydrogen bonding at biological or near-neutral pH. Examples of polar amino acids include serine, proline, threonine, cysteine, asparagine, glutamine, lysine, histidine, arginine, aspartate, tyrosine and glutamate. Examples of non-polar amino acids include glycine, alanine, valine leucine, isoleucine, methionine, phenylalanine, and tryptophan. Acidic amino acids have a net negative charge at a neutral pH. Examples of acidic amino acids include aspartate and glutamate. Basic amino acids have a net positive charge at a neutral pH. Examples of basic amino acids include arginine, lysine and histidine. Aromatic amino acids are generally nonpolar, and may participate in hydrophobic interactions. Examples of aromatic amino acids include phenylalanine, tyrosine and tryptophan. Tyrosine may also participate in hydrogen bonding through the hydroxyl group on the aromatic side chain. Neutral, aliphatic amino acids are generally nonpolar and hydrophobic. Examples of neutral amino acids include alanine, valine, leucine, isoleucine and methionine. An amino acid may be described by more than one descriptive category. Amino acids sharing a common descriptive category may be substitutable for each other in a peptide.

Nomenclature used to describe the peptide compounds of the present invention follows the conventional practice where the amino group is presented to the left and the carboxy group to the right of each amino acid residue. In the sequences representing selected specific embodiments of the present invention, the amino- and carboxy-terminal groups, although not specifically shown, will be understood to be in the form they would assume at physiologic pH values, unless otherwise specified. In the amino acid structure formulae, each residue may be generally represented by a one-letter or three-letter designation, corresponding to the trivial name of the amino acid, in accordance with Table 1.

TABLE 1

Nomenclature and abbreviations of the 20 standard L-amino acids commonly found in naturally occurring peptides.

| Full name | Three-letter abbreviation | One-letter abbreviation |
| --- | --- | --- |
| Alanine | Ala | A |
| Cysteine | Cys | C |
| Aspartic acid | Asp | D |
| Glutamic acid | Glu | E |
| Phenylalanine | Phe | F |
| Glycine | Gly | G |
| Histidine | His | H |
| Isoleucine | Ile | I |
| Lysine | Lys | K |
| Leucine | Leu | L |
| Methionine | Met | M |
| Asparagine | Asp | N |
| Proline | Pro | P |
| Glutamine | Gln | Q |
| Arginine | Arg | R |
| Serine | Ser | S |
| Threonine | Thr | T |
| Valine | Val | V |
| Tryptophan | Trp | W |
| Tyrosine | Tyr | T |

The hydropathy index of an amino acid is a scale indicating the tendency of an amino acid to seek out an aqueous environment (negative value) or a hydrophobic environment (positive value) (KYTE & DOOLITTLE 1982. *J Mol Biol* 157:105-132). Hydropathy indices of the standard amino acids include alanine (1.8), arginine (−4.5), asparagine (−3.5), aspartic acid (−3.5), cysteine (2.5), glutamine (−3.5), glutamic acid (−3.5), glycine (−0.4), histidine (−3.2), isoleucine (4.5), leucine (3.8), lysine (−3.9), methionine (1.9), phenylalanine (2.8), proline (−1.6), serine (−0.8), threonine (−0.7), tryptophan (−0.9), tyrosine (−1.3), and valine (4.2). Amino acids with similar hydropathy indices may be substitutable for each other in a peptide.

In order to further exemplify what is meant by a conservative amino acid substitution, Groups A-F are listed below. The replacement of one member of the following groups by another member of the same group is considered to be a conservative substitution.

Group A includes leucine, isoleucine, valine, methionine, phenylalanine, serine, cysteine, threonine, and modified amino acids having the following side chains: ethyl, iso-butyl, —$CH_2CH_2OH$, —$CH_2CH_2CH_2OH$, —$CH_2CHOHCH_3$ and $CH_2SCH_3$.

Group B includes glycine, alanine, valine, serine, cysteine, threonine, and a modified amino acid having an ethyl side chain.

Group C includes phenylalanine, phenylglycine, tyrosine, tryptophan, cyclohexylmethyl, and modified amino residues having substituted benzyl or phenyl side chains.

Group D includes glutamic acid, aspartic acid, a substituted or unsubstituted aliphatic, aromatic or benzylic ester of glutamic or aspartic acid (e.g., methyl, ethyl, n-propyl, iso-propyl, cyclohexyl, benzyl, or substituted benzyl), glutamine, asparagine, CO—NH-alkylated glutamine or asparagine (e.g., methyl, ethyl, n-propyl, and iso-propyl), and modified amino acids having the side chain —$(CH_2)_3COOH$, an ester thereof (substituted or unsubstituted aliphatic, aromatic, or benzylic ester), an amide thereof, and a substituted or unsubstituted N-alkylated amide thereof.

Group E includes histidine, lysine, arginine, N-nitroarginine, p-cycloarginine, g-hydroxyarginine, N-amidinocitrulline, 2-amino guanidinobutanoic acid, homologs of lysine, homologs of arginine, and ornithine.

Group F includes serine, threonine, cysteine, and modified amino acids having C1-C5 straight or branched alkyl side chains substituted with —OH or —SH.

Groups A-F are exemplary and are not intended to limit the invention.

Peptides or peptide analogues can be synthesised by chemical techniques known in the art, for example, by automated synthesis using solution or solid phase synthesis methodology. Automated peptide synthesisers are commercially available and use techniques well known in the art. Peptides and peptide analogues can also be prepared using recombinant DNA technology using methods such as those described in, for example, SAMBROOK J. AND RUSSELL D. (2000) Molecular Cloning: A Laboratory Manual (Third Edition) Cold Spring Harbor Laboratory, Cold Spring Harbor Laboratory Press, Cold Spring Harbor, N.Y.) or AUSUBEL et al. (Current Protocols in Molecular Biology, John Wiley & Sons, 1994).

A "peptidomimetic" is a compound comprising non-peptidic structural elements that mimics the biological action of a parent peptide. A peptidomimetic may not have classical peptide characteristics such as an enzymatically scissile peptidic bond. A parent peptide may initially be identified as a binding sequence or phosphorylation site on a protein of interest, or may be a naturally occurring peptide, for example a peptide hormone. Assays to identify peptidomimetics may include a parent peptide as a positive control for comparison purposes, when screening a library, such as a peptidomimetic library. A peptidomimetic library is a library of compounds that may have biological activity similar to that of a parent peptide.

Amino acids contained within the peptides described herein will be understood to be in the L- or D-configuration. In peptides and peptidomimetics of the present invention, D-amino acids may be substitutable for L-amino acids. Amino acids contained within the peptides of the present invention, and particularly at the carboxy- or amino-terminus, may be modified by methylation, amidation, acetylation or substitution with other chemical groups which may change the circulating half-life of the peptide without adversely affecting their biological activity. Additionally, a disulfide linkage may be present or absent in the peptides of the invention. Another approach for modification of an existing sequence is to synthesize the corresponding retro-inverso version. A retro-inverso peptide is one in which the sequence is reversed ie. reversal of the N to C terminal and synthesized using D-amino acids. Retro inverso analogs of L peptides when aligned alongside each other from N to C and C to N have all side chains in the same orientation, however the peptide bonds are reversed and sterically unavailable for cleavage by proteases. Nair et. al. 2003 *J. Immunol.* 170:1362-1373.

"Peptide nucleic acids" (PNA) as used herein refer to modified nucleic acids in which the sugar phosphate skeleton of a nucleic acid has been converted to an N-(2-aminoethyl)-glycine skeleton. Although the sugar-phosphate skeletons of DNA/RNA are subjected to a negative charge under neutral conditions resulting in electrostatic repulsion between complementary chains, the backbone structure of PNA does not inherently have a charge. Therefore, there is no electrostatic repulsion. Consequently, PNA has a higher ability to form double strands as compared with conventional nucleic acids, and has a high ability to recognize base sequences. Furthermore, PNAs are generally more robust than nucleic acids. PNAs may also be used in arrays and in other hybridization or other reactions as described above and herein for oligonucleotides.

As used herein, the term "vector" refers to a polynucleotide compound used for introducing exogenous or endogenous polynucleotide into host cells. A vector comprises a nucleotide sequence, which may encode one or more polypeptide molecules. Plasmids, cosmids, viruses and bacteriophages, in a natural state or which have undergone recombinant engineering, are non-limiting examples of commonly used vectors to provide recombinant vectors comprising at least one desired isolated polynucleotide molecule.

The nucleic acid molecules can be inserted into any suitable vector. Suitable vectors include, without limitation, viral vectors. Suitable viral vectors include, without limitation, retroviral vectors, alphaviral, vaccinial, adenoviral, adenoassociated viral, herpes viral, and fowl pox viral vectors. The vectors preferably have a native or engineered capacity to transform eukaryotic cells, e.g., CHO-K1 cells. Additionally, the vectors useful in the context of the invention can be "naked" nucleic acid vectors (i.e., vectors having little or no proteins, sugars, and/or lipids encapsulating them) such as plasmids or episomes, or the vectors can be complexed with other molecules. Other molecules that can be suitably combined with the inventive nucleic acids include without limitation viral coats, cationic lipids, liposomes, polyamines, gold particles, and targeting moieties such as ligands, receptors, or antibodies that target cellular molecules.

Nonstandard amino acids may occur in nature, and may or may not be genetically encoded. Examples of genetically encoded nonstandard amino acids include selenocysteine, sometimes incorporated into some proteins at a UGA codon, which may normally be a stop codon, or pyrrolysine, sometimes incorporated into some proteins at a UAG codon, which may normally be a stop codon. Some nonstandard amino acids that are not genetically encoded may result from modification of standard amino acids already incorporated in a peptide, or may be metabolic intermediates or precursors, for example. Examples of nonstandard amino acids include 4-hydroxyproline, 5-hydroxylysine, 6-N-methyllysine, gamma-carboxyglutamate, desmosine, selenocysteine, ornithine, citrulline, lanthionine, 1-aminocyclopropane-1-carboxylic acid, gamma-aminobutyric acid, carnitine, sarcosine, or N-formylmethionine. Synthetic variants of standard and non-standard amino acids are also known and may include chemically derivatized amino acids, amino acids labeled for identification or tracking, or amino acids with a variety of side groups on the alpha carbon. Examples of such side groups are known in the art and may include aliphatic, single aromatic, polycyclic aromatic, heterocyclic, heteronuclear, amino, alkylamino, carboxyl, carboxamide, carboxyl ester, guanidine, amidine, hydroxyl, alkoxy, mercapto-, alkylmercapto-, or other heteroatom-containing side chains. Other synthetic amino acids may include alpha-imino acids, non-alpha amino acids such as beta-amino acids, des-carboxy or des-amino acids. Synthetic variants of amino acids may be synthesized using general methods known in the art, or may be purchased from commercial suppliers, for example RSP Amino Acids LLC (Shirley, Mass.).

The B1SP fusion proteins described herein may be in isolation, or may be linked to or in combination with tracer compounds, liposomes, carbohydrate carriers, polymeric carriers or other agents or excipients as will be apparent to one of skill in the art. In an alternate embodiment, such compounds may comprise a medicament, wherein such compounds may be present in a pharmacologically effective amount.

The term "medicament" as used herein refers to a composition that may be administered to a patient or test subject and is capable of producing an effect in the patient or test subject. The effect may be chemical, biological or physical, and the patient or test subject may be human, or a non-human animal, such as a rodent or transgenic mouse, or a dog, cat, cow, sheep, horse, beaver, hamster, guinea pig, rabbit or pig. The medicament may be comprised of the effective chemical entity alone or in combination with a pharmaceutically acceptable excipient.

The term "pharmaceutically acceptable excipient" may include any and all solvents, dispersion media, coatings, antibacterial, antimicrobial or antifungal agents, isotonic and absorption delaying agents, and the like that are physiologically compatible. An excipient may be suitable for intravenous, intraperitoneal, intramuscular, subcutaneous, intrathecal, topical or oral administration. An excipient may include sterile aqueous solutions or dispersions for extemporaneous preparation of sterile injectable solutions or dispersion. Use of such media for preparation of medicaments is known in the art.

B1SP fusion proteins described herein may be administered in any of a variety of known routes. Examples of methods that may be suitable for the administration of a B1SP fusion protein described herein include orally, intravenous, inhalation, intramuscular, subcutaneous, topical, intraperitoneal, intra-rectal or intra-vaginal suppository, sublingual, and the like. A B1SP fusion protein as described herein may be administered as a sterile aqueous solution, or may be administered in a fat-soluble excipient, or in another solution, suspension, patch, tablet or paste format as is appropriate. A composition comprising the B1SP fusion protein described herein may be formulated for administration by inhalation. For instance, a B1SP fusion protein described herein may be combined with an excipient to allow dispersion in an aerosol. Examples of inhalation formulations will be known to those skilled in the art. Other agents may be included in combination with the B1SP fusion protein described herein to aid uptake or metabolism, or delay dispersion within the host, such as in a controlled-release formulation. Examples of controlled release formulations will be known to those of skill in the art, and may include microencapsulation, embolism within a carbohydrate or polymer matrix, and the like. Other methods known in the art for making formulations are found in, for example, "Remington's Pharmaceutical Sciences", (19th edition), ed. A. Gennaro, 1995, Mack Publishing Company, Easton, Pa.

The dosage of a B1SP fusion protein described herein may vary depending on the route of administration (oral, intravenous, inhalation, or the like) and the form in which the composition or compound is administered (solution, controlled release or the like). Determination of appropriate dosages is within the ability of one of skill in the art. As used herein, an "effective amount", a "therapeutically effective amount", or a "pharmacologically effective amount" of a medicament refers to an amount of a medicament present in such a concentration to result in a therapeutic level of drug delivered over the term that the drug is used. This may be dependent on mode of delivery, time period of the dosage, age, weight, general health, sex and diet of the subject receiving the medicament. Methods of determining effective amounts are known in the art. It is understood that it could be potentially beneficial to restrict delivery of a B1SP fusion protein is described herein to the target tissue or cell in which administration is desired. It is also understood that it may be desirable to target a B1SP fusion protein described herein to a desired tissue or cell type. The B1SP fusion protein described herein of the invention may be coupled to a cell uptake moiety. The targeting moiety may also function as the cell uptake moiety.

Delivery of bioactive molecules such as peptides, to a cell or cells in a reasonably efficient manner may require more than just the 'dumping' of the naked peptide onto the cell, or administering the naked peptide into the patient or test subject. Agents that enable delivery of bioactive molecules into cells in a suitable manner so as to provide an effective amount, such as a pharmacologically effective amount are known in the art, and are described in, for example, DIETZ et al 2004. *Mol Cell. Neurosci* 27:85-131. Examples of such agents include liposomes, lipid particles, antibodies or receptor ligands that may be coupled to the bioactive molecule, viral vectors, and protein transduction domains (PTD). Examples of PTDs include Antennapedia homeodomain (PEREZ et al 1992 *J. Cell Sci* 102:717-722), transportan (POOGA et al 1998 *FASEB J* 12: 67-77), the translocation domains of diphtheria toxin (STENMARK et al 1991 *J Cell Biol* 113:1025-1032; WIEDLOCHA et al 1994 *Cell* 76:1039-1051), anthrax toxin (BALLARD et al 1998 *Infect. Immun* 66:615-619; BLANKE et al 1996 *Proc Natl Acad Sci* 93: 8437-8442) and *Pseudomonas* exotoxin A (PRIOR et al 1992 *Biochemistry* 31:3555-3559), protegrin derivatives such as dermaseptin S4 (HARITON-GAZAL et al 2002 *Biochemistry* 41:9208-9214), HSV-1 VP22 (DILBER et al 1999 *Gene Ther.* 6:12-21), PEP-1 (MORRIS et al 2001 *Nature Biotechnol* 19:1173-1176), basic peptides such as poly-L and poly-D-lysine (WOLFERT et al 1996 *Gene Ther.* 3:269-273; RYSER et al 1980 *Cancer* 45:1207-1211;

SHEN et al 1978 *Proc Natl Acad Sci* 75:1872-1876), HSP70 (FUJIHARA et al 1999 *EMBO J* 18:411-419) and HIV-TAT (DEMARCHI et al 1996 *J Virol* 70:4427-4437). Other examples and related details of such protein transduction domains are described in DIETZ, supra and references therein.

As used herein, the term "cancer" refers to a proliferative disorder caused or characterized by the proliferation of cells which have lost susceptibility to normal growth control. The term cancer, as used in the present application, includes tumors and any other proliferative disorders, such as prostate adenocarcinoma. Cancers of the same tissue type usually originate in the same tissue, and may be divided into different subtypes based on their biological characteristics. Four general categories of cancers are carcinoma (epithelial tissue derived), sarcoma (connective tissue or mesodermal derived), leukemia (blood-forming tissue derived) and lymphoma (lymph tissue derived). Over 200 different types of cancers are known, and every organ and tissue of the body may be affected. Specific examples of cancers that do not limit the definition of cancer may include melanoma, leukemia, astrocytoma, glioblastoma, retinoblastoma, lymphoma, glioma, Hodgkins' lymphoma and chronic lymphocyte leukemia. Examples of organs and tissues that may be affected by various cancers include pancreas, breast, thyroid, ovary, uterus, testis, prostate, thyroid, pituitary gland, adrenal gland, kidney, stomach, esophagus, colon or rectum, head and neck, bone, nervous system, skin, blood, nasopharyngeal tissue, lung, urinary tract, cervix, vagina, exocrine glands and endocrine glands. Alternatively, a cancer may be multicentric or of unknown primary site (CUPS). The cancer may be selected from the group including: prostate cancer, breast cancer, ovarian cancer, bladder cancer, kidney cancer, glioblastoma and endometrial cancer. The cancer may be prostate cancer.

As used herein, a "cancerous cell" refers to a cell that has undergone a transformation event and whose growth is no longer regulated to the same extent as before said transformation event. A tumor refers to a collection of cancerous cells, often found as a solid or semi-solid lump in or on the tissue or a patient or test subject.

A cancer or cancerous cell may be described as "sensitive to" or "resistant to" a given therapeutic regimen or chemotherapeutic agent based on the ability of the regimen to kill cancer cells or decrease tumor size, reduce overall cancer growth (i.e. through reduction of angiogenesis), and/or inhibit metastasis. Cancer cells that are resistant to a therapeutic regimen may not respond to the regimen and may continue to proliferate. Cancer cells that are sensitive to a therapeutic regimen may respond to the regimen resulting in cell death, a reduction in tumor size, reduced overall growth (tumor burden) or inhibition of metastasis. For example, this desirably manifest itself in a reduction in tumor size, overall growth/tumor burden or the incidence of metastasis of about 10% or more, for example, about 30%, about 40%, about 50%, about 60%, about 70%, about 80%, or more, to about 2-fold, about 3-fold, about 4-fold, about 5-fold, about 10-fold, about 15-fold, about 20-fold or more. Monitoring of a response may be accomplished by numerous pathological, clinical and imaging methods as described herein and known to persons of skill in the art.

A common theme for a chemotherapeutic agent or combination of agents is to induce death of the cancerous cells. For example, DNA adducts such as nitrosoureas, busulfan, thiotepa, chlorambucil, cisplatin, mitomycin, procarbazine, or dacacarbazine slow the growth of the cancerous cell by forcing the replicating cell to repair the damaged DNA before the M-phase of the cell cycle, or may by themselves cause sufficient damage to trigger apoptosis of the cancerous cell. Other events such as gene expression or transcription, protein translation, or methylation of the replicated DNA, for example, may also be interfered with by the varied arsenal of chemotherapeutic agents available to the clinician and help to trigger apoptotic processes within the cancerous cells. Alternately, a chemotherapeutic agent may enable the cancerous cell to be killed by aspects of the patient or test subject's humoral or acquired immune system, for example, the complement cascade or lymphocyte attack.

The method for treating prostate cancer comprising administering a biologically effective amount of a B1SP fusion protein to cancer cells may be supplemented with a further therapeutic regimen. As used herein, a "therapeutic regimen" or "therapy" refers to the administration of at least one additional agent (i.e. other than the B1SP fusion protein) which is harmful to cancerous cells. Suitable therapeutic regimens for use in accordance with the invention include, but are not limited to, "chemotherapeutic regimens," "radiotherapeutic regimens," "alternative therapeutic regimen" and combinations thereof.

As used herein, a "chemotherapeutic regimen" or "chemotherapy" refers to the administration of at least one chemotherapy agent which is harmful to destroy cancerous cells. There are a myriad of such chemotherapy agents available to a clinician.

Chemotherapy agents may be administered to a subject in a single bolus dose, or may be administered in smaller doses over time. A single chemotherapeutic agent may be used (single-agent therapy) or more than one agent may be used in combination (combination therapy). Chemotherapy may be used alone to treat some types of cancer. Alternatively, chemotherapy may be used in combination with other types of treatment, for example, radiotherapy or alternative therapies (for example immunotherapy) as described herein. Additionally, a chemosensitizer may be administered as a combination therapy with a chemotherapy agent.

As used herein, a "chemotherapeutic agent" refers to a medicament that may be used to treat cancer, and generally has the ability to kill cancerous cells directly. Examples of chemotherapeutic agents include alkylating agents, antimetabolites, natural products, hormones and antagonists, and miscellaneous agents. Examples of alternate names are indicated in brackets. Examples of alkylating agents include nitrogen mustards such as mechlorethamine, cyclophosphamide, ifosfamide, melphalan (L-sarcolysin) and chlorambucil; ethylenimines and methylmelamines such as hexamethylmelamine and thiotepa; alkyl sulfonates such as busulfan; nitrosoureas such as carmustine (BCNU), semustine (methyl-CCNU), lomustine (CCNU) and streptozocin (streptozotocin); DNA synthesis antagonists such as estramustine phosphate; and triazines such as dacarbazine (DTIC, dimethyl-triazenoimidazolecarboxamide) and temozolomide. Examples of antimetabolites include folic acid analogs such as methotrexate (amethopterin); pyrimidine analogs such as fluorouracin (5-fluorouracil, 5-FU, 5FU), floxuridine (fluorodeoxyuridine, FUdR), cytarabine (cytosine arabinoside) and gemcitabine; purine analogs such as mercaptopurine (6-mercaptopurine, 6-MP), thioguanine (6-thioguanine, TG) and pentostatin (2'-deoxycoformycin, deoxycoformycin), cladribine and fludarabine; and topoisomerase inhibitors such as amsacrine. Examples of natural products include vinca alkaloids such as vinblastine (VLB) and vincristine; taxanes such as paclitaxel and docetaxel (Taxotere); epipodophyllotoxins such as etoposide and teniposide; camptothecins such as topotecan and irinotecan;

antibiotics such as dactinomycin (actinomycin D), daunorubicin (daunomycin, rubidomycin), doxorubicin, bleomycin, mitomycin (mitomycin C), idarubicin, epirubicin; enzymes such as L-asparaginase; and biological response modifiers such as interferon alpha and interlelukin 2. Examples of hormones and antagonists include luteinising releasing hormone agonists such as buserelin; adrenocorticosteroids such as prednisone and related preparations; progestins such as hydroxyprogesterone caproate, medroxyprogesterone acetate and megestrol acetate; estrogens such as diethylstilbestrol and ethinyl estradiol and related preparations; estrogen antagonists such as tamoxifen and anastrozole; androgens such as testosterone propionate and fluoxymesterone and related preparations; androgen antagonists such as flutamide and bicalutamide; and gonadotropin-releasing hormone analogs such as leuprolide. Examples of miscellaneous agents include thalidomide; platinum coordination complexes such as cisplatin (cis-DDP), oxaliplatin and carboplatin; anthracenediones such as mitoxantrone; substituted ureas such as hydroxyurea; methylhydrazine derivatives such as procarbazine (N-methylhydrazine, MIH); adrenocortical suppressants such as mitotane (o,p'-DDD) and aminoglutethimide; RXR agonists such as bexarotene; and tyrosine kinase inhibitors such as imatinib. Alternate names and trade-names of these and additional examples of chemotherapeutic agents, and their methods of use including dosing and administration regimens, will be known to a person versed in the art, and may be found in, for example "The Pharmacological basis of therapeutics", $10^{th}$ edition. HARDMAN H G., LIMBIRD L E. editors. McGraw-Hill, New York, and in "Clinical Oncology", $3^{rd}$ edition. Churchill Livingstone/Elsevier Press, 2004. ABELOFF, M D. editor. In particular, suitable chemotherapeutic agents for use in accordance with the invention include, without limitation, nanoparticle albumin-bound paclitaxels.

As used herein, the term "radiotherapeutic regimen" or "radiotherapy" refers to the administration of radiation to kill cancerous cells. Radiation interacts with various molecules within the cell, but the primary target, which results in cell death is the deoxyribonucleic acid (DNA). However, radiotherapy often also results in damage to the cellular and nuclear membranes and other organelles. DNA damage usually involves single and double strand breaks in the sugar-phosphate backbone. Furthermore, there can be cross-linking of DNA and proteins, which can disrupt cell function. Depending on the radiation type, the mechanism of DNA damage may vary as does the relative biologic effectiveness. For example, heavy particles (i.e. protons, neutrons) damage DNA directly and have a greater relative biologic effectiveness. Electromagnetic radiation results in indirect ionization acting through short-lived, hydroxyl free radicals produced primarily by the ionization of cellular water. Clinical applications of radiation consist of external beam radiation (from an outside source) and brachytherapy (using a source of radiation implanted or inserted into the patient). External beam radiation consists of X-rays and/or gamma rays, while brachytherapy employs radioactive nuclei that decay and emit alpha particles, or beta particles along with a gamma ray.

Radiotherapy may further be used in combination chemotherapy, with the chemotherapeutic agent acting as a radiosensitizer. The specific choice of radiotherapy suited to an individual patient may be determined by a skilled person at the point of care, taking into consideration the tissue and stage of the cancer. Examples of radiotherapy approaches to various cancers may be found in, for example "Clinical Oncology", $3^{rd}$ edition. Churchill Livingstone/Elsevier Press, 2004. ABELOFF, M D. editor.

As used herein, the term "alternative therapeutic regimen" or "alternative therapy" may include for example, biologic response modifiers (including polypeptide-, carbohydrate-, and lipid-biologic response modifiers), toxins, lectins, anti-angiogenic agents, receptor tyrosine kinase inhibitors (for example Iressa™ (gefitinib), Tarceva™ (erlotinib), Erbitux™ (cetuximab), imatinib mesilate (Gleevec™), proteosome inhibitors (for example bortezomib, Velcade™); VEGFR2 inhibitors such as PTK787 (ZK222584), aurora kinase inhibitors (for example ZM447439); mammalian target of rapamycin (mTOR) inhibitors, cyclooxygenase-2 (COX-2) inhibitors, rapamycin inhibitors (for example sirolimus, Rapamune™); farnesyltransferase inhibitors (for example tipifarnib, Zarnestra); matrix metalloproteinase inhibitors (for example BAY 12-9566; sulfated polysaccharide tecogalan); angiogenesis inhibitors (for example Avastin™ (bevacizumab); analogues of fumagillin such as TNP-4; carboxyaminotriazole; BB-94 and BB-2516; thalidomide; interleukin-12; linomide; peptide fragments; and antibodies to vascular growth factors and vascular growth factor receptors); platelet derived growth factor receptor inhibitors, protein kinase C inhibitors, mitogen-activated kinase inhibitors, mitogen-activated protein kinase kinase inhibitors, Rous sarcoma virus transforming oncogene (SRC) inhibitors, histonedeacetylase inhibitors, small hypoxia-inducible factor inhibitors, hedgehog inhibitors, and TGF-β signalling inhibitors. Furthermore, an immunotherapeutic agent would also be considered an alternative therapeutic regimen. Examples include chemokines, chemotaxins, cytokines, interleukins, or tissue factor. Suitable immunotherapeutic agents also include serum or gamma globulin containing preformed antibodies; nonspecific immunostimulating adjuvants; active specific immunotherapy; and adoptive immunotherapy. In addition, alternative therapies may include other biological-based chemical entities such as polynucleotides, including antisense molecules, polypeptides, antibodies, gene therapy vectors and the like. Such alternative therapeutics may be administered alone or in combination, or in combination with other therapeutic regimens described herein. Alternate names and trade-names of these agents used in alternative therapeutic regimens and additional examples of agents used in alternative therapeutic regimens, and their methods of use including dosing and administration regimens, will be known to a physician versed in the art. Furthermore, methods of use of chemotherapeutic agents and other agents used in alternative therapeutic regimens in combination therapies, including dosing and administration regimens, will also be known to a person versed in the art.

Prostate Cancer

The Semaphorins belong to a family of secreted and membrane bound proteins that contain a conserved SEMA domain. Semaphorins and their receptors (mainly plexins and neuropilins) are aberrantly expressed in human tumors. Semaphorin signals have an important role in the regulation of tumor angiogenesis, invasion and metastasis. The present disclosure details the use of a B1SP fusion proteins that target and inhibit semaphoring-mediated signalling pathways to treat prostate and other cancers. The results described herein show that B1SP fusion proteins are potent inhibitors of semaphoring signalling and use in the treatment of cancer. B1SP fusion proteins bind to neuropilin and plexin in a dose dependent manner. B1SP fusion protein treatment can lead to inhibition of cell viability and induction of cell death of prostate cancer cells in a dose and concentration dependent manner. Furthermore, B1SP fusion protein is shown herein to inhibit cell adhesion in prostate cancer cells. B1SP fusion protein is shown herein to inhibit EGFR phosphorylation and R1881-induced proliferation of prostate cancer cells.

Any terms not directly defined herein shall be understood to have the meanings commonly associated with them as understood within the art of the invention. Certain terms are discussed below, or elsewhere in the specification, to provide additional guidance to the practitioner in describing the compositions, devices, methods and the like of embodiments of the invention, and how to make or use them. It will be appreciated that the same thing may be said in more than one way. Consequently, alternative language and synonyms may be used for any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents, unless it is explicitly stated. Use of examples in the specification, including examples of terms, is for illustrative purposes only and does not limit the scope and meaning of the embodiments of the invention herein.

Other aspects and features of the present invention will become apparent to those ordinarily skilled in the art upon review of the following description of specific embodiments of the invention in conjunction with the accompanying figures. The invention is herein further described with reference to the following, non-limiting, examples. A description of the experimental procedures employed follows the examples.

Materials and Methods

Figure 3B:
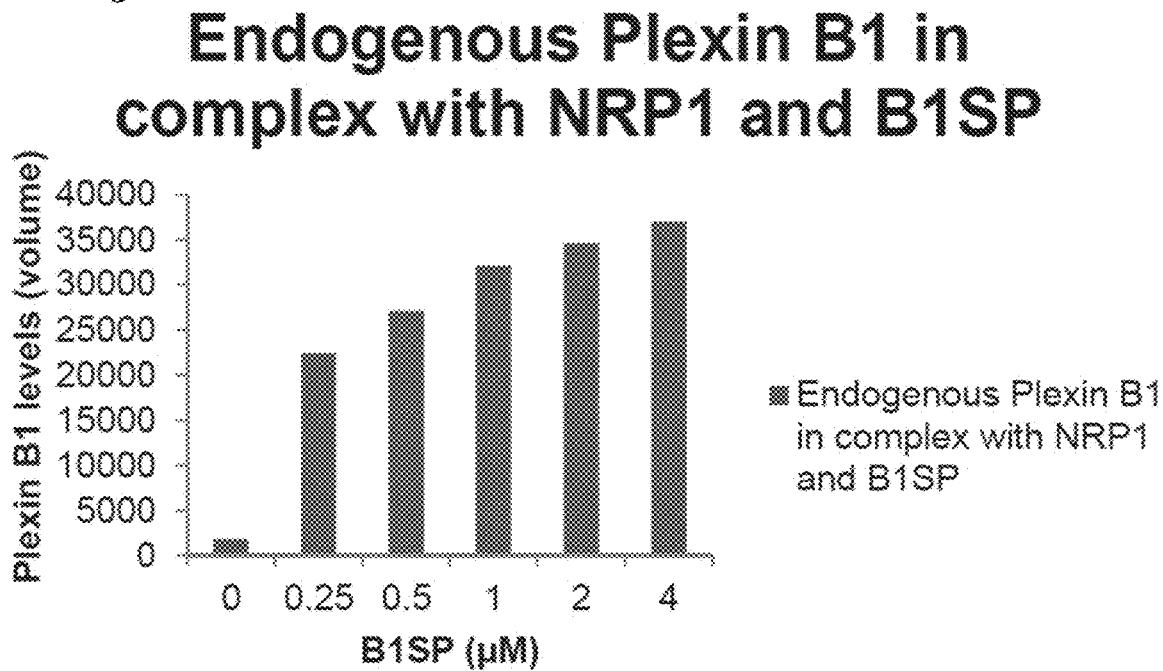
Figure 3C:
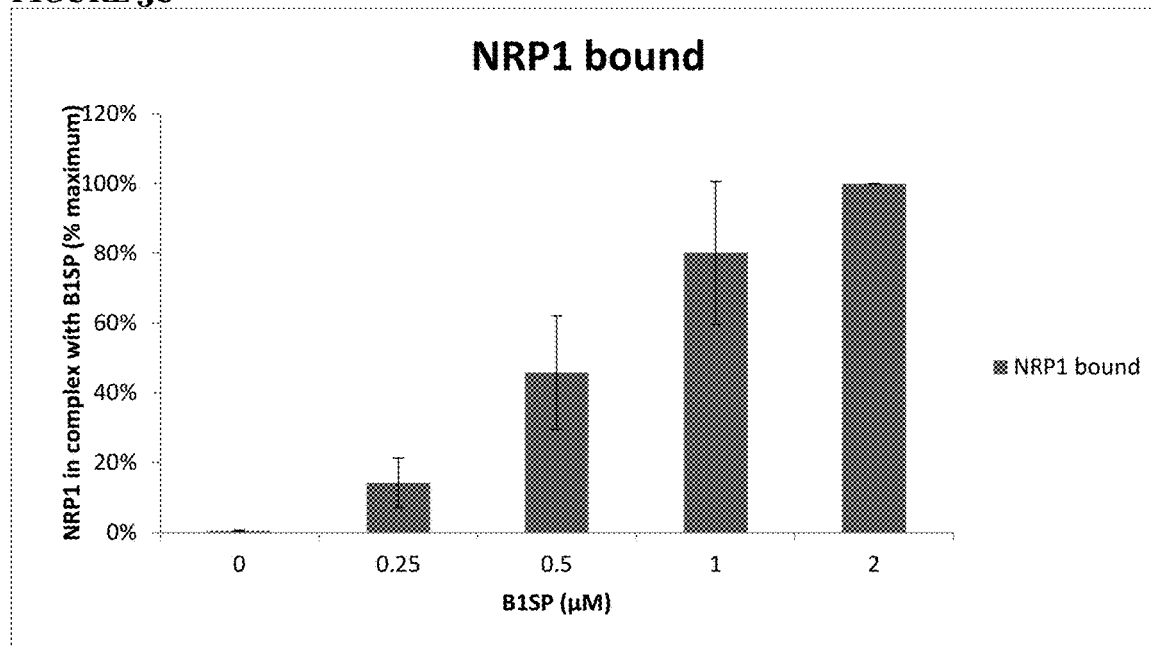
Figure 3D:
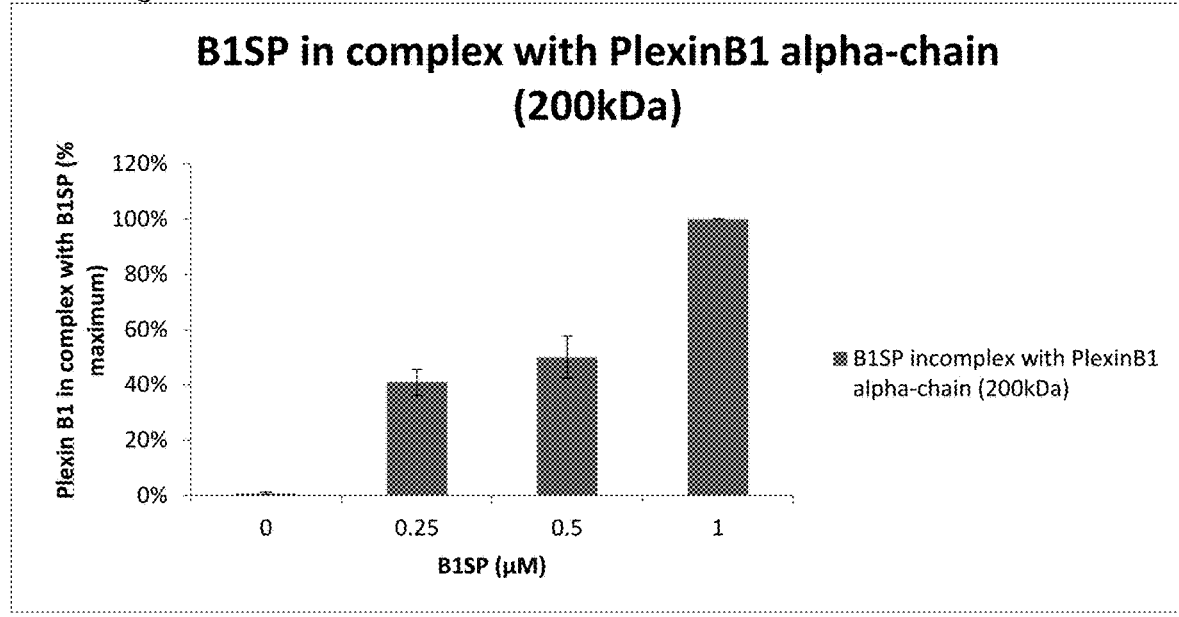

B1SP binds to Plexin B1 and NRP1 in a dose dependent manner. DU145 cells were washed and treated with the indicated dose of B1SP protein for 1 hour. Cells were then washed three times with DPBS and then lysed. B1SP protein in complex with cellular proteins were isolated using protein G agarose. Protein complexes were washed three times prior to the addition of sample buffer. Samples were boiled and analyzed by Western Blot. Shown are representative Dose-Responses to B1SP treatment. Recombinant human IgGFc was used as control. Densitometry analysis of NRP1 and PLEXIN B1 in complex with B1SP fusion protein was performed using Syngene Gene Tools™ version 4.02 (Synoptics Ltd.™, Cambridge, UK). In FIGS. 3C and 3D B1SP binding to Plexin B1 and NRP1 was measured. DU145 cells were washed and treated with the indicated dose of B1SP protein for 1 hour. Cells were then washed three times with DPBS and then lysed. B1SP protein in complex with cellular proteins were isolated using protein G agarose. Protein complexes were washed three times prior to the addition of sample buffer. Samples were boiled and analyzed by Western Blot. Shown are representative Dose-Responses to B1SP treatment. Recombinant human IgGFc was used as control. The relative amount of B1SP in complex with either NRP1 or, Plexin B1 was determined from three independent experiments followed by densitometry analysis of NRP1 and PLEXIN B1 in complex with B1SP fusion protein was performed using Syngene Gene Tools™ version 4.02 (Synoptics Ltd.™, Cambridge, UK).

Figure 3E:
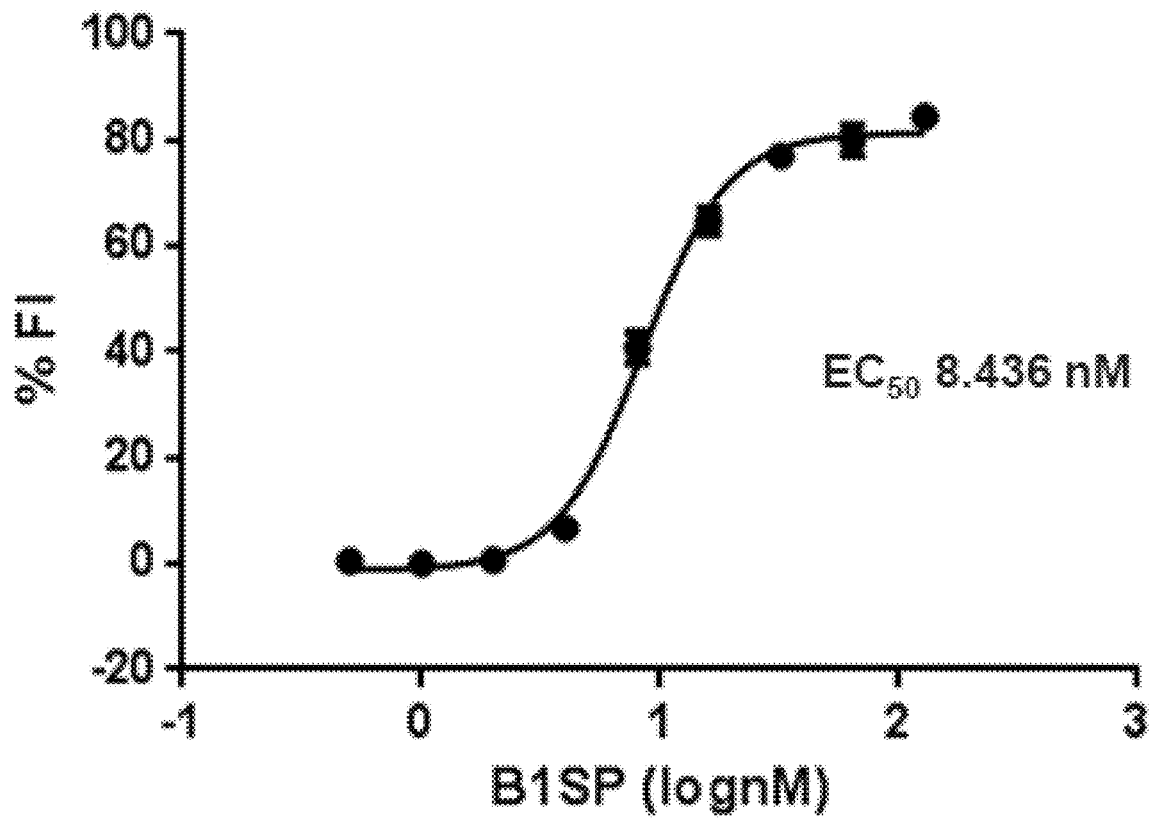
Figure 3F:
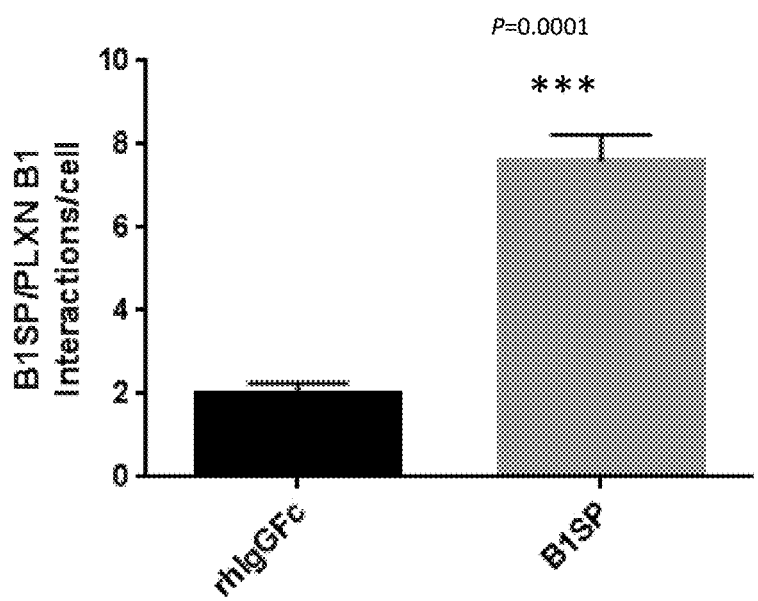
Figure 3G:
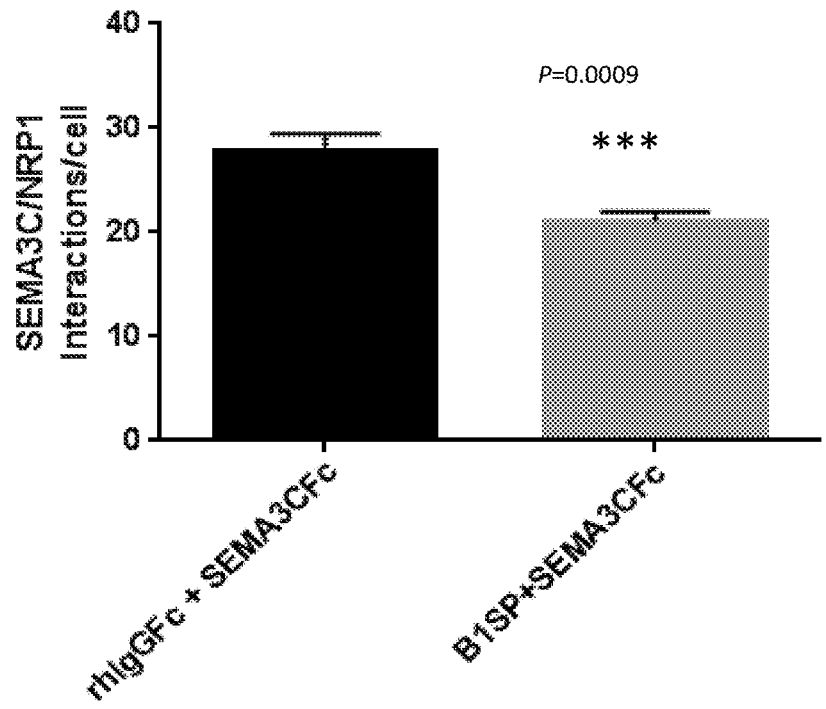
Figure 3H:
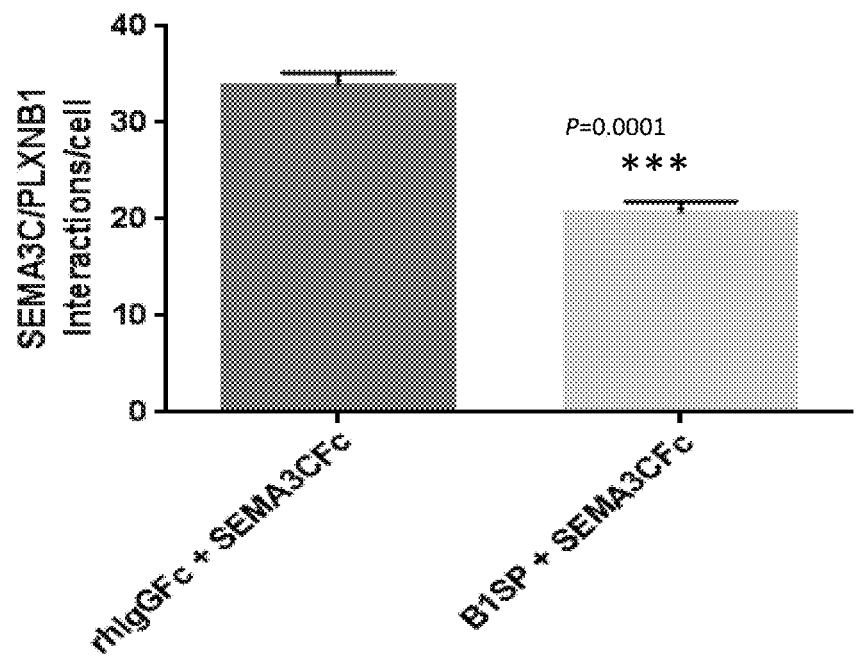

In FIGS. 3F, G and H, B1SP binding to PLEXINB1 was tested in DU145 cells. Photomicrographs of in-situ proximity ligation assay (PLA), showed punctate red fluorescence as an indication of protein interactions between the indicated molecules and were plotted on the Y-axis of the graphs from cells representative from 5-fields of view. PLA analysis was done by seeding 40,000 DU145 cells on 1 cm coverslips. Cells were then treated with either rhIgGFc as control or B1SP in HBHA binding buffer containing 5% BSA on ice for 1 h. The coverslips were then washed three times in HBHA buffer before PLA probe binding, ligation and amplification steps. PLA was carried out under the manufacturers protocol and analyzed using Duolink Image™ tool software. Bars represent Mean and SEM Interactions/cell. The data was statistically significant using the non-parametric Mann-Whitney statistical test as calculated in Graph Pad Prism™ software. Exact p-values are shown and the results are representative of independent repeated experiments. To distinguish between B1SP and endogenous PLEXIN B1, antibodies against the c-terminus of PLEXIN B1 were used. Mouse primary antibodies against hIgG-(Fc)-specific and Rabbit anti-human PLEXIN B1 c-terminal were used for PLA in (F). SEMA3C antibodies N20 (SantaCruz™) (Goat) and NRP1 (Rabbit) were used in (G). Anti-SEMA3C (N20) and PLEXINB1 c-terminal antibodies were used in (H).

Figure 4A:
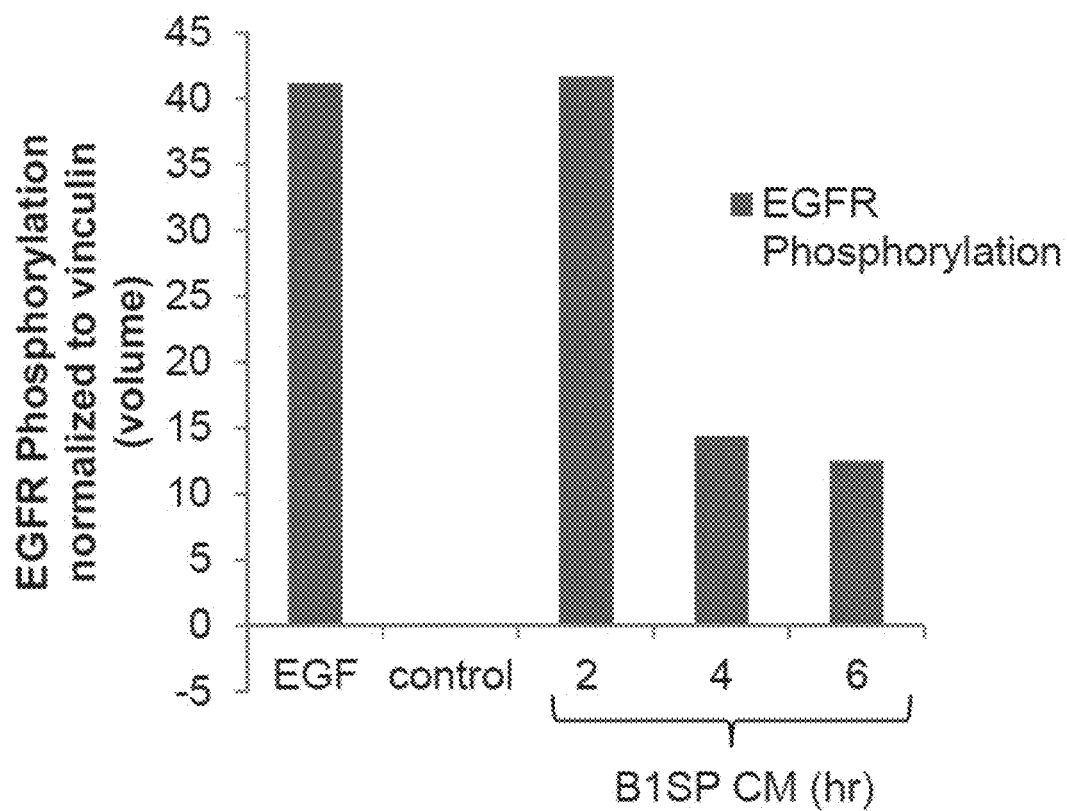
FIGS. 4A-4B shows inhibition of EGFR phosphorylation in LNCaP cells are time (FIG. 4A) and dose (FIG. 4B) dependent, where treated cells were harvested and evaluated for the expression of EGFR phosphorylation (pEGFR) and total EGFR expression as compared with anti-vinculin as loading control and untreated cell controls.
Figure 4B:
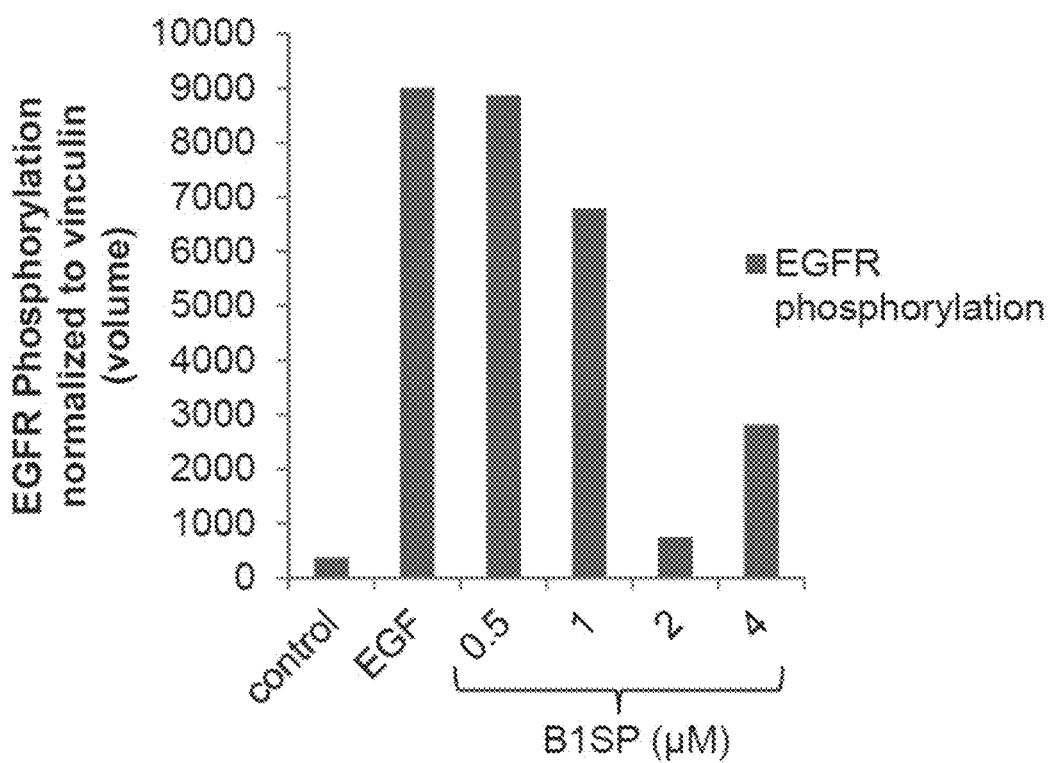

FIGS. 4A and 4B Inhibition of EGFR phosphorylation in LNCaP. Cells were serum starved for 24 hr. B1SP conditioned medium (CM) was added for the indicated time points followed by stimulation with EGF (5.0 ng/ml) for to min. Cells were harvested and evaluated for the expression of EGFR phosphorylation (pEGFR) and total EGFR expression. The Blot was reprobed with anti-vinculin as loading control. Untreated cells were either stimulated similarly or directly lysed at the 6 hour time point as a control for comparison of EGFR phosphorylation at the end of the time course and to control for any effect incubation time may have on the capacity to stimulate EGFR phosphorylation in LNCaP. Densitometric analysis of EGFR phosphorylation levels relative to vinculin expression levels in LNCaP treated with B1SP CM over a six hour time-course. B1SP inhibits EGFR phosphorylation in a time-dependent manner. LNCaP cells were serum starved for 24 hr. Cells were then treated with B1SP as indicated for 60 minutes followed by stimulation with EGF for to min. The blot shows EGF phosphorylation. The blot was then reprobed with vinculin as loading control. Densitometric analysis of EGF phosphorylation levels.

LNCaP cells were seeded at 4×105 cells/well in 6-well plates in RPMI medium containing 10% FBS. The next day, the medium was replaced with RPMI minus phenol-red and serum starved for 24 h. The medium was changed again just prior to stimulation to remove endogenous secreted SEMA3C. For EGF stimulations, cells were first treated with B1SP at the indicated concentration for the indicated time point (A) or, for 60 min (C) followed by stimulation with EGF for to min. Cells were washed once with PBS. Cells were immediately lysed with 250 µL lysis buffer (50 mM Tris pH7.5, 150 mM NaCl, 1% NP-40, 10 mM NaF, 10% Glycerol) containing Complete and PhosStop phosphatase protease inhibitors (Roche™, Mississauga, ON). Whole cell lysates were centrifuged at 14,000 rpm for 20 min at 40 C. The protein concentration in cleared whole cell lysates was determined using the BCA kit (Thermo Scientific™, Rockville, Ill.). Protein lysates (50 µg) were analysed by SDS-PAGE (8%) and transferred by Western Blot to nitrocellulose membranes (Bio-Rad™, Hercules, Calif.). Membranes were blocked in PBS containing 5% BSA for probing with phospho-antibodies or 5% non-fat milk for total and loading control antibodies as directed by the manufacturers. Membranes were washed 3×5 min with TBST followed by incubation with the appropriate HRP or IRdye-conjugated-secondary antibodies for 1 h. Blots were washed again 3× for 5 min with TBST. Detection was by ECL or by image analysis using a LICOR infrared imager and Image Studio Lite version 3.1, software. Densitometry analysis of EGFR phosphorylation was performed using Syngene Gene Tools™ version 4.02 (Synoptics™ Ltd., Cambridge, UK).

Figure 5A:
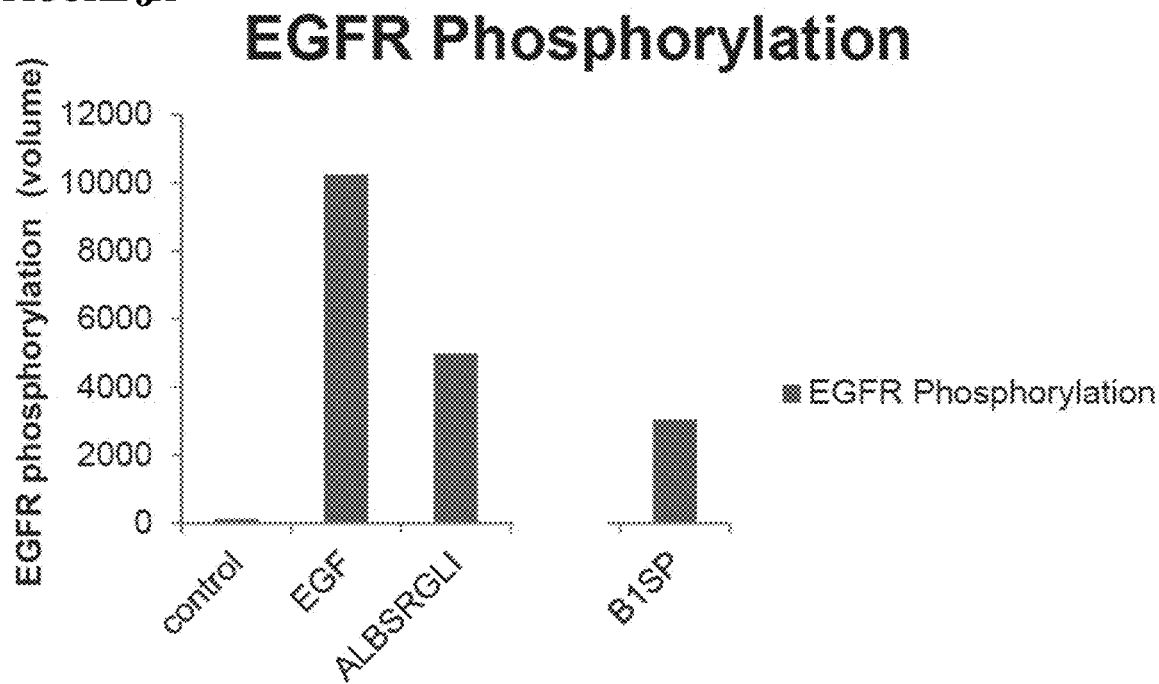
FIGS. 5A-5C FIG. 5A shows inhibition of EGFR phosphorylation in LNCaP cells, where the cells were treated with either truncated Semaphorin Fusion proteins (2.0 µM) (ALB SRGLI) or a Plexin B1 Fusion protein (B1SP) (2.0 µM) for 60 minutes followed by stimulation with EGF (10 ng/ml) for 10 min, before the cells were harvested and evaluated for the expression of EGFR phosphorylation (pEGFR), and EGFR levels with a vinculin loading control.
Figure 5B:
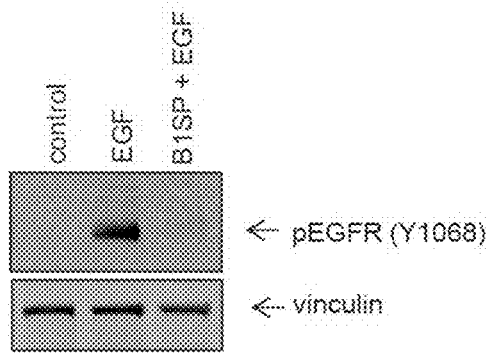
Figure 5C:
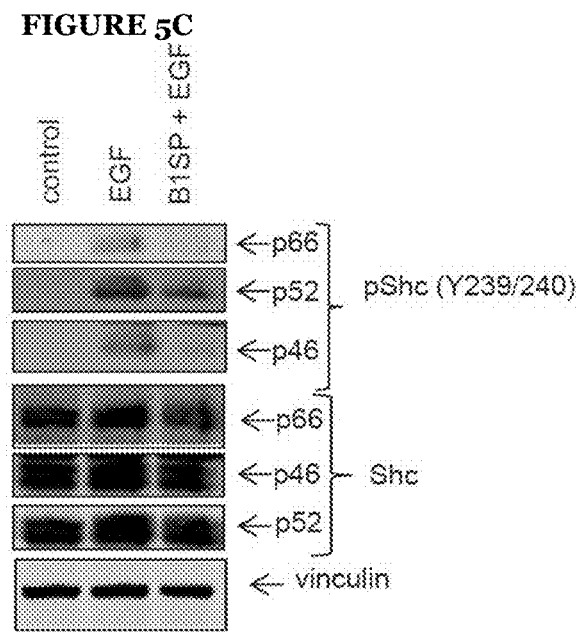

FIG. 5A-C (A) Inhibition of EGFR phosphorylation in LNCaP. LNCaP cells were serum starved, media was then changed and the cells were treated with either truncated Semaphorin Fusion proteins (2.0 µM) (ALB SRGLI) and Plexin B1 Fusion protein (B1SP) (2.0 µM) for 60 minutes. Cells were then stimulated with EGF (10 ng/ml) for to min. Cells were harvested and evaluated for the expression of EGFR phosphorylation (pEGFR), and EGFR levels. Blots were reprobed for Vinculin as loading control. Densitometry analysis EGFR phosphorylation levels was performed using Syngene Gene Tools version 4.02 (Synoptics Ltd.™, Cambridge, UK).

As shown, the inhibitory effect of B1SP on EGFR phosphorylation was stronger than other inhibitor proteins including ALB SRGLI. (B) B1SP inhibits phosphorylation of SHC isoforms downstream of the EGFR. LNCaP cells were treated with B1SP (2.0 µM) for 60 min. The cells were then stimulated with EGF (10 ng/ml) for 10 min, washed once with PBS and lysed with NP40 lysis buffer supplemented with protease inhibitors. Whole Cell protein Lystes (30 µg) were separated by SDS PAGE and immunoblotted with anti-phospho-SHC antibodies (2434, Cell Signaling Technology™, Inc. Beverly, Mass.) and ECL detection. Total SHC levels were determined by re-probing the blot with Anti-SHC antibodies (clone 30/SHC, BD Transduction Laboratories™, Lexington, Ky.) and detection using anti-mouse, IR 680 (Rockland™, Gilbertsville, Pa.) and image analysis using LICOR infrared imaging system and Image StudioLite™ version 3.1 software.

Figure 6A:
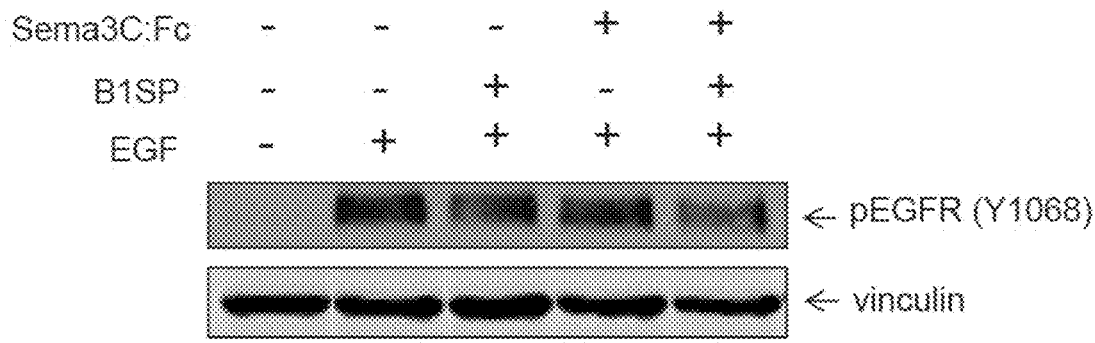
FIGS. 6A-6C FIG. 6A shows a blot where LNCaP cells when serum starved for 24 hr and then treated simultaneously with a B1SP and Semaphorin 3C:Fc for 60 minutes or a B1SP alone, or Sema3C:Fc alone or where left untreated, followed by stimulation with EGF (10 ng/ml) for 10 min, with resulting levels of EGFR phosphorylation as compared to vinculin as loading control.
Figure 6B:
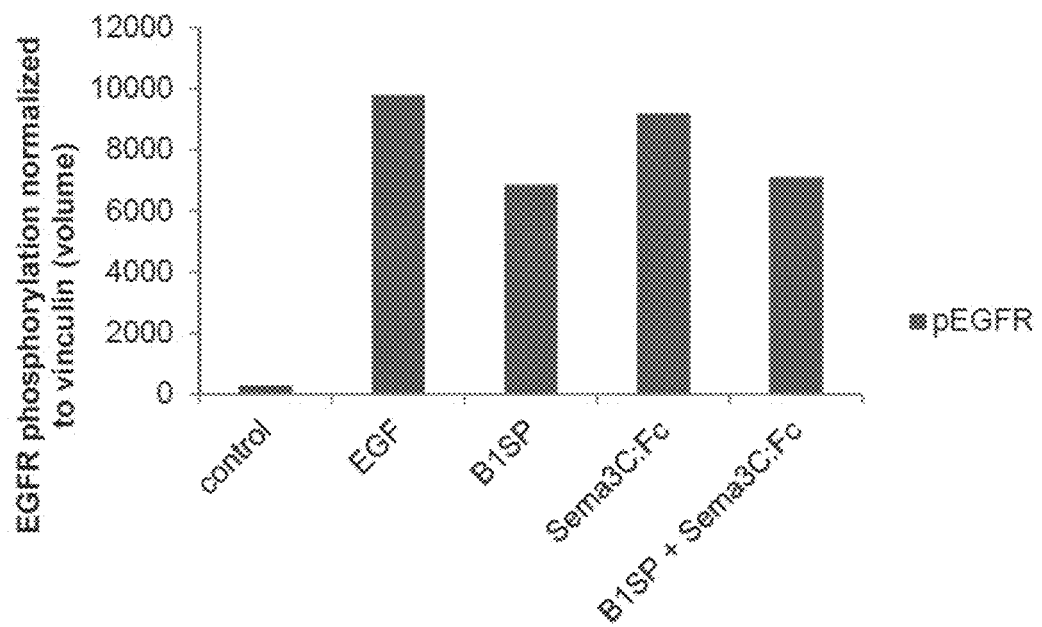
Figure 6C:
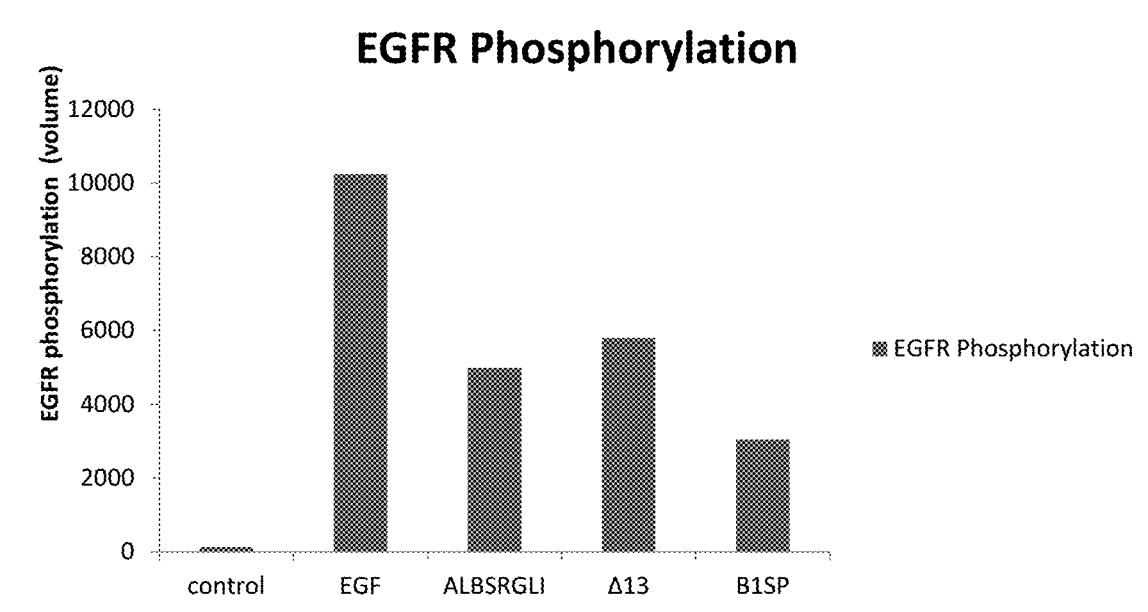

FIGS. 6A and 6B (A) LNCaP cells were serum starved for 24 hr. Cells were treated simultaneously with B1SP and Semaphorin 3C:Fc for 60 minutes, B1SP alone, Sema3C:Fc alone or, left untreated. Cells were then stimulated with EGF (10 ng/ml) for to min. The data shows the resulting levels of EGFR phosphorylation. The blot was re-probed with vinculin as loading control. (B) Quantitative densitometric analysis of the above blot. The data demonstrates that B1SP can inhibit Sema3C-mediated EGFR phosphorylation. Densitometry analysis EGFR phosphorylation levels was performed using Syngene Gene Tools version 4.02 (Synoptics Ltd.™, Cambridge, UK). In FIG. 6C, LNCaP cells were serum starved for 24 hr. Cells were treated simultaneously with B1SP and Semaphorin 3C:Fc for 60 minutes, B1SP alone, Sema3C:Fc alone or, left untreated. Cells were then stimulated with EGF (10 ng/ml) for to min. The resulting levels of EGFR phosphorylation were measured by quantitative densitometric analysis and the blot was re-probed with vinculin as loading control. Densitometry analysis EGFR phosphorylation levels was performed using Syngene Gene Tools™ version 4.02 (Synoptics Ltd.™, Cambridge, UK).

Figure 7A:
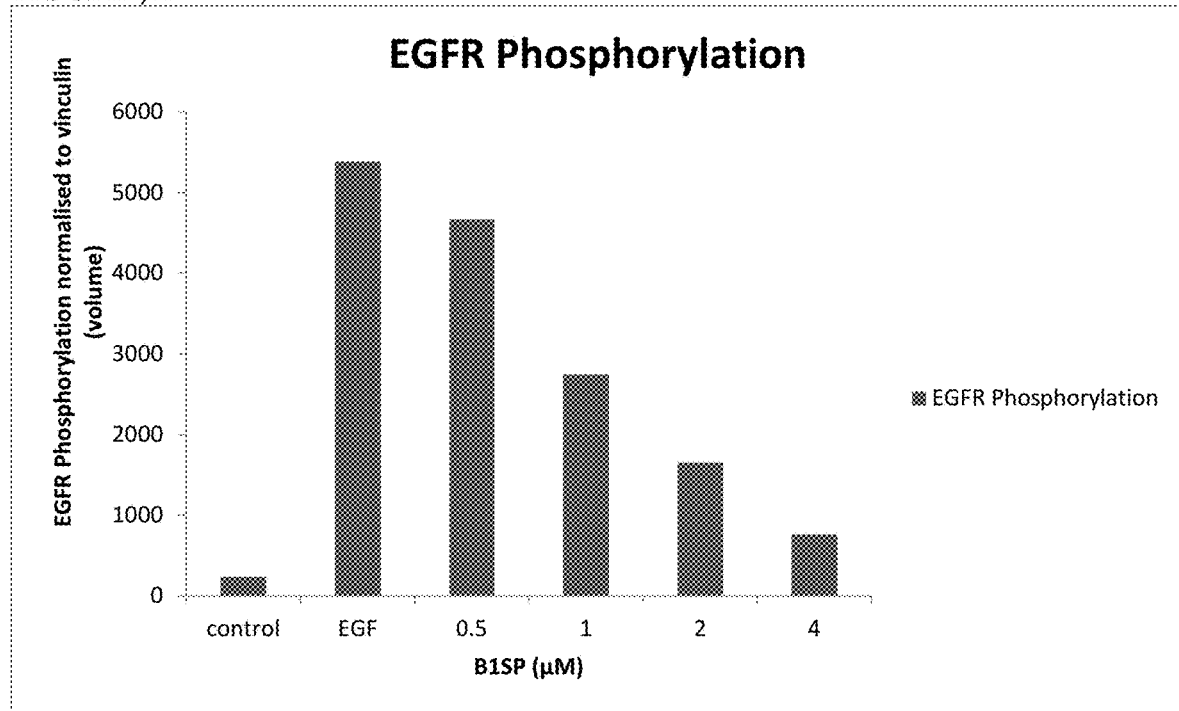
FIGS. 7A-7F shows inhibition of EGFR phosphorylation in LNCaP and 22RV1 PC cells, wherein EGF-mediated EGFR phosphorylation of LNCaP cells treated with increasing concentration B1SP are shown in FIG. 7A, where the LNCaP cells were serum starved for 24 hours, then treated with the indicated dose (0.5-4.0 µM) of B1SP for one hour followed by stimulation with EGF (10 ng/ml) and the levels of pEGFR, pHER2/ErbB2, pSHC and pMAPK were demonstrated by immunoblotting.
Figure 7B:
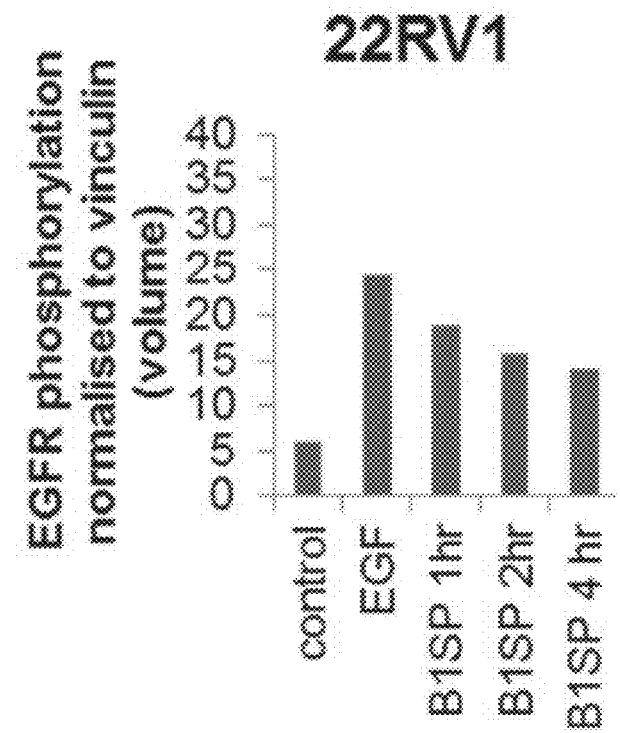
Figure 7C:
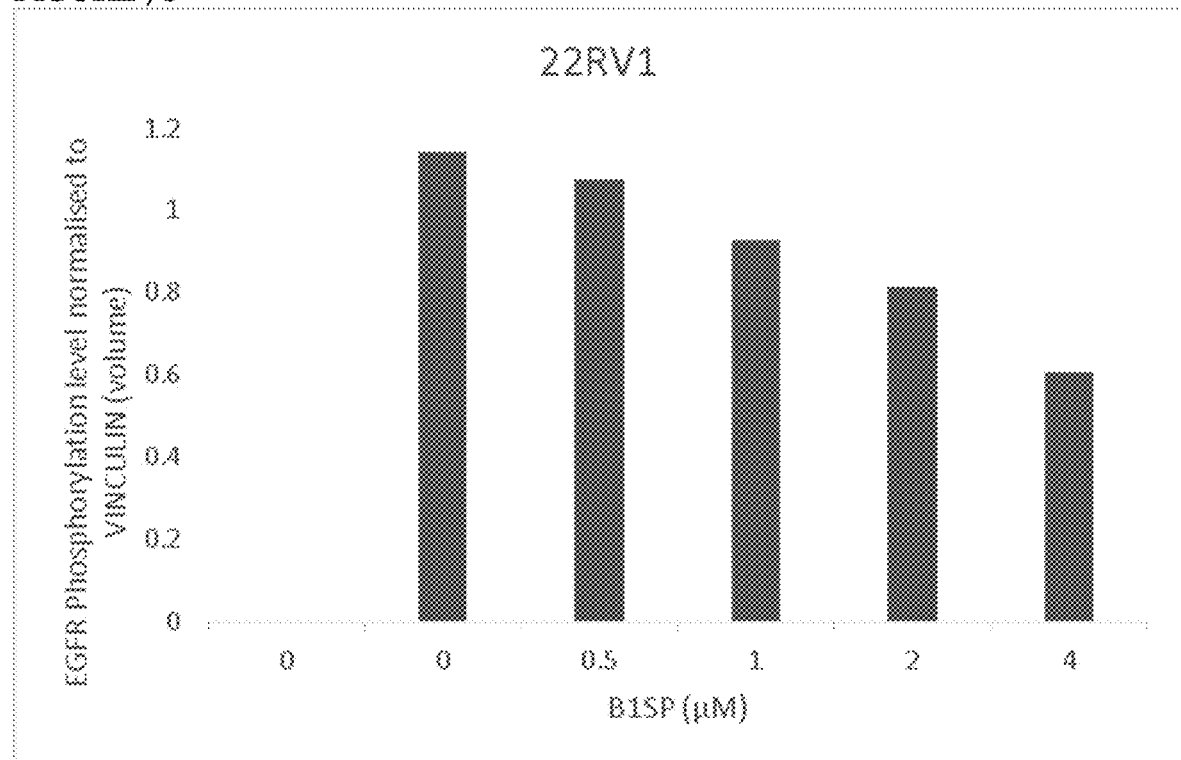
Figure 7D:
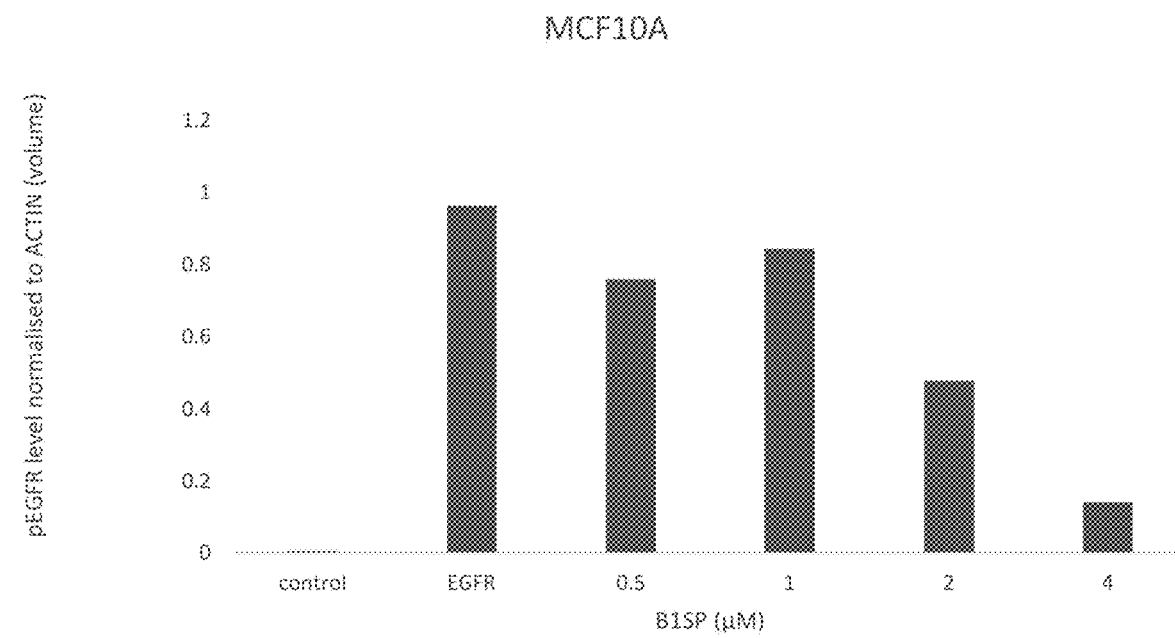
Figure 7E:
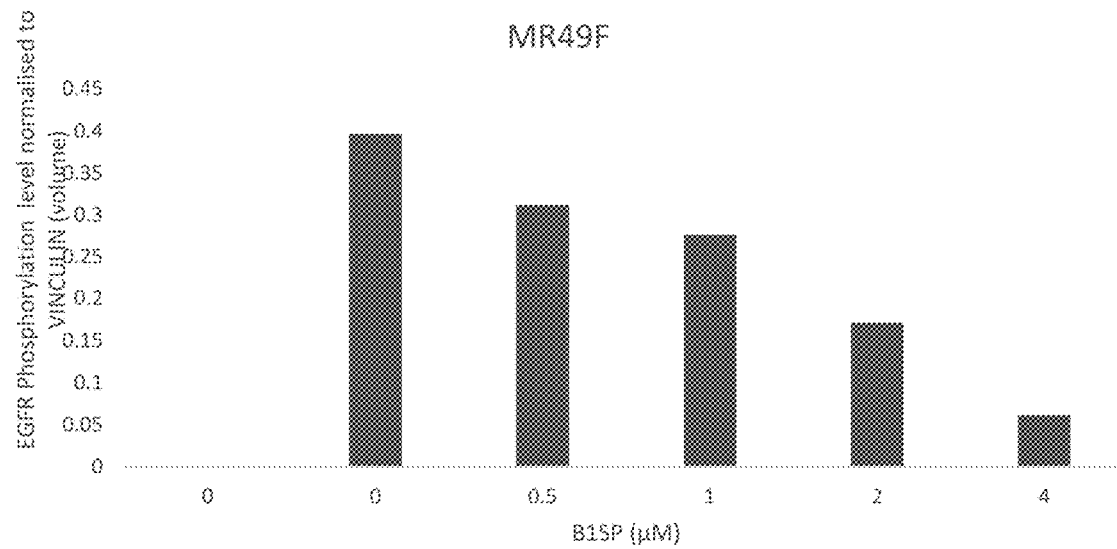
Figure 7F:
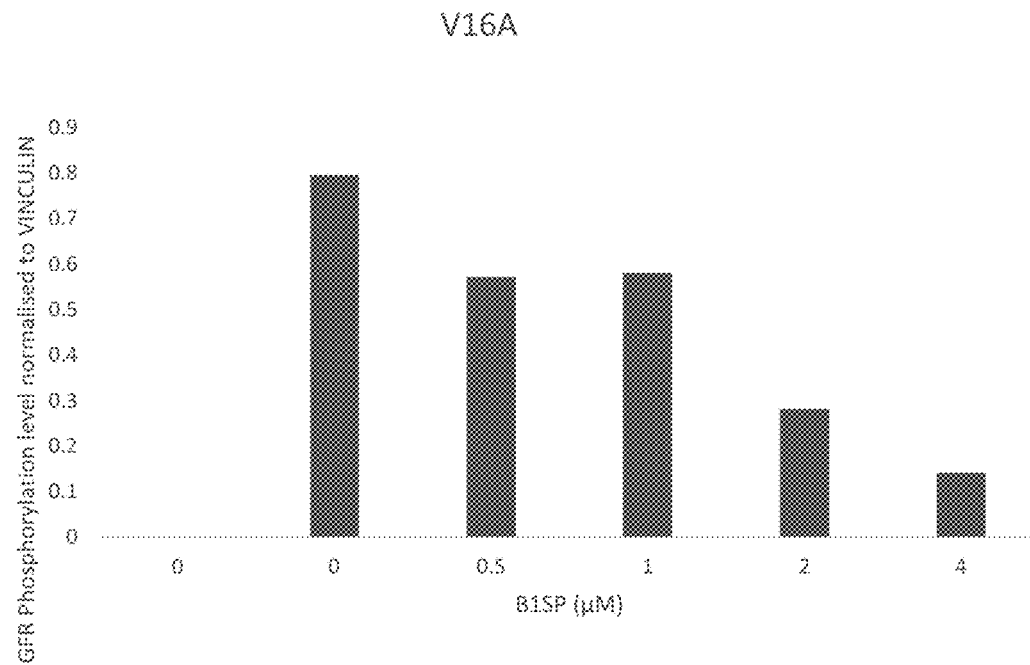

FIGS. 7A and 7B Inhibition of EGFR phosphorylation in LNCaP and 22RV1 PC cells, respectively. Cells were serum starved B1SP CM (1.0 ml) was added to the cells at the indicated concentrations (A) and at the indicated time-points (B) followed by stimulation with 10.0 ng/ml and 5.0 ng/ml EGF for to minutes, respectively. Cells were harvested, lysed and evaluated for the expression of pEGFR, and EGFR. Blots were re-probed for Vinculin as loading control. Control EGFR phosphorylation was evaluated in untreated cells at the termination of the time course. Densitometric analysis of a dose dependent and time dependent decrease of EGFR phosphorylation in response to B1SP CM treatment of LNCaP and 22Rv1 cells, respectively. Similarly, the inhibition of EGFR phosphorylation was tested in 22RV1 PC cells (C), MCF10A normal human mammary cells (D), MR49F PC cells (E) and V16A castration-resistant prostate cancer (CRPC) stem cells (F), with increasing concentrations of B1SP (i.e. 0.5, 1, 2 and 4.0 µM).

FIG. 8A-8D B1SP inhibits PC cell proliferation in LNCaP in a dose Dependent manner with an IC50 (1.145 µM). Cell viability was measured using fluorescent-based Presto-Blue™ staining. LNCaP ($3\times10^4$/ml) were plated in the presence or absence of B1SP (0-2.0 µM) in 96-well flat bottom tissue culture plates. Proliferation was assessed for 4 days later in response to B1SP treatment in the presence of R1881 (nM), wherein the R1881 vehicle (ethanol) was used as control. Cell growth was assayed using the using the Presto Blue™ proliferation viability reagent as directed by the manufacturer, (Life Technologies™ Corporation, Carlsbad, Calif.).

Figure 9A:
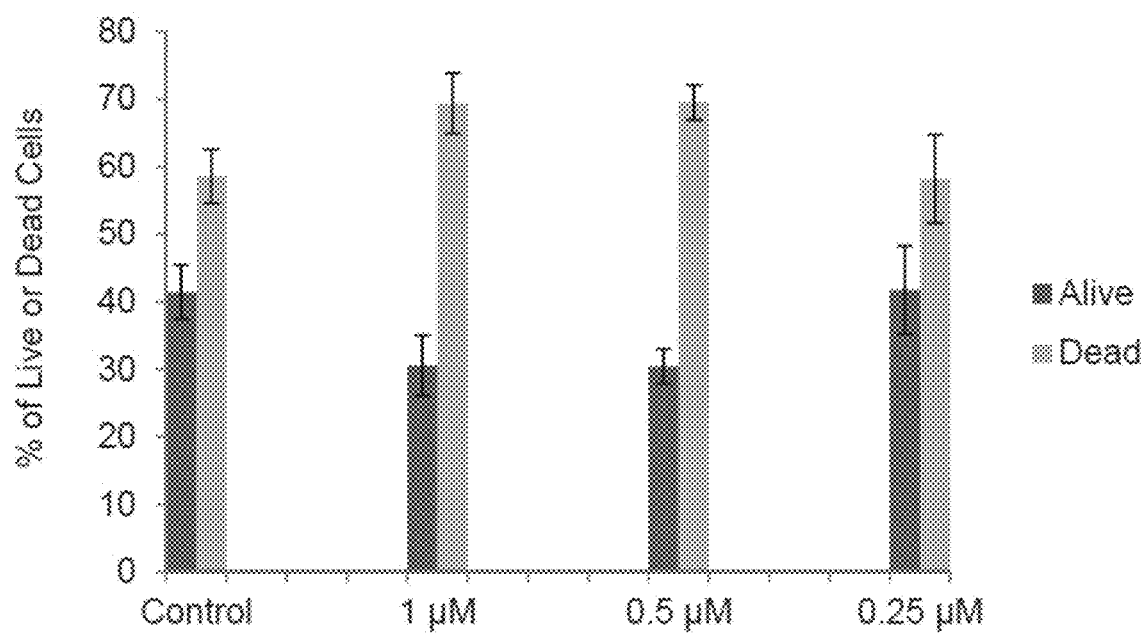
FIGS. 9A-9B shows two plots (two independent experiments) of LNCaP cells that were treated for 48 hours with a purified B1SP fusion protein before cell viability was analyzed using a fluorescence-based live/dead cell viability assay (Calcein/Propidium Iodide).
Figure 9B:
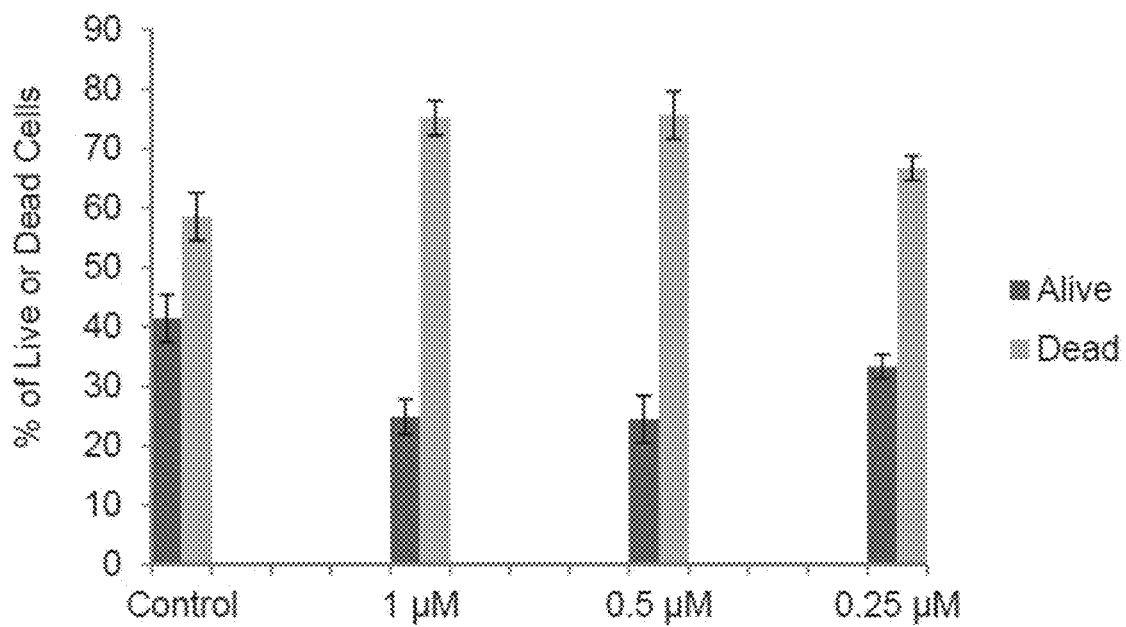

FIGS. 9A and 9B Purified and CM B1SP molecular weight confirmation Coomassie staining of purified B1SP protein under reducing (R) and non-reducing (NR) conditions. LNCaP cells were treated for 48 hours with purified B1SP protein. Cell viability was then analyzed using a fluorescence-based live/dead cell viability assay (Calcein/Propidium Iodide). Two independent experiments are shown. Transparent Corning 96-well multiwell Plates were coated with Fibronectin from human plasma (R&D 1918FN, Sigma F2006, 5.0 µg/cm$^2$) coat the culture surface with a minimal volume (50-75 µl), 1 h at 37 C. Allow to air dry for at least 45 minutes at room temperature. LNCaP cells were grown in media supplemented with 10% FBS and for assay were washed 3 times with serum free media and then serum starved for 8 h. Cells were detached with 10 mM EDTA in the media. Cells were washed to remove EDTA and resuspended in Dulbecco's PBS with calcium and magnesium (GIBCO™, Life Technologies™, Gaithersburg, Md., Catalog #14040-117) with 0.1% BSA at a concentration of $2.5\times10^6$ cells/mL. Calcein AM (Molecular Probes™, Catalog #C3099), (12.5 µM) was added and the cells were incubated at room temperature for 30 minutes in the dark. Cells were then washed twice in PBS with calcium and magnesium and then resuspended in PBS with calcium and magnesium at a concentration of ($1\times10^6$ cells/ml). 100 µL of the cell suspension was added to each well in triplicate. The plates were centrifuged at 411×g for 2 minutes to move the cells to the plate surface. Plates were then incubated for 30 minutes at 37° C. and then initially measured for "before wash" fluorescence of the samples using a fluorescence plate reader at excitation wavelength 485 nm and emission wavelength 520 nm. Forty-eight hours later, plates were washed to remove non-adherent cells using the following procedure: plates were inverted and the contents of the wells was tapped out. 200 µL/well of 1×PBS was added, the plate was then rotated horizontally 180°, inverted and tapped out again and repeated a second time. 100 µL/well of 1×PBS was added to all wells. Plates were read plate "after wash" on the fluorescence plate reader. Bars represent the average percent live cells of the initial cells plated using the following formula: [(RFU after wash)/(RFU before wash)]×100.

Figure 10A:
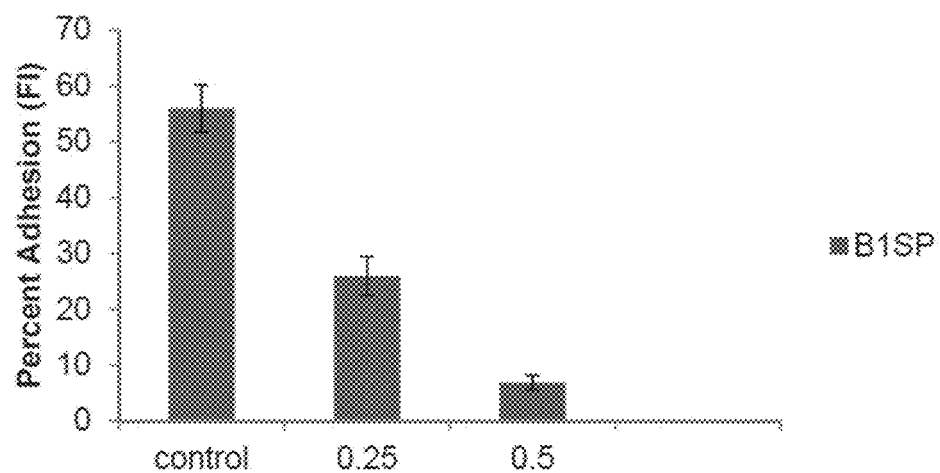
FIGS. 10A-10B shows a B1SP fusion protein treatment inhibiting adhesion of prostate cancer cells in two types of prostate cancer cells (i.e. (A) LNCaP or (B) DU145 cells), where the cells were pulsed with calcein AM (12.5 µM) and incubated for 30 min, then the cells ($1 \times 10^5$) were seeded on precoated, fibronectin (50 µg/ml) in 96-well plates and centrifuged briefly prior to incubation in the presence or absence of a B1SP fusion protein for 16-24 hr. before cell fluorescence was measured (both before and after removal of non-adhered cells by washing). The data represents the average (%) Adhesion of triplicate wells.
Figure 10B:
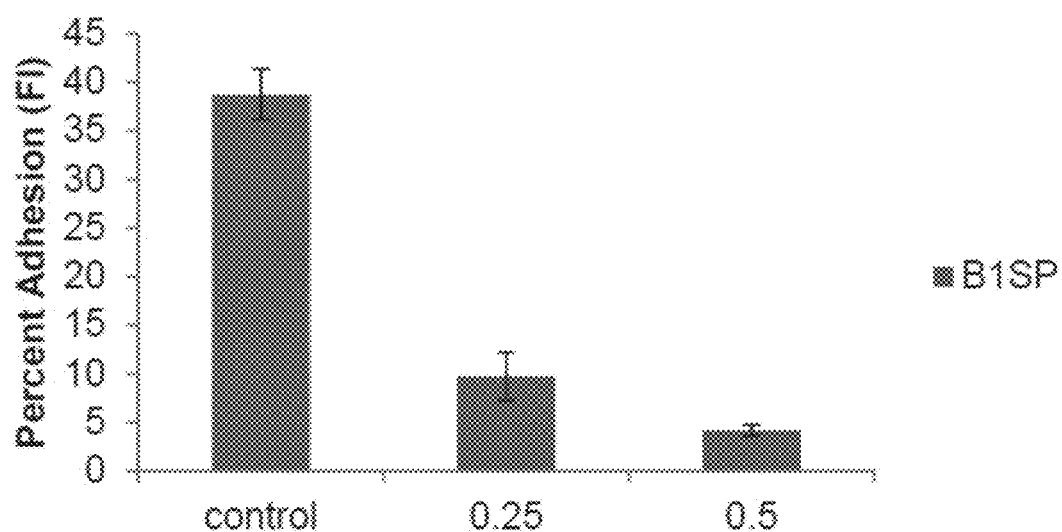

FIGS. 10A and 10B B1SP treatment inhibits adhesion of Prostate cancer cells. LNCaP or DU145 cells were pulsed with calcein AM (12.5 µM) and incubated for 30 min. Cells ($1\times10^5$) were seeded on precoated, fibronectin (509 g/ml) 96-well plates and centrifuged briefly prior to incubation in the presence or absence of B1SP for 16-24 hr. Cell Fluorescence was measured before and after removal of non-adhered cells by washing. Data represents the average (%) Adhesion of triplicate wells. Transparent Corning 96-well multiwell Plates were coated with Fibronectin from human plasma (R&D 1918FN, Sigma F2006, 5.0 μg/cm$^2$) coat the culture surface with a minimal volume (50-75 μl), 1 h at 37 C. Allow to air dry for at least 45 minutes at room temperature. LNCaP and DU145 cells were grown in media supplemented with 10% FBS and for assay were washed 3 times with serum free media and then serum starved for 8 h. Cells were detached with 10 mM EDTA in the media. Cells were washed to remove EDTA and resuspended in Dulbecco's PBS with calcium and magnesium (GIBCO™, Life Technologies™, Gaithersburg, Md., Catalog #14040-117) with 0.1% BSA at a concentration of 2.5×10$^6$ cells/mL. Calcein AM (Molecular Probes™, Catalog #C3099), (12.5 μM) was added and the cells were incubated at room temperature for 30 minutes in the dark. Cells were then washed twice in PBS with calcium and magnesium and then resuspended in PBS with calcium and magnesium at a concentration of (1×10$^6$ cells/ml). 100 μL of the cell suspension was added to each well in triplicate. The plates were centrifuged at 411×g for 2 minutes to move the cells to the plate surface. Plates were then incubated for 30 minutes at 37° C. and then initially measured for "before wash" fluorescence of the samples using a fluorescence plate reader at excitation wavelength 485 nm and emission wavelength 520 nm. Forty-eight hours later, plates were washed to remove non-adherent cells using the following procedure: plates were inverted and the contents of the wells was tapped out. 200 μL/well of 1×PBS was added, the plate was then rotated horizontally 180°, inverted and tapped out again and repeated a second time. 100 μL/well of 1×PBS was added to all wells. Plates were read plate "after wash" on the fluorescence plate reader. Bars represent the average and SD percent adhesion of initial cells plated using the following formula: [(RFU after wash)/(RFU before wash)]×100.

FIG. 3E Determination of B1SP EC50 (8.436 nM). PE-labelled B1SP (B1SP-PE) was serially diluted and added to DU145 cells in triplicate wells for 1 hour. Cells were washed with DPBS before measurement of PE-Fluorescence intensity (FI). DU145 cells (2×105/ml) were plated in 12-well plates. Twenty-four hours later the cells were incubated with serial diluted B1SP-PE in DPBS/20 mM HEPES in a volume of 1.0 ml. Cells were incubated at 370 C and 5% $CO_2$ for 60 min. Cells were then washed three times with DPBS/HEPES and then gently scraped and transferred to Flow Cytometry tubes. The cells were centrifuged at 1300 rpm for 5 minutes and finally resuspended in 0.5 ml PBS containing 2% FBS. As control, the cells were treated in parallel with rhIgGFc (100 nM) and then stained with secondary antibody, anti-IgGFc-specific conjugated to PE. The level of staining of control cells at 100 nM rhIgGFc was 6.01% whereas the level of B1SP-PE staining at 100 nM was 89.7%. The relative binding of B1SP-PE was determined by Flow Cytometry on a Bectin Dickenson FACSCantoII Flow Cytometer (BD Biosciences™, Mississauga, On).

Assessment of In Vivo Tumor Growth for Castration-Resistant C4-2 (CRPC) Xenografts.

For C4-2 castration-resistant (CRPC) xenograft model, C4-2 cells (1×10$^6$) were inoculated subcutaneously in bilateral flank regions of 6-8 week-old male athymic nude mice (Harlan Sprague Dawley, Inc.™, Indianapolis, Ind.) via a 27-gauge needle under methoxyfluorane anesthesia. Body weight, tumor volume and serum PSA levels were measured once a week. Blood samples were obtained from tail vein incisions and serum PSA was determined by the Roche Diagnostics Cobas411™ immunoassay system which is an automated, random access multichannel analyzer for immunological analysis using enhanced chemiluminescent technology (ECL™). When mice bearing C-42 tumors reached a tumor volume over 200 mm$^3$ or serum PSA reached levels greater than, 75 ng/ml, castration was performed via the scrotum under isoflurane anesthesia. Treatment commenced three times per week when PSA recovered to pre-castration levels. Tumor volume was monitored by caliper measurement and calculated by the formula length×width×depth×0.5236. Eighteen mice were randomized into 2 groups for treatment with 10 mg/Kg B1SP or PBS control. Serum PSA levels were measured once a week. Blood samples were obtained from tail vein incisions and serum PSA measured by the Roche Diagnostics Cobas411™ immunoassay system which is an automated, random access multichannel analyzer for immunological analysis using enhanced chemiluminescent technology (ECL™). When mice bearing LNCaP tumors reached a tumor volume over 200 mm$^3$ or serum PSA levels reached greater than 75 ng/ml, castration was performed via the scrotum under isoflurane anesthesia. Treatment commenced when PSA recovered to pre-castration levels.

Plexin B1 siRNA

Plexin B1 siRNA1 was validated (Hs_PLXNB1_6, Qiagen™, Montreal,PQ) and Plexin B1 siRNA2 was previously validated by (Swiercz et al., 2008) and was synthesized (ThermoScientific™, Rockford, Ill.). LNCaP cells were transfected with either scramble siRNA (AUCAAACU-GUUGUCAGCGCUGUU) (SEQ ID NO: 7), PlexinB1siRNA1 (CCGGGUGGAAUUUAUCC-UUGAUU) (SEQ ID NO: 8), or, Plexin B1siRNA2 (AC-CACGGUCACCCGGAUUCUU) (SEQ ID NO: 9), (10 nM) using HiPerFect™ reagent (Qiagen™, Montreal PQ) as described by the manufactuer. Transfected cells were incubated for 72 hours and then incubated in the presence or absence of SEMA3C:Fc (100 nM) for 10 minutes. Cells were washed and then lysed. Plexin B1 levels were analyzed from lysates (30 μg) by polyacrylamide gel electrophoresis (PAGE). Western Blots were probed with anti-Plexin B1 and anti-phospho-Shc.

Blots were re-probed with anti-vinculin and anti-Shc as loading control. DU145 cells were transfected with scramble siRNA, Plexin B1siRNA1 or PlexinB1 siRNA2 (10 nM) using RNAiMax™ reagent as directed by the manufacturer, (Invitrogen™, Mississauga, Ontario). Following 72 hours incubation the cells were replated at 20,000 cells/well in a 96-well flat bottom plate and let adhere for 4 hours. The remaining cells were lysed and assayed for PlexinB1 expression by Western Blot. The blot was reprobed with vinculin as loading control. Medium was replaced with DMEM without serum for 16 hours prior to the binding assay. Cells were then washed once with HBHA [20 mM HEPES, 150 mM NaCl, 5 mM $CaCl2$, 1 mM $MgCl2$], buffer containing, 0.5% BSA. The Opti-MEM1-conditioned medium from 293T cells expressing either the APTag vector alone or, the AP-SEMA 3C construct was assayed in a PNPP assay to find the linear and equivalent range of AP-enzymatic activity. The AP-SEMA3C was applied by diluting an equal volume of AP-SEMA3C CM to an equal volume of HBHA buffer that gave an enzymatic activity of 0.877. The APTag was first diluted 1:4 in Opti-MEM and then an equal volume of the 1:4 diluted—APTag CM was diluted to an equal volume of HBHA. The enzymatic activity of AP-Tag CM was 1.069.

The binding assay was performed as previously described by FLANAGAN, J G. and LEDER, P. (1990), endogenous phosphatase heat inactivation was done in HBHA at 65° C. following the fixation step. Plate readings at 562 nm were taken initially and then every 24 hours. The data was done in quadruplet. The binding of the APTag vector CM was subtracted from the binding to APSEMA3C in each case.

Apoptosis Assay

Figure 13:
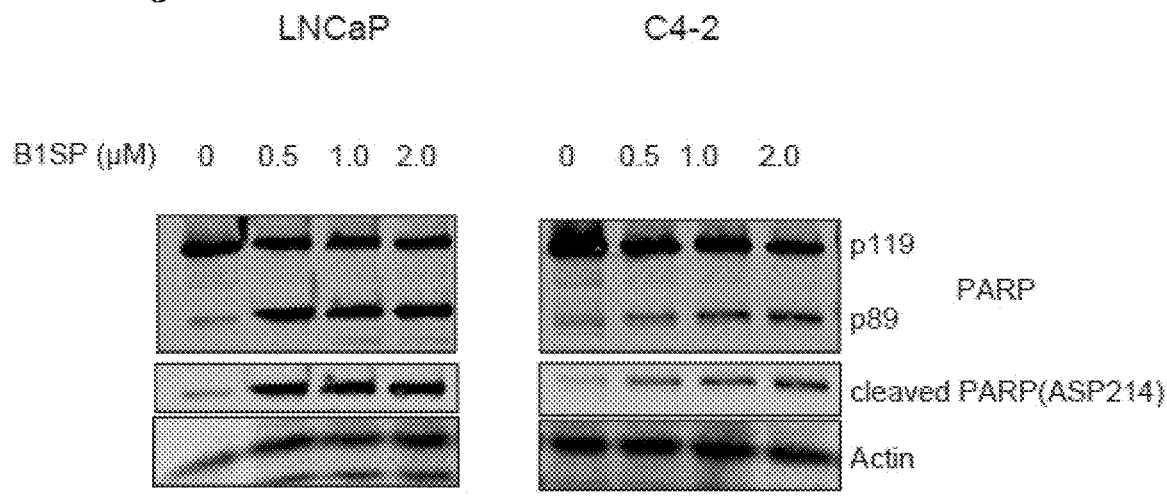
FIG. 13 shows immunoblots of LNCaP and C4-2 prostate cancer cells treated with B1SP stained with Total PARP and Cleaved PARP, which shows that these cells undergo apoptosis.

In FIG. 13, LNCaP and C4-2 cells (2.5×104) were plated in 6-well plates for twenty-four hrs when the medium was replaced with RPMI in the absence of Phenol red or serum. B1SP at the indicated concentrations was added and the cells were incubated at 37° C. and 5% CO2 for 4 days. The cells were harvested from medium and adherent cells by gentle scraping. The cells were then centrifuged at 1300 rpm, washed once in PBS and lysed with 200 µl NP40 lysis buffer containing protease inhibitors. Samples (30 µg) were separated by SDS PAGE. The gel was immunoblotted with Total PARP and Cleaved PARP (9542, 9541, Cell Signaling Technologies Inc.™, Beverly, Mass.). The blot was re-probed with anti-Actin to demonstrate equal loading of protein lysates.

Figure 14:
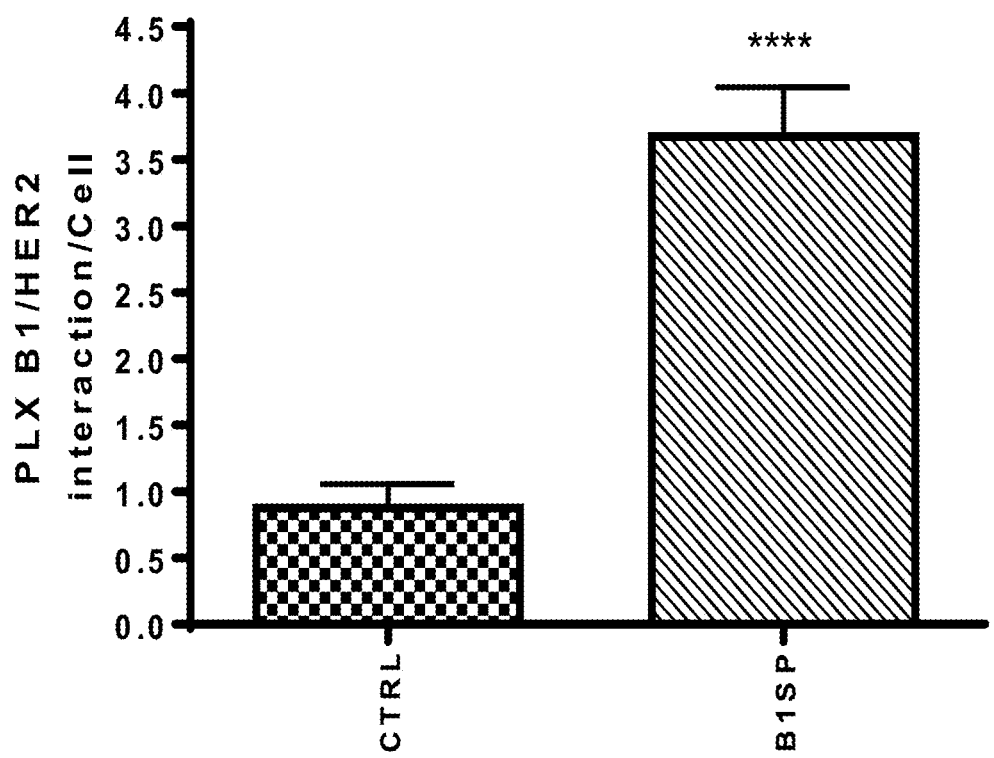
FIG. 14 shows that B1SP enhances the interaction of PLEXIN B1 with HER2/ErbB2 in DU145 cells, based on PLA analysis using the Duolink in-situ PLA kit.

In FIG. 14, PLA analysis was performed as previously described using the Duolink™ in-situ PLA kit (Sigma-Aldrich™, Oakville, ON), where C-terminal anti-PLEXIN B1 was used to distinguish the endogenous PLEXIN B1 and B1SP and Mouse Anti-HER2 were used.

EXAMPLES

The following working examples are provided for illustrative purposes, and are not intended to be limiting, as such.

Example 1A: A B1SP Fusion Protein Binds NRP1 and Plexin B1 in a Dose Dependent Manner Semaphorins and their receptors (mainly plexins and neuropilins) are aberrantly expressed in human tumors. Semaphorin 3C binding and signaling requires the interaction of neuropilin1 or 2, co-receptors for Plexin B1. A B1SP fusion protein has potential to inhibit Semaphorin signaling by competing for Semaphorin binding to neuropilin and thereby inhibiting signaling via Plexin B1. As shown in FIGS. 3A and 3B a B1SP fusion protein co-immunoprecipitates with NRP1 and Plexin B1 in a dose dependent manner. FIGS. 3C and 3D show B1SP binding to Plexin B1 and NRP1 in a dose dependent manner. The bar graphs represent the relative amount of B1SP in complex with either NRP1 or, Plexin B1 obtained from three independent Western blotting experiments followed by densitometry analysis of NRP1 and PLEXIN B1 in complex with B1SP fusion protein was performed.

Example 1B: Plexin B1 Silencing Inhibits SEMA3C Signaling

DU145 cells transfected with scramble siRNA or, two distinct siRNAs targeting Plexin B1. Inhibition of Plexin B1 protein levels following 72 hr incubation from whole cell lysates and Western Blot analysis probed with Plexin B1 antibodies (data not shown). The blot was then probed with anti-Vinculin to demonstrate equal loading of protein lysates. AP-Sema3C binding to DU145 cells that were transfected with scramble or Plexin B1 siRNAs, where the mean and SEM AP-Sema3C binding performed was calculated in quadruplicate. Knockdown of Plexin B1 resulted in a reduced binding of AP-Sema3C by 2.4-fold with Plexin siRNA1 and 1.9-fold with Plexin B1 siRNA2 compared to control scramble siRNA. There was also a decrease in Sema3C-mediated SHC phosphorylation in response to silencing of Plexin B1. LNCaP cells were transfected with scramble or, Plexin B1 siRNAs and then incubated for 72 hours. Cells were serum starved for 16 hr and then incubated in the presence or absence of SEMA 3C (100 nM) for 10 minutes. Western Blots were probed with Plexin B1 antibodies to demonstrate specific inhibition of Plexin B1 and anti-phospho-SHC. Blots were re-probed anti-SHC and anti-Vinculin as loading controls (data not shown).

Example IC: B1SP Enhances PLEXIN B1 and HER2/ErbB2 Interaction

Surprisingly, the addition of B1SP enhances the interaction of PLEXIN B1 with HER2/ErbB2 in DU145 cells (i.e. based on U.S. Pat. No. 9,198,966), as shown in FIG. 14.

Example 2: A B1SP Fusion Protein Inhibits EGFR Phosphorylation

FIG. 4 shows inhibition of EGFR phosphorylation in LNCaP cells. The LNCaP cells were serum starved for 24 hrs. before a B1SP fusion protein conditioned medium (CM) was added 2, 4 and 6 hour time points followed by stimulation with EGF (5.0 ng/ml) for to min. The cells were harvested and evaluated for the expression of EGFR phosphorylation (pEGFR) and total EGFR expression. The blots were reprobed with anti-vinculin as loading control. Untreated cells were either stimulated similarly or directly lysed at the 6 hour time point as a controls for comparison of EGFR phosphorylation at the end of the time course and to control for any effect incubation time may have on the capacity to stimulate EGFR phosphorylation in LNCaP.

FIG. 5A also shows inhibition of EGFR phosphorylation in LNCaP cells. LNCaP cells were serum starved, media was then changed and the cells were treated with either truncated Semaphorin Fusion proteins (2.0 µM) (ALB SRGLI) and Plexin B1 Fusion protein (B1SP fusion protein) (2.0 µM) for 60 minutes. The cells were then stimulated with EGF (10 ng/ml) for 10 min before the cells were harvested and evaluated for the expression of EGFR phosphorylation (pEGFR), and EGFR levels. Blots were then reprobed for vinculin as loading control. The inhibitory effect of a B1SP fusion protein on EGFR phosphorylation was stronger than other inhibitor proteins including ALB. Furthermore, an alternative c-terminal Albumin fusion (SDPSI-L-ALB) was tested (data not shown). SDPSI-L-ALB showed activity identical to the n-terminal Albumin fusion (ALB-L-SDPSI or ALB SRGLI).

FIGS. 5B and C show that a B1SP fusion protein inhibits phosphorylation of She isoforms downstream of the EGFR.

FIG. 6A shows LNCaP cells that were serum starved for 24 hrs. before the cells were treated simultaneously with a B1SP fusion protein and Semaphorin 3C:Fc for 60 minutes, B1SP alone, Sema3C:Fc alone or, left untreated. The cells were then stimulated with EGF (10 ng/ml) for to min. The blot was re-probed with vinculin as loading control. FIG. 6B shows quantitative densitometric analysis of the blot of FIG. 6A. The data demonstrates that B1SP can inhibit Sema3C-mediated EGFR phosphorylation. The data shows the resulting levels of EGFR phosphorylation. Similarly, FIG. 3C demonstrates that B1SP can inhibit Sema3C-mediated EGFR phosphorylation and is not inhibited by SEMA3C:Fc alone.

FIG. 7 also shows inhibition of EGFR phosphorylation in LNCaP and 22RV1 PC cells. The cells were serum starved before a B1SP fusion protein conditioned medium (CM) was added to the cells at the indicated concentrations (i.e. 0.5, 1, 2 and 4 µM—A) and for the indicated time-points (i.e. 1, 2 and 4 hrs.—B) followed by stimulation with 5.0 ng/ml EGF for 10 minutes. The cells were harvested and evaluated for the expression of pEGFR, and EGFR. The blots were re-probed for vinculin as a loading control. Control EGFR phosphorylation was evaluated in untreated cells at the termination of the time course. FIGS. 7A and 7B show plots of a quantitative densitometric analysis. Similarly, the inhibition of EGFR phosphorylation was also tested in 22RV1 PC cells (C), MCF10A normal human mammary cells (D), MR49F PC cells (E) and V16A castration-resistant prostate cancer (CRPC) stem cells (F), with increasing concentrations of B1SP (i.e. 0.5, 1, 2 and 4.0 μM) and showed a similar decline in EGFR phosphorylation.

B1SP inhibition of SEMA3C-mediated EGFR phosphorylation was also seen in U87MG glioblastoma cells, which were seeded at 2.5×105 cells in 6-well dishes and incubated overnight. The medium was then replaced with RPM1 without serum and Phenol red and incubated for 24 h. The cells were then treated with PBS as control or B1SP (2 μM) for 1 hour. The cells were then either stimulated with SEMA3C:Fc (1 μM) or PBS control for 20 minutes at 370 C and 5% CO2. Cells were processed for immunoblotting as previously described (immunoblot not shown). Additionally, dosage dependent inhibition of HGF-mediated MET and MAPK phosphorylation in serum-starved T24 Bladder cancer cells treated for 3 h with B1SP (0-4 μM) or PBS control was also tested. Cells were stimulated as indicated with HGF (1 nM) for 20 min followed by a wash in cold PBS and lysis in NP40 lysis buffer. The immunoblot showed the relative MET and MAPK phosphorylation decreased as the concentration of B1SP increased. Immunoblots were re-probed with MET and MAPK antibodies and Vinculin as loading controls (immunoblot not shown).

Example 3: B1SP Fusion Protein Inhibits LNCaP Cell Proliferation

Figure 8A:
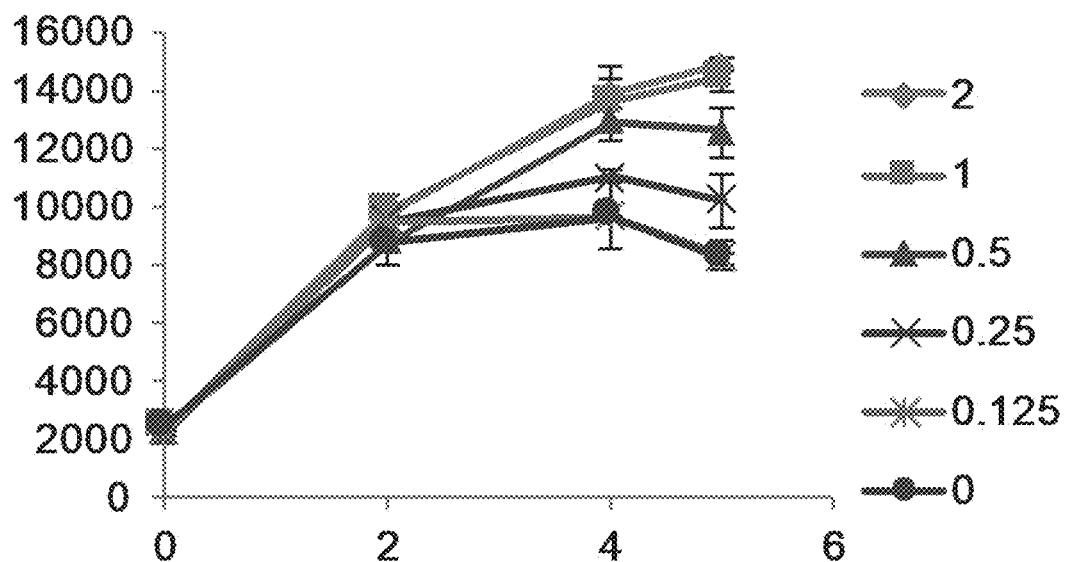
FIGS. 8A-D shows that B1SP inhibits PC cell (LNCaP) proliferation in a dose dependent manner with an IC50 of 1.145 µM, where (FIG. 8A) shows cells were treated with synthetic androgen (R1881) as indicated and cell proliferation was evaluated using the PrestoBlue proliferation assay over a period of 5 days; in (FIG. 8B) LNCaP cells were treated with R1881 (1 nM) in combination with increasing concentration B1SP and cell proliferation was monitored over a period of 4 days.
Figure 8B:
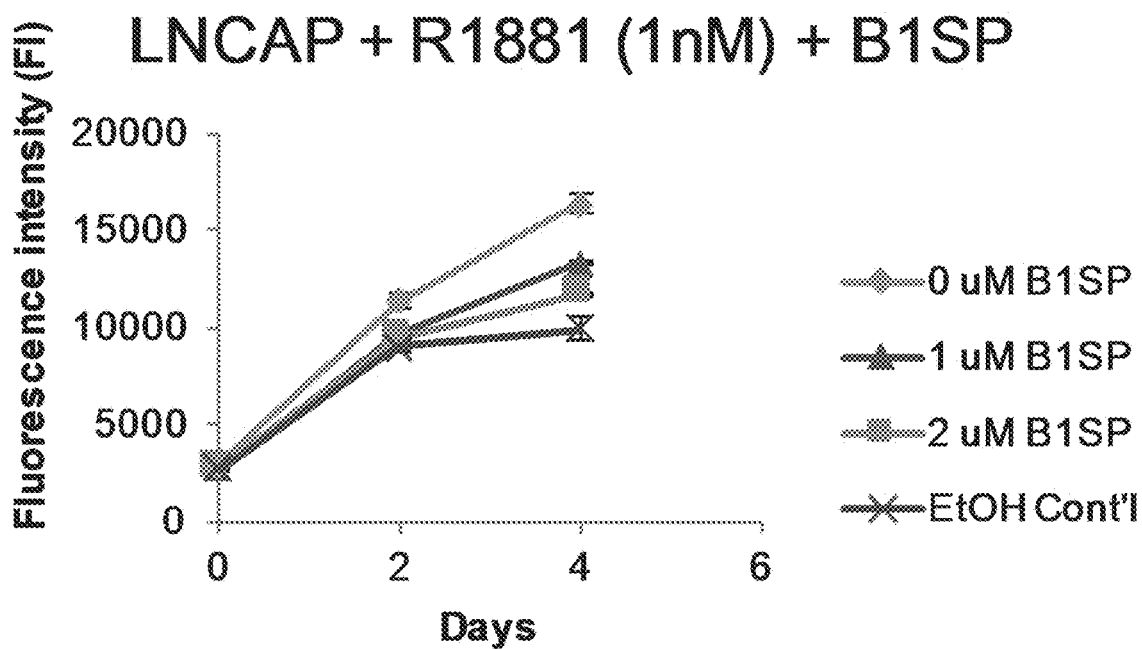
Figure 8C:
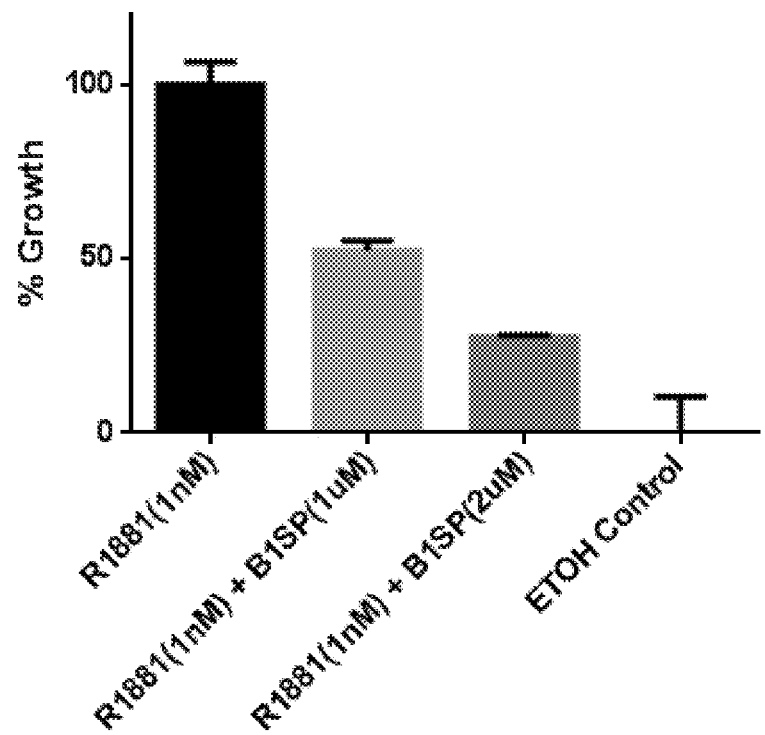
Figure 8D:
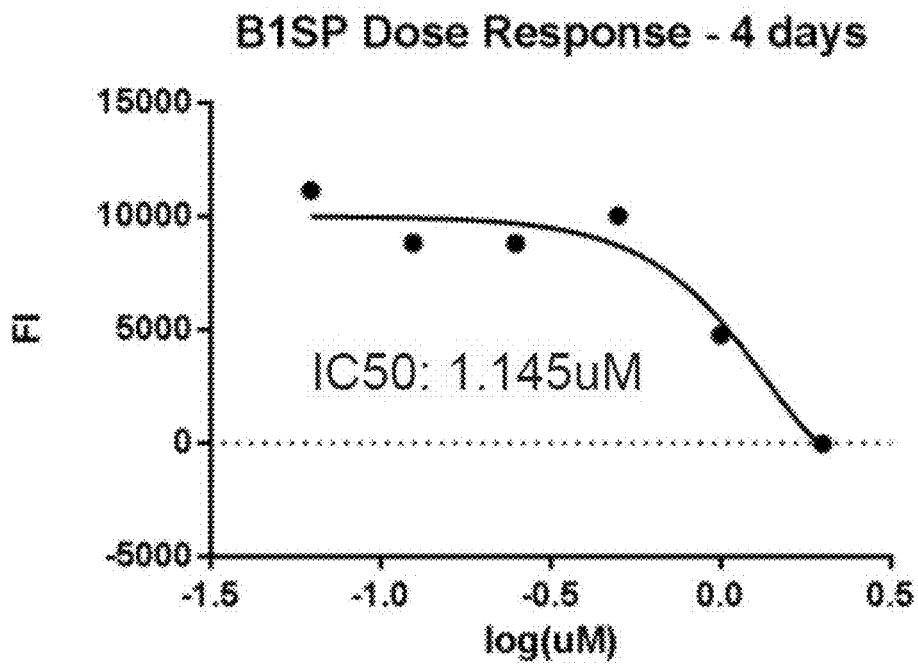

In (A), cells were treated with synthetic androgen (R1881) as indicated and cell proliferation was evaluated using the PrestoBlue proliferation assay over a period of 5 days. In (B), LNCaP cells were treated with R1881 (nM) in combination with increasing concentration B1SP and cell proliferation was monitored over a period of 4 days. In (C), the inhibitory effect of B1SP on growth expressed as percentage of maximum androgen (R1881) sensitive growth. FIG. 8A shows fluorescence intensity (FI) as a representation of cell proliferation over a 4 day period for a B1SP fusion protein at 2 μM, 1 μM, 0.5 μM, 0.25 μM, 0.125 μM and 0 μM. Similarly, FIG. 8B shows fluorescence intensity (FI) as a representation of cell proliferation over a 4 day period in LNCaP cells treated with R1881 (mM) and B1SP fusion protein at 2 μM, 1 μM and 0 μM, with EtOH control. FIG. 8D shows a plot of B1SP fusion protein dose response on a log scale.

Example 4: A B1SP Fusion Protein Increases LNCaP Cell Death

Purified and CM B1SP molecular weight was confirmed by Coomassie staining of purified B1SP protein under reducing (R) and non-reducing (NR) conditions (data not shown). Coomassie blue staining for a B1SP fusion protein showed a 97 kDa monomer (R) and 193 kDa dimer (NR). Similarly, conditioned medium harvested from CHO cells secreting a B1SP fusion protein was evaluated by Western blot with N-terminal, anti-Plexin B1 antibodies (data not shown).

As shown in FIGS. 9A and 9B, LNCaP cells were treated for 48 hours with purified a B1SP fusion protein and cell viability was then analyzed using a fluorescence-based live/dead cell viability assay (Calcein/Propidium Iodide). FIGS. 9A and 9B show two independent experiments.

Example 5: A B1SP Fusion Protein Inhibits Adhesion of Prostate Cancer Cells (LNCaP and DU145) to Fibronectin As shown in FIGS. 10A and 10B, a B1SP fusion protein treatment inhibits adhesion of prostate cancer cells (i.e. LNCaP or DU145 cells). The cells were pulsed with calcein AM (12.5 μM) and incubated for 30 min. The cells (1×10$^5$) were seeded on precoated fibronectin (50 μg/ml) 96-well plates and centrifuged briefly prior to incubation in the presence or absence of a B1SP fusion protein for 16-24 hr. Cell Fluorescence was measured before and after removal of non-adhered cells by washing. Data represents the average (%) Adhesion of triplicate wells.

Figure 11A:
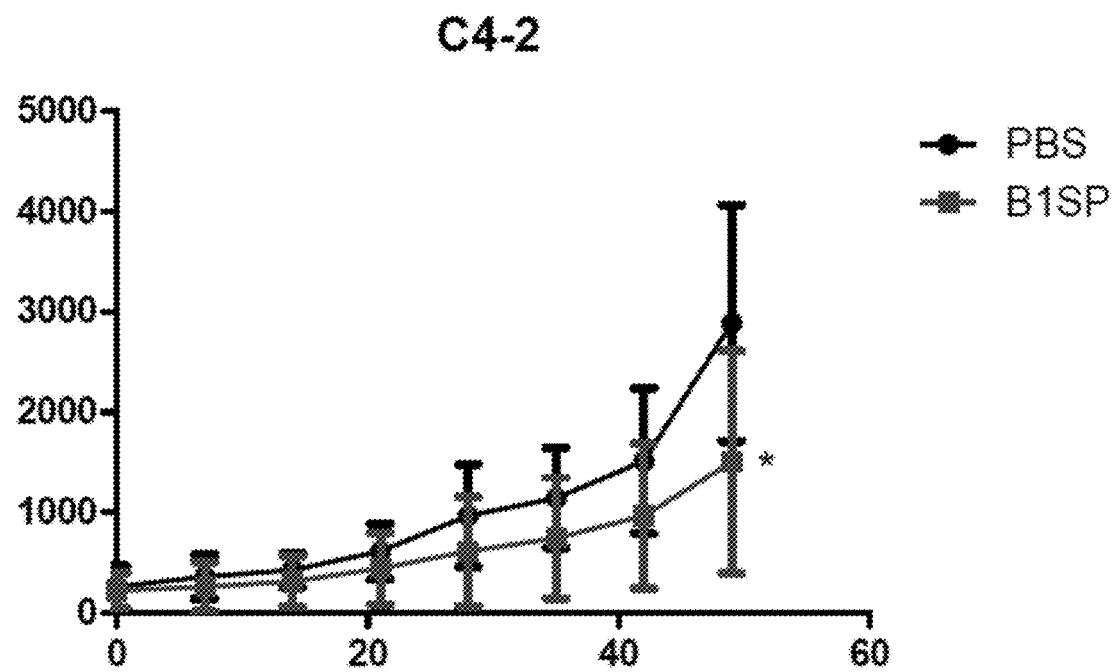
FIGS. 11A and 11B show treatment of mice bearing castration resistant C4-2 xenograft tumors with B1SP fusion protein inhibits tumor growth in vivo as shown by decreased tumor volume (FIG. 11A) and serum PSA levels (FIG. 11B) as compared to PBS treated control mice.
Figure 11B:
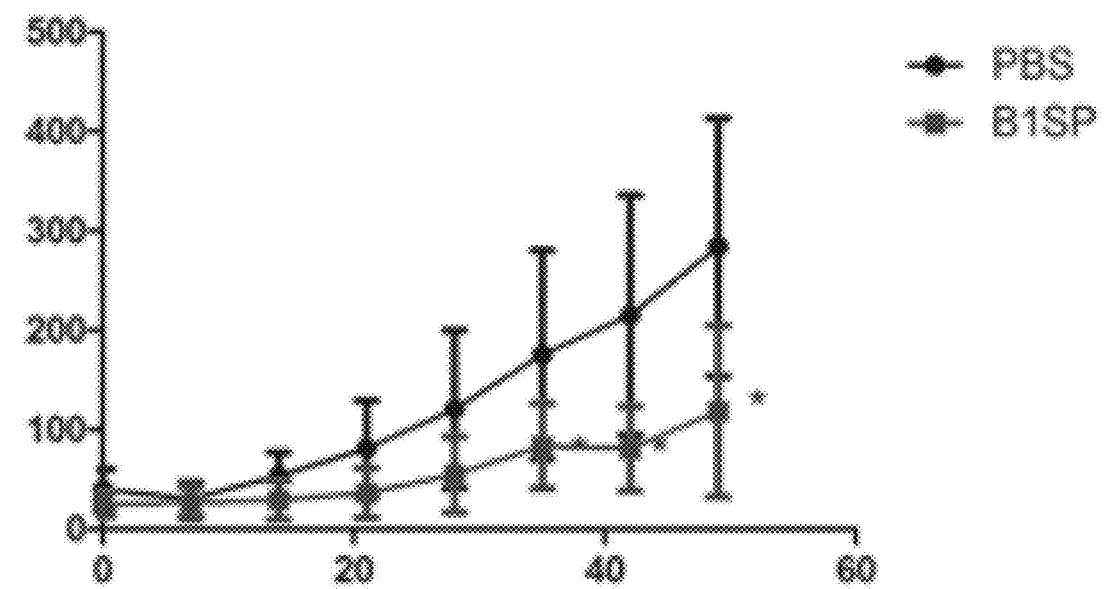

Example 6: A B1SP Fusion Protein Inhibits R1881-Induced Proliferation of LNCaP Cells in a Dose Dependent Manner FIGS. 11A-C shows a B1SP fusion protein inhibits proliferation of androgen sensitive LNCaP cells. A Cells were treated with synthetic androgen (R1881) as indicated. Cell proliferation was evaluated using the PrestoBlue proliferation assay over a period of 5 days. B LNCaP cells were treated with R1881 (1 nM) in combination with increasing concentration B1SP. Cell proliferation was monitored over a period of 4 days. C Represents the inhibitory effect of a B1SP fusion protein on growth expressed as percentage of maximum androgen (R1881) sensitive growth.

Example 7: In Vivo Assay

Figure 12A:
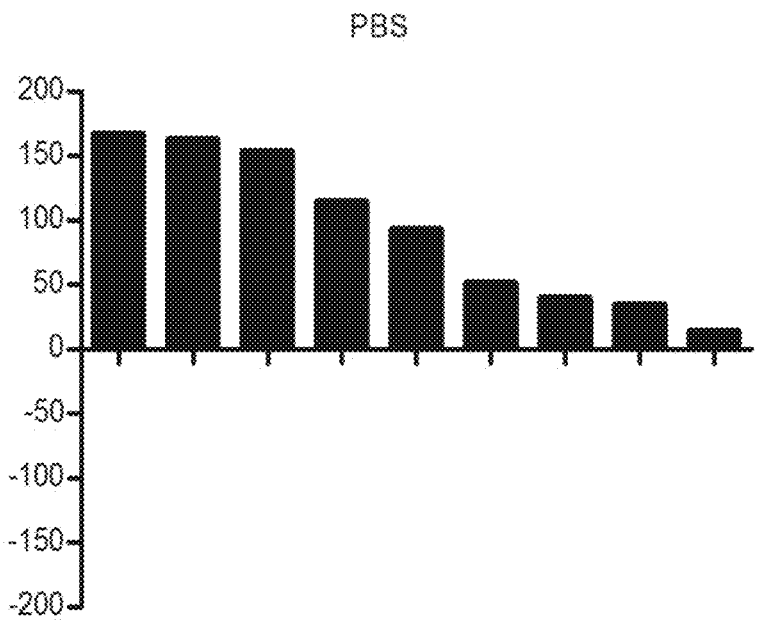
FIGS. 12A and 12B show two waterfall plots of percent change in serum PSA levels of individual C4-2 xenograft bearing mice from day 7 to day 14 treated with PBS (n=9) and B1SP (n=7), respectively.
Figure 12B:
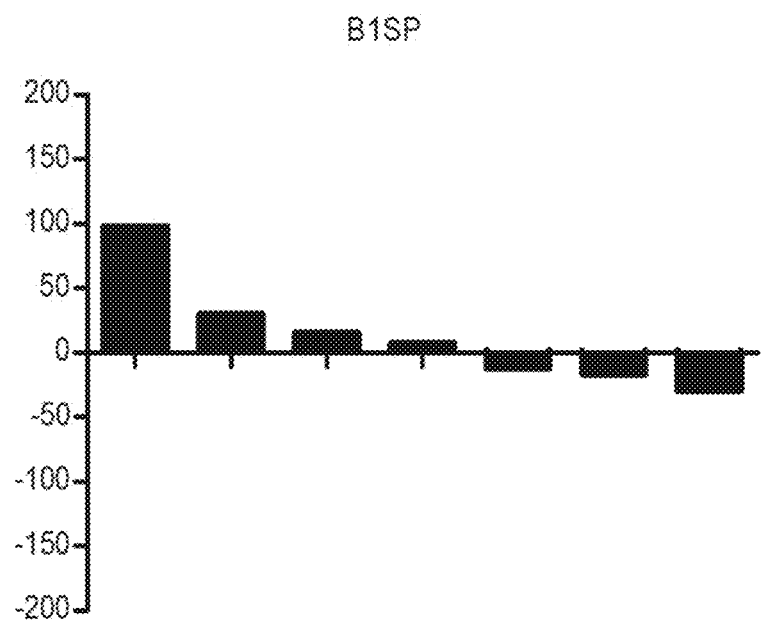

Athymic nu$^{-/-}$ mice bearing castrate resistant C4-2 xenografts were castrated and treated twice per week with 20 mg/kg B1SP or PBS control. Treatment with B1SP fusion protein suppressed C4-2 tumor growth (FIG. 11A) and serum PSA progression (FIG. 11B). FIG. 12 shows the change in serum PSA levels from Day 7 to Day 14 of individual castrate resistant C4-2 xenograft bearing mice (CRPC) treated with (A) PBS control (n=9) or (B) B1SP (n=7). FIG. 13 shows that treatment of LNCaP and C4-2 cells with B1SP fusion protein induces apoptosis in a dose dependent manner as monitored by immunoblot analysis for PARP cleavage.

Example 8: IC$_{50}$ Values for Various Cancer Cell-lines Tested for B1SP-mediated Proliferation Sensitivity A variety of cancer cell lines were tested for B1SP-mediated proliferation sensitivity to calculate the IC$_{50}$ value for each cell type as a representation of B1SP's effectiveness in the treatment of the cancer type. Inhibition of LNCaP, C42, MR49F, U87MG, Caki-1, Caki-2 and T24 cells were tested for proliferation in response to increasing doses of B1SP (i.e. 2, 1, 0.5, 0.25 and 0.125 μM) as compared to PBS controls. LNCaP cells were also administered R1881 as described above and used a EtOH and PBS control. Day 4 data were normalized to day 0 using GraphPad prism software. C4-2 are CRPC cells, MR49F cells are Enzalutamide-dependent (10 μM) LNCaP-derivative cells, U87MG are glioblastoma cells, Caki-1 and Caki-2 are renal carcinoma cells and T24 are bladder cancer cells.

TABLE 2 below summarizes the $IC_{50}$ values of the various cancer cell-lines tested for B1SP-mediated proliferation sensitivity.

TABLE 2

$IC_{50}$ Values by Cell Line and Cancer Type

| Type of Cancer | Cell Line | $IC_{50}$ (μM) |
|---|---|---|
| Prostate | LNCap | 0.2509 |
| | C42 | 0.9636 |
| | MR49F | 0.981 |
| Glioblastoma | U87MG | 2.965 |
| Kidney | Caki-1 | 2.215 |
| | Caki-2 | 0.1725 |
| Bladder | T24 | 0.06164 |

Example 9: Expression of SEMA Peptides with More than One PSI Domain

B1SP and B1R4 were expressed in HEK 293T cells but only B1SP was secreted into the conditioned medium. HEK 293T cells were transfected with B1SP and B1R4 expression clones. Twenty four hours later the medium was replaced with Opti-Mem and incubated at 37° C. in 5% $CO_2$ for an additional 48 h. Conditioned medium was harvested, concentrated and analysed by immunoblotting using anti-Plexin B1 for whole cell lysates (WCL) and HRP conjugated anti-Fc antibodies for conditioned medium (CM). It is suspected that the B1R4 secretion was inhibited by the additional PSI domains (i.e. B1SP has only one PSI domain).

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to the present invention.

REFERENCES

BALLARD et al 1998 Infect. Immun 66:615-619.
BLANKE et al 1996 Proc Natl Acad Sci 93: 8437-8442.
BRUCHOVSKY, N., P. RENNIE, et al. (1988). Mechanisms and effects of androgen withdrawal therapies. *Prostatic Cancer: Rationale of endocrine management.* Berlin, Walter De Gruyer & Co.: 3-14.
BRUCHOVSKY, N., P. S. RENNIE, et al. (1989). Limitations of androgen withdrawal therapy of prostatic carcinoma—the next step? *Prostate Cancer-The Second Tokyo Symposium.* New York, Elsevier: 1-10.
DEMARCHI et al 1996 *J Virol* 70:4427-4437.
DIETZ et al 2004. *Mol Cell. Neurosci* 27:85-131.
DILBER et al 1999 *Gene Ther.* 6:12-21.
FUJIHARA et al 1999 *EMBO J* 18:411-419.
GHERARDI E. et al. Current Opinion in Structural Biology (2004) 14:669-678.
GIORDANO, S., S. CORSO, et al. (2002). "The semaphorin 4D receptor controls invasive growth by coupling with Met." *Nat Cell Biol* 4(9): 720-4.
GOLDENBERG, S. L., N. BRUCHOVSKY, et al. (1988). "The combination of cyproterone acetate and low dose diethylstilbestrol in the treatment of advanced prostatic carcinoma." *J Urol* 140(6): 1460-5.
HARITON-GAZAL et al 2002 *Biochemistry* 41:9208-9214.
HEINLEIN, C. A. and CHANG C. (2004), "Androgen Receptor in Prostate Cancer." *Endocrine Reviews* 25(2): 276-308.
HERMAN, J. G. and G. G. MEADOWS (2007). "Increased class 3 semaphorin expression modulates the invasive and adhesive properties of prostate cancer cells." *Int J Oncol* 30(5): 1231-8.
HUGGINS, C. and C. HODGES (1941). "Studies on prostatic cancer. I. the effect of castration, of estrogen and of androgen injection on serum phosphatases in metastatic carcinoma of the prostate." *Cancer Res* 1: 293-297.
HUTT M. et al. The Journal of Biological Chemistry (2012) 287(7):4462-4469.
ISAACS, J., O. CUSSENOT, et al. (1997). "Growth regulation of normal and malignant prostatic cells." *First International Consultation on Prostate Cancer:* 31-87.
KOLODKIN, A. L., D. J. MATTHES, et al. (1993). "The semaphorin genes encode a family of transmembrane and secreted growth cone guidance molecules." *Cell* 75(7): 1389-99.
KRUGER, R. P., J. AURANDT, et al. (2005). "Semaphorins command cells to move." *Nat Rev Mol Cell Biol* 6(10): 789-800.
FLANAGAN, J G. and LEDER, P. (1990) "The kit ligand: a cell surface molecule altered in steel mutant fibroblasts" *Cell* Vol. 63(1):185-194.
MORRIS et al 2001 *Nature Biotechnol* 19:1173-1176.
NAIR et. al. 2003 *J. Immunol.* 170:1362-1373.
NEGISHI, M., I. OINUMA, and H. KATOH (2005). Plexins: axon guidance and signal transduction. *Cell Mol Life Sci* 62:1363-1371.
PEREZ et al 1992 *J. Cell Sci* 1002:717-722.
PETRYLAK, D. P., C. M. TANGEN, et al. (2004). "Docetaxel and estramustine compared with mitoxantrone and prednisone for advanced refractory prostate cancer." *N Engl J Med* 351(15): 1513-20.
POOGA et al 1998 *FASEB J* 12: 67-77.
PRIOR et al 1992 *Biochemistry* 31:3555-3559.
RATTAN et al. (1992), *Protein Synthesis: Posttranslational Modifications and Aging,* "Ann NY Acad Sci 663: 48-62.
RYSER et al 1980 *Cancer* 45:1207-1211.
SEIFTER et al., *Analysis for protein modifications and nonprotein cofactors, Meth. Enzymol.* (1990) 182: 626-646
SHEN et al 1978 *Proc Natl Acad Sci* 75:1872-1876.
SWIERCZ, J. M., R. KUNER, et al. (2004). "Plexin-B1/RhoGEF-mediated RhoA activation involves the receptor tyrosine kinase ErbB-2." *J Cell Biol* 165(6): 869-80.
SWIERCZ, J. M., T. WORZFELD, et al. (2008). "ErbB-2 and met reciprocally regulate cellular signaling via plexin-B1." *J Biol Chem* 283(4): 1893-901.
STENMARK et al 1991 *J Cell Biol* 113:1025-1032.
TAMAGNONE, L. and P. M. COMOGLIO (2000). "Signalling by semaphorin receptors: cell guidance and beyond." *Trends Cell Biol* 10(9): 377-83.

TANNOCK, I. F., R. de WIT, et al. (2004). "Docetaxel plus prednisone or mitoxantrone plus prednisone for advanced prostate cancer." *N Engl J Med* 351(15): 1502-12.

VERRAS, M., J. LEE, et al. (2007). "The androgen receptor negatively regulates the expression of c-Met: implications for a novel mechanism of prostate cancer progression." *Cancer Res* 67(3): 967-75.

WIEDLOCHA et al 1994 *Cell* 76:1039-1051.

WOLFERT et al 1996 *Gene Ther.* 3:269-273.

Proteins-Structure and Molecular Properties, $2^{nd}$ ed., T. E. Creighton, W. H. Freeman and Company, New York, 1993.

WOLD F, Posttranslational Protein Modifications: Perspectives and Prospects, pgs. 1-12 in Posttranslational Covalent Modification of Proteins, B. C. Johnson, ed., Academic Press, New York, 1983.

ALTSCHUL et al. 1990, *J Mol. Biol.* 215: 403-410.

ALTSCHUL et al. (1997), *Nucleic Acids Res.* 25: 3389-3402.

KYTE & DOOLITTLE 1982. *J Mol Biol* 157:105-132.

SAMBROOK J. AND RUSSELL D. (2000) Molecular Cloning: A Laboratory Manual (Third Edition) Cold Spring Harbor Laboratory, Cold Spring Harbor Laboratory Press, Cold Spring Harbor, N.Y.

AUSUBEL et al. (Current Protocols in Molecular Biology, John Wiley & Sons, 1994).

"Remington's Pharmaceutical Sciences", (19th edition), ed. A. Gennaro, 1995, Mack Publishing Company, Easton, Pa.

"The Pharmacological basis of therapeutics", $10^{th}$ edition. HARDMAN H G., LIMBIRD L E. editors.

"Clinical Oncology", $3^{rd}$ edition. Churchill Livingstone/Elsevier Press, 2004. ABELOFF, M D. editor.

```
INFORMAL SEQUENCE LISTING
                                                        SEQ ID NO: 1
SCAQHLDCAS CLAHRDPYCG WCVLLGRCSR RSECSRGQGP EQ (B1SP FUSION-molecular weight homodimer 168kD Amino Acid sequence)
                                                        SEQ ID NO: 2
MPALGPALLQALWAGWVLTLQPLPPTAFTPNGTYLQHLARDPTSGTLYLGATNFLFQLSPGLQLEATV

STGPVLDSRDCLPPVMPDECPQAQPTNNPNQLLLVSPGALVVCGSVHQGVCEQRRLGQLEQLLLRPER

PGDTQYVAANDPAVSTVGLVAQGLAGEPLLFVGRGYTSRGVGGGIPPITTRALWPPDPQAAFSYEETA

KLAVGRLSEYSHHFVSAFARGASAYFLFLRRDLQAQSRAFRAYVSRVCLRDQHYYSYVELPLACEGGR

YGLIQAAAVATSREVAHGEVLFAAFSSAAPPTVGRPPSAAAGASGASALCAFPLDEVDRLANRTRDAC

YTREGRAEDGTEVAYIEYDVNSDCAQLPVDTLDAYPCGSDHTPSPMASRVPLEATPILEWPGIQLTAV

AVTMEDGHTIAFLGDSQGQLHRVYLGPGSDGHPYSTQSIQQGSAVSRDLTFDGTFEHLYVMTQSTLLK

VPVASCAQHLDCASCLAHRDPYCGWCVLLGRCSRRSECSRGQGPEQWLWSFQPELGCLGSGGGSGGGG

GSGGGGSDKTHTCPPCPAPELLGGPSVFLFPPKPKDQLMISRTPEVTCVVVDVSHEDPEVKFNWYVDG

VEVHNAKTKPREEQYNSTYRVVSVLTVLHQDWLNGKEYKCKVSNKALPAPIEKTISKAKGQPREPQVY

TLPPSREEMTKNQVSLTCLVKGFYPSDIAVEWESNGQPENNYKTTPPVLDSDGSFFLYSKLTVDKSRW

QQGNVFSCSVLHEALHNHYTQKSLSLSPGK*

SEMA DOMAIN-no annotation
structural stabilization domain (PSI=plexin-semaphorin-integrin
domain)
linker
Hinge
Half life extending domain (FC region)

(B1SP FUSION-nucleic acid sequence encoding fusion protein of SEQ ID
NO: 2)
                                                        SEQ ID NO: 3
atgcctgctctgggcccagctcttctccaggctctctgggccgggtgggtcctcaccctccagcccct tccaccaactgcattcactcccaatggcacgtatctgcagcacctggcaagggacccacctcaggca ccctctacctgggggctaccaacttcctgttccagctgagccctgggctgcagctggaggccacagtg tccaccggccctgtgctagacagcagggactgcctgccacctgtgatgcctgatgagtgcccccaggc ccagcctaccaacaacccgaatcagctgctcctggtgagcccaggggccctggtggtatgcgggagcg tgcaccaggggtctgtgaacagcggcgcctggggcagctcgagcagctgctgctgcggccagagcgg cctggggacacacaatatgtggctgccaatgatcctgcggtcagcacggtggggctggtagcccaggg cttggcaggggagcccctcctgtttgtggggcgaggatacaccagcagggtgtgggggggtggcattc
```

-continued

```
cacccatcacaacccgggccctgtggccgcccgaccccaagctgccttctcctatgaggagacagcc aagctggcagtgggccgcctctccgagtacagccaccacttcgtgagtgcctttgcacgtggggccag cgcctacttcctgttcctgcggcgggacctgcaggctcagtctagagcttttcgtgcctatgtatctc gagtgtgtctccgggaccagcactactactcctatgtggagttgcctctggcctgcgaaggtggccgc tacgggctgatccaggctgcagctgtggccacgtccagggaggtggcgcatgggaggtgctctttgc agctttctcctcggctgcaccccccactgtgggccggcccccatcggcggctgctggggcatctggag cctctgccctctgtgccttcccctggatgaggtggaccggcttgctaatcgcacgcgagatgcctgc tacacccgggagggtcgtgctgaggatgggaccgaggtggcctacatcgagtatgatgtcaattctga ctgtgcacagctgccagtggacaccctggatgcttatccctgtggctcagaccacacgcccagcccca tggccagccgggtcccgctggaagccacaccaattctggagtggccagggattcagctaacagctgtg gcagtcaccatggaagatggacacaccatcgctttcctgggtgatagtcaagggcagctgcacagggt ctacttgggcccagggagcgatggccacccatactccacacagagcatccagcagggtctgcagtga gcagagacctcacctttgatgggacctttgagcacctgtatgtcatgacccagagcacactctgaag gttcctgtggcttcctgtgctcagcacctggactgtgcatcttgccttgctcacagggacccatactg tgggtggtgcgtgctccttggcaggtgcagtcgccgttctgagtgctcgaggggccagggcccagagc agtggctatggagcttccagcctgagctgggctgtctgggatccggtggcggttccggtggtggaggc ggaagcggcggtggaggatcaGACAAAACTCACACATGCCCACCGTGCCCAGCACCTGAACTCCTGGG

GGGACCGTCAGTCTTCCTCTTCCCCCCAAAACCCAAGGACCAACTGATGATCTCCCGGACCCCTGAGG

TCACATGCGTGGTGGTGGACGTGAGCCACGAAGACCCTGAGGTCAAGTTCAACTGGTACGTGGACGGC

GTGGAGGTGCATAATGCCAAGACAAAGCCGCGGGAGGAGCAGTACAACAGCACGTACCGTGTGGTCAG

CGTCCTCACCGTCCTGCACCAGGACTGGCTGAATGGCAAGGAGTACAAGTGCAAGGTCTCCAACAAAG

CCCTCCCAGCCCCCATCGAGAAAACCATCTCCAAAGCCAAAGGGCAGCCCCGAGAACCACAGGTGTAC

ACCCTGCCCCCATCCCGGGAGGAGATGACCAAGAACCAGGTCAGCCTGACCTGCCTGGTCAAAGGCTT

CTATCCCAGCGACATCGCCGTGGAGTGGGAGAGCAATGGGCAGCCGGAGAACAACTACAAGACCACGC

CTCCCGTGCTGGACTCCGACGGCTCCTTCTTCCTCTACAGCAAGCTCACCGTGGACAAGAGCAGGTGG

CAGCAGGGGAACGTCTTCTCATGCTCCGTGCTGCATGAGGCTCTGCACAACCACTACACGCAGAAGAG

CCTCTCCCTGTCTCCGGGTAAATGA
```

(ALB-L-SDPSI or ALB SRGLI) has albumin at the N-terminus fused to
linker then to SEMA3C sema domain then to psi truncated at the
natural cleavage of the furin site

SEQ ID NO: 4

MAFRTICVLVGVFICSICVKHHHHHHHHMKWVTFISLLFLFSSAYSRGVFRRDAHKSEVAHRFKDLGE

ENFKALVLIAFAQYLQQCPFEDHVKLVNEVTEFAKTCVADESAENCDKSLHTLFGDKLCTVATLRETY

GEMADCCAKQEPERNECFLQHKDDNPNLPRLVRPEVDVMCTAFHDNEETFLKKYLYEIARRHPYFYAP

ELLFFAKRYKAAFTECCQAADKAACLLPKLDELRDEGKASSAKQRLKCASLQKFGERAFKAWAVARLS

QRFPKAEFAEVSKLVTDLTKVHTECCHGDLLECADDRADLAKYICENQDSISSKLKECCEKPLLEKSH

CIAEVENDEMPADLPSLAADFVESKDVCKNYAEAKDVFLGMFLYEYARRHPDYSVVLLLRIAKTYETT

LEKCCAAADPHECYAKVFDEFKPLVEEPQNLIKQNCELFEQLGEYKFQNALLVRYTKKVPQVSTPTLV

EVSRNLGKVGSKCCKHPEAKRMPCAEDYLSVVLNQLCVLHEKTPVSDRVTKCCTESLVNRRPCFSALE

VDETYVPKEFNAETFTFHADICTLSEKERQIKKQTALVELVKHKPKATKEQLKAVMDDFAAFVEKCCK

ADDKETCFAEEGKKLVAASQAALGLGSGGGSGGGGSGGGGSGSSQPQARVYLTFDELRETKTSEYFS

LSHHPLDYRILLMDEDQDRIYVGSKDHILSLNINNISQEALSVFWPASTIKVEECKMAGKDPTHGCGN

-continued

FVRVIQTFNRTHLYVCGSGAFSPVCTYLNRGRRSEDQVFMIDSKCESGKGRCSFNPNVNTVSVMINEE

LFSGMYIDFMGTDAAIFRSLTKRNAVRTDQHNSKWLSEPMFVDAHVIPDGTDPNDAKVYFFFKEKLTD

NNRSTKQIHSMIARICPNDTGGLRSLVNKWTTFLKARLVCSVTDEDGPETHFDELEDVFLLETDNPRT

TLVYGIFTTSSSVFKGSAVCVYHLSDIQTVFNGPFAHKEGPNHQLISYQGRIPYPRPGTCPGGAFTPN

MRTTKEFPDDVVTFIRNHPLMYNSIYPIHKRPLIVRIGTDYKYTKIAVDRVNAADGRYHVLFLGTDRG

TVQKVVVLPTNNSVSGELILEELEVFKNHAPITTMKISSKKQQLYVSSNEGVSQVSLHRCHIYGTACA

DCCLARDPYCAWDGHSCSRFYPTGKR (SDPSI-L-ALB) has the SEMA3C sema domain and psi domain cleaved at
the furin cleavage site fused to GS linker then tc albumin

SEQ ID NO: 5

MAFRTICVLVGVFICSICVKGSSQPQARVYLTFDELRETKTSEYFSLSHHPLKYRILLMDFDQDRIYV

GSKDHILSLNINNISQEALSVFWPASTIKVEECKMAGKDPTHGCGNFVRVIQTFNRTHLYVCGSGAFS

PVCTYLNRGRRSEDQVFMIDSKCESGKGRCSFNPNVNTVSVMINEELFSGMYIDFMGTDAAIFRSLTK

RNAVRTDQHNSKWLSEPMFVDAHVIPDGTDPNDAKVYFFFKEKLTDNNRSTKQIHSMIARICPNDTGG

LRSLVNKWTTFLKARLVCSVTDEDGPETHFDELEDVFLLETDNPRTTLVYGIFTTSSSVFKGSAVCVY

HLSDIQTVFNGPFAHKEGPNHQLISYQGRIPYPRPGTCPGGAFTPNMRTTKEFPDDVVTFIRNHPLMY

NSIYPIHKRPLIVRIGTDYKYTKIAVDRVNAADGRYHVLFLGTDRGTVQKVVVLPTNNSVSGELILEE

LEVFKNHAPITTMKISSKKQQLYVSSNEGVSQVSLHRCHIYGTACADCCLARDPYCAWDGHSCSRFYP

TGKGSGGGSGGGGSGGGGSDAHKSEVAHRFKDLGEENFKALVLIAFAQYLQQCPFEDHVKLVNEVTE

FAKTCVADESAENCDKSLHTLFGDKLCTVATLRETYGEMADCCAKQEPERNECFLQHKDDNPNLPRLV

RPEVDVMCTAFHDNEETFLKKYLYEIARRHPYFYAPELLFFAKRYKAAFTECCQAADKAACLLPKLDE

LRDEGKASSAKQRLKCASLQKFGERAFKAWAVARLSQRFPKAEFAEVSKLVTDLTKVHTECCHGDLLE

CADDRADLAKYICENQDSISSKLKECCEKPLLEKSHCIAEVENDEMPADLPSLAADFVESKDVCKNYA

EAKDVFLGMFLYEYARRHPDYSVVLLLRLAKTYETTLEKCCAAADPHECYAKVFDEFKPLVEEPQNLI

KQNCELFEQLGEYKFQNALLVRYTKKVPQVSTPTLVEVSRNLGKVGSKCCKHPEAKRMPCAEDYLSVV

LNQLCVLHEKTPVSDRVTKCCTESLVNRRPCFSALEVDETYVPKEFNAETFTFHADICTLSEKERQIK

KQTALVELVKHKPKATKEQLKAVMDDFAAFVEKCCKADDKETCFAEEGKKLVAASQAALGLHHHHHH

H*

SEMA3C:FC full length SEMA3C with mutations in two furin
cleavage sites with a linker and Fc region at the C terminus. Human Semaphorin 3C amino acids 1-20 encodes signal peptide;
(human SEMA3C Gly21-Ser738: Arg551Ala, Arg552Ala, Arg611Ala,
Arg612Ala); IEGRMD linker peptide sequence; Human IgG1 (Pro100-
Lys330) and linker DKTHTCPPCP.

SEQ ID NO: 6

MAFRTICVLVGVFICSICVKGSSQPQARVYLTFDELRETKTSEYFSLSHHPLKYRILLMDIDQDRIYV

GSKDHILSLNINNISQEALSVFWPASTIKVEECKMAGKDPTHGCGNFVRVIQTFNRTHLYVCGSGAFS

PVCTYLNRGRRSEDQVFMIDSKCESGKGRCSFNPNVNTVSVMINEELFSGMYIDFMGTDAAIFRSLTK

RNAVRTDQHNSKWLSEPMFVDAHVIPDGTDPNDAKVYFFFKEKLTDNNRSTKQIHSMIARICPNDTGG

LRSLVNKWTTFLKARLVCSVTDEDGPETHFDELEDVFLLETDNPRTTLVYGIFTTSSSVFKGSAVCVY

HLSDIQTVFNGPFAHKEGPNHQLISYQGRIPYPRPGTCPGGAFTPNMRTTKEFPDDVVTFIRNHPLMY

NSIYPIHKRPLIVRIGTDYKYTKIAVDRVNAADGRYHVLFLGTDRGTVQKVVVLPTNNSVSGELILEE

LEVFKNHAPITTMKISSKKQQLYVSSNEGVSQVSLHRCHIYGTACADCCLARDPYCAWDGHSCSRFYP

TGKRRSAAQDVRHGNPLTQCRGFNLKAYRNAAEIVQYGVKNNTTFLECAPKSPQASIKWLLQKDKDAA

KEVKLNERIIATSQGLLIRSVQGSDQGLYHCIATENSFKQTIAKINFKVLDSEMVAVVTDKWSPWTWA

-continued

SSVRALPFHPKDIMGAFSHSEMQMINQYCKDTRQQHQQGDESQKMRGDYGKLKALINSIEGRMDPKSC

DKTHTCPPCPAPELLGGPSVFLFPPKPKDTLMISRTPEVTCVVVDVSHEDPEVKFNWYVDGVEVHNAK

TKPREEQYNSTYRVVSVLTVLHQDWLNGKEYKCKVSNKALPAPIEKTISKAKGQPREPQVYTLPPSRD

ELTKNQVSLTCLVKGFYPSDIAVEWESNGQPENNYKTTPPVLDSDGSFFLYSKLTVDKSRWQQGNVFS

CSVMHEALHNHYTQKSLSLSPGKHHHHHHHH*

(scramble siRNA)
SEQ ID NO: 7
AUCAAACUGUUGUCAGCGCUGUU (PlexinB1siRNA1)
SEQ ID NO: 8
CCGGGUGGAAUUUAUCCUUGAUU (Plexin B1siRNA2)
SEQ ID NO: 9
ACCACGGUCACCCGGAUUCUU B1R4
SEQ ID NO: 10
MPALGPALLQALWAGWVLTLQPLPPTAFTPNGTYLQHLARDPTSGTLYLGATNFLFQLSPGLQLEATV

STGPVLDSRDCLPPVMPDECPQAQPTNNPNQLLLVSPGALVVCGSVHQGVCEQRRLGQLEQLLLRPER

PGDTQYVAANDPAVSTVGLVAQGLAGEPLLFVGRGYTSRGVGGGIPPITTRALWPPDPQAAFSYEETA

KLAVGRLSEYSHHFVSAFARGASAYFLFLRRDLQAQSRAFRAYVSRVCLRDQHYYSYVELPLACEGGR

YGLIQAAAVATSREVAHGEVLFAAFSSAAPPTVGRPPSAAAGASGASALCAFPLDEVDRLANRTRDAC

YTREGRAEDGTEVAYIEYDVNSDCAQLPVDTLDAYPCGSDHTPSPMASRVPLEATPILEWPGIQLTAV

AVTMEDGHTIAFLGDSQGQLHRVYLGPGSDGHPYSTQSIQQGSAVSRDLTFDGTFEHLYVMTQSTLLK

VPVASCAQHLDCASCLAHRDPYCGWCVLLGRCSRRSECSRGQGPEQWLWSFQPELGCLQVAAMSPANI

SREETREVFLSVPDLPPLWPGESYSCHFGEHQSPALLTGSGVMCPSPDPSEAPVLPRGADYVSVSVEL

RFGAVVIAKTSLSFYDCVAVTELRPSAQCQACVSSRWGCNWCVWQHLCTHKASCDAGPMVASHQSPLV

SPDPPARGGPSPSPPTAPKALATPAPDTLPVEPGAPSTATASDISPGASPSLLSPWGPWAGSGSISSP

GSTGSPLHEEPSPPSPQNGPGTAVPAPTDFRPSATPEDLLASPLSPSEVAAVPPADPGPEALHPTVPL

DLPPATVPATTFPGAMGSVKPALDWLTREGGELPEADEWTGGDAPAFSTSTLLSGDGDSAELEGPPAP

LILPSSLDYQYDTPGLWELEEATLGASSCPCVESVQGSTLMPVHVEREIRLLGRNLHLFQDGPGDNEC

VMELEGLEVVVEARVECEPPPDTQCHVTCQQHQLSYEALQPELRVGLFLRRAGRLRVDSAEGLHVVLY

DCSVGHGDCSRCQTAMPQYGCVWCEGERPRCVTREACGEAEAVATQCPAPLIHSVEPLTGPVDGGTRV

TIRGSNLGQHVQDVLGMVTVAGVPCAVDAQEYEVSSSLVCITGASGEEVAGATAVEVPGRGRGVSEHD

FAYQDPKVHSIFPARGPRAGGTRLTLNGSKLLTGRLEDIRVVVGDQPCHLLPEQQSEQLRCETSPRPT

PATLPVAVWFGATERRLQRGQFKYTLDPNITSAGPTKSFLSGGREICVRGQNLDVVQTPRIRVTVVSR

MLWPSQGLGGSGGGSGGGGSGGGGSDKTHTCPPCPAPELLGGPSVFLFPPKPKDQLMISRTPEVTCV

VVDVSHEDPEVKFNWYVDGVEVHNAKTKPREEQYNSTYRVVSVLTVLHQDWLNGKEYKCKVSNKALPA

PIEKTISKAKGQPREPQVYTLPPSREEMTKNQVSLTCLVKGFYPSDIAVEWESNGQPENNYKTTPPVL

DSDGSFFLYSKLTVDKSRWQQGNVFSCSVLHEALHNHYTQKSLSLSPGK*

The invention claimed is:

1. A fusion protein comprising:
   (a) a SEMA3C sema domain or Plexin B 1 sema domain;
   (b) a single Plexins-Semaphorins-Integrins domain (PSI domain); and
   (c) a half life extending moiety, provided that when the sema domain is from SEMA3C then the half-life extending moiety is albumin and provided that when the sema domain is from Plexin B 1 then the half-life extending moiety is a fragment crystallizable region (Fc region) and the Fc region forms a dimer,
   provided that when the sema domain is from SEMA3C the fusion protein lacks an immunoglobulin-like domain.

2. The fusion protein of claim 1, wherein the fusion protein further comprises one or more of a linker and a hinge between the PSI domain and the half life extending moiety.

3. The fusion protein of claim 1, wherein the single PSI domain comprises the amino acid sequence SCAQHLDCASCLAHRDPYCG WCVLLGRCSRRSECSRGQGPEQ (SEQ ID NO: 1).

4. The fusion protein of claim 1, wherein the fusion protein has an amino acid sequence comprising SEQ ID NO:2.

5. The fusion protein of claim 1, wherein the single PSI domain is a Plexin B1 PSI domain; a Plexin B2 PSI domain; or a Plexin B3 PSI domain.

6. The fusion protein of claim 1, wherein the fusion protein has an amino acid sequence comprising SEQ ID NO:4 or SEQ ID NO:5.

7. The fusion protein of claim 1, wherein the fusion protein comprises
   (a) a Plexin B1 sema domain;
   (b) a single Plexins-Semaphorins-Integrins domain (PSI domain); and
   (c) a fragment crystallizable region (Fc region),
   wherein the Fc region forms a dimer.

8. The fusion protein of claim 1, wherein the fusion protein comprises
   (a) a SEMA3C sema domain;
   (b) a single Plexins-Semaphorins-Integrins domain (PSI domain); and
   (c) an albumin,
   provided that the fusion protein lacks an immunoglobulin-like domain.

9. A pharmaceutical composition comprising a fusion protein in combination with a physiologically acceptable carrier, wherein the fusion protein comprises:
   (a) a SEMA3C sema domain or Plexin B1 sema domain;
   (b) a single Plexins-Semaphorins-Integrins domain (PSI domain); and
   (c) a half life extending moiety, provided that when the sema domain is from SEMA3C then the half-life extending moiety is albumin, and provided that when the sema domain is from Plexin B1 then the half-life extending moiety is a fragment crystallizable region (Fc region) and the Fc region forms a dimer,
   provided that when the sema domain is from SEMA3C the fusion protein lacks an immunoglobulin-like domain.

10. The pharmaceutical composition of claim 9, wherein the fusion protein further comprises one or more of a linker and a hinge between the PSI domain and the half life extending moiety.

11. The pharmaceutical composition of claim 9, wherein the single PSI domain comprises SCAQHLDCASCLAHRDPYCG WCVLLGRCSRRSECSRGQGPEQ (SEQ ID NO: 1).

12. The pharmaceutical composition of claim 9, comprising an amount of the fusion protein sufficient to cause cell death of a cancer cell or to inhibit proliferation of the cancer cell.

13. The pharmaceutical composition of claim 12, wherein the cancer cell is a prostate cancer cell, a breast cancer cell, an ovarian cancer cell, a bladder cancer cell, a kidney cancer cell, a glioblastoma cell or an endometrial cancer cell.

14. The pharmaceutical composition of claim 13, wherein the cancer cell is a prostate cancer cell, and wherein the prostate cancer cell is an androgen receptor (AR) positive prostate cancer cell.

15. The pharmaceutical composition of claim 9, wherein the fusion protein has an amino acid sequence comprising SEQ ID NO:2.

16. The pharmaceutical composition of claim 9, wherein the single PSI domain is a Plexin B1 PSI domain; a Plexin B2 PSI domain; or a Plexin B3 PSI domain.

17. The pharmaceutical composition of claim 9, wherein the fusion protein comprises the amino acid sequence of SEQ ID NO:4 or SEQ ID NO:5.

18. The pharmaceutical composition of claim 9, wherein the fusion protein comprises:
  (a) a Plexin B1 sema domain;
  (b) a single Plexins-Semaphorins-Integrins domain (PSI domain); and
  (c) a fragment crystallizable region (Fc region),
wherein the Fc region forms a dimer.

19. The pharmaceutical composition of claim 9, wherein the fusion protein comprises:
  (a) a SEMA3C sema domain;
  (b) a single Plexins-Semaphorins-Integrins domain (PSI domain); and
  (c) an albumin;
provided that the fusion protein lacks an immunoglobulin-like domain.

20. A method for treating cancer in a patient, the method comprising administering an effective amount of the fusion protein of claim 1 to the patient.

21. The method of claim 20, wherein the fusion protein further comprises one or more of a linker and a hinge between the single PSI domain and the half life extending moiety.

22. The method of claim 20, wherein the single PSI domain comprises SCAQHLDCASCLAHRDPYCGWCVLLGRCSRRSECSRGQGPEQ (SEQ ID NO:1).

23. The method of claim 20, wherein the cancer is prostate cancer, breast cancer, ovarian cancer, bladder cancer, kidney cancer, glioblastoma or endometrial cancer.

24. The method of claim 23, wherein the cancer is prostate cancer, and wherein the prostate cancer is an androgen receptor (AR) positive prostate cancer.

25. The method of claim 20, wherein the cancer is an androgen receptor (AR) positive prostate cancer and the effective amount of the fusion protein is sufficient for killing or inhibiting the proliferation of androgen receptor (AR) positive prostate cancer.

26. The method of claim 25, wherein the fusion protein further comprises one or more of a linker and a hinge between the PSI domain and the half life extending domain.

27. The method of claim 20, wherein the cancer is an androgen dependent prostate cancer, the method further comprises administering androgen deprivation therapy to the patient.

28. The method of claim 27, wherein administration of the androgen deprivation therapy and the fusion protein are initiated at about the same time; or wherein administration of the fusion protein is initiated after androgen deprivation therapy and before the androgen dependent prostate cancer becomes androgen independent.

29. The method of claim 27, wherein the androgen deprivation therapy comprises administering a luteinizing hormone-releasing hormone (LHRH) analog.

30. The method of claim 27, wherein the androgen deprivation therapy comprises administering anti-androgen treatment.

31. The method of claim 27, wherein the androgen deprivation therapy comprises administering an adrenal androgen inhibitor.

32. The method of claim 27, wherein the androgen deprivation therapy is surgical.

33. The method of claim 27, wherein the androgen deprivation therapy and the fusion protein are administered with one or more further therapeutic regimen(s).

34. The method of claim 33, wherein the therapeutic regimen is a chemotherapeutic regimen.

35. The method of claim 33, wherein the therapeutic regimen is a radiotherapeutic regimen.

36. The method of claim 20, wherein the fusion protein comprises SEQ ID NO:2.

* * * * *

UNITED STATES PATENT AND TRADEMARK OFFICE
CERTIFICATE OF CORRECTION

| | | |
|---|---|---|
| PATENT NO. | : 11,142,561 B2 | Page 1 of 1 |
| APPLICATION NO. | : 15/737605 | |
| DATED | : October 12, 2021 | |
| INVENTOR(S) | : Ong et al. | |

It is certified that error appears in the above-identified patent and that said Letters Patent is hereby corrected as shown below:

In the Specification

In Column 6, Line 54, please change "03" to --β--;

In Column 20, Line 22, please change "for to" to --for 10--;

In Column 20, Line 37, please change "for to" to --for 10--;

In Column 20, Line 49, please change "for to" to --for 10--;

In Column 21, Line 10, please change "for to" to --for 10--;

In Column 21, Line 38, please change "for to" to --for 10--;

In Column 21, Line 49, please change "for to" to --for 10--;

In Column 26, Line 22, please change "for to" to --for 10--;

In Column 26, Line 53, please change "for to" to --for 10--.

Signed and Sealed this
First Day of March, 2022

Drew Hirshfeld
*Performing the Functions and Duties of the
Under Secretary of Commerce for Intellectual Property and
Director of the United States Patent and Trademark Office*

SEQUENCE LISTING

<160> NUMBER OF SEQ ID NOS: 167

<210> SEQ ID NO 1
<211> LENGTH: 42
<212> TYPE: PRT
<213> ORGANISM: Homo sapiens

<400> SEQUENCE: 1

Ser Cys Ala Gln His Leu Asp Cys Ala Ser Cys Leu Ala His Arg Asp
1               5                   10                  15

Pro Tyr Cys Gly Trp Cys Val Leu Leu Gly Arg Cys Ser Arg Arg Ser
            20                  25                  30

Glu Cys Ser Arg Gly Gln Gly Pro Glu Gln
        35                  40

<210> SEQ ID NO 2
<211> LENGTH: 778
<212> TYPE: PRT
<213> ORGANISM: Artificial Sequence
<220> FEATURE:
<223> OTHER INFORMATION: B1SP Fusion
<220> FEATURE:
<221> NAME/KEY: Fusion Protein B1SP
<222> LOCATION: (1)..(778)

<400> SEQUENCE: 2

Met Pro Ala Leu Gly Pro Ala Leu Leu Gln Ala Leu Trp Ala Gly Trp
1               5                   10                  15

Val Leu Thr Leu Gln Pro Leu Pro Pro Thr Ala Phe Thr Pro Asn Gly
            20                  25                  30

Thr Tyr Leu Gln His Leu Ala Arg Asp Pro Thr Ser Gly Thr Leu Tyr
        35                  40                  45

Leu Gly Ala Thr Asn Phe Leu Phe Gln Leu Ser Pro Gly Leu Gln Leu
    50                  55                  60

Glu Ala Thr Val Ser Thr Gly Pro Val Leu Asp Ser Arg Asp Cys Leu
65                  70                  75                  80

Pro Pro Val Met Pro Asp Glu Cys Pro Gln Ala Gln Pro Thr Asn Asn
                85                  90                  95

Pro Asn Gln Leu Leu Leu Val Ser Pro Gly Ala Leu Val Val Cys Gly
            100                 105                 110

Ser Val His Gln Gly Val Cys Glu Gln Arg Arg Leu Gly Gln Leu Glu
        115                 120                 125

Gln Leu Leu Leu Arg Pro Glu Arg Pro Gly Asp Thr Gln Tyr Val Ala
    130                 135                 140

Ala Asn Asp Pro Ala Val Ser Thr Val Gly Leu Val Ala Gln Gly Leu
145                 150                 155                 160

Ala Gly Glu Pro Leu Leu Phe Val Gly Arg Gly Tyr Thr Ser Arg Gly
                165                 170                 175

Val Gly Gly Gly Ile Pro Pro Ile Thr Thr Arg Ala Leu Trp Pro Pro
            180                 185                 190

Asp Pro Gln Ala Ala Phe Ser Tyr Glu Glu Thr Ala Lys Leu Ala Val
        195                 200                 205

Gly Arg Leu Ser Glu Tyr Ser His His Phe Val Ser Ala Phe Ala Arg
    210                 215                 220

Gly Ala Ser Ala Tyr Phe Leu Phe Leu Arg Arg Asp Leu Gln Ala Gln
225                 230                 235                 240

Ser Arg Ala Phe Arg Ala Tyr Val Ser Arg Val Cys Leu Arg Asp Gln
                245                 250                 255

```
His Tyr Tyr Ser Tyr Val Glu Leu Pro Leu Ala Cys Glu Gly Gly Arg
            260                 265                 270

Tyr Gly Leu Ile Gln Ala Ala Val Ala Thr Ser Arg Glu Val Ala
        275                 280                 285

His Gly Glu Val Leu Phe Ala Ala Phe Ser Ser Ala Ala Pro Pro Thr
    290                 295                 300

Val Gly Arg Pro Pro Ser Ala Ala Gly Ala Ser Gly Ala Ser Ala
305                 310                 315                 320

Leu Cys Ala Phe Pro Leu Asp Glu Val Asp Arg Leu Ala Asn Arg Thr
                325                 330                 335

Arg Asp Ala Cys Tyr Thr Arg Glu Gly Arg Ala Glu Asp Gly Thr Glu
        340                 345                 350

Val Ala Tyr Ile Glu Tyr Asp Val Asn Ser Asp Cys Ala Gln Leu Pro
        355                 360                 365

Val Asp Thr Leu Asp Ala Tyr Pro Cys Gly Ser Asp His Thr Pro Ser
    370                 375                 380

Pro Met Ala Ser Arg Val Pro Leu Glu Ala Thr Pro Ile Leu Glu Trp
385                 390                 395                 400

Pro Gly Ile Gln Leu Thr Ala Val Ala Val Thr Met Glu Asp Gly His
                405                 410                 415

Thr Ile Ala Phe Leu Gly Asp Ser Gln Gly Gln Leu His Arg Val Tyr
        420                 425                 430

Leu Gly Pro Gly Ser Asp Gly His Pro Tyr Ser Thr Gln Ser Ile Gln
    435                 440                 445

Gln Gly Ser Ala Val Ser Arg Asp Leu Thr Phe Asp Gly Thr Phe Glu
450                 455                 460

His Leu Tyr Val Met Thr Gln Ser Thr Leu Leu Lys Val Pro Val Ala
465                 470                 475                 480

Ser Cys Ala Gln His Leu Asp Cys Ala Ser Cys Leu Ala His Arg Asp
                485                 490                 495

Pro Tyr Cys Gly Trp Cys Val Leu Leu Gly Arg Cys Ser Arg Arg Ser
        500                 505                 510

Glu Cys Ser Arg Gly Gln Gly Pro Glu Gln Trp Leu Trp Ser Phe Gln
        515                 520                 525

Pro Glu Leu Gly Cys Leu Gly Ser Gly Gly Ser Gly Gly Gly Gly
    530                 535                 540

Gly Ser Gly Gly Gly Ser Asp Lys Thr His Thr Cys Pro Pro Cys
545                 550                 555                 560

Pro Ala Pro Glu Leu Leu Gly Gly Pro Ser Val Phe Leu Phe Pro Pro
                565                 570                 575

Lys Pro Lys Asp Gln Leu Met Ile Ser Arg Thr Pro Glu Val Thr Cys
        580                 585                 590

Val Val Val Asp Val Ser His Glu Asp Pro Glu Val Lys Phe Asn Trp
        595                 600                 605

Tyr Val Asp Gly Val Glu Val His Asn Ala Lys Thr Lys Pro Arg Glu
    610                 615                 620

Glu Gln Tyr Asn Ser Thr Tyr Arg Val Val Ser Val Leu Thr Val Leu
625                 630                 635                 640

His Gln Asp Trp Leu Asn Gly Lys Glu Tyr Lys Cys Lys Val Ser Asn
                645                 650                 655

Lys Ala Leu Pro Ala Pro Ile Glu Lys Thr Ile Ser Lys Ala Lys Gly
        660                 665                 670
```

```
Gln Pro Arg Glu Pro Gln Val Tyr Thr Leu Pro Ser Arg Glu Glu
            675                 680                 685

Met Thr Lys Asn Gln Val Ser Leu Thr Cys Leu Val Lys Gly Phe Tyr
    690                 695                 700

Pro Ser Asp Ile Ala Val Glu Trp Glu Ser Asn Gly Gln Pro Glu Asn
705                 710                 715                 720

Asn Tyr Lys Thr Thr Pro Pro Val Leu Asp Ser Asp Gly Ser Phe Phe
            725                 730                 735

Leu Tyr Ser Lys Leu Thr Val Asp Lys Ser Arg Trp Gln Gln Gly Asn
            740                 745                 750

Val Phe Ser Cys Ser Val Leu His Glu Ala Leu His Asn His Tyr Thr
            755                 760                 765

Gln Lys Ser Leu Ser Leu Ser Pro Gly Lys
            770                 775

<210> SEQ ID NO 3
<211> LENGTH: 2337
<212> TYPE: DNA
<213> ORGANISM: Artificial Sequence
<220> FEATURE:
<223> OTHER INFORMATION: DNA Sequence encoding B1SP fusion protein of
      SEQ ID NO:2
<220> FEATURE:
<221> NAME/KEY: encoding B1SP Fusion DNA
<222> LOCATION: (1)..(2337)

<400> SEQUENCE: 3
atgcctgctc tgggcccagc tcttctccag gctctctggg ccgggtgggt cctcaccctc        60
cagccccttc caccaactgc attcactccc aatggcacgt atctgcagca cctggcaagg       120
gaccccacct caggcaccct ctacctgggg gctaccaact tcctgttcca gctgagccct       180
gggctgcagc tggaggccac agtgtccacc ggccctgtgc tagacagcag ggactgcctg       240
ccacctgtga tgcctgatga gtgccccag gcccagccta ccaacaaccc gaatcagctg       300
ctcctggtga cccaggggc cctggtggta tgcgggagcg tgcaccaggg ggtctgtgaa       360
cagcggcgcc tggggcagct cgagcagctg ctgctgcggc cagagcggcc tgggacaca       420 caatatgtgg ctgccaatga tcctgcgtc agcacggtgg ggctggtagc ccagggcttg       480
gcaggggagc ccctcctgtt tgtggggcga ggatacacca gcaggggtgt gggggtggc       540 attccaccca tcacaacccg ggccctgtgg ccgcccgacc cccaagctgc cttctcctat       600
gaggagacag ccaagctggc agtgggccgc ctctccgagt acagccacca cttcgtgagt       660
gcctttgcac gtgggggccag cgcctacttc ctgttcctgc ggcgggacct gcaggctcag       720
tctagagctt tcgtgcctta tgtatctcga gtgtgtctcc gggaccagca ctactactcc       780
tatgtggagt gcctctggc ctgcgaaggt ggccgctacg gctgatccca ggctgcagct       840
gtggccacgt ccagggaggt ggcgcatggg gaggtgctct ttgcagcttt ctcctcggct       900
gcacccccca ctgtgggccg gcccccatcg gcggctgctg ggcatctgg agcctctgcc       960 ctctgtgcct tcccctgga tgaggtggac cggcttgcta atcgcacgcg agatgcctgc      1020
tacacccggg agggtcgtgc tgaggatggg accgaggtgg cctacatcga gtatgatgtc      1080
aattctgact gtgcacagct gccagtgac acctgatgt cttatccctg ggctcagac      1140 cacacgccca gcccatggc cagccgggtc cgctggaag ccacaccaat tctggagtgg      1200
ccagggattc agctaacagc tgtggcagtc accatgaag atggacacac catcgctttc      1260
ctgggtgata gtcaagggca gctgcacagg gtctacttgg gcccagggag cgatggccac      1320
```

```
ccatactcca cacagagcat ccagcagggg tctgcagtga gcagagacct cacctttgat    1380
gggacctttg agcacctgta tgtcatgacc cagagcacac ttctgaaggt tcctgtggct    1440
tcctgtgctc agcacctgga ctgtgcatct tgccttgctc acagggaccc atactgtggg    1500
tggtgcgtgc tccttggcag gtgcagtcgc cgttctgagt gctcgagggg ccagggccca    1560
gagcagtggc tatggagctt ccagcctgag ctgggctgtc tgggatccgg tggcggttcc    1620
ggtggtggag gcggaagcgg cggtggagga tcagacaaaa ctcacacatg cccaccgtgc    1680
ccagcacctg aactcctggg gggaccgtca gtcttcctct tccccccaaa acccaaggac    1740
caactgatga tctcccggac ccctgaggtc acatgcgtgg tggtggacgt gagccacgaa    1800
gaccctgagg tcaagttcaa ctggtacgtg gacggcgtgg aggtgcataa tgccaagaca    1860
aagccgcggg aggagcagta acagcacg taccgtgtgg tcagcgtcct caccgtcctg    1920
caccaggact ggctgaatgg caaggagtac aagtgcaagg tctccaacaa agccctccca    1980
gcccccatcg agaaaaccat ctccaaagcc aaagggcagc cccgagaacc acaggtgtac    2040
accctgcccc catcccggga ggagatgacc aagaaccagg tcagcctgac ctgcctggtc    2100
aaaggcttct atcccagcga catcgccgtg gagtgggaga gcaatgggca gccggagaac    2160
aactacaaga ccacgcctcc cgtgctggac tccgacggct ccttcttcct ctacagcaag    2220
ctcaccgtgg acaagagcag gtggcagcag gggaacgtct tctcatgctc cgtgctgcat    2280
gaggctctgc acaaccacta cacgcagaag agcctctccc tgtctccggg taaatga    2337
```

<210> SEQ ID NO 4
<211> LENGTH: 1182
<212> TYPE: PRT
<213> ORGANISM: Artificial Sequence
<220> FEATURE:
<223> OTHER INFORMATION: ALB-L-SDPSI or ALB SRGLI
<220> FEATURE:
<221> NAME/KEY: Fusion Protein ALB-L-SDPSI Albumin
<222> LOCATION: (1)..(1182)

<400> SEQUENCE: 4

```
Met Ala Phe Arg Thr Ile Cys Val Leu Val Gly Val Phe Ile Cys Ser
1               5                   10                  15

Ile Cys Val Lys His His His His His His Met Lys Trp Val
                20                  25                  30

Thr Phe Ile Ser Leu Leu Phe Leu Phe Ser Ser Ala Tyr Ser Arg Gly
            35                  40                  45

Val Phe Arg Arg Asp Ala His Lys Ser Glu Val Ala His Arg Phe Lys
        50                  55                  60

Asp Leu Gly Glu Glu Asn Phe Lys Ala Leu Val Leu Ile Ala Phe Ala
65                  70                  75                  80

Gln Tyr Leu Gln Gln Cys Pro Phe Glu Asp His Val Lys Leu Val Asn
                85                  90                  95

Glu Val Thr Glu Phe Ala Lys Thr Cys Val Ala Asp Glu Ser Ala Glu
            100                 105                 110

Asn Cys Asp Lys Ser Leu His Thr Leu Phe Gly Asp Lys Leu Cys Thr
        115                 120                 125

Val Ala Thr Leu Arg Glu Thr Tyr Gly Glu Met Ala Asp Cys Cys Ala
    130                 135                 140

Lys Gln Glu Pro Glu Arg Asn Glu Cys Phe Leu Gln His Lys Asp Asp
145                 150                 155                 160

Asn Pro Asn Leu Pro Arg Leu Val Arg Pro Glu Val Asp Val Met Cys
                165                 170                 175
```

Thr Ala Phe His Asp Asn Glu Glu Thr Phe Leu Lys Lys Tyr Leu Tyr
            180                 185                 190

Glu Ile Ala Arg Arg His Pro Tyr Phe Tyr Ala Pro Glu Leu Leu Phe
        195                 200                 205

Phe Ala Lys Arg Tyr Lys Ala Ala Phe Thr Glu Cys Cys Gln Ala Ala
    210                 215                 220

Asp Lys Ala Ala Cys Leu Leu Pro Lys Leu Asp Glu Leu Arg Asp Glu
225                 230                 235                 240

Gly Lys Ala Ser Ser Ala Lys Gln Arg Leu Lys Cys Ala Ser Leu Gln
                245                 250                 255

Lys Phe Gly Glu Arg Ala Phe Lys Ala Trp Ala Val Ala Arg Leu Ser
            260                 265                 270

Gln Arg Phe Pro Lys Ala Glu Phe Ala Glu Val Ser Lys Leu Val Thr
        275                 280                 285

Asp Leu Thr Lys Val His Thr Glu Cys Cys His Gly Asp Leu Leu Glu
    290                 295                 300

Cys Ala Asp Asp Arg Ala Asp Leu Ala Lys Tyr Ile Cys Glu Asn Gln
305                 310                 315                 320

Asp Ser Ile Ser Ser Lys Leu Lys Glu Cys Cys Glu Lys Pro Leu Leu
                325                 330                 335

Glu Lys Ser His Cys Ile Ala Glu Val Glu Asn Asp Glu Met Pro Ala
            340                 345                 350

Asp Leu Pro Ser Leu Ala Ala Asp Phe Val Glu Ser Lys Asp Val Cys
        355                 360                 365

Lys Asn Tyr Ala Glu Ala Lys Asp Val Phe Leu Gly Met Phe Leu Tyr
    370                 375                 380

Glu Tyr Ala Arg Arg His Pro Asp Tyr Ser Val Val Leu Leu Leu Arg
385                 390                 395                 400

Leu Ala Lys Thr Tyr Glu Thr Thr Leu Glu Lys Cys Cys Ala Ala Ala
                405                 410                 415

Asp Pro His Glu Cys Tyr Ala Lys Val Phe Asp Glu Phe Lys Pro Leu
            420                 425                 430

Val Glu Glu Pro Gln Asn Leu Ile Lys Gln Asn Cys Glu Leu Phe Glu
        435                 440                 445

Gln Leu Gly Glu Tyr Lys Phe Gln Asn Ala Leu Leu Val Arg Tyr Thr
    450                 455                 460

Lys Lys Val Pro Gln Val Ser Thr Pro Thr Leu Val Glu Val Ser Arg
465                 470                 475                 480

Asn Leu Gly Lys Val Gly Ser Lys Cys Cys Lys His Pro Glu Ala Lys
                485                 490                 495

Arg Met Pro Cys Ala Glu Asp Tyr Leu Ser Val Val Leu Asn Gln Leu
            500                 505                 510

Cys Val Leu His Glu Lys Thr Pro Val Ser Asp Arg Val Thr Lys Cys
        515                 520                 525

Cys Thr Glu Ser Leu Val Asn Arg Arg Pro Cys Phe Ser Ala Leu Glu
    530                 535                 540

Val Asp Glu Thr Tyr Val Pro Lys Glu Phe Asn Ala Glu Thr Phe Thr
545                 550                 555                 560

Phe His Ala Asp Ile Cys Thr Leu Ser Glu Lys Glu Arg Gln Ile Lys
                565                 570                 575

Lys Gln Thr Ala Leu Val Glu Leu Val Lys His Lys Pro Lys Ala Thr
            580                 585                 590

```
Lys Glu Gln Leu Lys Ala Val Met Asp Asp Phe Ala Ala Phe Val Glu
            595                 600                 605

Lys Cys Cys Lys Ala Asp Asp Lys Glu Thr Cys Phe Ala Glu Glu Gly
        610                 615                 620

Lys Lys Leu Val Ala Ala Ser Gln Ala Ala Leu Gly Leu Gly Ser Gly
625                 630                 635                 640

Gly Gly Ser Gly Gly Gly Gly Ser Gly Gly Gly Ser Gly Ser
                645                 650                 655

Ser Gln Pro Gln Ala Arg Val Tyr Leu Thr Phe Asp Glu Leu Arg Glu
                660                 665                 670

Thr Lys Thr Ser Glu Tyr Phe Ser Leu Ser His His Pro Leu Asp Tyr
        675                 680                 685

Arg Ile Leu Leu Met Asp Glu Asp Gln Asp Arg Ile Tyr Val Gly Ser
        690                 695                 700

Lys Asp His Ile Leu Ser Leu Asn Ile Asn Asn Ile Ser Gln Glu Ala
705                 710                 715                 720

Leu Ser Val Phe Trp Pro Ala Ser Thr Ile Lys Val Glu Glu Cys Lys
                725                 730                 735

Met Ala Gly Lys Asp Pro Thr His Gly Cys Gly Asn Phe Val Arg Val
                740                 745                 750

Ile Gln Thr Phe Asn Arg Thr His Leu Tyr Val Cys Gly Ser Gly Ala
                755                 760                 765

Phe Ser Pro Val Cys Thr Tyr Leu Asn Arg Gly Arg Arg Ser Glu Asp
        770                 775                 780

Gln Val Phe Met Ile Asp Ser Lys Cys Glu Ser Gly Lys Gly Arg Cys
785                 790                 795                 800

Ser Phe Asn Pro Asn Val Asn Thr Val Ser Val Met Ile Asn Glu Glu
                805                 810                 815

Leu Phe Ser Gly Met Tyr Ile Asp Phe Met Gly Thr Asp Ala Ala Ile
                820                 825                 830

Phe Arg Ser Leu Thr Lys Arg Asn Ala Val Arg Thr Asp Gln His Asn
                835                 840                 845

Ser Lys Trp Leu Ser Glu Pro Met Phe Val Asp Ala His Val Ile Pro
        850                 855                 860

Asp Gly Thr Asp Pro Asn Asp Ala Lys Val Tyr Phe Phe Phe Lys Glu
865                 870                 875                 880

Lys Leu Thr Asp Asn Asn Arg Ser Thr Lys Gln Ile His Ser Met Ile
                885                 890                 895

Ala Arg Ile Cys Pro Asn Asp Thr Gly Gly Leu Arg Ser Leu Val Asn
                900                 905                 910

Lys Trp Thr Thr Phe Leu Lys Ala Arg Leu Val Cys Ser Val Thr Asp
        915                 920                 925

Glu Asp Gly Pro Glu Thr His Phe Asp Glu Leu Glu Asp Val Phe Leu
930                 935                 940

Leu Glu Thr Asp Asn Pro Arg Thr Thr Leu Val Tyr Gly Ile Phe Thr
945                 950                 955                 960

Thr Ser Ser Ser Val Phe Lys Gly Ser Ala Val Cys Val Tyr His Leu
                965                 970                 975

Ser Asp Ile Gln Thr Val Phe Asn Gly Pro Phe Ala His Lys Glu Gly
            980                 985                 990

Pro Asn His Gln Leu Ile Ser Tyr Gln Gly Arg Ile Pro Tyr Pro Arg
            995                 1000                1005

Pro Gly Thr Cys Pro Gly Gly Ala Phe Thr Pro Asn Met Arg Thr
```

```
            1010                1015                1020

Thr Lys Glu Phe Pro Asp Asp Val Val Thr Phe Ile Arg Asn His
    1025                1030                1035

Pro Leu Met Tyr Asn Ser Ile Tyr Pro Ile His Lys Arg Pro Leu
    1040                1045                1050

Ile Val Arg Ile Gly Thr Asp Tyr Lys Tyr Thr Lys Ile Ala Val
    1055                1060                1065

Asp Arg Val Asn Ala Ala Asp Gly Arg Tyr His Val Leu Phe Leu
    1070                1075                1080

Gly Thr Asp Arg Gly Thr Val Gln Lys Val Val Leu Pro Thr
    1085                1090                1095

Asn Asn Ser Val Ser Gly Glu Leu Ile Leu Glu Glu Leu Glu Val
    1100                1105                1110

Phe Lys Asn His Ala Pro Ile Thr Thr Met Lys Ile Ser Ser Lys
    1115                1120                1125

Lys Gln Gln Leu Tyr Val Ser Ser Asn Glu Gly Val Ser Gln Val
    1130                1135                1140

Ser Leu His Arg Cys His Ile Tyr Gly Thr Ala Cys Ala Asp Cys
    1145                1150                1155

Cys Leu Ala Arg Asp Pro Tyr Cys Ala Trp Asp Gly His Ser Cys
    1160                1165                1170

Ser Arg Phe Tyr Pro Thr Gly Lys Arg
    1175                1180

<210> SEQ ID NO 5
<211> LENGTH: 1157
<212> TYPE: PRT
<213> ORGANISM: Artificial Sequence
<220> FEATURE:
<223> OTHER INFORMATION: SDPSI-L-ALB
<220> FEATURE:
<221> NAME/KEY: Fusion Protein SDPSI-L-ALB
<222> LOCATION: (1)..(1157)

<400> SEQUENCE: 5

Met Ala Phe Arg Thr Ile Cys Val Leu Val Gly Val Phe Ile Cys Ser
1               5                   10                  15

Ile Cys Val Lys Gly Ser Ser Gln Pro Gln Ala Arg Val Tyr Leu Thr
                20                  25                  30

Phe Asp Glu Leu Arg Glu Thr Lys Thr Ser Glu Tyr Phe Ser Leu Ser
            35                  40                  45

His His Pro Leu Asp Tyr Arg Ile Leu Leu Met Asp Glu Asp Gln Asp
        50                  55                  60

Arg Ile Tyr Val Gly Ser Lys Asp His Ile Leu Ser Leu Asn Ile Asn
65                  70                  75                  80

Asn Ile Ser Gln Glu Ala Leu Ser Val Phe Trp Pro Ala Ser Thr Ile
                85                  90                  95

Lys Val Glu Glu Cys Lys Met Ala Gly Lys Asp Pro Thr His Gly Cys
                100                 105                 110

Gly Asn Phe Val Arg Val Ile Gln Thr Phe Asn Arg Thr His Leu Tyr
            115                 120                 125

Val Cys Gly Ser Gly Ala Phe Ser Pro Val Cys Thr Tyr Leu Asn Arg
        130                 135                 140

Gly Arg Arg Ser Glu Asp Gln Val Phe Met Ile Asp Ser Lys Cys Glu
145                 150                 155                 160

Ser Gly Lys Gly Arg Cys Ser Phe Asn Pro Asn Val Asn Thr Val Ser
```

-continued

```
                165                 170                 175
Val Met Ile Asn Glu Leu Phe Ser Gly Met Tyr Ile Asp Phe Met
            180                 185                 190
Gly Thr Asp Ala Ala Ile Phe Arg Ser Leu Thr Lys Arg Asn Ala Val
            195                 200                 205
Arg Thr Asp Gln His Asn Ser Lys Trp Leu Ser Glu Pro Met Phe Val
            210                 215                 220
Asp Ala His Val Ile Pro Asp Gly Thr Asp Pro Asn Asp Ala Lys Val
225                 230                 235                 240
Tyr Phe Phe Phe Lys Glu Lys Leu Thr Asp Asn Asn Arg Ser Thr Lys
                245                 250                 255
Gln Ile His Ser Met Ile Ala Arg Ile Cys Pro Asn Asp Thr Gly Gly
            260                 265                 270
Leu Arg Ser Leu Val Asn Lys Trp Thr Thr Phe Leu Lys Ala Arg Leu
            275                 280                 285
Val Cys Ser Val Thr Asp Glu Asp Gly Pro Glu Thr His Phe Asp Glu
            290                 295                 300
Leu Glu Asp Val Phe Leu Leu Glu Thr Asp Asn Pro Arg Thr Thr Leu
305                 310                 315                 320
Val Tyr Gly Ile Phe Thr Thr Ser Ser Ser Val Phe Lys Gly Ser Ala
                325                 330                 335
Val Cys Val Tyr His Leu Ser Asp Ile Gln Thr Val Phe Asn Gly Pro
            340                 345                 350
Phe Ala His Lys Glu Gly Pro Asn His Gln Leu Ile Ser Tyr Gln Gly
            355                 360                 365
Arg Ile Pro Tyr Pro Arg Pro Gly Thr Cys Pro Gly Gly Ala Phe Thr
            370                 375                 380
Pro Asn Met Arg Thr Thr Lys Glu Phe Pro Asp Asp Val Val Thr Phe
385                 390                 395                 400
Ile Arg Asn His Pro Leu Met Tyr Asn Ser Ile Tyr Pro Ile His Lys
                405                 410                 415
Arg Pro Leu Ile Val Arg Ile Gly Thr Asp Tyr Lys Tyr Thr Lys Ile
            420                 425                 430
Ala Val Asp Arg Val Asn Ala Ala Asp Gly Arg Tyr His Val Leu Phe
            435                 440                 445
Leu Gly Thr Asp Arg Gly Thr Val Gln Lys Val Val Leu Pro Thr
            450                 455                 460
Asn Asn Ser Val Ser Gly Glu Leu Ile Leu Glu Glu Leu Glu Val Phe
465                 470                 475                 480
Lys Asn His Ala Pro Ile Thr Thr Met Lys Ile Ser Ser Lys Lys Gln
                485                 490                 495
Gln Leu Tyr Val Ser Ser Asn Glu Gly Val Ser Gln Val Ser Leu His
            500                 505                 510
Arg Cys His Ile Tyr Gly Thr Ala Cys Ala Asp Cys Cys Leu Ala Arg
            515                 520                 525
Asp Pro Tyr Cys Ala Trp Asp Gly His Ser Cys Ser Arg Phe Tyr Pro
            530                 535                 540
Thr Gly Lys Gly Ser Gly Gly Ser Gly Gly Gly Gly Ser Gly
545                 550                 555                 560
Gly Gly Gly Ser Asp Ala His Lys Ser Glu Val Ala His Arg Phe Lys
                565                 570                 575
Asp Leu Gly Glu Glu Asn Phe Lys Ala Leu Val Leu Ile Ala Phe Ala
            580                 585                 590
```

Gln Tyr Leu Gln Gln Cys Pro Phe Glu Asp His Val Lys Leu Val Asn
            595                 600                 605

Glu Val Thr Glu Phe Ala Lys Thr Cys Val Ala Asp Glu Ser Ala Glu
            610                 615                 620

Asn Cys Asp Lys Ser Leu His Thr Leu Phe Gly Asp Lys Leu Cys Thr
625                 630                 635                 640

Val Ala Thr Leu Arg Glu Thr Tyr Gly Glu Met Ala Asp Cys Cys Ala
                645                 650                 655

Lys Gln Glu Pro Glu Arg Asn Glu Cys Phe Leu Gln His Lys Asp Asp
                660                 665                 670

Asn Pro Asn Leu Pro Arg Leu Val Arg Pro Glu Val Asp Val Met Cys
                675                 680                 685

Thr Ala Phe His Asp Asn Glu Glu Thr Phe Leu Lys Lys Tyr Leu Tyr
            690                 695                 700

Glu Ile Ala Arg Arg His Pro Tyr Phe Tyr Ala Pro Glu Leu Leu Phe
705                 710                 715                 720

Phe Ala Lys Arg Tyr Lys Ala Ala Phe Thr Glu Cys Cys Gln Ala Ala
                725                 730                 735

Asp Lys Ala Ala Cys Leu Leu Pro Lys Leu Asp Glu Leu Arg Asp Glu
                740                 745                 750

Gly Lys Ala Ser Ser Ala Lys Gln Arg Leu Lys Cys Ala Ser Leu Gln
            755                 760                 765

Lys Phe Gly Glu Arg Ala Phe Lys Ala Trp Ala Val Ala Arg Leu Ser
770                 775                 780

Gln Arg Phe Pro Lys Ala Glu Phe Ala Glu Val Ser Lys Leu Val Thr
785                 790                 795                 800

Asp Leu Thr Lys Val His Thr Glu Cys Cys His Gly Asp Leu Leu Glu
            805                 810                 815

Cys Ala Asp Asp Arg Ala Asp Leu Ala Lys Tyr Ile Cys Glu Asn Gln
                820                 825                 830

Asp Ser Ile Ser Ser Lys Leu Lys Glu Cys Cys Glu Lys Pro Leu Leu
            835                 840                 845

Glu Lys Ser His Cys Ile Ala Glu Val Glu Asn Asp Glu Met Pro Ala
            850                 855                 860

Asp Leu Pro Ser Leu Ala Ala Asp Phe Val Glu Ser Lys Asp Val Cys
865                 870                 875                 880

Lys Asn Tyr Ala Glu Ala Lys Asp Val Phe Leu Gly Met Phe Leu Tyr
                885                 890                 895

Glu Tyr Ala Arg Arg His Pro Asp Tyr Ser Val Val Leu Leu Leu Arg
                900                 905                 910

Leu Ala Lys Thr Tyr Glu Thr Thr Leu Glu Lys Cys Cys Ala Ala Ala
            915                 920                 925

Asp Pro His Glu Cys Tyr Ala Lys Val Phe Asp Glu Phe Lys Pro Leu
            930                 935                 940

Val Glu Glu Pro Gln Asn Leu Ile Lys Gln Asn Cys Glu Leu Phe Glu
945                 950                 955                 960

Gln Leu Gly Glu Tyr Lys Phe Gln Asn Ala Leu Leu Val Arg Tyr Thr
                965                 970                 975

Lys Lys Val Pro Gln Val Ser Thr Pro Thr Leu Val Glu Val Ser Arg
            980                 985                 990

Asn Leu Gly Lys Val Gly Ser Lys Cys Cys Lys His Pro Glu Ala Lys
            995                1000                1005

```
Arg Met Pro Cys Ala Glu Asp Tyr Leu Ser Val Val Leu Asn Gln
    1010            1015                1020

Leu Cys Val Leu His Glu Lys Thr Pro Val Ser Asp Arg Val Thr
    1025            1030                1035

Lys Cys Cys Thr Glu Ser Leu Val Asn Arg Arg Pro Cys Phe Ser
    1040            1045                1050

Ala Leu Glu Val Asp Glu Thr Tyr Val Pro Lys Glu Phe Asn Ala
    1055            1060                1065

Glu Thr Phe Thr Phe His Ala Asp Ile Cys Thr Leu Ser Glu Lys
    1070            1075                1080

Glu Arg Gln Ile Lys Lys Gln Thr Ala Leu Val Glu Leu Val Lys
    1085            1090                1095

His Lys Pro Lys Ala Thr Lys Glu Gln Leu Lys Ala Val Met Asp
    1100            1105                1110

Asp Phe Ala Ala Phe Val Glu Lys Cys Cys Lys Ala Asp Asp Lys
    1115            1120                1125

Glu Thr Cys Phe Ala Glu Glu Gly Lys Lys Leu Val Ala Ala Ser
    1130            1135                1140

Gln Ala Ala Leu Gly Leu His His His His His His His
    1145            1150                1155

<210> SEQ ID NO 6
<211> LENGTH: 983
<212> TYPE: PRT
<213> ORGANISM: Artificial Sequence
<220> FEATURE:
<223> OTHER INFORMATION: SEMA3C:FC full length SEMA3C with mutations in
      two furin cleavage sites, a linker and Fc region at the C terminus
<220> FEATURE:
<221> NAME/KEY: SEMA3C:FC full length SEMA3C with mutations in two furin
      cleavage sites, a linker and Fc region at the C terminus
<222> LOCATION: (1)..(983)

<400> SEQUENCE: 6

Met Ala Phe Arg Thr Ile Cys Val Leu Val Gly Val Phe Ile Cys Ser
1               5                   10                  15

Ile Cys Val Lys Gly Ser Ser Gln Pro Gln Ala Arg Val Tyr Leu Thr
            20                  25                  30

Phe Asp Glu Leu Arg Glu Thr Lys Thr Ser Glu Tyr Phe Ser Leu Ser
        35                  40                  45

His His Pro Leu Asp Tyr Arg Ile Leu Leu Met Asp Glu Asp Gln Asp
    50                  55                  60

Arg Ile Tyr Val Gly Ser Lys Asp His Ile Leu Ser Leu Asn Ile Asn
65                  70                  75                  80

Asn Ile Ser Gln Glu Ala Leu Ser Val Phe Trp Pro Ala Ser Thr Ile
                85                  90                  95

Lys Val Glu Glu Cys Lys Met Ala Gly Lys Asp Pro Thr His Gly Cys
            100                 105                 110

Gly Asn Phe Val Arg Val Ile Gln Thr Phe Asn Arg Thr His Leu Tyr
        115                 120                 125

Val Cys Gly Ser Gly Ala Phe Ser Pro Val Cys Thr Tyr Leu Asn Arg
    130                 135                 140

Gly Arg Arg Ser Glu Asp Gln Val Phe Met Ile Asp Ser Lys Cys Glu
145                 150                 155                 160

Ser Gly Lys Gly Arg Cys Ser Phe Asn Pro Asn Val Asn Thr Val Ser
                165                 170                 175

Val Met Ile Asn Glu Glu Leu Phe Ser Gly Met Tyr Ile Asp Phe Met
```

```
            180                 185                 190
Gly Thr Asp Ala Ala Ile Phe Arg Ser Leu Thr Lys Arg Asn Ala Val
            195                 200                 205
Arg Thr Asp Gln His Asn Ser Lys Trp Leu Ser Glu Pro Met Phe Val
            210                 215                 220
Asp Ala His Val Ile Pro Asp Gly Thr Asp Pro Asn Asp Ala Lys Val
225                 230                 235                 240
Tyr Phe Phe Lys Glu Lys Leu Thr Asp Asn Asn Arg Ser Thr Lys
                245                 250                 255
Gln Ile His Ser Met Ile Ala Arg Ile Cys Pro Asn Asp Thr Gly Gly
            260                 265                 270
Leu Arg Ser Leu Val Asn Lys Trp Thr Thr Phe Leu Lys Ala Arg Leu
            275                 280                 285
Val Cys Ser Val Thr Asp Glu Asp Gly Pro Thr His Phe Asp Glu
            290                 295                 300
Leu Glu Asp Val Phe Leu Leu Glu Thr Asp Asn Pro Arg Thr Thr Leu
305                 310                 315                 320
Val Tyr Gly Ile Phe Thr Thr Ser Ser Ser Val Phe Lys Gly Ser Ala
                325                 330                 335
Val Cys Val Tyr His Leu Ser Asp Ile Gln Thr Val Phe Asn Gly Pro
            340                 345                 350
Phe Ala His Lys Glu Gly Pro Asn His Gln Leu Ile Ser Tyr Gln Gly
            355                 360                 365
Arg Ile Pro Tyr Pro Arg Pro Gly Thr Cys Pro Gly Gly Ala Phe Thr
            370                 375                 380
Pro Asn Met Arg Thr Thr Lys Glu Phe Pro Asp Asp Val Val Thr Phe
385                 390                 395                 400
Ile Arg Asn His Pro Leu Met Tyr Asn Ser Ile Tyr Pro Ile His Lys
                405                 410                 415
Arg Pro Leu Ile Val Arg Ile Gly Thr Asp Tyr Lys Tyr Thr Lys Ile
            420                 425                 430
Ala Val Asp Arg Val Asn Ala Ala Asp Gly Arg Tyr His Val Leu Phe
            435                 440                 445
Leu Gly Thr Asp Arg Gly Thr Val Gln Lys Val Val Val Leu Pro Thr
            450                 455                 460
Asn Asn Ser Val Ser Gly Glu Leu Ile Leu Glu Glu Leu Glu Val Phe
465                 470                 475                 480
Lys Asn His Ala Pro Ile Thr Thr Met Lys Ile Ser Ser Lys Lys Gln
                485                 490                 495
Gln Leu Tyr Val Ser Ser Asn Glu Gly Val Ser Gln Val Ser Leu His
            500                 505                 510
Arg Cys His Ile Tyr Gly Thr Ala Cys Ala Asp Cys Cys Leu Ala Arg
            515                 520                 525
Asp Pro Tyr Cys Ala Trp Asp Gly His Ser Cys Ser Arg Phe Tyr Pro
            530                 535                 540
Thr Gly Lys Arg Arg Ser Ala Ala Gln Asp Val Arg His Gly Asn Pro
545                 550                 555                 560
Leu Thr Gln Cys Arg Gly Phe Asn Leu Lys Ala Tyr Arg Asn Ala Ala
                565                 570                 575
Glu Ile Val Gln Tyr Gly Val Lys Asn Asn Thr Thr Phe Leu Glu Cys
            580                 585                 590
Ala Pro Lys Ser Pro Gln Ala Ser Ile Lys Trp Leu Leu Gln Lys Asp
            595                 600                 605
```

```
Lys Asp Ala Ala Lys Glu Val Lys Leu Asn Glu Arg Ile Ile Ala Thr
            610                 615                 620
Ser Gln Gly Leu Leu Ile Arg Ser Val Gln Gly Ser Asp Gln Gly Leu
625                 630                 635                 640
Tyr His Cys Ile Ala Thr Glu Asn Ser Phe Lys Gln Thr Ile Ala Lys
                    645                 650                 655
Ile Asn Phe Lys Val Leu Asp Ser Glu Met Val Ala Val Thr Asp
                660                 665                 670
Lys Trp Ser Pro Trp Thr Trp Ala Ser Ser Val Arg Ala Leu Pro Phe
            675                 680                 685
His Pro Lys Asp Ile Met Gly Ala Phe Ser His Ser Glu Met Gln Met
690                 695                 700
Ile Asn Gln Tyr Cys Lys Asp Thr Arg Gln Gln His Gln Gln Gly Asp
705                 710                 715                 720
Glu Ser Gln Lys Met Arg Gly Asp Tyr Gly Lys Leu Lys Ala Leu Ile
                725                 730                 735
Asn Ser Ile Glu Gly Arg Met Asp Pro Lys Ser Cys Asp Lys Thr His
                740                 745                 750
Thr Cys Pro Pro Cys Pro Ala Pro Glu Leu Leu Gly Gly Pro Ser Val
            755                 760                 765
Phe Leu Phe Pro Pro Lys Pro Lys Asp Thr Leu Met Ile Ser Arg Thr
770                 775                 780
Pro Glu Val Thr Cys Val Val Val Asp Val Ser His Glu Asp Pro Glu
785                 790                 795                 800
Val Lys Phe Asn Trp Tyr Val Asp Gly Val Glu Val His Asn Ala Lys
                805                 810                 815
Thr Lys Pro Arg Glu Glu Gln Tyr Asn Ser Thr Tyr Arg Val Val Ser
            820                 825                 830
Val Leu Thr Val Leu His Gln Asp Trp Leu Asn Gly Lys Glu Tyr Lys
            835                 840                 845
Cys Lys Val Ser Asn Lys Ala Leu Pro Ala Pro Ile Glu Lys Thr Ile
850                 855                 860
Ser Lys Ala Lys Gly Gln Pro Arg Glu Pro Gln Val Tyr Thr Leu Pro
865                 870                 875                 880
Pro Ser Arg Asp Glu Leu Thr Lys Asn Gln Val Ser Leu Thr Cys Leu
                885                 890                 895
Val Lys Gly Phe Tyr Pro Ser Asp Ile Ala Val Glu Trp Glu Ser Asn
                900                 905                 910
Gly Gln Pro Glu Asn Asn Tyr Lys Thr Thr Pro Pro Val Leu Asp Ser
            915                 920                 925
Asp Gly Ser Phe Phe Leu Tyr Ser Lys Leu Thr Val Asp Lys Ser Arg
930                 935                 940
Trp Gln Gln Gly Asn Val Phe Ser Cys Ser Val Met His Glu Ala Leu
945                 950                 955                 960
His Asn His Tyr Thr Gln Lys Ser Leu Ser Leu Ser Pro Gly Lys His
                965                 970                 975
His His His His His His
            980

<210> SEQ ID NO 7
<211> LENGTH: 23
<212> TYPE: RNA
<213> ORGANISM: Artificial Sequence
<220> FEATURE:
```

```
<223> OTHER INFORMATION: scramble siRNA
<220> FEATURE:
<221> NAME/KEY: siRNA scamrable
<222> LOCATION: (1)..(23)

<400> SEQUENCE: 7
aucaaacugu ugucagcgcu guu                                              23

<210> SEQ ID NO 8
<211> LENGTH: 23
<212> TYPE: RNA
<213> ORGANISM: Homo sapiens

<400> SEQUENCE: 8
ccggguggaa uuuauccuug auu                                              23

<210> SEQ ID NO 9
<211> LENGTH: 21
<212> TYPE: RNA
<213> ORGANISM: Homo sapiens

<400> SEQUENCE: 9
accacgguca cccggauucu u                                                21

<210> SEQ ID NO 10
<211> LENGTH: 1545
<212> TYPE: PRT
<213> ORGANISM: Artificial Sequence
<220> FEATURE:
<223> OTHER INFORMATION: B1R4 Fusion Protein
<220> FEATURE:
<221> NAME/KEY: B1R4 Protein Fusion
<222> LOCATION: (1)..(1545)

<400> SEQUENCE: 10
```

Met Pro Ala Leu Gly Pro Ala Leu Leu Gln Ala Leu Trp Ala Gly Trp
1               5                   10                  15

Val Leu Thr Leu Gln Pro Leu Pro Pro Thr Ala Phe Thr Pro Asn Gly
            20                  25                  30

Thr Tyr Leu Gln His Leu Ala Arg Asp Pro Thr Ser Gly Thr Leu Tyr
        35                  40                  45

Leu Gly Ala Thr Asn Phe Leu Phe Gln Leu Ser Pro Gly Leu Gln Leu
    50                  55                  60

Glu Ala Thr Val Ser Thr Gly Pro Val Leu Asp Ser Arg Asp Cys Leu
65                  70                  75                  80

Pro Pro Val Met Pro Asp Glu Cys Pro Gln Ala Gln Pro Thr Asn Asn
                85                  90                  95

Pro Asn Gln Leu Leu Leu Val Ser Pro Gly Ala Leu Val Val Cys Gly
            100                 105                 110

Ser Val His Gln Gly Val Cys Glu Gln Arg Arg Leu Gly Gln Leu Glu
        115                 120                 125

Gln Leu Leu Leu Arg Pro Glu Arg Pro Gly Asp Thr Gln Tyr Val Ala
    130                 135                 140

Ala Asn Asp Pro Ala Val Ser Thr Val Gly Leu Val Ala Gln Gly Leu
145                 150                 155                 160

Ala Gly Glu Pro Leu Leu Phe Val Gly Arg Gly Tyr Thr Ser Arg Gly
                165                 170                 175

Val Gly Gly Gly Ile Pro Pro Ile Thr Thr Arg Ala Leu Trp Pro Pro
            180                 185                 190

Asp Pro Gln Ala Ala Phe Ser Tyr Glu Glu Thr Ala Lys Leu Ala Val

```
            195                 200                 205
Gly Arg Leu Ser Glu Tyr Ser His His Phe Val Ser Ala Phe Ala Arg
210                 215                 220

Gly Ala Ser Ala Tyr Phe Leu Phe Leu Arg Arg Asp Leu Gln Ala Gln
225                 230                 235                 240

Ser Arg Ala Phe Arg Ala Tyr Val Ser Arg Val Cys Leu Arg Asp Gln
                    245                 250                 255

His Tyr Tyr Ser Tyr Val Glu Leu Pro Leu Ala Cys Glu Gly Gly Arg
                260                 265                 270

Tyr Gly Leu Ile Gln Ala Ala Val Ala Thr Ser Arg Glu Val Ala
            275                 280                 285

His Gly Glu Val Leu Phe Ala Ala Phe Ser Ser Ala Ala Pro Pro Thr
290                 295                 300

Val Gly Arg Pro Pro Ser Ala Ala Ala Gly Ala Ser Gly Ala Ser Ala
305                 310                 315                 320

Leu Cys Ala Phe Pro Leu Asp Glu Val Asp Arg Leu Ala Asn Arg Thr
                    325                 330                 335

Arg Asp Ala Cys Tyr Thr Arg Glu Gly Arg Ala Glu Asp Gly Thr Glu
                340                 345                 350

Val Ala Tyr Ile Glu Tyr Asp Val Asn Ser Asp Cys Ala Gln Leu Pro
            355                 360                 365

Val Asp Thr Leu Asp Ala Tyr Pro Cys Gly Ser Asp His Thr Pro Ser
370                 375                 380

Pro Met Ala Ser Arg Val Pro Leu Glu Ala Thr Pro Ile Leu Glu Trp
385                 390                 395                 400

Pro Gly Ile Gln Leu Thr Ala Val Ala Val Thr Met Glu Asp Gly His
                    405                 410                 415

Thr Ile Ala Phe Leu Gly Asp Ser Gln Gly Gln Leu His Arg Val Tyr
                420                 425                 430

Leu Gly Pro Gly Ser Asp Gly His Pro Tyr Ser Thr Gln Ser Ile Gln
            435                 440                 445

Gln Gly Ser Ala Val Ser Arg Asp Leu Thr Phe Asp Gly Thr Phe Glu
450                 455                 460

His Leu Tyr Val Met Thr Gln Ser Thr Leu Leu Lys Val Pro Val Ala
465                 470                 475                 480

Ser Cys Ala Gln His Leu Asp Cys Ala Ser Cys Leu Ala His Arg Asp
                    485                 490                 495

Pro Tyr Cys Gly Trp Cys Val Leu Leu Gly Arg Cys Ser Arg Arg Ser
                500                 505                 510

Glu Cys Ser Arg Gly Gln Gly Pro Glu Gln Trp Leu Trp Ser Phe Gln
            515                 520                 525

Pro Glu Leu Gly Cys Leu Gln Val Ala Ala Met Ser Pro Ala Asn Ile
530                 535                 540

Ser Arg Glu Glu Thr Arg Glu Val Phe Leu Ser Val Pro Asp Leu Pro
545                 550                 555                 560

Pro Leu Trp Pro Gly Glu Ser Tyr Ser Cys His Phe Gly Glu His Gln
                    565                 570                 575

Ser Pro Ala Leu Leu Thr Gly Ser Gly Val Met Cys Pro Ser Pro Asp
                580                 585                 590

Pro Ser Glu Ala Pro Val Leu Pro Arg Gly Ala Asp Tyr Val Ser Val
            595                 600                 605

Ser Val Glu Leu Arg Phe Gly Ala Val Val Ile Ala Lys Thr Ser Leu
610                 615                 620
```

```
Ser Phe Tyr Asp Cys Val Ala Val Thr Glu Leu Arg Pro Ser Ala Gln
625                 630                 635                 640

Cys Gln Ala Cys Val Ser Ser Arg Trp Gly Cys Asn Trp Cys Val Trp
            645                 650                 655

Gln His Leu Cys Thr His Lys Ala Ser Cys Asp Ala Gly Pro Met Val
        660                 665                 670

Ala Ser His Gln Ser Pro Leu Val Ser Pro Asp Pro Ala Arg Gly
    675                 680                 685

Gly Pro Ser Pro Ser Pro Pro Thr Ala Pro Lys Ala Leu Ala Thr Pro
690                 695                 700

Ala Pro Asp Thr Leu Pro Val Glu Pro Gly Ala Pro Ser Thr Ala Thr
705                 710                 715                 720

Ala Ser Asp Ile Ser Pro Gly Ala Ser Pro Ser Leu Leu Ser Pro Trp
                725                 730                 735

Gly Pro Trp Ala Gly Ser Gly Ser Ile Ser Ser Pro Gly Ser Thr Gly
            740                 745                 750

Ser Pro Leu His Glu Glu Pro Ser Pro Ser Pro Gln Asn Gly Pro
    755                 760                 765

Gly Thr Ala Val Pro Ala Pro Thr Asp Phe Arg Pro Ser Ala Thr Pro
770                 775                 780

Glu Asp Leu Leu Ala Ser Pro Leu Ser Pro Ser Glu Val Ala Ala Val
785                 790                 795                 800

Pro Pro Ala Asp Pro Gly Pro Glu Ala Leu His Pro Thr Val Pro Leu
                805                 810                 815

Asp Leu Pro Pro Ala Thr Val Pro Ala Thr Thr Phe Pro Gly Ala Met
                820                 825                 830

Gly Ser Val Lys Pro Ala Leu Asp Trp Leu Thr Arg Glu Gly Gly Glu
            835                 840                 845

Leu Pro Glu Ala Asp Glu Trp Thr Gly Gly Asp Ala Pro Ala Phe Ser
850                 855                 860

Thr Ser Thr Leu Leu Ser Gly Asp Gly Asp Ser Ala Glu Leu Glu Gly
865                 870                 875                 880

Pro Pro Ala Pro Leu Ile Leu Pro Ser Ser Leu Asp Tyr Gln Tyr Asp
                885                 890                 895

Thr Pro Gly Leu Trp Glu Leu Glu Glu Ala Thr Leu Gly Ala Ser Ser
            900                 905                 910

Cys Pro Cys Val Glu Ser Val Gln Gly Ser Thr Leu Met Pro Val His
            915                 920                 925

Val Glu Arg Glu Ile Arg Leu Leu Gly Arg Asn Leu His Leu Phe Gln
            930                 935                 940

Asp Gly Pro Gly Asp Asn Glu Cys Val Met Glu Leu Glu Gly Leu Glu
945                 950                 955                 960

Val Val Val Glu Ala Arg Val Glu Cys Glu Pro Pro Asp Thr Gln
            965                 970                 975

Cys His Val Thr Cys Gln Gln His Gln Leu Ser Tyr Glu Ala Leu Gln
                980                 985                 990

Pro Glu Leu Arg Val Gly Leu Phe Leu Arg Arg Ala Gly Arg Leu Arg
    995                 1000                1005

Val Asp Ser Ala Glu Gly Leu His Val Val Leu Tyr Asp Cys Ser
    1010                1015                1020

Val Gly His Gly Asp Cys Ser Arg Cys Gln Thr Ala Met Pro Gln
    1025                1030                1035
```

-continued

| | | | | | | | | | | | |
|---|---|---|---|---|---|---|---|---|---|---|---|
|Tyr|Gly|Cys|Val|Trp|Cys|Glu|Gly|Glu|Arg|Pro|Arg|
| |1040| | | |1045| | | |1050| | |
| | | | | | | | | | | | |
|Cys|Val|Thr| | | | | | | | | |

Arg Glu Ala Cys Gly Glu Ala Glu Ala Val Ala Thr Gln Cys Pro
 1055           1060           1065

Ala Pro Leu Ile His Ser Val Glu Pro Leu Thr Gly Pro Val Asp
 1070           1075           1080

Gly Gly Thr Arg Val Thr Ile Arg Gly Ser Asn Leu Gly Gln His
 1085           1090           1095

Val Gln Asp Val Leu Gly Met Val Thr Val Ala Gly Val Pro Cys
 1100           1105           1110

Ala Val Asp Ala Gln Glu Tyr Glu Val Ser Ser Leu Val Cys
 1115           1120           1125

Ile Thr Gly Ala Ser Gly Glu Glu Val Ala Gly Thr Ala Val
 1130           1135           1140

Glu Val Pro Gly Arg Gly Arg Gly Val Ser Glu His Asp Phe Ala
 1145           1150           1155

Tyr Gln Asp Pro Lys Val His Ser Ile Phe Pro Ala Arg Gly Pro
 1160           1165           1170

Arg Ala Gly Gly Thr Arg Leu Thr Leu Asn Gly Ser Lys Leu Leu
 1175           1180           1185

Thr Gly Arg Leu Glu Asp Ile Arg Val Val Gly Asp Gln Pro
 1190           1195           1200

Cys His Leu Leu Pro Glu Gln Gln Ser Glu Gln Leu Arg Cys Glu
 1205           1210           1215

Thr Ser Pro Arg Pro Thr Pro Ala Thr Leu Pro Val Ala Val Trp
 1220           1225           1230

Phe Gly Ala Thr Glu Arg Arg Leu Gln Arg Gly Gln Phe Lys Tyr
 1235           1240           1245

Thr Leu Asp Pro Asn Ile Thr Ser Ala Gly Pro Thr Lys Ser Phe
 1250           1255           1260

Leu Ser Gly Gly Arg Glu Ile Cys Val Arg Gly Gln Asn Leu Asp
 1265           1270           1275

Val Val Gln Thr Pro Arg Ile Arg Val Thr Val Val Ser Arg Met
 1280           1285           1290

Leu Gln Pro Ser Gln Gly Leu Gly Gly Ser Gly Gly Ser Gly
 1295           1300           1305

Gly Gly Gly Gly Ser Gly Gly Gly Ser Asp Lys Thr His Thr
 1310           1315           1320

Cys Pro Pro Cys Pro Ala Pro Glu Leu Leu Gly Gly Pro Ser Val
 1325           1330           1335

Phe Leu Phe Pro Pro Lys Pro Lys Asp Gln Leu Met Ile Ser Arg
 1340           1345           1350

Thr Pro Glu Val Thr Cys Val Val Val Asp Val Ser His Glu Asp
 1355           1360           1365

Pro Glu Val Lys Phe Asn Trp Tyr Val Asp Gly Val Glu Val His
 1370           1375           1380

Asn Ala Lys Thr Lys Pro Arg Glu Glu Gln Tyr Asn Ser Thr Tyr
 1385           1390           1395

Arg Val Val Ser Val Leu Thr Val Leu His Gln Asp Trp Leu Asn
 1400           1405           1410

Gly Lys Glu Tyr Lys Cys Lys Val Ser Asn Lys Ala Leu Pro Ala
 1415           1420           1425

Pro Ile Glu Lys Thr Ile Ser Lys Ala Lys Gly Gln Pro Arg Glu

```
                         1430                1435                1440

Pro Gln Val Tyr Thr Leu Pro Pro Ser Arg Glu Glu Met Thr Lys
                  1445                1450                1455

Asn Gln Val Ser Leu Thr Cys Leu Val Lys Gly Phe Tyr Pro Ser
                  1460                1465                1470

Asp Ile Ala Val Glu Trp Glu Ser Asn Gly Gln Pro Glu Asn Asn
                  1475                1480                1485

Tyr Lys Thr Thr Pro Pro Val Leu Asp Ser Asp Gly Ser Phe Phe
                  1490                1495                1500

Leu Tyr Ser Lys Leu Thr Val Asp Lys Ser Arg Trp Gln Gln Gly
                  1505                1510                1515

Asn Val Phe Ser Cys Ser Val Leu His Glu Ala Leu His Asn His
                  1520                1525                1530

Tyr Thr Gln Lys Ser Leu Ser Leu Ser Pro Gly Lys
                  1535                1540                1545

<210> SEQ ID NO 11
      <211> LENGTH: 442
      <212> TYPE: PRT
      <213> ORGANISM: Gallus gallus domesticus

<400> SEQUENCE: 11

Tyr His Thr Phe Leu Leu Asp Glu Glu Arg Ser Arg Leu Tyr Val Gly
      1               5                   10                  15

Ala Lys Asp His Ile Phe Ser Phe Asn Leu Val Asn Ile Lys Glu Tyr
                      20                  25                  30

Gln Lys Ile Val Trp Pro Val Ser His Ser Arg Arg Asp Glu Cys Lys
                  35                  40                  45

Trp Ala Gly Lys Asp Ile Leu Arg Glu Cys Ala Asn Phe Ile Lys Val
              50                  55                  60

Leu Lys Thr Tyr Asn Gln Thr His Leu Tyr Ala Cys Gly Thr Gly Ala
      65              70                  75                  80

Phe His Pro Met Cys Thr Tyr Ile Glu Val Gly Ser His Pro Glu Asp
                      85                  90                  95

Asn Ile Phe Arg Met Glu Asp Ser His Phe Glu Asn Gly Arg Gly Lys
                  100                 105                 110

Ser Pro Tyr Asp Pro Lys Leu Leu Thr Ala Ser Leu Leu Val Asp Gly
                  115                 120                 125

Glu Leu Tyr Ser Gly Thr Ala Ala Asp Phe Met Gly Arg Asp Phe Ala
              130                 135                 140

Ile Phe Arg Thr Leu Gly His His Pro Ile Arg Thr Glu Gln His
      145                 150                 155                 160

Asp Ser Arg Trp Leu Asn Asp Pro Arg Phe Ile Ser Ala His Leu Ile
                      165                 170                 175

Pro Glu Ser Asp Asn Pro Glu Asp Lys Ile Tyr Phe Phe Phe Arg
                  180                 185                 190

Glu Asn Ala Ile Asp Gly Glu His Thr Gly Lys Ala Thr His Ala Arg
                  195                 200                 205

Ile Gly Gln Ile Cys Lys Asn Asp Phe Gly Gly His Arg Ser Leu Val
              210                 215                 220

Asn Lys Trp Thr Thr Phe Leu Lys Ala Arg Leu Ile Cys Ser Val Pro
      225                 230                 235                 240

Gly Pro Asn Gly Ile Asp Thr His Phe Asp Glu Leu Gln Asp Val Phe
                      245                 250                 255
```

-continued

```
Leu Met Asn Ser Lys Asp Pro Lys Asn Pro Ile Val Tyr Gly Val Phe
            260                 265                 270

Thr Thr Ser Ser Asn Ile Phe Lys Gly Ser Ala Val Cys Met Tyr Ser
        275                 280                 285

Met Thr Asp Val Arg Arg Val Phe Leu Gly Pro Tyr Ala His Arg Asp
    290                 295                 300

Gly Pro Asn Tyr Gln Trp Val Pro Tyr Gln Gly Arg Val Pro Tyr Pro
305                 310                 315                 320

Arg Pro Gly Thr Cys Pro Ser Lys Thr Phe Gly Phe Asp Ser Thr
                325                 330                 335

Lys Asp Leu Pro Asp Glu Val Ile Thr Phe Ala Arg Ser His Pro Ala
                340                 345                 350

Met Tyr Asn Pro Val Phe Pro Ile Asn Ser Arg Pro Ile Met Ile Lys
                355                 360                 365

Thr Asp Val Asp Tyr Gln Phe Thr Gln Ile Val Val Asp Arg Val Asp
        370                 375                 380

Ala Glu Asp Gly Gln Tyr Asp Val Met Phe Ile Gly Thr Asp Ile Gly
385                 390                 395                 400

Thr Val Leu Lys Val Val Ser Ile Pro Lys Glu Thr Trp His Glu Leu
                405                 410                 415

Glu Glu Val Leu Leu Glu Glu Met Thr Val Phe Arg Glu Pro Thr Val
                420                 425                 430

Ile Ser Ala Met Lys Ile Ser Thr Lys Gln
                435                 440

<210> SEQ ID NO 12
<211> LENGTH: 443
<212> TYPE: PRT
<213> ORGANISM: Homo sapiens

<400> SEQUENCE: 12

Leu His Thr Met Leu Leu Asp Glu Tyr Gln Glu Arg Leu Phe Val Gly
1               5                   10                  15

Gly Arg Asp Leu Val Tyr Ser Leu Ser Leu Glu Arg Ile Ser Asp Gly
                20                  25                  30

Tyr Lys Glu Ile His Trp Pro Ser Thr Ala Leu Lys Met Glu Glu Cys
            35                  40                  45

Ile Met Lys Gly Lys Asp Ala Gly Glu Cys Ala Asn Tyr Val Arg Val
        50                  55                  60

Leu His His Tyr Asn Arg Thr His Leu Leu Thr Cys Gly Thr Gly Ala
65                  70                  75                  80

Phe Asp Pro Val Cys Ala Phe Ile Arg Val Gly Tyr His Leu Glu Asp
                85                  90                  95

Pro Leu Phe His Leu Glu Ser Pro Arg Ser Glu Arg Gly Arg Gly Arg
                100                 105                 110

Cys Pro Phe Asp Pro Ser Ser Ser Phe Ile Ser Thr Leu Ile Gly Ser
            115                 120                 125

Glu Leu Phe Ala Gly Leu Tyr Ser Asp Tyr Trp Ser Arg Asp Ala Ala
        130                 135                 140

Ile Phe Arg Ser Met Gly Arg Leu Ala His Ile Arg Thr Glu His Asp
145                 150                 155                 160

Asp Glu Arg Leu Leu Lys Glu Pro Lys Phe Val Gly Ser Tyr Met Ile
                165                 170                 175

Pro Asp Asn Glu Asp Arg Asp Asp Asn Lys Val Tyr Phe Phe Phe Thr
                180                 185                 190
```

Glu Lys Ala Leu Glu Ala Glu Asn Asn Ala His Ala Ile Tyr Thr Arg
            195                 200                 205

Val Gly Arg Leu Cys Val Asn Asp Val Gly Gln Arg Ile Leu Val
    210                 215                 220

Asn Lys Trp Ser Thr Phe Leu Lys Ala Arg Leu Val Cys Ser Val Pro
225                 230                 235                 240

Gly Met Asn Gly Ile Asp Thr Tyr Phe Asp Glu Leu Glu Asp Val Phe
                245                 250                 255

Leu Leu Pro Thr Arg Asp His Lys Asn Pro Val Ile Phe Gly Leu Phe
            260                 265                 270

Asn Thr Thr Ser Asn Ile Phe Arg Gly His Ala Ile Cys Val Tyr His
            275                 280                 285

Met Ser Ser Ile Arg Ala Ala Phe Asn Gly Pro Tyr Ala His Lys Glu
        290                 295                 300

Gly Pro Glu Tyr His Trp Ser Val Tyr Glu Gly Lys Val Pro Tyr Pro
305                 310                 315                 320

Arg Pro Gly Ser Cys Ala Ser Lys Val Asn Gly Gly Arg Tyr Gly Thr
                325                 330                 335

Thr Lys Asp Tyr Pro Asp Asp Ala Ile Arg Phe Ala Arg Ser His Pro
            340                 345                 350

Leu Met Tyr Gln Ala Ile Lys Pro Ala His Lys Lys Pro Ile Leu Val
            355                 360                 365

Lys Thr Asp Gly Lys Tyr Asn Leu Lys Gln Ile Ala Val Asp Arg Val
        370                 375                 380

Glu Ala Glu Asp Gly Gln Tyr Asp Val Leu Phe Ile Gly Thr Asp Asn
385                 390                 395                 400

Gly Ile Val Leu Lys Val Ile Thr Ile Tyr Asn Gln Glu Met Glu Ser
                405                 410                 415

Met Glu Glu Val Ile Leu Glu Glu Leu Gln Ile Phe Lys Asp Pro Val
            420                 425                 430

Pro Ile Ile Ser Met Glu Ile Ser Ser Lys Arg
            435                 440

<210> SEQ ID NO 13
<211> LENGTH: 406
<212> TYPE: PRT
<213> ORGANISM: Mus musculus

<400> SEQUENCE: 13

Tyr Arg Ile Leu Leu Met Asp Glu Asp Gln Asp Arg Ile Tyr Val Gly
1               5                   10                  15

Ser Lys Asp His Ile Leu Ser Leu Asn Ile Asn Asn Ile Ser Gln Glu
            20                  25                  30

Pro Leu Ser Val Phe Trp Pro Ala Ser Thr Ile Lys Val Glu Glu Cys
        35                  40                  45

Lys Met Ala Gly Lys Asp Pro Thr His Gly Cys Gly Asn Phe Val Arg
    50                  55                  60

Val Ile Gln Thr Phe Asn Arg Thr His Leu Tyr Val Cys Gly Ser Gly
65                  70                  75                  80

Ala Phe Ser Pro Val Cys Thr Tyr Leu Asn Arg Gly Arg Arg Ser Glu
                85                  90                  95

Asp Gln Val Phe Met Ile Asp Ser Lys Cys Glu Ser Gly Lys Gly Arg
            100                 105                 110

Cys Ser Phe Asn Pro Asn Val Asn Thr Val Ser Val Met Ile Asn Glu

```
                115                 120                 125
Glu Leu Phe Ser Gly Met Tyr Ile Asp Phe Met Gly Thr Asp Ala Ala
130                 135                 140

Ile Phe Arg Ser Leu Thr Lys Arg Met Gln Leu Arg Thr Asp Gln His
145                 150                 155                 160

Asn Ser Lys Trp Leu Ser Glu Pro Met Phe Val Asp Ala His Val Ile
                165                 170                 175

Pro Asp Gly Thr Asp Pro Asn Asp Ala Lys Val Tyr Phe Phe Phe Lys
            180                 185                 190

Glu Arg Leu Thr Asp Asn Asn Arg Ser Thr Lys Gln Ile His Ser Met
        195                 200                 205

Ile Ala Arg Ile Cys Pro Asn Asp Thr Gly Gly Gln Arg Ser Leu Val
210                 215                 220

Asn Lys Trp Thr Thr Phe Leu Lys Ala Arg Leu Val Cys Ser Val Thr
225                 230                 235                 240

Asp Glu Asp Gly Pro Glu Thr His Phe Asp Glu Leu Glu Asp Val Phe
                245                 250                 255

Leu Leu Glu Thr Asp Asn Pro Arg Thr Thr Leu Val Tyr Gly Ile Phe
            260                 265                 270

Thr Thr Ser Ser Ser Val Phe Lys Gly Ser Ala Val Cys Val Tyr His
        275                 280                 285

Leu Ser Asp Ile Gln Thr Val Phe Asn Gly Pro Phe Ala His Lys Glu
290                 295                 300

Gly Pro Asn His Gln Leu Ile Ser Tyr Gln Gly Arg Ile Pro Tyr Pro
305                 310                 315                 320

Arg Pro Gly Thr Cys Pro Gly Gly Ala Phe Thr Pro Asn Met Arg Thr
                325                 330                 335

Thr Lys Asp Phe Pro Asp Asp Val Val Thr Phe Ile Arg Asn His Pro
            340                 345                 350

Leu Met Tyr Asn Ser Ile Ser Pro Ile His Arg Arg Pro Leu Ile Val
        355                 360                 365

Arg Ile Gly Thr Asp Tyr Lys Tyr Thr Lys Ile Ala Val Asp Arg Val
370                 375                 380

Asn Ala Ala Asp Gly Arg Tyr His Val Leu Phe Leu Gly Thr Asp Arg
385                 390                 395                 400

Gly Thr Val Gln Lys Val
                405

<210> SEQ ID NO 14
<211> LENGTH: 446
<212> TYPE: PRT
<213> ORGANISM: Homo sapiens

<400> SEQUENCE: 14

Leu Gln Ala Met Tyr Leu Asp Glu Tyr Arg Asp Arg Leu Phe Leu Gly
1               5                   10                  15

Gly Leu Asp Ala Leu Tyr Ser Leu Arg Leu Asp Gln Ala Trp Pro Asp
            20                  25                  30

Pro Arg Glu Val Leu Trp Pro Pro Gln Pro Gly Gln Arg Glu Glu Cys
        35                  40                  45

Val Arg Lys Gly Arg Asp Pro Leu Thr Glu Cys Ala Asn Phe Val Arg
    50                  55                  60

Val Leu Gln Pro His Asn Arg Thr His Leu Leu Ala Cys Gly Thr Gly
65                  70                  75                  80
```

Ala Phe Gln Pro Thr Cys Ala Leu Ile Thr Val Gly His Arg Gly Glu
                85                  90                  95

His Val Leu His Leu Glu Pro Gly Ser Val Glu Ser Gly Arg Gly Arg
            100                 105                 110

Cys Pro His Glu Pro Ser Arg Pro Phe Ala Ser Thr Phe Ile Asp Gly
            115                 120                 125

Glu Leu Tyr Thr Gly Leu Thr Ala Asp Phe Leu Gly Arg Glu Ala Met
        130                 135                 140

Ile Phe Arg Ser Gly Gly Pro Arg Pro Ala Leu Arg Ser Asp Ser Asp
145                 150                 155                 160

Gln Ser Leu Leu His Asp Pro Arg Phe Val Met Ala Ala Arg Ile Pro
                165                 170                 175

Glu Asn Ser Asp Gln Asp Asn Asp Lys Val Tyr Phe Phe Ser Glu
            180                 185                 190

Thr Val Pro Ser Pro Asp Gly Gly Ser Asn His Val Thr Val Ser Arg
            195                 200                 205

Val Gly Arg Val Cys Val Asn Asp Ala Gly Gly Gln Arg Val Leu Val
        210                 215                 220

Asn Lys Trp Ser Thr Phe Leu Lys Ala Arg Leu Val Cys Ser Val Pro
225                 230                 235                 240

Gly Pro Gly Gly Ala Glu Thr His Phe Asp Gln Leu Glu Asp Val Phe
                245                 250                 255

Leu Leu Trp Pro Lys Ala Gly Lys Ser Leu Glu Val Tyr Ala Leu Phe
            260                 265                 270

Ser Thr Val Ser Ala Val Phe Gln Gly Phe Ala Val Cys Val Tyr His
        275                 280                 285

Met Ala Asp Ile Trp Glu Val Phe Asn Gly Pro Phe Ala His Arg Asp
    290                 295                 300

Gly Pro Gln His Gln Trp Gly Pro Tyr Gly Gly Lys Val Pro Phe Pro
305                 310                 315                 320

Arg Pro Gly Val Cys Pro Ser Lys Met Thr Ala Gln Pro Gly Arg Pro
                325                 330                 335

Phe Gly Ser Thr Lys Asp Tyr Pro Asp Glu Val Leu Gln Phe Ala Arg
            340                 345                 350

Ala His Pro Leu Met Phe Trp Pro Val Arg Pro Arg His Gly Arg Pro
        355                 360                 365

Val Leu Val Lys Thr His Leu Ala Gln Gln Leu His Gln Ile Val Val
    370                 375                 380

Asp Arg Val Glu Ala Glu Asp Gly Thr Tyr Asp Val Ile Phe Leu Gly
385                 390                 395                 400

Thr Asp Ser Gly Ser Val Leu Lys Val Ile Ala Leu Gln Ala Gly Gly
                405                 410                 415

Ser Ala Glu Pro Glu Glu Val Val Leu Glu Glu Leu Gln Val Phe Lys
            420                 425                 430

Val Pro Thr Pro Ile Thr Glu Met Glu Ile Ser Val Lys Arg
        435                 440                 445

<210> SEQ ID NO 15
<211> LENGTH: 446
<212> TYPE: PRT
<213> ORGANISM: Gallus gallus domesticus

<400> SEQUENCE: 15

Phe Arg Thr Leu Leu Leu Asp Glu Glu Arg Gly Arg Leu Leu Val Gly
1               5                   10                  15

-continued

```
Ala Lys Asp His Ile Phe Leu Leu Asn Leu Val Asp Leu Asn Lys Asn
         20                  25                  30

Val Lys Lys Ile Tyr Trp Pro Ala Lys Glu Lys Met Glu Leu Cys
     35                  40                  45

Lys Leu Ala Gly Lys Asp Ala His Thr Asp Cys Ala Asn Phe Ile Arg
 50                  55                  60

Val Leu Gln Pro Tyr Asn Arg Thr His Val Tyr Val Cys Gly Thr Gly
 65                  70                  75                  80

Ala Phe His Pro Leu Cys Gly Tyr Ile Glu Leu Gly Thr His Lys Glu
                 85                  90                  95

Glu Thr Ile Phe Arg Leu Asp Thr Gln Asn Leu Glu Ser Gly Arg Leu
             100                 105                 110

Lys Cys Pro Phe Asp Pro Gln Gln Pro Phe Ala Ser Val Met Ala Asp
             115                 120                 125

Glu Tyr Leu Tyr Ala Gly Thr Ala Ser Asp Phe Leu Gly Lys Asp Thr
             130                 135                 140

Ala Leu Thr Arg Ser Leu Gly Pro Ser His Asp His His Tyr Ile Arg
145                 150                 155                 160

Thr Asp Ile Ser Glu His Tyr Trp Leu Thr Gly Ala Lys Phe Ile Ala
                165                 170                 175

Thr Phe Pro Ile Pro Asp Thr Tyr Asn Pro Asp Asp Lys Ile Tyr
                 180                 185                 190

Phe Phe Phe Arg Glu Ile Ser Gln Asp Ser Ser Thr Ser Asp Lys Thr
                 195                 200                 205

Ile Leu Ser Arg Val Gly Arg Val Cys Lys Asn Asp Met Gly Gly Gln
             210                 215                 220

Arg Ser Leu Ile Asn Lys Trp Thr Thr Phe Leu Lys Ala Arg Leu Val
225                 230                 235                 240

Cys Ser Ile Pro Gly Pro Glu Gly Ala Asp Thr His Phe Asp Glu Leu
                 245                 250                 255

Gln Asp Ile Phe Leu Leu Ser Thr Arg Asp Glu Arg Asn Pro Leu Val
             260                 265                 270

Tyr Gly Val Phe Thr Thr Thr Ser Ser Val Phe Lys Gly Ser Ala Val
             275                 280                 285

Cys Val Tyr Ser Met Ala Asp Ile Arg Ala Val Phe Asn Gly Pro Tyr
290                 295                 300

Ala His Lys Glu Ser Ala Asp His Arg Trp Val Gln Tyr Glu Gly Arg
305                 310                 315                 320

Ile Pro Tyr Pro Arg Pro Gly Thr Cys Pro Ser Lys Thr Tyr Asp Pro
                 325                 330                 335

Leu Ile Lys Ser Thr Arg Asp Phe Pro Asp Glu Val Ile Ser Phe Ile
             340                 345                 350

Lys Arg His Pro Leu Met Tyr Lys Ser Val Tyr Pro Leu Thr Gly Gly
             355                 360                 365

Pro Val Phe Thr Arg Ile Asn Val Asp Tyr Arg Leu Thr Gln Ile Val
             370                 375                 380

Val Asp His Val Met Ala Glu Asp Gly Gln Tyr Asp Val Ile Phe Leu
385                 390                 395                 400

Gly Thr Asp Ile Gly Thr Val Leu Lys Ala Val Ser Ile Thr Lys Glu
                 405                 410                 415

Lys Trp Thr Lys Glu Glu Val Val Leu Glu Glu Leu Gln Ile Phe Lys
             420                 425                 430
```

```
His Pro Ser Phe Ile Ser Thr Met Glu Ile Ser Gln Lys Gln
            435                 440                 445

<210> SEQ ID NO 16
<211> LENGTH: 446
<212> TYPE: PRT
<213> ORGANISM: Danio rerio

<400> SEQUENCE: 16

Phe Gln Thr Val Leu Leu Asp Glu Glu Arg Ser Arg Leu Leu Leu Gly
1               5                   10                  15

Ala Lys Asp His Val Tyr Leu Leu Asp Pro Asp Asn Ile Asn Lys His
            20                  25                  30

Pro Lys Lys Leu Ser Trp Pro Ala Ser Arg Asp Arg Val Glu Met Cys
        35                  40                  45

Ile Leu Ala Gly Lys Asn Pro Leu Thr Glu Cys Ala Asn Phe Ile Arg
    50                  55                  60

Val Leu His Ser Tyr Asn Arg Thr His Val Tyr Ala Cys Gly Thr Gly
65                  70                  75                  80

Ala Phe His Pro Thr Cys Ala Phe Leu Glu Ile Lys Gly His Lys Glu
                85                  90                  95

Asp Arg Trp Leu Leu His Ser Asn Thr Met Glu Ser Gly Arg Met
            100                 105                 110

Lys Cys Pro Phe Asp Pro Asn Gln Pro Phe Ala Ser Val Leu Thr Asp
        115                 120                 125

Gln Tyr Leu Tyr Ala Gly Thr Ala Ser Asp Phe Leu Gly Lys Asp Ser
    130                 135                 140

Thr Phe Thr Arg Ser Leu Gly Pro Pro His Gln Gln Tyr Ile Arg
145                 150                 155                 160

Thr Asp Ile Ser Glu Asp Tyr Trp Ile Asn Glu Gly Lys Phe Ile Ser
                165                 170                 175

Ala His Pro Ile Ser Asp Thr Tyr Asn Pro Asp Asp Lys Ile Tyr
            180                 185                 190

Phe Phe Phe Arg Glu Ala Ser Arg Asp Gly Ser Thr Thr Asp Lys Ser
        195                 200                 205

Val Leu Ser Arg Val Ala Arg Ile Cys Arg Asn Asp Val Gly Gly Leu
    210                 215                 220

Arg Ser Leu Thr Asn Lys Trp Thr Thr Phe Leu Lys Ala Arg Leu Val
225                 230                 235                 240

Cys Ser Ile Pro Gly Pro Asp Gly Val Asp Thr His Phe Asp Glu Leu
                245                 250                 255

Gln Asp Ile Phe Leu Leu Pro Ser Arg Asp Glu Lys Asn Pro Met Val
            260                 265                 270

Tyr Gly Val Phe Thr Thr Thr Ser Ser Ile Phe Lys Gly Ser Ala Val
        275                 280                 285

Cys Val Tyr Thr Met Glu Asp Ile Arg Ala Ala Phe Asn Gly Pro Tyr
    290                 295                 300

Ala His Lys Glu Gly Pro Asp His Arg Trp Val Glu Tyr Glu Gly Arg
305                 310                 315                 320

Ile Pro Tyr Pro Arg Pro Gly Thr Cys Pro Ser Arg Tyr Asp Pro
                325                 330                 335

His Ile Lys Thr Thr Lys Asp Phe Pro Asp Glu Val Ile Ser Phe Ile
            340                 345                 350

Arg Leu His Pro Leu Met Tyr Gln Ser Val His Pro Met Thr Gly Arg
        355                 360                 365
```

```
Pro Ile Phe Thr Arg Ile Asn Thr Glu Tyr Arg Leu Thr Gln Ile Ile
    370                 375                 380

Val Asp Arg Val Ala Ala Glu Asp Gly Gln Tyr Ala Val Met Phe Leu
385                 390                 395                 400

Gly Thr Asp Met Gly Ser Val Leu Lys Val Val Ser Ile Thr Gln Glu
                405                 410                 415

Asn Trp Ser Ser Glu Glu Ile Ile Leu Glu Glu Leu Gln Val Phe Lys
            420                 425                 430

Asn Pro Ser Pro Ile Leu Asn Met Glu Val Ser Ser Lys Gln
            435                 440                 445

<210> SEQ ID NO 17
<211> LENGTH: 443
<212> TYPE: PRT
<213> ORGANISM: Homo sapiens

<400> SEQUENCE: 17

Tyr Gln Ala Leu Leu Val Asp Glu Glu Arg Gly Arg Leu Phe Val Gly
1               5                   10                  15

Ala Glu Asn His Val Ala Ser Leu Asn Leu Asp Asn Ile Ser Lys Arg
            20                  25                  30

Ala Lys Lys Leu Ala Trp Pro Ala Pro Val Glu Trp Arg Glu Glu Cys
        35                  40                  45

Asn Trp Ala Gly Lys Asp Ile Gly Thr Glu Cys Met Asn Phe Val Lys
50                  55                  60

Leu Leu His Ala Tyr Asn Arg Thr His Leu Leu Ala Cys Gly Thr Gly
65                  70                  75                  80

Ala Phe His Pro Thr Cys Ala Phe Val Glu Val Gly His Arg Ala Glu
                85                  90                  95

Glu Pro Val Leu Arg Leu Asp Pro Gly Arg Ile Glu Asp Gly Lys Gly
            100                 105                 110

Lys Ser Pro Tyr Asp Pro Arg His Arg Ala Ala Ser Val Leu Val Gly
        115                 120                 125

Glu Glu Leu Tyr Ser Gly Val Ala Ala Asp Leu Met Gly Arg Asp Phe
130                 135                 140

Thr Ile Phe Arg Ser Leu Gly Gln Arg Pro Ser Leu Arg Thr Glu Pro
145                 150                 155                 160

His Asp Ser Arg Trp Leu Asn Glu Pro Lys Phe Val Lys Val Phe Trp
                165                 170                 175

Ile Pro Glu Ser Glu Asn Pro Asp Asp Asp Lys Ile Tyr Phe Phe Phe
            180                 185                 190

Arg Glu Thr Ala Val Glu Ala Ala Pro Ala Leu Gly Arg Leu Ser Val
        195                 200                 205

Ser Arg Val Gly Gln Ile Cys Arg Asn Asp Val Gly Gly Gln Arg Ser
210                 215                 220

Leu Val Asn Lys Trp Thr Thr Phe Leu Lys Ala Arg Leu Val Cys Ser
225                 230                 235                 240

Val Pro Gly Val Glu Gly Asp Thr His Phe Asp Gln Leu Gln Asp Val
                245                 250                 255

Phe Leu Leu Ser Ser Arg Asp His Arg Thr Pro Leu Leu Tyr Ala Val
            260                 265                 270

Phe Ser Thr Ser Ser Ser Ile Phe Gln Gly Ser Ala Val Cys Val Tyr
        275                 280                 285

Ser Met Asn Asp Val Arg Arg Ala Phe Leu Gly Pro Phe Ala His Lys
```

```
                290                 295                 300
Glu Gly Pro Met His Gln Trp Val Ser Tyr Gln Gly Arg Val Pro Tyr
305                 310                 315                 320

Pro Arg Pro Gly Met Cys Pro Ser Lys Thr Phe Gly Thr Phe Ser Ser
                325                 330                 335

Thr Lys Asp Phe Pro Asp Val Ile Gln Phe Ala Arg Asn His Pro
                340                 345                 350

Leu Met Tyr Asn Ser Val Leu Pro Thr Gly Gly Arg Pro Leu Phe Leu
                355                 360                 365

Gln Val Gly Ala Asn Tyr Thr Phe Thr Gln Ile Ala Ala Asp Arg Val
            370                 375                 380

Ala Ala Ala Asp Gly His Tyr Asp Val Leu Phe Ile Gly Thr Asp Val
385                 390                 395                 400

Gly Thr Val Leu Lys Val Ile Ser Val Pro Lys Gly Ser Arg Pro Ser
                405                 410                 415

Ala Glu Gly Leu Leu Leu Glu Glu Leu His Val Phe Glu Asp Ser Ala
                420                 425                 430

Ala Val Thr Ser Met Gln Ile Ser Ser Lys Arg
                435                 440

<210> SEQ ID NO 18
<211> LENGTH: 443
<212> TYPE: PRT
<213> ORGANISM: Danio rerio

<400> SEQUENCE: 18

Tyr Asp Thr Phe Leu Met Asp Gly Glu Arg Gly Arg Leu Leu Val Gly
1               5                   10                  15

Ala Glu Asp His Val Phe Ser Phe Asp Leu Val Asn Ile Asn Arg Asp
                20                  25                  30

Val Lys Gln Ile Ala Trp Pro Ala Thr Pro Ser Lys Arg Asp Glu Cys
            35                  40                  45

Lys Trp Ala Gly Lys Asp Leu Arg Lys Asp Cys Ser Asn Phe Val Arg
        50                  55                  60

Val Leu Gln Ser Tyr Asn Gln Thr His Ile Tyr Ile Cys Gly Thr Gly
65                  70                  75                  80

Ala Phe His Pro Ile Cys Ser Phe Leu Glu Met Gly Lys Arg Ala Glu
                85                  90                  95

Asp Asn Ile Phe Arg Leu Asp Ala Asn Tyr Phe Glu Asn Gly Arg Gly
                100                 105                 110

Lys Ser Pro Tyr Asp Pro Lys Met Gln Ser Ser Ser Leu Leu Leu Asp
            115                 120                 125

Gly Glu Leu Tyr Ser Gly Thr Ser Ala Asp Phe Met Gly Arg Asp Phe
        130                 135                 140

Ala Ile Phe Arg Thr Leu Gly Ser His His Pro Ile Arg Thr Glu Gln
145                 150                 155                 160

His Asp Ser Arg Trp Leu Asn Glu Pro Arg Phe Leu Gly Ile His Leu
                165                 170                 175

Ile Pro Glu Ser Asp Asn Pro Glu Asp Asp Lys Ile Phe Leu Phe Phe
                180                 185                 190

Lys Glu Asn Ala Met Asp Gly Glu His Thr Gly Lys Ala Thr Ile Ser
            195                 200                 205

Arg Ile Gly Gln Leu Cys Lys Asn Asp Met Gly Gly His Arg Ser Leu
        210                 215                 220
```

Val Asn Lys Trp Thr Thr Phe Leu Lys Ala Lys Leu Thr Cys Ser Val
225                 230                 235                 240

Pro Gly Leu Asn Gly Ile Asp Thr His Phe Asp Glu Leu Gln Asp Val
            245                 250                 255

Phe Leu Met Ser Ala Lys Asp Pro Lys Asn Pro Val Ile Tyr Ala Val
            260                 265                 270

Phe Thr Thr Ser Ser Asn Ile Phe Arg Gly Ser Ala Ile Cys Met Tyr
            275                 280                 285

Ser Met Ala Asp Ile Arg Arg Val Phe Leu Gly Pro Tyr Ala His Arg
            290                 295                 300

Asp Gly Pro Asn Tyr Gln Trp Val Pro Phe Gln Gly Arg Val Pro Tyr
305                 310                 315                 320

Pro Arg Pro Gly Thr Cys Pro Ser Lys Thr Phe Gly Gly Phe Asp Ser
            325                 330                 335

Thr Lys Asp Leu Pro Asp Asp Val Ile Thr Phe Ala Arg Leu His Pro
            340                 345                 350

Ala Met Tyr Asn Pro Val Gln Pro Met Gly Gly Lys Pro Ile Val Val
            355                 360                 365

Arg Thr Asn Val Glu Tyr Gln Phe Thr Gln Leu Val Val Asp Arg Val
370                 375                 380

Glu Ala Glu Asp Gly Gln Tyr Asp Val Met Phe Ile Gly Thr Asp Leu
385                 390                 395                 400

Gly Thr Val Leu Lys Val Val Thr Ile Pro Arg Glu Ser Trp His Asp
            405                 410                 415

Leu Glu Glu Val Val Leu Glu Glu Met Thr Val Phe Arg Glu Pro Thr
            420                 425                 430

Pro Ile Thr Ala Met Glu Leu Ser Thr Lys Gln
            435                 440

<210> SEQ ID NO 19
<211> LENGTH: 473
<212> TYPE: PRT
<213> ORGANISM: Homo sapiens

<400> SEQUENCE: 19

Tyr Arg Ile Leu Leu Lys Asp Glu Asp His Asp Arg Met Tyr Val Gly
1               5                   10                  15

Ser Lys Asp Tyr Val Leu Ser Leu Asp Leu His Asp Ile Asn Arg Glu
            20                  25                  30

Pro Leu Ile Ile His Trp Ala Ala Ser Pro Gln Arg Ile Glu Glu Cys
            35                  40                  45

Val Leu Ser Gly Lys Asp Val Asn Gly Glu Cys Gly Asn Phe Val Arg
50                  55                  60

Leu Ile Gln Pro Trp Asn Arg Thr His Leu Tyr Val Cys Gly Thr Gly
65                  70                  75                  80

Ala Tyr Asn Pro Met Cys Thr Tyr Val Asn Arg Gly Arg Arg Ala Gln
            85                  90                  95

Ala Thr Pro Trp Thr Gln Thr Gln Ala Val Arg Gly Arg Gly Ser Arg
            100                 105                 110

Ala Thr Asp Gly Ala Leu Arg Pro Met Pro Thr Ala Pro Arg Gln Asp
            115                 120                 125

Tyr Ile Phe Tyr Leu Glu Pro Glu Arg Leu Glu Ser Gly Lys Gly Lys
            130                 135                 140

Cys Pro Tyr Asp Pro Lys Leu Asp Thr Ala Ser Ala Leu Ile Asn Glu
145                 150                 155                 160

Glu Leu Tyr Ala Gly Val Tyr Ile Asp Phe Met Gly Thr Asp Ala Ala
                165                 170                 175
Ile Phe Arg Thr Leu Gly Lys Gln Thr Ala Met Arg Thr Asp Gln Tyr
                180                 185                 190
Asn Ser Arg Trp Leu Asn Asp Pro Ser Phe Ile His Ala Glu Leu Ile
                195                 200                 205
Pro Asp Ser Ala Glu Arg Asn Asp Lys Leu Tyr Phe Phe Arg
                210                 215                 220
Glu Arg Ser Ala Glu Ala Pro Gln Ser Pro Ala Val Tyr Ala Arg Ile
225                 230                 235                 240
Gly Arg Ile Cys Leu Asn Asp Gly Gly His Cys Cys Leu Val Asn
                245                 250                 255
Lys Trp Ser Thr Phe Leu Lys Ala Arg Leu Val Cys Ser Val Pro Gly
                260                 265                 270
Glu Asp Gly Ile Glu Thr His Phe Asp Glu Leu Gln Asp Val Phe Val
                275                 280                 285
Gln Gln Thr Gln Asp Val Arg Asn Pro Val Ile Tyr Ala Val Phe Thr
                290                 295                 300
Ser Ser Gly Ser Val Phe Arg Gly Ser Ala Val Cys Val Tyr Ser Met
305                 310                 315                 320
Ala Asp Ile Arg Met Val Phe Asn Gly Pro Phe Ala His Lys Glu Gly
                325                 330                 335
Pro Asn Tyr Gln Trp Met Pro Phe Ser Gly Lys Met Pro Tyr Pro Arg
                340                 345                 350
Pro Gly Thr Cys Pro Gly Gly Thr Phe Thr Pro Ser Met Lys Ser Thr
                355                 360                 365
Lys Asp Tyr Pro Asp Glu Val Ile Asn Phe Met Arg Ser His Pro Leu
                370                 375                 380
Met Tyr Gln Ala Val Tyr Pro Leu Gln Arg Arg Pro Leu Val Val Arg
385                 390                 395                 400
Thr Gly Ala Pro Tyr Arg Leu Thr Thr Ile Ala Val Asp Gln Val Asp
                405                 410                 415
Ala Gly Asp Gly Arg Tyr Glu Val Leu Phe Leu Gly Thr Asp Arg Gly
                420                 425                 430
Thr Val Gln Lys Val Ile Val Leu Pro Lys Asp Asp Gln Glu Met Glu
                435                 440                 445
Glu Leu Met Leu Glu Glu Val Glu Val Phe Lys Asp Pro Ala Pro Val
                450                 455                 460
Lys Thr Met Thr Ile Ser Ser Lys Arg
465                 470

<210> SEQ ID NO 20
<211> LENGTH: 461
<212> TYPE: PRT
<213> ORGANISM: Homo sapiens

<400> SEQUENCE: 20

Phe Leu Thr Leu Thr Leu Thr Glu Pro Thr Gly Leu Leu Tyr Val Gly
1               5                   10                  15
Ala Arg Glu Ala Leu Phe Ala Phe Ser Met Glu Ala Leu Glu Leu Gln
                20                  25                  30
Gly Ala Ile Ser Trp Glu Ala Pro Val Glu Lys Lys Thr Glu Cys Ile
                35                  40                  45
Gln Lys Gly Lys Asn Asn Gln Thr Glu Cys Phe Asn Phe Ile Arg Phe

```
            50                  55                  60
Leu Gln Pro Tyr Asn Ala Ser His Leu Tyr Val Cys Gly Thr Tyr Ala
 65                  70                  75                  80

Phe Gln Pro Lys Cys Thr Tyr Val Asn Met Leu Thr Phe Thr Arg Phe
                     85                  90                  95

Leu Gln Pro Tyr Asn Ala Ser His Leu Tyr Val Cys Gly Thr Tyr Ala
                    100                 105                 110

Phe Gln Pro Lys Cys Thr Tyr Val Asn Met Leu Thr Phe Thr Leu Glu
                115                 120                 125

His Gly Glu Phe Glu Asp Gly Lys Gly Lys Cys Pro Tyr Asp Pro Ala
            130                 135                 140

Lys Gly His Ala Gly Leu Leu Val Asp Gly Glu Leu Tyr Ser Ala Thr
145                 150                 155                 160

Leu Asn Asn Phe Leu Gly Thr Glu Pro Ile Ile Leu Arg Asn Met Gly
                    165                 170                 175

Pro His His Ser Met Lys Thr Glu Tyr Leu Ala Phe Trp Leu Asn Glu
                180                 185                 190

Pro His Phe Val Gly Ser Ala Tyr Val Pro Glu Ser Val Gly Ser Phe
                195                 200                 205

Thr Gly Asp Asp Lys Val Tyr Phe Phe Arg Glu Arg Ala Val
210                 215                 220

Glu Ser Asp Cys Tyr Ala Glu Gln Val Val Ala Arg Val Ala Arg Val
225                 230                 235                 240

Cys Lys Gly Asp Met Gly Gly Ala Arg Thr Leu Gln Arg Lys Trp Thr
                245                 250                 255

Thr Phe Leu Lys Ala Arg Leu Ala Cys Ser Ala Pro Asn Trp Gln Leu
                260                 265                 270

Tyr Phe Asn Gln Leu Gln Ala Met His Thr Leu Gln Asp Thr Ser Trp
                275                 280                 285

His Asn Thr Thr Phe Phe Gly Val Phe Gln Ala Gln Trp Gly Asp Met
            290                 295                 300

Tyr Leu Ser Ala Ile Cys Glu Tyr Gln Leu Glu Glu Ile Gln Arg Val
305                 310                 315                 320

Phe Glu Gly Pro Tyr Lys Glu Tyr His Glu Glu Ala Gln Lys Trp Asp
                325                 330                 335

Arg Tyr Thr Asp Pro Val Pro Ser Pro Arg Pro Gly Cys Ile Asn
                340                 345                 350

Asn Trp His Arg Arg His Gly Tyr Thr Ser Ser Leu Glu Leu Pro Asp
                355                 360                 365

Asn Ile Leu Asn Phe Val Lys Lys His Pro Leu Met Glu Glu Gln Val
                370                 375                 380

Gly Pro Arg Trp Ser Arg Pro Leu Leu Val Lys Lys Gly Thr Asn Phe
385                 390                 395                 400

Thr His Leu Val Ala Asp Arg Val Thr Gly Leu Asp Gly Ala Thr Tyr
                405                 410                 415

Thr Val Leu Phe Ile Gly Thr Gly Asp Gly Trp Leu Leu Lys Ala Val
                420                 425                 430

Ser Leu Gly Pro Trp Val His Leu Ile Glu Glu Leu Gln Leu Phe Asp
                435                 440                 445

Gln Glu Pro Met Arg Ser Leu Val Leu Ser Gln Ser Lys
450                 455                 460

<210> SEQ ID NO 21
```

```
<211> LENGTH: 432
<212> TYPE: PRT
<213> ORGANISM: Mus musculus

<400> SEQUENCE: 21

Tyr Ser Ala Leu Leu Val Asp Pro Ala Ser His Thr Leu Tyr Val Gly
1               5                   10                  15

Ala Arg Asp Ser Ile Phe Ala Leu Thr Leu Pro Phe Ser Gly Glu Lys
            20                  25                  30

Pro Arg Arg Ile Asp Trp Met Val Pro Glu Thr His Arg Gln Asn Cys
        35                  40                  45

Arg Lys Lys Gly Lys Lys Glu Asp Glu Cys His Asn Phe Ile Gln Ile
    50                  55                  60

Leu Ala Ile Ala Asn Ala Ser His Leu Leu Thr Cys Gly Thr Phe Ala
65                  70                  75                  80

Phe Asp Pro Lys Cys Gly Val Ile Asp Val Ser Ser Phe Gln Gln Val
                85                  90                  95

Glu Arg Leu Glu Ser Gly Arg Gly Lys Cys Pro Phe Glu Pro Ala Gln
            100                 105                 110

Arg Ser Ala Ala Val Met Ala Gly Gly Val Leu Tyr Thr Ala Thr Val
        115                 120                 125

Lys Asn Phe Leu Gly Thr Glu Pro Ile Ile Ser Arg Ala Val Gly Arg
130                 135                 140

Ala Glu Asp Trp Ile Arg Thr Glu Thr Leu Ser Ser Trp Leu Asn Ala
145                 150                 155                 160

Pro Ala Phe Val Ala Ala Met Val Leu Ser Pro Ala Glu Trp Gly Asp
                165                 170                 175

Glu Asp Gly Asp Asp Glu Ile Phe Phe Phe Thr Glu Thr Ser Arg
            180                 185                 190

Val Leu Asp Ser Tyr Glu Arg Ile Lys Val Pro Arg Val Ala Arg Val
        195                 200                 205

Cys Ala Gly Asp Leu Gly Gly Arg Lys Thr Leu Gln Gln Arg Trp Thr
    210                 215                 220

Thr Phe Leu Lys Ala Asp Leu Leu Cys Pro Gly Pro Glu His Gly Arg
225                 230                 235                 240

Ala Ser Gly Val Leu Gln Asp Met Thr Glu Leu Arg Pro Gln Pro Gly
                245                 250                 255

Ala Gly Thr Pro Leu Phe Tyr Gly Ile Phe Ser Ser Gln Trp Glu Gly
            260                 265                 270

Ala Ala Ile Ser Ala Val Cys Ala Phe Arg Pro Gln Asp Ile Arg Ala
        275                 280                 285

Val Leu Asn Gly Pro Phe Arg Glu Leu Lys His Asp Cys Asn Arg Gly
    290                 295                 300

Leu Pro Val Met Asp Asn Glu Val Pro Gln Pro Arg Pro Gly Glu Cys
305                 310                 315                 320

Ile Thr Asn Asn Met Lys Phe Gln Gln Phe Gly Ser Ser Leu Ser Leu
                325                 330                 335

Pro Asp Arg Val Leu Thr Phe Ile Arg Asp His Pro Leu Met Asp Arg
            340                 345                 350

Pro Val Phe Pro Ala Asp Gly Arg Pro Leu Leu Val Thr Thr Asp Thr
        355                 360                 365

Ala Tyr Leu Arg Val Val Ala His Arg Val Thr Ser Leu Ser Gly Lys
    370                 375                 380

Glu Tyr Asp Val Leu Tyr Leu Gly Thr Glu Asp Gly His Leu His Arg
```

```
                385                 390                 395                 400
Ala Val Arg Ile Gly Ala Gln Leu Ser Val Leu Glu Asp Leu Ala Leu
                    405                 410                 415

Phe Pro Glu Pro Gln Pro Val Glu Ser Met Lys Leu Tyr His Asp Trp
                    420                 425                 430

<210> SEQ ID NO 22
<211> LENGTH: 433
<212> TYPE: PRT
<213> ORGANISM: Mus musculus

<400> SEQUENCE: 22

Tyr Ser Ala Leu Leu Met Ser Glu Asp Lys Asp Thr Leu Tyr Val Gly
1               5                   10                  15

Ala Arg Glu Ala Val Phe Ala Val Asn Ala Leu Asn Ile Ser Glu Lys
                20                  25                  30

Gln His Glu Val Tyr Trp Lys Val Ser Glu Asp Lys Lys Ser Lys Cys
            35                  40                  45

Ala Glu Lys Gly Lys Ser Lys Gln Thr Glu Cys Leu Asn Tyr Ile Arg
        50                  55                  60

Val Leu Gln Pro Leu Ser Ser Thr Ser Leu Tyr Val Cys Gly Thr Asn
65                  70                  75                  80

Ala Phe Gln Pro Thr Cys Asp His Leu Asn Leu Thr Ser Phe Lys Phe
                85                  90                  95

Leu Gly Lys Ser Glu Asp Gly Lys Gly Arg Cys Pro Phe Asp Pro Ala
                100                 105                 110

His Ser Tyr Thr Ser Val Met Val Gly Gly Glu Leu Tyr Ser Gly Thr
            115                 120                 125

Ser Tyr Asn Phe Leu Gly Ser Glu Pro Ile Ile Ser Arg Asn Ser Ser
        130                 135                 140

His Ser Pro Leu Arg Thr Glu Tyr Ala Ile Pro Trp Leu Asn Glu Pro
145                 150                 155                 160

Ser Phe Val Phe Ala Asp Val Ile Gln Lys Ser Pro Asp Gly Pro Glu
                165                 170                 175

Gly Glu Asp Asp Lys Val Tyr Phe Phe Phe Thr Glu Val Ser Val Glu
            180                 185                 190

Tyr Glu Phe Val Phe Lys Leu Met Ile Pro Arg Val Ala Arg Val Cys
        195                 200                 205

Lys Gly Asp Gln Gly Gly Leu Arg Thr Leu Gln Lys Lys Trp Thr Ser
    210                 215                 220

Phe Leu Lys Ala Arg Leu Ile Cys Ser Lys Pro Asp Ser Gly Leu Val
225                 230                 235                 240

Phe Asn Ile Leu Gln Asp Val Phe Val Leu Arg Ala Pro Gly Leu Lys
                245                 250                 255

Glu Pro Val Phe Tyr Ala Val Phe Thr Pro Gln Leu Asn Asn Val Gly
            260                 265                 270

Leu Ser Ala Val Cys Ala Tyr Thr Leu Ala Thr Val Glu Ala Val Phe
        275                 280                 285

Ser Arg Gly Lys Tyr Met Gln Ser Ala Thr Val Glu Gln Ser His Thr
    290                 295                 300

Lys Trp Val Arg Tyr Asn Gly Pro Val Pro Thr Pro Arg Pro Gly Ala
305                 310                 315                 320

Cys Ile Asp Ser Glu Ala Arg Ala Ala Asn Tyr Thr Ser Ser Leu Asn
                325                 330                 335
```

```
Leu Pro Asp Lys Thr Leu Gln Phe Val Lys Asp His Pro Leu Met Asp
                340                 345                 350

Asp Ser Val Thr Pro Ile Asp Asn Arg Pro Lys Leu Ile Lys Lys Asp
            355                 360                 365

Val Asn Tyr Thr Gln Ile Val Asp Arg Thr Gln Ala Leu Asp Gly
        370                 375                 380

Thr Phe Tyr Asp Val Met Phe Ile Ser Thr Asp Arg Gly Ala Leu His
385                 390                 395                 400

Lys Ala Val Ile Leu Thr Lys Glu Val His Val Ile Glu Glu Thr Gln
                405                 410                 415

Leu Phe Arg Asp Phe Glu Pro Val Leu Thr Leu Leu Leu Ser Ser Lys
                420                 425                 430

Lys

<210> SEQ ID NO 23
<211> LENGTH: 431
<212> TYPE: PRT
<213> ORGANISM: Danio rerio

<400> SEQUENCE: 23

Tyr Thr Thr Met Leu Leu Arg Asp Asp Leu Asn Leu Ile Leu Gly
1               5                   10                  15

Ala Arg Glu Ala Ile Phe Ala Leu Asp Leu Asp Ile Thr Ile Lys
                20                  25                  30

Lys Ala Met Leu Lys Trp Glu Val Thr Arg Asp Gln Gln Asn Asp Cys
                35                  40                  45

Ser Asn Lys Gly Lys Asp Ala Thr Asn Asp Cys Lys Asn Tyr Ile Arg
    50                  55                  60

Ile Leu His Lys Lys Asn Asp Gly Arg Met Tyr Val Cys Gly Thr Lys
65                  70                  75                  80

Ala Phe Asn Pro Thr Cys Gly Tyr Leu Ser Tyr Ala Asp Gly Lys Leu
                85                  90                  95

Thr Leu Glu Ile Leu Gln Glu Asp Thr Lys Gly Lys Cys Pro Phe Asp
                100                 105                 110

Pro Phe Gln Arg Tyr Thr Ser Ala Met Val Asp Gly Ala Tyr Tyr Ser
                115                 120                 125

Ala Thr Ser Met Asn Phe Arg Gly Ser Glu Pro Val Met Met Arg Ser
            130                 135                 140

Thr Glu Glu Ser Ile Arg Thr Glu Phe Thr Ser Thr Trp Leu Ser Glu
145                 150                 155                 160

Pro Asn Phe Ile His Met Ala His Ile Pro Glu Gly Gln Ser Asn Pro
                165                 170                 175

Asp Gly Asp Asp Asp Lys Ile Tyr Leu Phe Phe Ser Glu Thr Ala Val
            180                 185                 190

Glu Tyr Glu Ser Tyr Thr Lys Val Asp Val Ser Arg Val Ala Arg Val
        195                 200                 205

Cys Lys Gly Asp Leu Gly Gly Gln Arg Thr Leu Gln Lys Lys Trp Thr
    210                 215                 220

Ser Phe Leu Lys Ala Arg Leu Asp Cys Gln Val Pro Asn Thr Asn Leu
225                 230                 235                 240

Pro Leu Leu Val Gln Asp Val Phe His Leu Cys Pro Asp Asp Trp Thr
                245                 250                 255

Thr Cys Val Phe Tyr Ala Val Phe Thr Pro Gln Ser Asp Ser Ser Gln
            260                 265                 270
```

```
Tyr Ser Ala Val Cys Ser Tyr Lys Ile Glu Asp Ile Lys Thr Val Phe
            275                 280                 285

Ser Lys Gly Lys Phe Lys Ala Pro Phe Asn Val Glu Thr Ser Phe Val
290                 295                 300

Lys Trp Val Met Tyr Ser Gly Glu Leu Pro Asp Pro Arg Pro Gly Ala
305                 310                 315                 320

Cys Ile Asp Asn His Ala Arg Glu Lys Gly Ile Thr Lys Ser Leu Glu
                325                 330                 335

Leu Pro Asp Lys Thr Leu Gln Phe Val Lys Asp Lys Pro Leu Met Asp
                340                 345                 350

Gln Ala Val Thr Ala Glu Gln Pro Leu Val Lys Arg Gly Ala Ala
                355                 360                 365

Phe Thr Arg Ile Val Val Thr Thr Ala Thr Ala Leu Asn Gly Thr Ser
    370                 375                 380

His Gln Val Met Phe Ile Gly Thr Lys Ser Gly Ser Val Leu Lys Ala
385                 390                 395                 400

Val Asn Tyr Asn Gly Glu Met Val Ile Met Glu Ile Gln Leu Phe
                405                 410                 415

Asp Pro Ser Glu Pro Ile Lys Ile Leu Arg Leu Ser Ser Ser Lys
                420                 425                 430

<210> SEQ ID NO 24
<211> LENGTH: 428
<212> TYPE: PRT
<213> ORGANISM: Homo sapiens

<400> SEQUENCE: 24

Tyr Ser Thr Leu Leu Glu Glu Ala Ser Ala Arg Leu Leu Val Gly
1               5                   10                  15

Ala Arg Gly Ala Leu Phe Ser Leu Ser Ala Asn Asp Ile Gly Asp Gly
                20                  25                  30

Ala His Lys Glu Ile His Trp Glu Ala Ser Pro Glu Met Gln Ser Lys
            35                  40                  45

Cys His Gln Lys Gly Lys Asn Asn Gln Thr Glu Cys Phe Asn His Val
        50                  55                  60

Arg Phe Leu Gln Arg Leu Asn Ser Thr His Leu Tyr Ala Cys Gly Thr
65                  70                  75                  80

His Ala Phe Gln Pro Leu Cys Ala Ala Ile Asp Ala Glu Ala Phe Thr
                85                  90                  95

Leu Pro Thr Ser Phe Glu Glu Gly Lys Glu Lys Cys Pro Tyr Asp Pro
                100                 105                 110

Ala Arg Gly Phe Thr Gly Leu Ile Ile Asp Gly Gly Leu Tyr Thr Ala
            115                 120                 125

Thr Arg Tyr Glu Phe Arg Ser Ile Pro Asp Ile Arg Arg Ser Arg His
        130                 135                 140

Pro His Ser Leu Arg Thr Glu Glu Thr Pro Met His Trp Leu Asn Asp
145                 150                 155                 160

Ala Glu Phe Val Phe Ser Val Leu Val Arg Glu Ser Lys Ala Ser Ala
                165                 170                 175

Val Gly Asp Asp Asp Lys Val Tyr Tyr Phe Phe Thr Glu Arg Ala Thr
            180                 185                 190

Glu Glu Gln Ser Arg Ser Ser His Arg Val Ala Arg Val Ala Arg Val
        195                 200                 205

Cys Lys Gly Asp Leu Gly Gly Lys Lys Ile Leu Gln Lys Lys Trp Thr
    210                 215                 220
```

-continued

```
Ser Phe Leu Lys Ala Arg Leu Ile Cys His Ile Pro Leu Tyr Glu Thr
225                 230                 235                 240

Leu Arg Gly Val Cys Ser Leu Asp Ala Glu Thr Ser Ser Arg Thr His
                245                 250                 255

Phe Tyr Ala Ala Phe Thr Leu Ser Thr Gln Trp Lys Thr Leu Glu Ala
            260                 265                 270

Ser Ala Ile Cys Arg Tyr Asp Leu Ala Glu Ile Gln Ala Val Phe Ala
        275                 280                 285

Gly Pro Tyr Met Glu Tyr Gln Asp Gly Ser Arg Arg Trp Gly Arg Tyr
    290                 295                 300

Glu Gly Gly Val Pro Glu Pro Arg Pro Gly Ser Cys Ile Thr Asp Ser
305                 310                 315                 320

Leu Arg Ser Gln Gly Tyr Asn Ser Ser Gln Asp Leu Pro Ser Leu Val
                325                 330                 335

Leu Asp Phe Val Lys Leu His Pro Leu Met Ala Arg Pro Val Val Pro
            340                 345                 350

Thr Arg Gly Arg Pro Leu Leu Leu Lys Arg Asn Ile Arg Tyr Thr His
        355                 360                 365

Leu Thr Gly Thr Pro Val Thr Thr Pro Ala Gly Pro Thr Tyr Asp Leu
    370                 375                 380

Leu Phe Leu Gly Thr Ala Asp Gly Trp Ile His Lys Ala Val Val Leu
385                 390                 395                 400

Gly Ser Gly Met His Ile Ile Glu Glu Thr Gln Val Phe Arg Glu Ser
                405                 410                 415

Gln Ser Val Glu Asn Leu Val Ile Ser Leu Leu Gln
            420                 425

<210> SEQ ID NO 25
<211> LENGTH: 438
<212> TYPE: PRT
<213> ORGANISM: Homo sapiens

<400> SEQUENCE: 25

Tyr Thr Ala Leu Leu Leu Ser Arg Asp Gly Arg Thr Leu Tyr Val Gly
1               5                   10                  15

Ala Arg Glu Ala Leu Phe Ala Leu Ser Ser Asn Leu Ser Phe Leu Pro
            20                  25                  30

Gly Gly Glu Tyr Gln Glu Leu Leu Trp Gly Ala Asp Ala Glu Lys Lys
        35                  40                  45

Gln Gln Cys Ser Phe Lys Gly Lys Asp Pro Gln Arg Asp Cys Gln Asn
    50                  55                  60

Tyr Ile Lys Ile Leu Leu Pro Leu Ser Gly Ser His Leu Phe Thr Cys
65                  70                  75                  80

Gly Thr Ala Ala Phe Ser Pro Met Cys Thr Tyr Ile Asn Met Glu Asn
                85                  90                  95

Phe Thr Leu Ala Arg Asp Glu Lys Gly Asn Val Leu Leu Glu Asp Gly
            100                 105                 110

Lys Gly Arg Cys Pro Phe Asp Pro Asn Phe Lys Ser Thr Ala Leu Val
        115                 120                 125

Val Asp Gly Glu Leu Tyr Thr Gly Thr Val Ser Ser Phe Gln Gly Asn
    130                 135                 140

Asp Pro Ala Ile Ser Arg Ser Gln Ser Leu Arg Pro Thr Lys Thr Glu
145                 150                 155                 160

Ser Ser Leu Asn Trp Leu Gln Asp Pro Ala Phe Val Ala Ser Ala Tyr
```

```
                    165                 170                 175
Ile Pro Glu Ser Leu Gly Ser Leu Gln Gly Asp Asp Lys Ile Tyr
                180                 185                 190

Phe Phe Phe Ser Glu Thr Gly Gln Glu Phe Glu Phe Glu Asn Thr
                195                 200                 205

Ile Val Ser Arg Ile Ala Arg Ile Cys Lys Gly Asp Glu Gly Glu
            210                 215                 220

Arg Val Leu Gln Gln Arg Trp Thr Ser Phe Leu Lys Ala Gln Leu Leu
225                 230                 235                 240

Cys Ser Arg Pro Asp Asp Gly Phe Pro Phe Asn Val Leu Gln Asp Val
                245                 250                 255

Phe Thr Leu Ser Pro Ser Pro Gln Asp Trp Arg Asp Thr Leu Phe Tyr
                260                 265                 270

Gly Val Phe Thr Ser Gln Trp His Arg Gly Thr Thr Glu Gly Ser Ala
                275                 280                 285

Val Cys Val Phe Thr Met Lys Asp Val Gln Arg Val Phe Ser Gly Leu
                290                 295                 300

Tyr Lys Glu Val Asn Arg Glu Thr Gln Gln Trp Tyr Thr Val Thr His
305                 310                 315                 320

Pro Val Pro Thr Pro Arg Pro Gly Ala Cys Ile Thr Asn Ser Ala Arg
                325                 330                 335

Glu Arg Lys Ile Asn Ser Ser Leu Gln Leu Pro Asp Arg Val Leu Asn
                340                 345                 350

Phe Leu Lys Asp His Phe Leu Met Asp Gly Gln Val Arg Ser Arg Met
                355                 360                 365

Leu Leu Leu Gln Pro Gln Ala Arg Tyr Gln Arg Val Ala Val His Arg
                370                 375                 380

Val Pro Gly Leu His His Thr Tyr Asp Val Leu Phe Leu Gly Thr Gly
385                 390                 395                 400

Asp Gly Arg Leu His Lys Ala Val Ser Val Gly Pro Arg Val His Ile
                405                 410                 415

Ile Glu Glu Leu Gln Ile Phe Ser Ser Gly Gln Pro Val Gln Asn Leu
                420                 425                 430

Leu Leu Asp Thr His Arg
            435

<210> SEQ ID NO 26
<211> LENGTH: 415
<212> TYPE: PRT
<213> ORGANISM: Mus musculus

<400> SEQUENCE: 26

Phe Asp Thr Leu Leu Leu Ser Asp Asp Gly Asn Thr Leu Tyr Val Gly
1               5                   10                  15

Ala Arg Glu Thr Val Leu Ala Leu Asn Ile Gln Asn Pro Gly Ile Pro
                20                  25                  30

Arg Leu Lys Asn Met Ile Pro Trp Pro Ala Ser Glu Arg Lys Lys Thr
            35                  40                  45

Glu Cys Ala Phe Lys Lys Lys Ser Asn Glu Thr Gln Cys Phe Asn Phe
        50                  55                  60

Ile Arg Val Leu Val Ser Tyr Asn Ala Thr His Leu Tyr Ala Cys Gly
65                  70                  75                  80

Thr Phe Ala Phe Ser Pro Ala Cys Thr Phe Ile Glu Leu Gln Asp Ser
                85                  90                  95
```

```
Leu Leu Leu Pro Ile Leu Ile Asp Lys Val Met Asp Gly Lys Gly Gln
                100                 105                 110

Ser Pro Leu Thr Leu Phe Thr Ser Thr Gln Ala Val Leu Val Asp Gly
            115                 120                 125

Met Leu Tyr Ser Gly Thr Met Asn Asn Phe Leu Gly Ser Glu Pro Ile
        130                 135                 140

Leu Met Arg Thr Leu Gly Ser His Pro Val Leu Lys Thr Asp Ile Phe
145                 150                 155                 160

Leu Arg Trp Leu His Ala Asp Ala Ser Phe Val Ala Ala Ile Pro Ser
                165                 170                 175

Thr Gln Val Val Tyr Phe Phe Glu Glu Thr Ala Ser Glu Phe Asp
            180                 185                 190

Phe Phe Glu Glu Leu Tyr Ile Ser Arg Val Ala Gln Val Cys Lys Asn
        195                 200                 205

Asp Val Gly Gly Glu Lys Leu Leu Gln Lys Lys Trp Thr Thr Phe Leu
210                 215                 220

Lys Ala Gln Leu Leu Cys Ala Gln Pro Gly Gln Leu Pro Phe Asn Ile
225                 230                 235                 240

Ile Arg His Ala Val Leu Leu Pro Ala Asp Ser Pro Ser Val Ser Arg
                245                 250                 255

Ile Tyr Ala Val Phe Thr Ser Gln Trp Gln Val Gly Gly Thr Arg Ser
            260                 265                 270

Ser Ala Val Cys Ala Phe Ser Leu Thr Asp Ile Glu Arg Val Phe Lys
        275                 280                 285

Gly Lys Tyr Lys Glu Leu Asn Lys Glu Thr Ser Arg Trp Thr Thr Tyr
290                 295                 300

Arg Gly Ser Glu Val Ser Pro Arg Pro Gly Ser Cys Ser Met Gly Pro
305                 310                 315                 320

Ser Ser Asp Lys Ala Leu Thr Phe Met Lys Asp His Phe Leu Met Asp
                325                 330                 335

Glu His Val Val Gly Thr Pro Leu Leu Val Lys Ser Gly Val Glu Tyr
            340                 345                 350

Thr Arg Leu Ala Val Glu Ser Ala Arg Gly Leu Asp Gly Ser Ser His
        355                 360                 365

Val Val Met Tyr Leu Gly Thr Ser Thr Gly Pro Leu His Lys Ala Val
        370                 375                 380

Val Pro Gln Asp Ser Ser Ala Tyr Leu Val Glu Ile Gln Leu Ser
385                 390                 395                 400

Pro Asp Ser Glu Pro Val Arg Asn Leu Gln Leu Ala Pro Ala Gln
                405                 410                 415

<210> SEQ ID NO 27
<211> LENGTH: 439
<212> TYPE: PRT
<213> ORGANISM: Mus musculus

<400> SEQUENCE: 27

Ile Gln Asn Val Val Leu Tyr Lys His His Val Tyr Ile Gly Ala Val
1               5                   10                  15

Asn Lys Ile Tyr Val Leu Asn Glu Thr Leu Gln Asn Ile Ser Val Tyr
            20                  25                  30

Lys Thr Gly Pro Ile Leu Glu Ser Pro Gly Cys Ala Pro Cys Glu Asp
        35                  40                  45

Cys Lys Asp Lys Ala Asn Leu Ser Asn Ser Val Trp Lys Asp Asn Val
50                  55                  60
```

Asn Met Ala Leu Leu Leu Glu Thr Tyr Tyr Asp Asp Gln Leu Ile Ser
65                  70                  75                  80

Cys Gly Ser Val Ser Gly Val Cys His Arg His Ile Ile Pro Pro
            85                  90                  95

Asp Asn Pro Ala Asp Ile Glu Ser Glu Val His Cys Met Tyr Ser Pro
                100                 105                 110

Gln Val Asp Gly Glu Ala Asp Asn Cys Pro Asp Cys Val Val Ser Thr
            115                 120                 125

Leu Gly Thr Lys Val Leu Val Thr Glu Lys Asp Arg Phe Val Asn Phe
            130                 135                 140

Phe Val Gly Asn Thr Met Thr Ser Ala Phe Gln Pro Pro His Val Leu
145                 150                 155                 160

His Ser Ile Ser Val Arg Arg Leu Lys Glu Thr Gln Asp Gly Phe Glu
                165                 170                 175

Phe Leu Thr Asp Gln Ser Tyr Ile Asp Ile Leu Pro Gln Phe Arg Asp
                180                 185                 190

Ser Tyr Pro Ile Lys Tyr Val His Ala Phe Glu His Asp His Phe Val
            195                 200                 205

Tyr Phe Leu Thr Val Gln Arg Glu Ser Leu Asp Ser Gln Thr Phe His
210                 215                 220

Thr Arg Ile Ile Arg Phe Cys Thr Leu Asp Ser Glu Met Arg Ser Tyr
225                 230                 235                 240

Met Glu Met Pro Leu Glu Cys Ile Phe Thr Glu Ile Arg Lys Glu Val
                245                 250                 255

Phe Asn Ile Leu Gln Ala Ala Tyr Val Ser Lys Pro Gly Ala Ala Leu
                260                 265                 270

Ala His Glu Met Gly Leu Gly Leu Ile Asp Asp Ile Leu Tyr Gly Val
            275                 280                 285

Phe Ala Gln Thr Asn Gln Ile Pro Gln Glu Pro Thr Asn Arg Ser Ala
290                 295                 300

Val Cys Ala Val Ser Val Arg Thr Ile Asn Glu Phe Phe Asn Lys Ile
305                 310                 315                 320

Val Asp Lys Gln Asn Met Lys Cys Leu Gln His Phe Tyr Gly Lys Asp
                325                 330                 335

Ser Lys Tyr Cys Leu Asn Arg Ala Phe Ser Arg Asn Ala Ser Tyr Cys
            340                 345                 350

Arg Ala Gln Asp Asp Glu Tyr Arg Leu Glu Val Thr Thr Pro Leu Gln
            355                 360                 365

Arg Val Asp Leu Phe Met Gly Gln Phe Asn Asn Ile Leu Leu Thr Ser
            370                 375                 380

Ile Ser Val Phe Thr Lys Gly Asn Leu Thr Ile Ala Asn Leu Gly Thr
385                 390                 395                 400

Ser Glu Gly Arg Phe Met Gln Ile Val Val Ser Arg Ser Glu Pro Thr
                405                 410                 415

Ala Pro His Val Ser Phe Gln Leu Asp Ser His Ala Val Ser Pro Gln
            420                 425                 430

Val Val Val Glu Gln Ser Ala
            435

<210> SEQ ID NO 28
<211> LENGTH: 439
<212> TYPE: PRT
<213> ORGANISM: Homo sapiens

```
<400> SEQUENCE: 28

Ile Gln Asn Val Ile Leu His Glu His His Ile Phe Leu Gly Ala Thr
1               5                   10                  15

Asn Tyr Ile Tyr Val Leu Asn Glu Glu Asp Leu Gln Lys Val Ala Glu
            20                  25                  30

Tyr Lys Thr Gly Pro Val Leu Glu His Pro Asp Cys Phe Pro Cys Gln
        35                  40                  45

Asp Cys Ser Ser Lys Ala Asn Leu Ser Gly Gly Val Trp Lys Asp Asn
    50                  55                  60

Ile Asn Met Ala Leu Val Val Asp Thr Tyr Tyr Asp Asp Gln Leu Ile
65              70                  75                  80

Ser Cys Gly Ser Val Asn Arg Gly Thr Cys Gln Arg His Val Phe Pro
            85                  90                  95

His Asn His Thr Ala Asp Ile Gln Ser Glu Val His Cys Ile Phe Ser
            100                 105                 110

Pro Gln Ile Glu Glu Pro Ser Gln Cys Pro Asp Cys Val Val Ser Ala
        115                 120                 125

Leu Gly Ala Lys Val Leu Ser Ser Val Lys Asp Arg Phe Ile Asn Phe
    130                 135                 140

Phe Val Gly Asn Thr Ile Asn Ser Ser Tyr Phe Pro Asp His Pro Leu
145                 150                 155                 160

His Ser Ile Ser Val Arg Arg Leu Lys Glu Thr Lys Asp Gly Phe Met
            165                 170                 175

Phe Leu Thr Asp Gln Ser Tyr Ile Asp Val Leu Pro Glu Phe Arg Asp
        180                 185                 190

Ser Tyr Pro Ile Lys Tyr Val His Ala Phe Glu Ser Asn Asn Phe Ile
    195                 200                 205

Tyr Phe Leu Thr Val Gln Arg Glu Thr Leu Asp Ala Gln Thr Phe His
210                 215                 220

Thr Arg Ile Ile Arg Phe Cys Ser Ile Asn Ser Gly Leu His Ser Tyr
225                 230                 235                 240

Met Glu Met Pro Leu Glu Cys Ile Leu Thr Glu Thr Lys Lys Glu Val
            245                 250                 255

Phe Asn Ile Leu Gln Ala Ala Tyr Val Ser Lys Pro Gly Ala Gln Leu
        260                 265                 270

Ala Arg Gln Ile Gly Ala Ser Leu Asn Asp Asp Ile Leu Phe Gly Val
    275                 280                 285

Phe Ala Gln Ser Lys Pro Asp Ser Ala Glu Pro Met Asp Arg Ser Ala
290                 295                 300

Met Cys Ala Phe Pro Ile Lys Tyr Val Asn Asp Phe Phe Asn Lys Ile
305                 310                 315                 320

Val Asn Lys Asn Asn Val Arg Cys Leu Gln His Phe Tyr Gly Pro Asn
            325                 330                 335

His Glu His Cys Phe Asn Arg Thr Leu Leu Arg Asn Ser Ser Gly Cys
        340                 345                 350

Glu Ala Arg Arg Asp Glu Tyr Arg Thr Glu Phe Thr Thr Ala Leu Gln
    355                 360                 365

Arg Val Asp Leu Phe Met Gly Gln Phe Ser Glu Val Leu Leu Thr Ser
370                 375                 380

Ile Ser Thr Phe Ile Lys Gly Asp Leu Thr Ile Ala Asn Leu Gly Thr
385                 390                 395                 400

Ser Glu Gly Arg Phe Met Gln Val Val Val Ser Arg Ser Gly Pro Ser
            405                 410                 415
```

```
Thr Pro His Val Asn Phe Leu Leu Asp Ser His Pro Val Ser Pro Glu
            420                 425                 430

Val Ile Val Glu His Thr Leu
        435
```

<210> SEQ ID NO 29
<211> LENGTH: 439
<212> TYPE: PRT
<213> ORGANISM: Apteryx australis mantelli

<400> SEQUENCE: 29

```
Ile Gln Ser Ile Ile Met Phe Lys Gly Tyr Val Tyr Gly Ala Val
1               5                   10                  15

Asn Lys Ile Tyr Val Leu Asn Glu Asn Leu Thr Lys Ile Ser Glu Tyr
                20                  25                  30

Lys Thr Gly Pro Leu Leu Lys His Ser Asp Cys Leu Pro Cys Lys Asn
            35                  40                  45

Cys Thr Asp Asn Leu Leu Ser Pro Asn Gly Thr Trp Lys Asp Ser Val
50                  55                  60

Asn Met Ala Leu Phe Val Gln Asp Phe Tyr Asp Asp Gln Leu Ile Ser
65                  70                  75                  80

Cys Gly Asn Ile Arg Lys Gly Glu Cys Gln Arg His Thr Leu His Ser
                85                  90                  95

Asp Lys Pro Trp Asp Ile Ala Ser Asp Val His Cys Leu Tyr Ser Ser
            100                 105                 110

Gln Met Val Glu Asp Lys Asp Ser Cys Pro Asp Cys Ile Val Ser Thr
        115                 120                 125

Ala Gly Ser Lys Ile Leu Val Thr Val Gly Asp Arg Phe Val Lys Phe
    130                 135                 140

Phe Val Gly Ser Thr Leu Thr Gly Gln Pro Ser Thr Ile His Ser Val
145                 150                 155                 160

Ser Val Arg Arg Leu Lys Glu Thr Gln Asp Gly Phe Glu Tyr Leu Thr
                165                 170                 175

Asp Gln Ser Tyr Ile Asp Val Leu Pro His Leu Arg Asp Ile Tyr Pro
            180                 185                 190

Ile Arg Tyr Ile Tyr Thr Phe Glu Ser Asn Asn Phe Val Tyr Phe Leu
        195                 200                 205

Thr Val Gln Arg Glu Ser Leu Asp Ser Gln Ala Tyr His Thr Arg Ile
    210                 215                 220

Val Arg Ile Cys Ser Ser Asp Ser Glu Leu Arg Ser Tyr Ile Glu Met
225                 230                 235                 240

Pro Leu Glu Cys Ile Phe Thr Glu Lys Arg Arg Lys Arg Ser Thr Ala
                245                 250                 255

Ser Ala Val Phe Asn Ile Val Gln Ala Ala Tyr Leu Gly Arg Ala Gly
            260                 265                 270

Glu Asp Leu Ala Glu Glu Met Gly Val Lys Pro Asp Asp Ile Leu
        275                 280                 285

Tyr Gly Val Phe Ala Gln Ser Lys Pro Asp Ser Pro Glu Pro Asn Asn
    290                 295                 300

Arg Ser Ala Val Cys Ala Val Ser Val Lys Thr Ile Asn Glu Phe Phe
305                 310                 315                 320

Asn Ser Ala Ala Asp Lys Gln Asn Thr Lys Cys Leu Glu His Phe Tyr
                325                 330                 335

Gly Lys Asp Asn Arg Leu Cys Ile Asn Asn Lys Arg Phe Leu Arg Cys
```

-continued

```
                340                 345                 350
Ser Thr Pro Ile Asp Glu Tyr Arg Val Glu Val Thr Thr Val Leu Arg
            355                 360                 365

Arg Leu Asp Leu Phe Met Asp Gln Phe Arg Asn Val Leu Leu Thr Ser
        370                 375                 380

Ile Ser Val Phe Thr Gln Gly Arg Leu Thr Ile Ala Asn Leu Gly Thr
385                 390                 395                 400

Ser Glu Gly Arg Phe Met Gln Val Ile Ile Ser Arg Thr Gly Gln Pro
                405                 410                 415

Lys Pro His Val Asn Phe Leu Leu Glu Ala Arg Pro Ile Ser Pro Glu
            420                 425                 430

Ile Val Ile Asn Thr Ala Ser
            435

<210> SEQ ID NO 30
<211> LENGTH: 443
<212> TYPE: PRT
<213> ORGANISM: Takifugu rubripes

<400> SEQUENCE: 30

Ile Gln Asn Val Val Thr Leu Asp Gly Ile Ile Tyr Val Gly Ala Thr
1               5                   10                  15

Asn Arg Ile Tyr Ala Leu Ala Pro Ser Leu Thr Lys Leu Ser Glu Tyr
            20                  25                  30

Arg Thr Gly Pro Leu Leu Ala Asn Gln Thr Cys Gly Gln Lys Val Ala
        35                  40                  45

Asn Ala Ser Ser Gly Gly Arg Lys Asp Asn Leu Asn Val Ala Leu
    50                  55                  60

Val Val Glu Asn Ile Tyr Asp Lys Gly Leu Phe Ser Cys Gly Ser Ala
65              70                  75                  80

Asp Asn Gly Val Cys Arg Arg His Val Leu Glu Asp Asp Val Ser Leu
            85                  90                  95

Asp Glu Glu Gly Val Asp Glu Phe Thr Asp Leu Lys Gln Asp Lys Gly
            100                 105                 110

Gln Pro Arg Asp Ser Asp Val Val Val Ser Pro Ser Gly Ser Gln Val
        115                 120                 125

Leu Asn Val Glu Ser Asn Met Ile Met Phe Phe Val Gly Asn Ser Glu
    130                 135                 140

Ile Pro Gly Ser Gly Asn Val Thr Gly Pro Thr Ala Arg Pro His Thr
145             150                 155                 160

Met Ser Leu Arg Lys Met Lys Thr Ser Gln Asn Gly Phe Thr Phe Phe
            165                 170                 175

Ser Asn Arg Ser Tyr Met Asp Leu Ile Pro Pro Leu Arg Gly Ser Tyr
        180                 185                 190

Tyr Leu Arg Tyr Val Tyr Ser Phe His Ser Gly Pro Phe Thr Tyr Phe
    195                 200                 205

Leu Thr Val Gln Gln Val Ser Lys Asp Ser Gln Thr Tyr His Thr Arg
    210                 215                 220

Ile Val Arg Met Cys Ser Ser Asp His Asp Ile Arg Arg Tyr Val Glu
225             230                 235                 240

Met Pro Leu Glu Cys Ile Ser Thr Asp Ser Met Glu Asp Val Lys Val
            245                 250                 255

Phe Asn Ile Leu Gln Ala Ala Thr Val Thr Lys Val Gly Ser Asp Val
        260                 265                 270
```

Glu Leu Gln Arg Gln Leu Arg Leu Glu Glu Gly Asp Asp Val Leu Phe
275 280 285

Ala Ala Phe Ala Arg Gly Lys Pro Asn Ser Thr Glu Ala Thr Pro Asn
290 295 300

Ser Ala Ile Cys Val Met Ser Leu Lys Leu Ile Asn Ser Met Phe Lys
305 310 315 320

Met Tyr Met Gln Lys Cys Asn Thr Val Asp Leu Tyr His Phe Thr Gly
325 330 335

Ser Asp Lys Lys Ser Cys Tyr Asn Val Ser Ser Ser Asp Cys Asp
340 345 350

Pro His Glu Gly Ile His Glu Gly Lys Glu Gly Lys Tyr Arg Leu Gln
355 360 365

Val Thr Gln Phe Val Gln Arg Leu Glu Tyr Trp Gln Lys Val Leu Thr
370 375 380

Asn Thr Leu Val Thr Ser Ile Thr Val Thr Val His Gly Arg Ala
385 390 395 400

Val Gly Tyr Leu Gly Thr Ala Asp Gly Arg His Ile Gln Val Val Phe
405 410 415

Ser Arg Phe Ala Ser Pro His Val Asn Ile Arg Leu Asp Ser Arg Pro
420 425 430

Val Ser Gly Ser Val Val Leu Pro Gly Gln Asp
435 440

<210> SEQ ID NO 31
<211> LENGTH: 443
<212> TYPE: PRT
<213> ORGANISM: Gallus gallus

<400> SEQUENCE: 31

Val Gln Asn Ile Ala Val Phe Pro Asp Pro Thr Val Phe Val Ala
1 5 10 15

Val Arg Asn Arg Ile Leu Val Val Asp Pro Glu Leu Arg Leu Arg Ser
20 25 30

Val Leu Val Thr Gly Pro Thr Gly Ser Ala Pro Cys Glu Ile Cys Arg
35 40 45

Leu Cys Pro Ala Ala Val Asp Ala Pro Gly Pro Glu Asp Val Asp Asn
50 55 60

Val Leu Leu Leu Leu Asp Pro Val Glu Pro Trp Leu Tyr Ser Cys Gly
65 70 75 80

Thr Ala Arg Arg Gly Leu Cys Tyr Leu His Gln Leu Asp Val Arg Gly
85 90 95

Ser Glu Val Thr Ile Ala Ser Thr Arg Cys Leu Tyr Ser Ala Ala Ala
100 105 110

Asn Ser Pro Val Asn Cys Pro Asp Cys Val Ala Ser Pro Leu Gly Ser
115 120 125

Thr Ala Thr Val Val Ala Asp Arg Tyr Thr Ala Ser Phe Tyr Leu Gly
130 135 140

Ser Thr Val Asn Ser Ser Val Ala Ala Arg Tyr Ser Pro Arg Ser Val
145 150 155 160

Ser Val Arg Arg Leu Lys Gly Thr Arg Asp Gly Phe Ala Asp Pro Phe
165 170 175

His Ser Leu Thr Val Leu Pro His Tyr Gln Asp Val Tyr Pro Ile His
180 185 190

Tyr Val His Ser Phe Thr Asp Gly Asp His Val Tyr Leu Val Thr Val
195 200 205

```
Gln Pro Glu Phe Pro Gly Ser Ser Thr Phe His Thr Arg Leu Val Arg
    210                 215                 220

Leu Ser Ala His Glu Pro Glu Leu Arg Arg Tyr Arg Glu Ile Val Leu
225                 230                 235                 240

Asp Cys Arg Tyr Glu Ser Glu Glu Thr Glu Arg Asp Val Ala Tyr Asn
                245                 250                 255

Val Leu Gln Ala Ala His Ala Ala Arg Pro Gly Ala Arg Leu Ala Arg
            260                 265                 270

Asp Leu Gly Ile Asp Gly Thr Glu Thr Val Leu Phe Gly Ala Phe Ala
        275                 280                 285

Glu Ser His Pro Glu Ser Arg Ala Pro Gln His Asn Ser Ala Val Cys
    290                 295                 300

Ala Phe Pro Leu Arg Leu Leu Asn Gln Ala Ile Arg Glu Gly Met Asp
305                 310                 315                 320

Lys Cys Cys Gly Thr Gly Thr Gln Thr Leu Lys Arg Gly Leu Ala Phe
                325                 330                 335

Phe Gln Pro Gln Gln Tyr Cys Pro His Ser Val Asn Leu Ser Ala Pro
            340                 345                 350

Val Thr Asn Thr Ser Cys Trp Asp Gln Pro Thr Leu Val Pro Ala Ala
        355                 360                 365

Ser His Lys Val Asp Leu Phe Asn Gly Arg Leu Ser Gly Thr Leu Leu
    370                 375                 380

Thr Ser Ile Phe Val Thr Val Leu Gln Asn Val Thr Val Ala His Leu
385                 390                 395                 400

Gly Thr Ala Gln Gly Arg Val Leu Gln Met Val Leu Gln Arg Ser Ser
                405                 410                 415

Ser Tyr Val Val Ala Leu Thr Asn Phe Ser Leu Gly Glu Pro Gly Leu
            420                 425                 430

Val Gln His Ala Thr Gly Leu Gln Gly His Ser
        435                 440

<210> SEQ ID NO 32
<211> LENGTH: 405
<212> TYPE: PRT
<213> ORGANISM: Takifugu rubripes

<400> SEQUENCE: 32

Ile Gln Asn Ile Val Asn Asn Ser Phe Tyr Gln Glu Val Tyr Val Ala
1               5                   10                  15

Ser Gln Asn Val Ile Glu Ala Val Asn Gln Ser Leu Glu Lys Val Trp
            20                  25                  30

Glu Leu Arg Thr Gly Pro Val Gly Ser Pro Glu Cys Lys Ile Cys Asp
        35                  40                  45

Leu Cys Asn Thr Asp Lys Asp Pro Ser Leu Glu Asp Thr Asn Asn Glu
    50                  55                  60

Val Leu Leu Leu Asp Thr Leu Phe Met Tyr Leu Tyr Thr Cys Gly Ser
65                  70                  75                  80

Ser Gln Tyr Gly Val Cys Tyr Phe His Gln Leu Asn Ser Thr Gly Glu
                85                  90                  95

Pro Pro Ser Leu Ser Lys Cys Leu Tyr Arg Lys Lys Ser Asn Ser Ala
            100                 105                 110

Ala Tyr Cys Pro Asp Cys Val Ala Ser Ser Leu Gly Thr Lys Val Thr
        115                 120                 125

Met Val Glu Glu Gly Gln Thr Val Tyr Phe Phe Val Ala Thr Thr Val
```

```
            130                 135                 140
Asn Asp Ser Val Thr Gln Arg Tyr Gly Arg Lys Ser Leu Ser Val Arg
145                 150                 155                 160

Arg Pro Leu Ala Thr Glu Asp Gly Phe Tyr Ser Asp Val Arg Gly Leu
                165                 170                 175

Thr Val Leu Pro Ser Leu Arg Asn Thr Tyr His Ile Glu Tyr Val Tyr
                180                 185                 190

Ser Phe Phe Thr Gln Glu Phe Val Phe Phe Leu Ser Val Gln Arg Glu
            195                 200                 205

Ser Pro Asp Gln Glu Ser Ser Pro Phe Gln Thr Arg Leu Gly Arg Leu
        210                 215                 220

Pro Arg Asn Glu Trp Glu Met Lys Arg Tyr Arg Glu Val Ile Leu Glu
225                 230                 235                 240

Cys Arg Phe Glu Pro Gly Ser Glu Pro Tyr Lys Asp Val Val Tyr Asn
                245                 250                 255

Val Val Gln Ala Ala His Phe Ala Lys Ala Gly Arg Glu Leu Ala Glu
                260                 265                 270

Glu Leu Gly Ala Glu Glu Asp Asp Ile Leu Tyr Gly Val Phe Ala
            275                 280                 285

Val Thr Asp Asp Asn Gly Val Thr Glu His Asp Ser Ala Leu Cys Ala
        290                 295                 300

Phe Pro Val Asp Asn Val Asn Lys Ala Ile Ala Asp Gly Val Asp Asp
305                 310                 315                 320

Cys Cys Gln Ser Gly Pro Glu Gln Leu Ser Arg Gly Leu Cys His Phe
                325                 330                 335

Gln Pro Cys Glu Ser Cys Pro His Glu Ser Met Glu Asn Asn Ala Thr
                340                 345                 350

Cys Arg Asp Gln Pro Thr Met Val Ser Lys Pro Tyr Tyr Arg Val Asp
            355                 360                 365

Leu Phe Asn Arg Gln Met Thr Asp Val Leu Thr Ser Leu Leu Val
        370                 375                 380

Thr Thr Ile Glu Asn Lys Thr Val Ala His Ile Gly Thr Ser Thr Gly
385                 390                 395                 400

Arg Leu Leu Gln Leu
            405

<210> SEQ ID NO 33
<211> LENGTH: 435
<212> TYPE: PRT
<213> ORGANISM: Takifugu rubripes

<400> SEQUENCE: 33

Val Gln Asn Ile Ala Val Asn Trp Asp Ser Gln Gln Lys Glu Ile Tyr
1               5                   10                  15

Ile Gly Cys Gln Asn Ala Ile Lys Ala Val Ser Gly Thr Leu Glu Glu
            20                  25                  30

Met Trp Glu Val Lys Thr Gly Pro Val Gly Ser Pro Asp Cys Glu Thr
        35                  40                  45

Cys Lys Leu Cys Asp Val Glu Ala Asp Pro Glu Asp Pro Val Asp Thr
    50                  55                  60

Asp Ser Glu Val Leu Val Leu Asp Pro Ala Gly Ile Leu Leu Pro Tyr
65              70                  75                  80

Leu Tyr Val Cys Gly Ser Thr Gln His Gly Ile Cys Tyr Phe Ile Asp
                85                  90                  95
```

```
Ile Glu Ser Pro Glu His Ala Pro Gln Cys Leu Tyr Lys Lys Gln Arg
            100                 105                 110

Asn Ser Pro Thr Arg Cys Pro Asp Cys Leu Ala Ser Pro Leu Gly Thr
        115                 120                 125

Lys Val Ser Ile Ile Glu Asp Gly Ser Thr Thr Tyr Phe Phe Val Ala
    130                 135                 140

Ala Ala Val Asp Asp Arg Val Ala Gln Arg Tyr Pro Arg Arg Ser Ile
145                 150                 155                 160

Ser Val Met Arg Pro Leu Ser Thr Glu Asp Gly Phe Glu Met Val Thr
                165                 170                 175

Asp Gly Leu Thr Val Leu Pro Ser Arg Ser Thr Tyr Lys Ile Asp Tyr
            180                 185                 190

Ile His Ser Phe Ala Thr Lys Glu Tyr Val Tyr Phe Leu Ser Leu Gln
        195                 200                 205

Arg Glu Asn Pro Ser Asn Ser Asn Ser Pro Leu Gln Thr Arg Leu Gly
    210                 215                 220

Arg Leu Pro Ile Ser Ile Arg Glu Val Trp Met Tyr Arg Glu Val Val
225                 230                 235                 240

Leu Glu Cys His Phe Asn Pro Gly Asp Phe Arg Gly Ile Val Tyr Asn
                245                 250                 255

Gly Leu Gln Ala Ala His Phe Gly Arg Ala Gly Lys Asp Leu Ala Glu
            260                 265                 270

Glu Leu Arg Val Asp Glu Gln Glu Asp Ile Leu Tyr Gly Val Phe Ala
        275                 280                 285

Val Val Asn Glu Leu Gly Glu Thr Gln Arg Asn Ser Ala Leu Cys Ala
    290                 295                 300

Phe Pro Leu Ser Lys Val Asn His Ala Ile Asp Glu Gly Val Glu Ala
305                 310                 315                 320

Cys Cys Arg Ser Gly Thr Glu Gln Leu Ser Arg Gly Leu Gly His Phe
                325                 330                 335

Gln Pro Leu Glu Ser Cys Pro His Glu Ser Ser Glu Asp Lys Tyr Thr
            340                 345                 350

Cys Arg Ser Lys Pro Thr Leu Val Ala Gln Pro His Tyr Arg Leu Asp
        355                 360                 365

Leu Phe Asn Arg Lys Met Arg Asp Val Leu Phe Thr Thr Val Met Val
    370                 375                 380

Thr Thr Thr Gly Asn His Thr Leu Gly His Phe Gly Thr Ser Asp Gly
385                 390                 395                 400

Arg Ile Leu Gln Val Ile Leu Ser Leu Tyr Arg Pro Ile Val Phe Ala
                405                 410                 415

Asn Tyr Ser Leu Gly Asp Gly Glu Val Ser Arg Thr Ala Ala Val Tyr
            420                 425                 430

Ser Glu Asp
        435

<210> SEQ ID NO 34
<211> LENGTH: 449
<212> TYPE: PRT
<213> ORGANISM: Homo sapiens

<400> SEQUENCE: 34

Val Gln Ala Met Val Thr Tyr Glu Gly Asp Arg Asn Glu Ser Ala Val
1               5                   10                  15

Phe Val Ala Ile Arg Asn Arg Leu His Val Leu Gly Pro Asp Leu Lys
            20                  25                  30
```

```
Ser Val Gln Ser Leu Ala Thr Gly Pro Ala Gly Asp Pro Gly Cys Gln
            35                  40                  45

Thr Cys Ala Ala Cys Gly Pro Gly His Gly Pro Pro Gly Asp Thr
    50                  55                  60

Asp Thr Lys Val Leu Val Leu Asp Pro Ala Leu Pro Ala Leu Val Ser
65                  70                  75                  80

Cys Gly Ser Ser Leu Gln Gly Arg Cys Phe Leu His Asp Leu Glu Pro
                85                  90                  95

Gln Gly Thr Ala Val His Leu Ala Ala Pro Ala Cys Leu Phe Ser Ala
            100                 105                 110

His His Asn Arg Pro Asp Asp Cys Pro Asp Cys Val Ala Ser Pro Leu
            115                 120                 125

Gly Thr Arg Val Thr Val Val Glu Gln Gly Gln Ala Ser Tyr Phe Tyr
            130                 135                 140

Val Ala Ser Ser Leu Asp Ala Ala Val Ala Gly Ser Phe Ser Pro Arg
145                 150                 155                 160

Ser Val Ser Ile Arg Arg Leu Lys Ala Asp Ala Ser Gly Phe Ala Pro
                165                 170                 175

Gly Phe Val Ala Leu Ser Val Leu Pro Lys His Leu Val Ser Tyr Ser
            180                 185                 190

Ile Glu Tyr Val His Ser Phe His Thr Gly Ala Phe Val Tyr Phe Leu
            195                 200                 205

Thr Val Gln Pro Ala Ser Val Thr Asp Asp Pro Ser Ala Leu His Thr
            210                 215                 220

Arg Leu Ala Arg Leu Ser Ala Thr Glu Pro Glu Leu Gly Asp Tyr Arg
225                 230                 235                 240

Glu Leu Val Leu Asp Cys Arg Phe Ala Pro Gly Ala Pro Glu Gly Gly
                245                 250                 255

Gln Pro Tyr Pro Val Leu Gln Val Ala His Ser Ala Pro Val Gly Ala
            260                 265                 270

Gln Leu Ala Thr Glu Leu Ser Ile Ala Glu Gly Gln Glu Val Leu Phe
            275                 280                 285

Gly Val Phe Val Thr Gly Lys Asp Gly Gly Pro Gly Val Gly Pro Asn
            290                 295                 300

Ser Val Val Cys Ala Phe Pro Ile Asp Leu Leu Asp Thr Leu Ile Asp
305                 310                 315                 320

Glu Gly Val Glu Arg Cys Cys Glu Ser Pro Val His Pro Gly Leu Arg
                325                 330                 335

Arg Gly Leu Asp Phe Phe Gln Ser Pro Ser Phe Cys Pro Asn Pro Pro
            340                 345                 350

Gly Leu Glu Ala Leu Ser Pro Asn Thr Ser Cys Arg His Phe Pro Leu
            355                 360                 365

Leu Val Ser Ser Ser Phe Ser Arg Val Asp Leu Phe Asn Gly Leu Leu
370                 375                 380

Gly Pro Val Gln Val Thr Ala Leu Tyr Val Thr Arg Leu Asp Asn Val
385                 390                 395                 400

Thr Val Ala His Met Gly Thr Met Asp Gly Arg Ile Leu Gln Val Glu
                405                 410                 415

Leu Val Arg Ser Leu Asn Tyr Leu Leu Tyr Val Ser Asn Phe Ser Leu
            420                 425                 430

Gly Asp Ser Gly Gln Pro Val Gln Arg Asp Val Ser Arg Leu Gly Asp
            435                 440                 445
```

His

<210> SEQ ID NO 35
<211> LENGTH: 444
<212> TYPE: PRT
<213> ORGANISM: Mus musculus

<400> SEQUENCE: 35

```
Val Gln Ala Thr Ala Ala Tyr Glu Asp Ser Thr Asn Ser Ala Val Phe
1               5                   10                  15

Val Ala Thr Arg Asn His Leu His Val Leu Gly Pro Asp Leu Gln Phe
            20                  25                  30

Ile Glu Asn Leu Thr Thr Gly Pro Ile Gly Asn Pro Gly Cys Gln Thr
        35                  40                  45

Cys Ala Ser Cys Gly Pro Gly Pro His Gly Pro Pro Lys Asp Thr Asp
    50                  55                  60

Thr Leu Val Leu Val Met Glu Pro Gly Leu Pro Ala Leu Val Ser Cys
65                  70                  75                  80

Gly Ser Thr Leu Gln Gly Arg Cys Phe Leu His Glu Leu Glu Pro Arg
                85                  90                  95

Gly Lys Ala Leu His Leu Ala Ala Pro Ala Cys Leu Phe Ser Ala Asn
            100                 105                 110

Asn Asn Lys Pro Glu Ala Cys Thr Asp Cys Val Ala Ser Pro Leu Gly
        115                 120                 125

Thr Arg Val Thr Val Glu Gln Gly His Ala Ser Tyr Phe Tyr Val
    130                 135                 140

Ala Ser Ser Leu Asp Pro Glu Leu Ala Ala Ser Phe Ser Pro Arg Ser
145                 150                 155                 160

Val Ser Ile Arg Arg Leu Lys Ser Asp Thr Ser Gly Phe Gln Pro Gly
                165                 170                 175

Phe Pro Ser Leu Ser Val Leu Pro Lys Tyr Leu Ala Ser Tyr Leu Ile
            180                 185                 190

Lys Tyr Val Tyr Ser Phe His Ser Gly Asp Phe Val Tyr Phe Leu Thr
        195                 200                 205

Val Gln Pro Ile Ser Val Thr Ser Pro Pro Ser Ala Leu His Thr Arg
    210                 215                 220

Leu Val Arg Leu Asn Ala Val Glu Pro Glu Ile Gly Asp Tyr Arg Glu
225                 230                 235                 240

Leu Val Leu Asp Cys His Phe Ala Pro Ala Pro Glu Gly Thr Gln Pro
                245                 250                 255

Tyr Pro Val Leu Gln Ala Ala His Ser Ala Pro Val Asp Ala Lys Leu
            260                 265                 270

Ala Val Glu Leu Ser Ile Ser Glu Gly Gln Glu Val Leu Phe Gly Val
        275                 280                 285

Phe Val Thr Val Lys Asp Gly Gly Ser Gly Met Gly Pro Asn Ser Val
    290                 295                 300

Val Cys Ala Phe Pro Ile Tyr His Leu Asn Ile Leu Ile Glu Glu Gly
305                 310                 315                 320

Val Glu Tyr Cys Cys His Ser Ser Asn Ser Ser Ser Leu Leu Ser Arg
                325                 330                 335

Gly Leu Asp Phe Phe Gln Thr Pro Ser Phe Cys Pro Asn Pro Pro Gly
            340                 345                 350

Gly Pro Ser Ser Arg Cys His Tyr Phe Pro Leu Met Val His Ala Ser
        355                 360                 365
```

-continued

```
Phe Thr Arg Val Asp Leu Phe Asn Gly Leu Leu Gly Ser Val Lys Val
    370                 375                 380
Thr Ala Leu His Val Thr Arg Leu Gly Asn Val Thr Val Ala His Met
385                 390                 395                 400
Gly Thr Val Asp Gly Arg Val Leu Gln Val Glu Ile Ala Arg Ser Leu
                405                 410                 415
Asn Tyr Leu Leu Tyr Val Ser Asn Phe Ser Leu Gly Ser Ser Gly Gln
            420                 425                 430
Pro Val His Arg Asp Val Ser Arg Leu Gly Asn Asp
        435                 440

<210> SEQ ID NO 36
<211> LENGTH: 434
<212> TYPE: PRT
<213> ORGANISM: Xenopus laevis

<400> SEQUENCE: 36

Ile Gln Asn Leu Val Ser Gln Glu Asp Leu Leu Phe Leu Thr Thr Thr
1               5                   10                  15
Asn His Leu Tyr Val Leu Thr Gly Asn Glu Leu His Met Leu Gln Asn
            20                  25                  30
Leu Thr Thr Gly Pro Thr Asn Ser Gln Cys Thr Leu Cys Ser Lys Cys
        35                  40                  45
Gln Met Gly Asn Ala Leu Pro Ser Gln Pro Glu Asp Thr Glu Ser Gln
    50                  55                  60
Val Leu Val Ala Asp Pro Glu Glu Ser Val Ile Tyr Ser Cys Gly Ser
65                  70                  75                  80
Ser Leu His Gly Leu Cys Phe Met His Val Ile Ala Ser Ser Lys Ile
                85                  90                  95
Val Asp Ser Lys Cys Leu Phe Asn Gln Asn Arg Asn Asn Ala Ser Ser
            100                 105                 110
Cys Pro Asp Cys Ile Ala Ser Pro Leu Gly Thr Leu Leu Thr Val Val
        115                 120                 125
Thr Gln Ser Arg Val Val Tyr Phe Tyr Thr Ala Ser Ser Leu Asp Ser
    130                 135                 140
Pro Ile Ala Lys Ser Tyr Ser Pro Thr Ser Ile Ser Ile Arg Arg Leu
145                 150                 155                 160
Leu Gly Ser Glu Asp Gly Phe Gly Gly Gly Phe His Ser Leu Thr Val
                165                 170                 175
Leu Glu Thr Phe Arg Asp Ser Tyr Pro Ile His Tyr Val His Thr Phe
            180                 185                 190
Thr Ser Gly Ser Tyr Val Tyr Phe Leu Thr Val Gln Pro Glu His Pro
        195                 200                 205
Leu Ser Ser Thr Tyr His Ser Arg Val Val Arg Leu Tyr Lys Lys Glu
    210                 215                 220
Glu Glu Met Arg Ser Tyr Arg Glu Leu Ile Leu Glu Cys Arg Leu Glu
225                 230                 235                 240
Pro Arg Arg Arg Ala Glu Pro Arg Ile Phe Asn Val Leu Gln Ala Ala
                245                 250                 255
His Val Ala Thr Val Gly Ser Thr Leu Ala Gly Glu Leu Asp Ile Ser
            260                 265                 270
Glu Thr Asp Pro Val Leu Phe Ala Val Phe Ala Gln Ser Glu Pro Met
        275                 280                 285
Ser Ala Gln Pro Arg Lys Tyr Ser Ala Val Cys Ala Phe Pro Ile Ser
    290                 295                 300
```

```
Leu Ile Asp Leu Ser Ile Glu Asp Gly Met Asn Ala Cys Cys Ser Asn
305                 310                 315                 320

Thr Asn Ser Val Arg Leu Thr Arg Gly Leu Asn Phe Phe Gln Pro Glu
            325                 330                 335

Met Glu Cys Pro Gln Asn Asp Asn Gln Ser Asp Ile Thr Cys Lys Asn
            340                 345                 350

Val Pro Thr Leu Val Ser Pro Leu Arg Arg Val Asp Ile Phe Asn
            355                 360                 365

Gly Gln Leu Asp Gly Val Leu Leu Thr Ser Met Tyr Val Arg Pro Gln
    370                 375                 380

Glu Asp Leu Thr Ile Gly Phe Leu Gly Thr Ser Val Gly Arg Leu Leu
385                 390                 395                 400

Gln Val Val Leu Gln Arg Asn Ser Lys Pro Arg Thr Leu Ser Asn Phe
                405                 410                 415

Ser Ile Ser Asp Thr His Pro Val Ser Arg Glu Val Thr Arg Ile Arg
            420                 425                 430

Asp Ser

<210> SEQ ID NO 37
<211> LENGTH: 431
<212> TYPE: PRT
<213> ORGANISM: Mus musculus

<400> SEQUENCE: 37

Leu Thr His Leu Val His Asn Lys Thr Gly Glu Val Tyr Val Gly
1               5                   10                  15

Ala Ile Asn Arg Ile Tyr Lys Leu Ser Asn Asn Leu Thr Leu Leu Arg
                20                  25                  30

Thr His Val Thr Gly Pro Val Glu Asp Asn Glu Lys Cys Tyr Pro Pro
            35                  40                  45

Pro Ser Val Gln Ser Cys Pro His Gly Leu Ile Thr Thr Asn Asn Val
    50                  55                  60

Asn Lys Leu Leu Leu Ile Asp Tyr Ser Asp Asn Arg Leu Ile Ala Cys
65                  70                  75                  80

Gly Ser Ala Ser Gln Gly Ile Cys Gln Phe Leu Arg Leu Asp Asp Leu
                85                  90                  95

Phe Lys Leu Gly Arg Lys Glu His Tyr Leu Ser Ser Val Asn Glu Ser
            100                 105                 110

Gly Thr Met Ser Gly Val Ile Ile Glu Val Pro Asn Gly Gln Asn Lys
        115                 120                 125

Leu Phe Val Gly Thr Pro Ile Asp Gly Lys Ser Glu Tyr Phe Pro Thr
130                 135                 140

Leu Ser Ser Arg Lys Leu Leu Gly Asn Glu Asn Ala Glu Met Phe
145                 150                 155                 160

Gly Phe Val Tyr Gln Asp Glu Phe Val Ser Ser Gln Leu Lys Ile Pro
                165                 170                 175

Ser Phe Pro Thr Phe Asp Ile Tyr Tyr Val Tyr Ser Phe Ser Ser Glu
            180                 185                 190

Gln Phe Val Tyr Tyr Leu Thr Leu Gln Leu Asp Thr Gln Leu Ser Thr
        195                 200                 205

Gly Glu Gln Phe Phe Thr Ser Lys Ile Val Arg Leu Cys Val Asp Asp
    210                 215                 220

Pro Lys Phe Tyr Ser Tyr Val Glu Phe Pro Ile Gly Cys Met Lys Asp
225                 230                 235                 240
```

Gly Val Glu Tyr Arg Leu Ile Gln Asp Ala Tyr Leu Ser Lys Pro Gly
                245                 250                 255

Lys Arg Leu Ala Lys Glu Leu Gly Ile Ser Glu Arg Glu Asp Ile Leu
            260                 265                 270

Phe Thr Val Phe Ser Gln Gly Gln Lys Asn Arg Ile Lys Pro Pro Lys
        275                 280                 285

Glu Ser Val Leu Cys Leu Phe Thr Leu Lys Lys Ile Lys Asp Lys Ile
    290                 295                 300

Lys Glu Arg Ile Gln Ser Cys Tyr Arg Gly Asp Gly Lys Leu Ser Leu
305                 310                 315                 320

Pro Trp Leu Leu Asn Lys Glu Leu Gly Cys Ile Asn Ser Pro Leu Gln
                325                 330                 335

Ile Asp Asp Asn Phe Cys Gly Gln Asp Phe Asn Gln Pro Leu Gly Gly
            340                 345                 350

Thr Val Thr Ile Glu Gly Thr Pro Leu Phe Leu Asp Lys Glu Asp Gly
        355                 360                 365

Met Thr Ser Val Ala Ala Tyr Asp Tyr Arg Gly His Thr Val Val Phe
    370                 375                 380

Ala Gly Thr Arg Ser Gly Arg Val Lys Lys Ile Leu Val Asp Leu Ser
385                 390                 395                 400

Ala Ser Ser Ser His Leu Val Gln Gln Tyr Glu Asn Val Val His
                405                 410                 415

Glu Gly Asn Ala Ile Leu Arg Asp Leu Val Leu Ser Pro Asp Arg
            420                 425                 430

<210> SEQ ID NO 38
<211> LENGTH: 427
<212> TYPE: PRT
<213> ORGANISM: Mus musculus

<400> SEQUENCE: 38

Leu Thr His Leu Ala Val His Arg Val Thr Gly Glu Val Phe Val Gly
1               5                   10                  15

Ala Val Asn Arg Val Phe Lys Leu Ala Pro Asn Leu Thr Glu Leu Arg
            20                  25                  30

Ala His Val Thr Gly Pro Ile Glu Asp Asn Ala Arg Cys Tyr Pro Pro
        35                  40                  45

Pro Ser Met Arg Val Cys Ser His Arg Leu Val Pro Val Asp Asn Val
    50                  55                  60

Asn Lys Leu Leu Leu Ile Asp Tyr Ala Ala Arg Arg Leu Val Ala Cys
65                  70                  75                  80

Gly Ser Ile Trp Gln Gly Ile Cys Gln Phe Leu Arg Leu Asp Asp Leu
                85                  90                  95

Phe Lys Leu Gly Arg Lys Glu His Tyr Leu Ser Gly Ala Gln Glu Pro
            100                 105                 110

Asp Ser Met Ala Gly Val Ile Val Glu Gln Val Gln Gly Pro Ser Lys
        115                 120                 125

Leu Phe Val Gly Thr Ala Val Asp Gly Lys Ser Glu Tyr Phe Pro Thr
    130                 135                 140

Leu Ser Ser Arg Lys Leu Ile Asp Asp Glu Asp Ser Gly Asp Met Phe
145                 150                 155                 160

Ser Leu Val Tyr Gln Asp Glu Phe Val Ser Ser Gln Ile Lys Ile Pro
                165                 170                 175

Ser Tyr Pro Ala Phe Asp Ile Tyr Tyr Ile Tyr Gly Phe Val Ser Ala

```
                180                 185                 190
Ser Phe Val Tyr Phe Leu Thr Leu Gln Leu Asp Thr Gln Gln Thr Ala
                195                 200                 205

Gly Glu Lys Phe Phe Thr Ser Lys Ile Val Arg Met Cys Ala Gly Asp
            210                 215                 220

Ser Glu Phe Tyr Ser Tyr Val Glu Phe Pro Ile Gly Cys Ser Trp Arg
225                 230                 235                 240

Gly Val Glu Tyr Arg Leu Val Gln Ser Ala His Leu Ala Lys Pro Gly
                245                 250                 255

Leu Leu Leu Ala Gln Ala Leu Gly Val Pro Ala Asp Glu Asp Val Leu
            260                 265                 270

Phe Thr Ile Phe Ser Gln Gly Gln Lys Asn Arg Ala Asn Pro Pro Arg
                275                 280                 285

Gln Thr Ile Leu Cys Leu Phe Thr Leu Ser Ser Ile Asn Ala His Ile
                290                 295                 300

Arg Arg Arg Ile Gln Ser Cys Tyr Arg Gly Glu Gly Thr Leu Ala Leu
305                 310                 315                 320

Pro Trp Leu Leu Asn Lys Glu Leu Pro Cys Ile Asn Thr Pro Leu Gln
                325                 330                 335

Ile Asn Gly Asn Phe Cys Gly Leu Val Leu Asn Gln Pro Leu Gly Gly
                340                 345                 350

Leu His Val Ile Glu Gly Leu Pro Leu Leu Ala Asp Ser Thr Asp Gly
                355                 360                 365

Met Ala Ser Val Ala Ala Tyr Thr Tyr His Gln His Ser Val Val Phe
                370                 375                 380

Ile Gly Thr Arg Ser Gly Asn Leu Lys Lys Val Arg Val Asp Gly Ser
385                 390                 395                 400

Gln Asp Ala Gln Leu Tyr Glu Thr Val Ser Val Gln Gly Ser Pro
                405                 410                 415

Ile Leu Arg Asp Leu Leu Phe Ser Pro Asp His
                420                 425

<210> SEQ ID NO 39
<211> LENGTH: 433
<212> TYPE: PRT
<213> ORGANISM: Mus musculus

<400> SEQUENCE: 39

Leu Thr His Leu Val His Glu Gln Thr Gly Glu Val Tyr Val Gly
1               5                   10                  15

Ala Val Asn Arg Ile Tyr Lys Leu Ser Gly Asn Leu Thr Leu Leu Arg
                20                  25                  30

Ala His Val Thr Gly Pro Val Glu Asp Asn Glu Lys Cys Tyr Pro Pro
            35                  40                  45

Pro Ser Val Gln Ser Cys Pro His Gly Leu Gly Ser Thr Asp Asn Val
50                  55                  60

Asn Lys Leu Leu Leu Leu Asp Tyr Ala Ala Asn Arg Leu Leu Ala Cys
65                  70                  75                  80

Gly Ser Ala Ser Gln Gly Ile Cys Gln Phe Leu Arg Leu Asp Asp Leu
                85                  90                  95

Phe Lys Leu Gly Arg Lys Glu His Tyr Leu Ser Ser Val Arg Glu Ala
            100                 105                 110

Gly Ser Met Ala Gly Val Leu Ile Ala Gly Pro Pro Gly Gln Gly Gln
            115                 120                 125
```

Ala Lys Leu Phe Val Gly Thr Pro Ile Asp Gly Lys Ser Glu Tyr Phe
130                 135                 140

Pro Thr Leu Ser Ser Arg Arg Leu Met Ala Asn Glu Glu Asp Ala Asp
145                 150                 155                 160

Met Phe Gly Phe Val Tyr Gln Asp Glu Phe Val Ser Ser Gln Leu Lys
            165                 170                 175

Ile Pro Ser Phe Pro Ala Phe Asp Ile Tyr Tyr Val Tyr Ser Phe Arg
            180                 185                 190

Ser Glu Gln Phe Val Tyr Tyr Leu Thr Leu Gln Leu Asp Thr Gln Leu
            195                 200                 205

Ala Ala Gly Glu His Phe Phe Thr Ser Lys Ile Val Arg Leu Cys Val
210                 215                 220

Asn Asp Pro Lys Phe Tyr Ser Tyr Val Glu Phe Pro Ile Gly Cys Glu
225                 230                 235                 240

Gln Ala Gly Val Glu Tyr Arg Leu Val Gln Asp Ala Tyr Leu Ser Arg
            245                 250                 255

Pro Gly Gln Ala Leu Ala Lys Gln Leu Gly Leu Ala Glu Asp Glu Glu
            260                 265                 270

Val Leu Phe Thr Val Phe Ala Gln Gly Gln Lys Asn Arg Val Lys Pro
    275                 280                 285

Pro Lys Glu Ser Ala Leu Cys Leu Phe Thr Leu Arg Ala Ile Lys Glu
290                 295                 300

Lys Ile Lys Glu Arg Ile Gln Ser Cys Tyr Arg Gly Glu Gly Lys Leu
305                 310                 315                 320

Ser Leu Pro Trp Leu Leu Asn Lys Glu Leu Gly Cys Ile Asn Ser Pro
            325                 330                 335

Leu Gln Ile Asp Asp Asp Phe Cys Gly Gln Asp Phe Asn Gln Pro Leu
            340                 345                 350

Gly Gly Thr Val Thr Ile Glu Gly Thr Pro Leu Phe Val Asp Lys Glu
            355                 360                 365

Asp Gly Leu Thr Ala Val Ala Ala Tyr Asp Tyr Gln Gly Arg Thr Val
            370                 375                 380

Val Phe Ala Gly Thr Arg Ser Gly Arg Ile Arg Lys Ile Leu Val Asp
385                 390                 395                 400

Leu Ala Asn Pro Ser Gly Arg Pro Ala Leu Ala Tyr Glu Ser Val Val
            405                 410                 415

Ala Gln Glu Gly Asn Pro Ile Leu Arg Asp Leu Val Leu Ser Pro Asn
            420                 425                 430

Arg

<210> SEQ ID NO 40
<211> LENGTH: 429
<212> TYPE: PRT
<213> ORGANISM: Homo sapiens

<400> SEQUENCE: 40

Phe Asn His Leu Thr Val His Gln Gly Thr Gly Ala Val Tyr Val Gly
1               5                   10                  15

Ala Ile Asn Arg Val Tyr Lys Leu Thr Gly Asn Leu Thr Ile Gln Val
            20                  25                  30

Ala His Lys Thr Gly Pro Glu Glu Asp Asn Lys Ser Cys Tyr Pro Pro
        35                  40                  45

Leu Ile Val Gln Pro Cys Ser Glu Val Leu Thr Leu Thr Asn Asn Val
    50                  55                  60

```
Asn Lys Leu Leu Ile Ile Asp Tyr Ser Glu Asn Arg Leu Leu Ala Cys
 65                  70                  75                  80

Gly Ser Leu Tyr Gln Gly Val Cys Lys Leu Leu Arg Leu Asp Asp Leu
                 85                  90                  95

Phe Ile Leu Val Lys Lys Glu His Tyr Leu Ser Ser Val Asn Lys Thr
            100                 105                 110

Gly Thr Met Tyr Gly Val Ile Val Arg Ser Glu Gly Glu Asp Gly Lys
        115                 120                 125

Leu Phe Ile Gly Thr Ala Val Asp Gly Lys Gln Asp Tyr Phe Pro Thr
130                 135                 140

Leu Ser Ser Arg Lys Leu Pro Arg Asp Pro Glu Ser Ser Ala Met Leu
145                 150                 155                 160

Asp Tyr Glu Leu His Ser Asp Phe Val Ser Ser Leu Ile Lys Ile Pro
                165                 170                 175

Ser Val Ser His Phe Asp Ile Phe Tyr Ile Tyr Gly Phe Ala Ser Gly
            180                 185                 190

Gly Phe Val Tyr Phe Leu Thr Val Gln Pro Glu Thr Pro Glu Ser Ala
        195                 200                 205

Gly Asp Leu Phe Tyr Thr Ser Arg Ile Val Arg Leu Cys Lys Asp Asp
210                 215                 220

Pro Lys Phe His Ser Tyr Val Ser Leu Pro Phe Gly Cys Thr Arg Ala
225                 230                 235                 240

Gly Val Glu Tyr Arg Leu Leu Gln Ala Ala Tyr Leu Ala Lys Pro Gly
                245                 250                 255

Asp Ser Leu Ala Gln Ala Phe Asn Ile Thr Ser Gln Asp Asp Val Leu
            260                 265                 270

Phe Ala Ile Phe Ser Lys Gly Gln Lys Gln Tyr His His Pro Pro Asp
        275                 280                 285

Asp Ser Ala Leu Cys Ala Phe Pro Ile Arg Ala Ile Asn Leu Gln Ile
290                 295                 300

Lys Gly Arg Leu Gln Ser Cys Tyr Gln Gly Gly Asn Leu Glu Leu
305                 310                 315                 320

Asn Trp Leu Leu Gly Lys Asp Val Gln Cys Thr Lys Ala Pro Val Pro
                325                 330                 335

Ile Asp Asp Asn Phe Cys Gly Leu Asp Ile Asn Gln Pro Leu Gly Gly
            340                 345                 350

Ser Thr Pro Val Glu Gly Leu Thr Leu Tyr Thr Thr Ser Arg Asp Arg
        355                 360                 365

Met Thr Ser Val Ala Ser Tyr Val Tyr Asn Gly Tyr Ser Val Val Phe
370                 375                 380

Val Gly Thr Lys Ser Gly Lys Leu Lys Lys Ile Arg Ala Asp Gly Pro
385                 390                 395                 400

Pro His Gly Gly Val Gln Tyr Glu Met Val Ser Val Leu Lys Asp Gly
                405                 410                 415

Ser Pro Ile Leu Arg Asp Met Ala Phe Ser Ile Asp Gln
            420                 425

<210> SEQ ID NO 41
<211> LENGTH: 430
<212> TYPE: PRT
<213> ORGANISM: Drosophila melanogaster

<400> SEQUENCE: 41

Leu Asn His Leu Leu Val Asp Thr Ile Thr Gly Arg Val Phe Val Gly
  1               5                  10                  15
```

-continued

```
Gly Val Asn Arg Leu Tyr Gln Leu Ser Pro Asp Leu Glu Leu Ser Glu
             20                  25                  30

Thr Val Lys Thr Gly Pro Gln Asn Asp Ser Val Glu Cys Ser Ile Leu
             35                  40                  45

Asp Cys Pro Leu Asn Ala Val Arg Ser Pro Thr Asp Asn Tyr Asn Lys
 50                  55                  60

Val Leu Leu Ile Asp Arg Ala Thr Ser Arg Leu Ile Ala Cys Gly Ser
 65                  70                  75                  80

Leu Phe Gln Gly Thr Cys Thr Val Arg Asn Leu Gln Asn Val Ser Ile
             85                  90                  95

Ile Glu His Glu Val Pro Asp Ala Val Ala Asn Asp Ala Asn Ser
             100                 105                 110

Ser Thr Val Ala Phe Ile Ala Pro Gly Pro Gln His Pro Val Thr
             115                 120                 125

Asn Val Met Tyr Val Gly Val Thr Tyr Thr Asn Asn Ser Pro Tyr Arg
130                  135                 140

Ser Glu Ile Pro Ala Val Ala Ser Arg Ser Leu Glu Lys Thr Lys Met
145                  150                 155                 160

Phe Gln Ile Ala Ser Ser Ala Val Thr Thr Gly Thr Arg Thr Phe Ile
             165                 170                 175

Asn Ser Tyr Ala Arg Glu Thr Tyr Phe Val Asn Tyr Val Tyr Gly Phe
             180                 185                 190

Ser Ser Glu Arg Phe Ser Tyr Phe Leu Thr Thr Gln Leu Lys His Ser
             195                 200                 205

His His Ser Ser Pro Lys Glu Tyr Ile Thr Lys Leu Val Arg Ile Cys
             210                 215                 220

Gln Glu Asp Ser Asn Tyr Tyr Ser Tyr Thr Glu Ile Pro Val Glu Cys
225                  230                 235                 240

Ile Ser Asp Ala Gln Gly Gly Thr Lys Phe Asn Leu Val Gln Ala Gly
             245                 250                 255

Phe Leu Gly Lys Pro Ser Ser Asn Leu Ala Gln Ser Leu Gly Ile Ser
             260                 265                 270

Ile Gln Asn Asp Val Leu Phe Ala Val Phe Ser Lys Gly Glu Gly Asn
             275                 280                 285

Thr Pro Thr Asn Asn Ser Ala Leu Cys Ile Tyr Ser Leu Lys Ser Ile
             290                 295                 300

Arg Arg Lys Phe Met Gln Asn Ile Lys Ser Cys Phe Asn Gly Ser Gly
305                  310                 315                 320

Met Arg Gly Leu Asn Phe Ile Ser Pro Ser Met Pro Cys Val Leu Thr
             325                 330                 335

Lys Leu Gln Thr Ile Gly Glu Asp Phe Cys Gly Leu Asp Val Asn Ser
             340                 345                 350

Pro Leu Gly Gly Glu Thr Pro Ile Thr Ser Val Pro Val Ala Met Phe
             355                 360                 365

Asn Thr Lys Leu Thr Ser Val Ala Ala Thr Ser Thr Ser Gly Tyr Thr
             370                 375                 380

Val Val Phe Val Gly Thr Ser Asp Gly Phe Leu Lys Lys Val Val Ile
385                  390                 395                 400

Glu Ser Ser Ser Ile Ala Asn Glu Tyr Ala Ser Phe Ala Val Asp Leu
             405                 410                 415

Gly Ser Glu Ile Asn Arg Asp Met Gln Phe Asp Asn Gln Asn
             420                 425                 430
```

```
<210> SEQ ID NO 42
<211> LENGTH: 431
<212> TYPE: PRT
<213> ORGANISM: Drosophila melanogaster

<400> SEQUENCE: 42

Phe Thr His Met Ser Phe Asp Phe Met His Asn Val Leu Phe Ala Gly
1               5                   10                  15

Ala Thr Asn Lys Ile Leu Lys Leu Asn Glu Asn Leu Arg Val Leu Ala
            20                  25                  30

Glu Ala Val Thr Gly Pro Leu His Asp Ser Pro Gln Cys His Ala Gly
        35                  40                  45

Gly Cys Pro Glu Asp Ile Glu Thr Ser Leu Val Asn Asn Phe Asn Lys
    50                  55                  60

Ile Leu Val Val Ser Tyr Ala His Asp Gly Ile Leu Ile Ala Cys Gly
65                  70                  75                  80

Ser Ile Arg Gln Gly Ala Cys Glu Ile Tyr Ser Leu Pro Arg Phe Pro
                85                  90                  95

Ala Thr Pro Gln Phe Phe Ala Val Pro Leu Ala Ala Asn Asp Glu Asn
            100                 105                 110

Ala Ser Thr Tyr Ala Phe Val Gly Pro Ala Arg Tyr Ala Trp Lys Glu
        115                 120                 125

Glu Asp Ile Leu Tyr Val Gly Thr Thr Phe Thr Asn Val Gly Asp Tyr
    130                 135                 140

Arg His Asp Val Pro Ala Ile Ser Ser Arg Arg Leu Asp Asp Leu Asn
145                 150                 155                 160

Tyr Ala Glu Phe Ser Ile Gln Gln Ser Ile Ile Asn Ile Asp Val Lys
                165                 170                 175

Tyr Arg Asp His Phe Leu Val Asp Tyr Ile Tyr Gly Phe Asn Ser Ser
            180                 185                 190

Glu Tyr Ala Tyr Phe Ile Ile Val Gln Lys Lys Ser His Leu Ala Asp
        195                 200                 205

Glu Ala Gly Tyr Val Thr Arg Leu Ala Arg Ile Cys Ile Thr Asp Pro
    210                 215                 220

Asn Tyr Asp Ser Tyr Thr Glu Ile Thr Val Gln Cys Thr Ala Thr Glu
225                 230                 235                 240

Asn Asn Val Asp Tyr Asn Ile Val Arg Asp Ala Lys Val Thr Pro Ala
                245                 250                 255

Ser His Lys Leu Ala Gln Lys Met Gly Ile Lys Lys Asp Asp His Val
            260                 265                 270

Leu Val Thr Val Phe Ser Pro Ser Arg Glu Ile Ser Asn Gln Pro Glu
        275                 280                 285

Ser Lys Ser Ala Met Cys Ile Tyr Ser Ile Lys Asp Ile Glu Asp Met
    290                 295                 300

Phe Ile Glu Asn Ile His Leu Cys Phe Asn Gly Thr Thr Lys Asp Arg
305                 310                 315                 320

Asn Leu Gly Tyr Ile Ser Gly Thr Ile Asn Asp Gly Arg Cys Pro Ile
                325                 330                 335

Val Gly Ser Leu Gly Asn Ile Tyr Asn Phe Cys Ser Val Gly Leu Lys
            340                 345                 350

Ile Ser Gly Val Ser Pro Ile Thr Ala His Ala Leu Phe His Phe Asp
        355                 360                 365

Asn Val Ser Val Thr Ser Val Thr Ala Thr Ser Thr Asp Gln Gln
    370                 375                 380
```

His Ser Leu Ala Phe Leu Gly Thr Asn Met Gly Val Ile Lys Lys Val
385                 390                 395                 400

Leu Leu Ser Gly Gln Ser Pro Gly Glu Tyr Glu Ile Val Val Asp
            405                 410                 415

Ala Gly Asn Arg Ile Leu Pro Asn Thr Met Met Ser Pro Lys Lys
            420                 425                 430

<210> SEQ ID NO 43
<211> LENGTH: 421
<212> TYPE: PRT
<213> ORGANISM: Homo sapiens

<400> SEQUENCE: 43

Leu Gln His Leu Ala Arg Asp Pro Thr Ser Gly Thr Leu Tyr Leu Gly
1               5                   10                  15

Ala Thr Asn Phe Leu Phe Gln Leu Ser Pro Gly Leu Gln Leu Glu Ala
            20                  25                  30

Thr Val Ser Thr Gly Pro Val Leu Asp Ser Arg Asp Cys Leu Pro Pro
        35                  40                  45

Val Met Pro Asp Glu Cys Pro Gln Ala Gln Pro Thr Asn Asn Pro Asn
50                  55                  60

Gln Leu Leu Leu Val Ser Pro Gly Ala Leu Val Val Cys Gly Ser Val
65                  70                  75                  80

His Gln Gly Val Cys Glu Gln Arg Arg Leu Gly Gln Leu Glu Gln Leu
                85                  90                  95

Leu Leu Arg Pro Glu Arg Pro Gly Asp Thr Gln Tyr Val Ala Ala Asn
            100                 105                 110

Asp Pro Ala Val Ser Thr Val Gly Leu Val Ala Gln Gly Leu Ala Gly
        115                 120                 125

Glu Pro Leu Leu Phe Val Gly Arg Gly Tyr Thr Ser Arg Gly Val Gly
130                 135                 140

Gly Gly Ile Pro Pro Ile Thr Thr Arg Ala Leu Trp Pro Pro Asp Pro
145                 150                 155                 160

Gln Ala Ala Phe Ser Tyr Glu Glu Thr Ala Lys Leu Ala Val Gly Arg
                165                 170                 175

Leu Ser Glu Tyr Ser His His Phe Val Ser Ala Phe Ala Arg Gly Ala
            180                 185                 190

Ser Ala Tyr Phe Leu Phe Leu Arg Arg Asp Leu Gln Ala Gln Ser Arg
        195                 200                 205

Ala Phe Arg Ala Tyr Val Ser Arg Val Cys Leu Arg Asp Gln His Tyr
210                 215                 220

Tyr Ser Tyr Val Glu Leu Pro Leu Ala Cys Glu Gly Gly Arg Tyr Gly
225                 230                 235                 240

Leu Ile Gln Ala Ala Val Ala Thr Ser Arg Glu Val Ala His Gly
                245                 250                 255

Glu Val Leu Phe Ala Ala Phe Ser Ser Ala Ala Pro Pro Ala Ala Gly
            260                 265                 270

Ala Ser Gly Ala Ser Ala Leu Cys Ala Phe Pro Leu Asp Glu Val Asp
        275                 280                 285

Arg Leu Ala Asn Arg Thr Arg Asp Ala Cys Tyr Thr Arg Glu Gly Arg
290                 295                 300

Ala Glu Asp Gly Thr Glu Val Ala Tyr Ile Glu Tyr Asp Val Asn Ser
305                 310                 315                 320

Asp Cys Ala Gln Leu Pro Val Asp Thr Leu Asp Ala Tyr Pro Cys Gly

```
                    325                 330                 335
Ser Asp His Thr Pro Ser Pro Met Ala Ser Arg Val Pro Leu Glu Ala
                340                 345                 350

Thr Pro Ile Leu Glu Trp Pro Gly Ile Gln Leu Thr Ala Val Ala Val
            355                 360                 365

Thr Met Glu Asp Gly His Thr Ile Ala Phe Leu Gly Asp Ser Gln Gly
        370                 375                 380

Gln Leu His Arg Val Tyr Leu Gly Pro Gly Ser Asp Gly His Pro Tyr
385                 390                 395                 400

Ser Thr Gln Ser Ile Gln Gln Gly Ser Ala Val Ser Arg Asp Leu Thr
                405                 410                 415

Phe Asp Gly Thr Phe
                420

<210> SEQ ID NO 44
<211> LENGTH: 417
<212> TYPE: PRT
<213> ORGANISM: Homo sapiens

<400> SEQUENCE: 44

Leu Asn His Leu Ala Val Asp Glu Ala Ser Gly Val Val Tyr Leu Gly
1               5                   10                  15

Ala Val Asn Ala Leu Tyr Gln Leu Asp Ala Lys Leu Gln Leu Glu Gln
            20                  25                  30

Gln Val Ala Thr Gly Pro Ala Leu Asp Asn Lys Lys Cys Thr Pro Pro
        35                  40                  45

Ile Glu Ala Ser Gln Cys His Glu Ala Glu Met Thr Asp Asn Val Asn
    50                  55                  60

Gln Leu Leu Leu Asp Pro Pro Arg Lys Arg Leu Val Glu Cys Gly
65                  70                  75                  80

Ser Leu Phe Lys Gly Ile Cys Ala Leu Arg Ala Leu Ser Asn Ile Ser
                85                  90                  95

Leu Arg Leu Phe Tyr Glu Asp Gly Ser Gly Glu Lys Ser Phe Val Ala
            100                 105                 110

Ser Asn Asp Glu Gly Val Ala Thr Val Gly Leu Val Ser Ser Thr Gly
        115                 120                 125

Pro Gly Gly Asp Arg Val Leu Phe Val Gly Lys Gly Asn Gly Pro His
    130                 135                 140

Asp Asn Gly Ile Ile Val Ser Thr Arg Leu Leu Asp Arg Thr Asp Ser
145                 150                 155                 160

Arg Glu Ala Phe Glu Ala Tyr Thr Asp His Ala Thr Tyr Lys Ala Gly
                165                 170                 175

Tyr Leu Ser Thr Asn Thr Gln Gln Phe Val Ala Phe Glu Asp Gly
            180                 185                 190

Pro Tyr Val Phe Phe Val Phe Asn Gln Gln Asp Lys His Pro Ala Arg
        195                 200                 205

Asn Arg Thr Leu Leu Ala Arg Met Cys Arg Glu Asp Pro Asn Tyr Tyr
    210                 215                 220

Ser Tyr Leu Glu Met Asp Leu Gln Cys Arg Asp Pro Asp Ile His Ala
225                 230                 235                 240

Ala Ala Phe Gly Thr Cys Leu Ala Ala Ser Val Ala Ala Pro Gly Ser
                245                 250                 255

Gly Arg Val Leu Tyr Ala Val Phe Ser Arg Asp Ser Arg Ser Ser Gly
            260                 265                 270
```

```
Gly Pro Gly Ala Gly Leu Cys Leu Phe Pro Leu Asp Lys Val His Ala
            275                 280                 285
Lys Met Glu Ala Asn Arg Asn Ala Cys Tyr Thr Gly Thr Arg Glu Ala
        290                 295                 300
Arg Asp Ile Phe Tyr Lys Pro Phe His Gly Asp Ile Gln Cys Gly Gly
305                 310                 315                 320
His Ala Pro Gly Ser Ser Lys Ser Phe Pro Cys Gly Ser Glu His Leu
                325                 330                 335
Pro Tyr Pro Leu Gly Ser Arg Asp Gly Leu Arg Gly Thr Ala Val Leu
                340                 345                 350
Gln Arg Gly Gly Leu Asn Leu Thr Ala Val Thr Val Ala Ala Glu Asn
            355                 360                 365
Asn His Thr Val Ala Phe Leu Gly Thr Ser Asp Gly Arg Ile Leu Lys
        370                 375                 380
Val Tyr Leu Thr Pro Asp Gly Thr Ser Ser Glu Tyr Asp Ser Ile Leu
385                 390                 395                 400
Val Glu Ile Asn Lys Arg Val Lys Arg Asp Leu Val Leu Ser Gly Asp
                405                 410                 415
Leu

<210> SEQ ID NO 45
<211> LENGTH: 402
<212> TYPE: PRT
<213> ORGANISM: Mus musculus

<400> SEQUENCE: 45

Phe Asn His Leu Val Leu Ala Pro Asp Gln Gly Lys Leu Tyr Val Gly
1               5                   10                  15
Ala Val Asn His Leu Phe Gln Leu Ser Pro Glu Leu Lys Met Glu Ser
            20                  25                  30
Val Ala Val Thr Gly Pro Val Ile Asp Ser Pro Asp Cys Val Pro Phe
        35                  40                  45
Arg Asp Leu Ala Glu Cys Pro Gln Ala Gln Leu Thr Asp Asn Ala Asn
50                  55                  60
Gln Leu Leu Leu Val Ser Ser Arg Thr Gln Glu Leu Val Ala Cys Gly
65                  70                  75                  80
Gln Val Lys Gln Gly Val Cys Glu Lys Arg Arg Leu Gly Asp Val Thr
                85                  90                  95
Gln Val Leu Tyr Gln Ala Glu Asp Pro Gly Asp Gly Gln Phe Val Ala
            100                 105                 110
Ala Asn Thr Leu Gly Val Thr Thr Val Gly Leu Val Val Pro Leu Pro
        115                 120                 125
Gly Arg Asp Leu Leu Leu Val Ala Arg Gly Leu Ala Gly Lys Leu Ser
130                 135                 140
Ala Gly Val Pro Pro Leu Thr Val Arg Gln Leu Ala Gly Pro Gln Pro
145                 150                 155                 160
Phe Ser Ser Glu Gly Leu Gly Arg Leu Val Gly Asp Phe Ser Asp
                165                 170                 175
Tyr Asn Asn Ser Tyr Val Gly Ala Phe Ser Asp Ala His Ser Ala Tyr
            180                 185                 190
Phe Val Phe Arg Arg Arg Gly Ala Arg Ala Gln Thr Glu Tyr Arg Ser
        195                 200                 205
Tyr Val Ala Arg Val Cys Leu Arg Asp Val Asn Leu Tyr Ser Tyr Val
            210                 215                 220
```

-continued

```
Glu Met Pro Leu Thr Cys His Gly Gln Gly Leu Ile Gln Ala Ala Phe
225                 230                 235                 240

Leu Thr Pro Asp Thr Leu Leu Gly Ala Phe Ser Ala Gly Thr Ser Gln
            245                 250                 255

Ala Gln Ala Ala Leu Cys Ala Phe Pro Leu Ala Asp Leu Asp Arg Ser
        260                 265                 270

Met Glu Gln Ala Arg Arg Leu Cys Tyr Thr Thr Gly Gly Gln Gly Pro
    275                 280                 285

Ser Gly Met Glu Glu Ala Thr Val Glu Tyr Gly Val Thr Ser Arg Cys
290                 295                 300

Val Thr Leu Pro Pro Asp Ser Pro Glu Ser Tyr Pro Cys Gly Asp Glu
305                 310                 315                 320

His Thr Pro Ser Pro Ile Ala Gly Arg Gln Pro Leu Glu Ala Gln Pro
                325                 330                 335

Leu Leu Gln Leu Gly Gln Ser Ile Ser Ala Val Ala Ala Leu Gln Thr
            340                 345                 350

Asp Gly His Thr Ile Ala Phe Leu Gly Asp Thr Gln Gly Gln Leu His
        355                 360                 365

Lys Val Phe Leu Asn Ser Ser His Gly Gln Val Tyr His Ser Gln Gln
    370                 375                 380

Val Gly Pro Pro Gly Ser Ala Ile Ser Pro Asp Leu Leu Val Asp Ser
385                 390                 395                 400

Asn Gly

<210> SEQ ID NO 46
<211> LENGTH: 437
<212> TYPE: PRT
<213> ORGANISM: Caenorhabditis elegans

<400> SEQUENCE: 46

Phe Glu Lys Met Ala Ile Asp Pro Ser Thr Thr Arg Val Phe Val Gly
1               5                   10                  15

Ala Val Asn Ser Leu Tyr Asp Leu Thr Ser Ala Asp Leu Thr Val Arg
            20                  25                  30

Arg His Val Gln Thr Gly Pro Gln Asp Asp Ser Pro Leu Cys Arg Gly
        35                  40                  45

Lys Trp Asn Lys Lys Asn Ser Leu Lys Lys Leu Tyr Ser Arg Thr Asn
50                  55                  60

Ser His Thr Lys Ala Leu Ser Val Tyr Asp Lys Ser Ser Lys Leu Ile
65                  70                  75                  80

Glu Cys Ser Asn Leu Tyr Gln Gly Arg Cys Arg Leu Arg Asn Leu His
                85                  90                  95

Asn Ile Ser Glu Val Ile Ser Glu Ala Ile Glu Pro Arg Val Ser Asn
            100                 105                 110

Asp Thr Ser Ser Ser Val Val Ile Phe Val Gly Ser Gly Pro Ala Asn
        115                 120                 125

Leu Ser Ser Glu Pro Val Leu Tyr Val Gly Ala Thr Ile Gly Ser Gly
    130                 135                 140

Asp His Asp Arg Met Ser Val Ser Ser Leu Phe Leu Arg Pro Gln Lys
145                 150                 155                 160

Ala Phe Glu Val Val Phe Pro Gly Leu Tyr Gly Gly Thr His Val Ser
                165                 170                 175

Leu Asp Tyr Arg Ser Arg Gly Tyr Tyr Lys Tyr Gln Ile Asp Tyr Ile
            180                 185                 190
```

```
Asn Gly Phe Glu Ser Gly Asp Tyr Ala Tyr Phe Val Thr Arg Gln Arg
        195                 200                 205

Val Asn Ile Ala Asp Asp Ser Ser Ile Gln Ser Arg Leu Val Arg Val
    210                 215                 220

Cys Thr Gly Asp Lys Asn Phe His Ser Tyr Thr Glu Val Pro Leu Glu
225                 230                 235                 240

Cys Thr Gln Asn Gly Val Glu Phe Asn Leu Val Gln Asp Val Tyr Val
                245                 250                 255

Thr Arg Ala Gly Tyr Glu Leu Ala Lys Ser Leu Asp Ile Ser Val Ser
            260                 265                 270

Asp Pro Val Leu Tyr Gly Val Phe Trp Glu Gly Asp Lys Asn Ser Tyr
        275                 280                 285

Arg Ser Gln Glu Pro Thr Gly Lys Ser Ala Ile Cys Met Phe Thr Met
290                 295                 300

Arg Glu Ile Glu Thr Ser Phe Lys Gln Asn Ile Met Lys Cys Tyr Lys
305                 310                 315                 320

Gly Thr Ser Gly Leu Lys Lys Asn Leu Pro Trp Phe Ser Asn Asp
                325                 330                 335

Asp Cys Arg Phe Thr Thr Leu Pro Trp Glu Gly Ile Lys Cys Gly Lys
                340                 345                 350

Asp Val Asn Ser Lys Ile Gly Gly Asp Thr Pro Ile Ser Thr Ser Ala
            355                 360                 365

Thr Tyr Val Met Glu Asp Ser Ser Asn Leu Leu Thr Ala Ile Ala Ile
        370                 375                 380

Asn Thr Thr Arg Ser Ser Thr Val Ala Phe Val Gly Thr Gln Gly Gly
385                 390                 395                 400

Gln Leu His Lys Ile Leu Ile Glu Ser Lys Arg Ser Ala Glu Lys Tyr
                405                 410                 415

Ala Thr Glu Met Leu Thr Asp Asn Glu Pro Ile Leu Ser Asp Met Glu
            420                 425                 430

Phe Gly Gly Asp Gly
            435

<210> SEQ ID NO 47
<211> LENGTH: 467
<212> TYPE: PRT
<213> ORGANISM: Homo sapiens

<400> SEQUENCE: 47

Thr Asn Asn Phe Ala Leu Asp Gly Ala Ala Gly Thr Val Tyr Leu Ala
1               5                   10                  15

Ala Val Asn Arg Leu Tyr Gln Leu Ser Gly Ala Asn Leu Ser Leu Glu
            20                  25                  30

Ala Glu Ala Ala Val Gly Pro Val Pro Asp Ser Pro Leu Cys His Ala
        35                  40                  45

Pro Gln Leu Pro Gln Ala Ser Cys Glu His Pro Arg Arg Leu Thr Asp
    50                  55                  60

Asn Tyr Asn Lys Ile Leu Gln Leu Asp Pro Gly Gln Gly Leu Val Val
65                  70                  75                  80

Val Cys Gly Ser Ile Tyr Gln Gly Phe Cys Gln Leu Arg Arg Arg Gly
                85                  90                  95

Asn Ile Ser Ala Val Ala Val Arg Phe Pro Ala Glu Pro Val Thr
            100                 105                 110

Val Phe Pro Ser Met Leu Asn Val Ala Ala Asn His Pro Asn Ala Ser
        115                 120                 125
```

Thr Val Gly Leu Val Leu Pro Pro Ala Gly Ala Gly Gly Ser Arg
130                 135                 140

Leu Leu Val Gly Ala Thr Tyr Thr Gly Tyr Gly Ser Ser Phe Phe Pro
145                 150                 155                 160

Arg Asn Arg Ser Leu Glu Asp His Arg Phe Glu Asn Thr Pro Glu Ile
            165                 170                 175

Ala Ile Arg Ser Leu Asp Thr Arg Gly Asp Leu Ala Lys Leu Phe Thr
            180                 185                 190

Phe Asp Leu Asn Pro Ser Asp Asp Asn Ile Leu Lys Ile Lys Gln Gly
        195                 200                 205

Ala Lys Glu Gln His Lys Leu Gly Phe Val Ser Ala Phe Leu His Pro
210                 215                 220

Ser Asp Pro Pro Gly Ala Gln Ser Tyr Ala Tyr Leu Ala Leu Asn
225                 230                 235                 240

Ser Glu Ala Arg Ala Gly Asp Lys Glu Ser Gln Ala Arg Ser Leu Leu
            245                 250                 255

Ala Arg Ile Cys Leu Pro His Gly Ala Gly Gly Asp Ala Lys Lys Leu
            260                 265                 270

Thr Glu Ser Tyr Ile Gln Leu Gly Leu Gln Cys Ala Gly Gly Ala Gly
        275                 280                 285

Arg Gly Asp Leu Tyr Ser Arg Leu Val Ser Val Phe Pro Ala Arg Glu
290                 295                 300

Arg Leu Phe Ala Val Phe Glu Arg Pro Gln Gly Ser Pro Ala Ala Arg
305                 310                 315                 320

Ala Ala Pro Ala Ala Leu Cys Ala Phe Arg Phe Ala Asp Val Arg Ala
            325                 330                 335

Ala Ile Arg Ala Ala Arg Thr Ala Cys Phe Val Glu Pro Ala Pro Asp
            340                 345                 350

Val Val Ala Val Leu Asp Ser Val Gln Gly Thr Gly Pro Ala Cys
        355                 360                 365

Glu Arg Lys Leu Asn Ile Gln Leu Gln Pro Glu Gln Leu Asp Cys Gly
370                 375                 380

Ala Ala His Leu Gln His Pro Leu Ser Ile Leu Gln Pro Leu Lys Ala
385                 390                 395                 400

Thr Pro Val Phe Arg Ala Pro Gly Leu Thr Ser Val Ala Val Ala Ser
            405                 410                 415

Val Asn Asn Tyr Thr Ala Val Phe Leu Gly Thr Val Asn Gly Arg Leu
            420                 425                 430

Leu Lys Ile Asn Leu Asn Glu Ser Met Gln Val Val Ser Arg Arg Val
        435                 440                 445

Val Thr Val Ala Tyr Gly Glu Pro Val His His Val Met Gln Phe Asp
    450                 455                 460

Pro Ala Asp
465

<210> SEQ ID NO 48
<211> LENGTH: 390
<212> TYPE: PRT
<213> ORGANISM: Caenorhabditis elegans

<400> SEQUENCE: 48

Ile Asp Asp Phe Ile Val Ser Arg Asp Gln Gln Thr Ile Tyr Val Ala
1               5                   10                  15

Ser Leu Asn Arg Leu Thr Ser Leu Ser Ile Ser Asn Phe Ser Ile Gln

```
                20              25              30
His Glu Val Ser Leu Gly Pro Val Gln Asp Ser Pro Trp Cys Ser Ala
             35              40              45

Asp Gly Lys Ser Cys Leu Lys Leu Val Asn Phe Pro Thr Asp Val Arg
 50              55              60

Thr Lys Ile Leu Gln Ile Leu Pro Thr Asn Gln Ile Leu Gln Cys Gly
 65              70              75              80

Ser Val Lys Leu Gly Ser Cys Ser Thr Phe Asn Ser Lys Leu Ser Leu
             85              90              95

Ile Thr Glu Ser Thr Ile Ala Val Ala Ala Asn Ser Pro Asp Ala Ser
            100             105             110

Thr Val Ser Lys Ile Ile Asp Asn Arg Leu Ile Val Ala Ala Ser Ala
            115             120             125

Thr Lys Glu Ser Pro Tyr Arg Asp Pro Phe Pro Ala Val Ala Ile Arg
            130             135             140

Asn Leu Pro Gly Leu Asn Val Glu Asn Ala Gly Asp Leu Glu Gly Glu
145             150             155             160

Ala Ala Val Phe Leu Arg Ala Ala Tyr Lys Asn Ala Phe Lys Phe Leu
                165             170             175

Tyr Thr Phe Thr His Gln His Phe Val Phe Val Ala Met Val Thr
                180             185             190

Pro Arg Glu Ser Arg Leu Pro Met Thr Thr Arg Leu Ile Arg Phe Cys
            195             200             205

Arg Asn Asp Thr Lys Phe Glu Ser Tyr Ser Glu Ile Glu Leu Gln Cys
            210             215             220

Arg Gly Glu Asp Asn Thr Asn Tyr Pro Phe Leu Asn Ala Ile Ile Gln
225             230             235             240

Ser Tyr Asp Lys Leu Ile Ala Ser Phe Ser Thr Ser Thr Ser Pro
                245             250             255

Lys Ser Ser Ile Cys Val Phe Ser Met Gln Lys Val Lys Leu Thr Phe
                260             265             270

Trp Tyr Asn Val Asp Arg Cys Arg Ser Gly Thr Asp Ser Ile Arg Leu
            275             280             285

Pro His Ile Gly Arg Asp Thr Lys Cys Lys Ala His Ile Pro Leu Asp
            290             295             300

Glu Asp Ser Cys Glu Leu Gly Val Gly Gly Ser Ile Glu Leu Val Glu
305             310             315             320

Met Ser Thr Lys Asp Ile Met Gly Lys Val Thr Ser Leu Met Ala Val
                325             330             335

Asp Gln Lys Ala Ile Phe Ala Gly Thr Thr Thr Ser Gln Ile Val Met
                340             345             350

Phe Lys Trp Asp Glu His His Ser Asn Gln Leu Glu Glu Tyr Gly Arg
            355             360             365

Lys Glu Val Gly Asp Gly Arg Thr Gly Ser Glu Val Ser Lys Met Val
            370             375             380

Lys Phe Gly Asp Phe Val
385             390

<210> SEQ ID NO 49
<211> LENGTH: 391
<212> TYPE: PRT
<213> ORGANISM: Vaccinia virus

<400> SEQUENCE: 49
```

```
Leu Leu Phe Ile Leu Phe Tyr Phe Ala Asn Gly Ile Glu Trp His Lys
1               5                   10                  15

Phe Glu Thr Ser Glu Glu Ile Ile Ser Thr Tyr Leu Leu Asp Asp Val
            20                  25                  30

Leu Tyr Thr Gly Val Asn Gly Ala Val Tyr Thr Phe Ser Asn Asn Lys
            35                  40                  45

Leu Asn Lys Thr Gly Leu Thr Asn Asn Tyr Ile Thr Thr Ser Ile
50                  55                  60

Lys Val Glu Asp Ala Lys Asp Thr Leu Val Cys Gly Thr Asn Asn
65                  70                  75                  80

Gly Asn Pro Lys Cys Trp Lys Ile Asp Gly Ser Asp Pro Lys His
                85                  90                  95

Arg Gly Arg Gly Tyr Ala Pro Tyr Gln Asn Ser Lys Val Thr Ile Ile
                100                 105                 110

Ser His Asn Gly Cys Val Leu Ser Asp Ile Asn Ile Ser Lys Glu Gly
                115                 120                 125

Ile Lys Arg Trp Arg Arg Phe Asp Gly Pro Cys Gly Tyr Asp Leu Tyr
            130                 135                 140

Thr Ala Asp Asn Val Ile Pro Lys Asp Gly Leu Arg Gly Ala Phe Val
145                 150                 155                 160

Asp Lys Asp Gly Thr Tyr Asp Lys Val Tyr Ile Leu Phe Thr Asp Thr
                165                 170                 175

Ile Gly Ser Lys Arg Ile Val Lys Ile Pro Tyr Ile Ala Gln Met Cys
            180                 185                 190

Leu Asn Asp Glu Gly Gly Pro Ser Ser Leu Ser Ser His Arg Trp Ser
            195                 200                 205

Thr Phe Leu Lys Val Glu Leu Glu Cys Asp Ile Asp Gly Arg Ser Tyr
210                 215                 220

Arg Gln Ile Ile His Ser Arg Thr Ile Lys Thr Asp Asn Asp Thr Ile
225                 230                 235                 240

Leu Tyr Val Phe Phe Asp Ser Pro Tyr Ser Lys Ser Ala Leu Cys Thr
            245                 250                 255

Tyr Ser Met Asn Thr Ile Lys Gln Ser Phe Ser Thr Ser Lys Leu Glu
            260                 265                 270

Gly Tyr Thr Lys Gln Leu Pro Ser Pro Ala Ser Gly Ile Cys Leu Pro
            275                 280                 285

Ala Gly Lys Val Val Pro His Thr Thr Phe Glu Val Ile Glu Lys Tyr
            290                 295                 300

Asn Val Leu Asp Asp Ile Ile Lys Pro Leu Ser Asn Gln Pro Ile Phe
305                 310                 315                 320

Glu Gly Pro Ser Gly Val Lys Trp Phe Asp Ile Lys Glu Lys Glu Asn
            325                 330                 335

Glu His Arg Glu Tyr Arg Ile Tyr Phe Ile Lys Glu Asn Ser Ile Tyr
            340                 345                 350

Ser Phe Asp Thr Lys Ser Lys Gln Thr Arg Ser Ser Gln Val Asp Ala
            355                 360                 365

Arg Leu Phe Ser Val Met Val Thr Ser Lys Pro Leu Phe Ile Ala Asp
            370                 375                 380

Ile Gly Ile Gly Val Gly Met
385                 390
```

<210> SEQ ID NO 50
<211> LENGTH: 398
<212> TYPE: PRT

-continued

<213> ORGANISM: Caenorhabditis elegans

<400> SEQUENCE: 50

```
Leu Val Ile Leu His Lys Leu Pro Gly Glu Tyr Val Leu Leu Gly Gly
1               5                   10                  15

Arg Asn His Val Tyr Asn Ile Ser Ile Ser Ser Met Leu Glu Ile Ala
            20                  25                  30

Arg Tyr Glu Trp Thr Ser Ser Asp Glu Ala Arg Thr Asn Cys Ala Ala
        35                  40                  45

Ile Ser Gln Thr Pro Ala Ser Cys Glu Asn Phe Ile Arg Thr Tyr Phe
    50                  55                  60

Glu Leu Thr Asn Asp Thr Leu Ile Leu Cys Gly Thr His Ala Leu Gln
65                  70                  75                  80

Pro Thr Cys Ala Glu Phe Arg Lys Gly Asn Ala Lys Pro Gln Arg Leu
                85                  90                  95

Ile Ser Ala Val Gly Met Ser Pro Ile Asp Ala Asp Ser Thr Ala Pro
            100                 105                 110

Phe Ile Arg Ser Asn Glu Asn Ile Ile Thr Val Asn Val Ala Glu Leu
        115                 120                 125

Ser Ser Ser Glu Pro Leu Leu Val Arg Arg Asn Val Ile Lys Met Trp
    130                 135                 140

Lys Gly Ile Glu Asn Asp Val Ile Leu Arg Thr Pro Arg Gly Leu Ser
145                 150                 155                 160

Ser Phe Glu Gln Ala Asn Phe Leu Ser Met His Lys Val Lys Lys Val
                165                 170                 175

Arg Gly Val Glu Val Leu Phe Phe Phe Ser Glu Ser Pro Met Glu
            180                 185                 190

Thr Glu Gly Cys Gly Leu His Lys Val Ala Arg Val Gly Arg Val Cys
        195                 200                 205

Glu Asp Asp Pro Gly Gly Arg Leu Ser Tyr Asn Lys Glu Trp Ser Ser
    210                 215                 220

Tyr Glu Lys Ala Arg Ile Glu Cys Ser Ile Glu Glu Thr Asp Thr Asp
225                 230                 235                 240

Thr Phe Tyr Phe Asn Gln Phe Ala Gly Val Ala Glu Ser Pro Thr Ser
                245                 250                 255

Phe Tyr Gly Ala Phe Arg Ser Gln Leu Ala Gly Ile Gly Ala Ser Ala
            260                 265                 270

Ile Cys Lys Tyr Ser Lys Lys Val Ile Ser Gly Ser Phe Ala Ser Gly
        275                 280                 285

Tyr Lys Glu Ser Thr Pro Asp Thr Cys Ser Arg Ala Asn Asp Ile Glu
    290                 295                 300

Glu Leu Ser Arg Ile Arg Leu Lys Pro Leu Ile Lys Gln Lys Ile Ser
305                 310                 315                 320

Ala Asn Pro Ile Tyr Ile Phe His Gly Lys Asp Arg Phe Val His Val
                325                 330                 335

Leu Ala Gln Glu Asp Thr Arg Asp Leu Ser Asn Arg Ala Tyr Asp Ile
            340                 345                 350

Leu Tyr Val Ala Thr Asn Leu Gly Asn Ile Leu Lys Ile Val Val Pro
        355                 360                 365

Ser Thr Asp Lys Thr Gly Arg His Ala Val Thr Leu Lys Val Leu Pro
    370                 375                 380

Thr Asn Ser Lys Ile Val Asp Met Ser Leu Tyr Ser Lys Asn
385                 390                 395
```

```
<210> SEQ ID NO 51
<211> LENGTH: 403
<212> TYPE: PRT
<213> ORGANISM: Homo sapiens

<400> SEQUENCE: 51

His Thr Val Leu Phe His Glu Pro Gly Ser Ser Val Trp Val Gly
 1               5                  10                  15

Gly Arg Gly Lys Val Tyr Leu Phe Asp Phe Pro Glu Gly Lys Asn Ala
                20                  25                  30

Ser Val Arg Thr Val Asn Ile Gly Ser Thr Lys Gly Ser Cys Leu Asp
            35                  40                  45

Lys Arg Asp Cys Glu Asn Tyr Ile Thr Leu Leu Glu Arg Arg Ser Glu
50                  55                  60

Gly Leu Leu Ala Cys Gly Thr Asn Ala Arg His Pro Ser Cys Trp Asn
65                  70                  75                  80

Leu Val Asn Gly Thr Val Val Pro Leu Gly Glu Met Arg Gly Tyr Ala
                85                  90                  95

Pro Phe Ser Pro Asp Glu Asn Ser Leu Val Leu Phe Glu Gly Arg Ala
               100                 105                 110

Gly Asp Glu Val Tyr Ser Thr Ile Arg Lys Gln Glu Tyr Asn Gly Lys
            115                 120                 125

Ile Arg Arg Phe Arg Arg Ile Arg Gly Glu Ser Glu Leu Tyr Thr Ser
130                 135                 140

Asp Thr Val Met Gln Asn Pro Gln Phe Ile Lys Ala Thr Ile Val His
145                 150                 155                 160

Gln Asp Gln Ala Tyr Asp Asp Lys Ile Tyr Tyr Phe Phe Arg Glu Asp
                165                 170                 175

Asn Pro Asp Lys Asn Pro Glu Ala Pro Leu Asn Val Ser Arg Val Ala
            180                 185                 190

Gln Leu Cys Arg Gly Asp Gln Gly Gly Glu Ser Ser Leu Ser Val Ser
        195                 200                 205

Lys Trp Asn Thr Phe Leu Lys Ala Met Leu Val Cys Ser Asp Ala Ala
210                 215                 220

Thr Asn Lys Asn Phe Asn Arg Leu Gln Asp Val Phe Leu Leu Pro Asp
225                 230                 235                 240

Pro Ser Gly Gln Trp Arg Asp Thr Arg Val Tyr Gly Val Phe Ser Asn
                245                 250                 255

Pro Trp Asn Tyr Ser Ala Val Cys Val Tyr Ser Leu Gly Asp Ile Asp
            260                 265                 270

Lys Val Phe Arg Thr Ser Ser Leu Lys Gly Tyr His Ser Ser Leu Pro
        275                 280                 285

Asn Pro Arg Pro Gly Lys Cys Leu Pro Asp Gln Gln Pro Ile Pro Thr
290                 295                 300

Glu Thr Phe Gln Val Ala Asp Arg His Pro Glu Val Ala Gln Arg Val
305                 310                 315                 320

Glu Pro Met Gly Pro Leu Lys Thr Pro Leu Phe His Ser Lys Tyr His
                325                 330                 335

Tyr Gln Lys Val Ala Val His Arg Met Gln Ala Ser His Gly Glu Thr
            340                 345                 350

Phe His Val Leu Tyr Leu Thr Thr Asp Arg Gly Thr Ile His Lys Val
        355                 360                 365

Val Glu Pro Gly Glu Gln Glu His Ser Phe Ala Phe Asn Ile Met Glu
370                 375                 380
```

```
Ile Gln Pro Phe Arg Arg Ala Ala Ile Gln Thr Met Ser Leu Asp
385                 390                 395                 400

Ala Glu Arg
```

<210> SEQ ID NO 52
<211> LENGTH: 400
<212> TYPE: PRT
<213> ORGANISM: Alcelaphine herpesvirus 1

<400> SEQUENCE: 52

```
His Thr Val Leu Phe His Ser Leu Asn Ser Ser Asp Val Tyr Val Gly
1               5                   10                  15

Gly Asn Asn Thr Ile Tyr Leu Phe Asp Phe Ala His Ser Ser Asn Ala
            20                  25                  30

Ser Thr Ala Leu Ile Asn Ile Thr Ser Thr His Asn Thr His Arg Leu
        35                  40                  45

Ser Ser Thr Cys Glu Asn Phe Ile Thr Leu Leu His Asn Gln Thr Asp
    50                  55                  60

Gly Leu Leu Ala Cys Gly Thr Asn Ser Gln Lys Pro Ser Cys Trp Leu
65                  70                  75                  80

Ile Asn Asn Leu Thr Thr Gln Phe Leu Gly Pro Lys Leu Gly Leu Ala
                85                  90                  95

Pro Phe Ser Pro Ser Ser Gly Asn Leu Val Leu Phe Asp Gln Asn Asp
            100                 105                 110

Thr Tyr Ser Thr Ile Asn Leu Tyr Lys Ser Leu Ser Gly Ser His Lys
        115                 120                 125

Phe Arg Arg Ile Ala Gly Gln Val Glu Leu Tyr Thr Ser Asp Thr Ala
    130                 135                 140

Met His Arg Pro Gln Phe Val Gln Ala Thr Ala Val His Lys Asn Glu
145                 150                 155                 160

Ser Tyr Asp Asp Lys Ile Tyr Phe Phe Gln Glu Asn Ser His Ser
                165                 170                 175

Asp Phe Lys Gln Phe Pro His Thr Val Pro Arg Val Gly Gln Val Cys
            180                 185                 190

Ser Ser Asp Gln Gly Gly Glu Ser Ser Leu Ser Val Tyr Lys Trp Thr
        195                 200                 205

Thr Phe Leu Lys Ala Arg Leu Ala Cys Val Asp Tyr Asp Thr Gly Arg
    210                 215                 220

Ile Tyr Asn Glu Leu Gln Asp Ile Phe Ile Trp Gln Ala Pro Glu Asn
225                 230                 235                 240

Ser Trp Glu Glu Thr Leu Ile Tyr Gly Leu Phe Leu Ser Pro Trp Asn
                245                 250                 255

Phe Ser Ala Val Cys Val Phe Thr Val Lys Asp Ile Asp His Val Phe
            260                 265                 270

Lys Thr Ser Lys Leu Lys Asn Tyr His His Lys Leu Pro Thr Pro Arg
        275                 280                 285

Pro Gly Gln Cys Met Lys Asn His Gln His Val Pro Thr Glu Thr Phe
    290                 295                 300

Gln Val Ala Asp Arg Tyr Pro Glu Val Ala Asp Pro Tyr Gln Lys
305                 310                 315                 320

Asn Asn Ala Met Phe Pro Ile Ile Gln Ser Lys Tyr Ile Tyr Thr Lys
                325                 330                 335

Leu Leu Val Tyr Arg Val Glu Tyr Gly Gly Val Phe Trp Ala Thr Ile
            340                 345                 350
```

```
Phe Tyr Leu Thr Thr Ile Lys Gly Thr Ile His Ile Tyr Val Arg Tyr
            355                 360                 365

Glu Asp Ser Asn Ser Thr Thr Ala Leu Asn Ile Leu Glu Ile Asn Pro
370                 375                 380

Phe Gln Lys Pro Ala Pro Ile Gln Asn Ile Leu Leu Asp Asn Thr Asn
385                 390                 395                 400

<210> SEQ ID NO 53
<211> LENGTH: 370
<212> TYPE: PRT
<213> ORGANISM: Fowlpox virus

<400> SEQUENCE: 53

Val Val Ile Tyr Arg Thr Asp Cys Asn Thr Arg Leu Ile Ile Gly Val
1               5                   10                  15

Thr Asn Thr Val Tyr Val Asn Thr Thr Asp Lys Ser Asn Ile Thr
                20                  25                  30

Val Asp Phe Ser Pro Asp Asn Val Ser Thr Gln Ser Gly Ala Asn Tyr
            35                  40                  45

Ile Thr Phe Ile Gly Gly Tyr Asp Asp Lys Ile Leu Val Cys Gly Thr
        50                  55                  60

Asn Ser Ser Ser Pro Thr Cys Trp Tyr Ile Asn Gly Thr Ile Lys Glu
65                  70                  75                  80

Pro Thr Pro Tyr Gly Arg Gly Leu Ser Pro Glu Ser Tyr Asp Met Thr
                85                  90                  95

Gly Leu Val Leu Ile Asp Gly Lys Glu Ile Tyr Ser Thr Ile Lys Lys
            100                 105                 110

Tyr Ser His Leu Ser Thr Gly Phe Ser Arg Ile Val Gly Lys Pro Val
        115                 120                 125

Leu Tyr Thr Ser Ser Ser Thr Met Lys Asn Pro Lys Phe Val His Leu
    130                 135                 140

Val Ser Leu Gln Glu Thr Asn Ser Ile Asn Asp Thr Ile Tyr Ile Phe
145                 150                 155                 160

Phe Gln Glu Glu Gly Met Ala Lys Val Ser Arg Val Cys Lys His Asp
                165                 170                 175

Gln Gly Gly Ser Gly Ser Leu Ser Gly Ser Lys Trp Ser Thr Phe Leu
            180                 185                 190

Lys Ser Ile Met Ile Cys Glu Asp Leu Asn Val Arg Phe Asn Tyr Leu
        195                 200                 205

Lys Asp Val Val Ile Lys Gly Lys Ser Pro Asn Glu Thr Ile Ile
    210                 215                 220

Tyr Gly Leu Phe Phe Asn Glu Trp Asn Tyr Ser Ala Val Cys Met Phe
225                 230                 235                 240

Lys Phe Asp Lys Ile Gln Asn Asn Phe Asn Thr Ser Pro Leu Lys Gly
                245                 250                 255

Tyr Ser Gly Gly Lys Val Leu Ser Val Arg Pro Gly Thr Cys Leu Asn
            260                 265                 270

Thr Ser Thr Pro Arg Asp Thr Phe Glu Val Ile Asp Leu Tyr Pro Glu
        275                 280                 285

Thr Leu Tyr Gly Val Lys Gly Asp Phe Ile Phe Lys Thr Lys Tyr Thr
    290                 295                 300

Tyr Thr His Ile Val Ile Asn Thr Ala Val Ile Asn Tyr Gln His Lys
305                 310                 315                 320

Asp Tyr Arg Val Thr Thr Phe Tyr Leu Ser Thr Ser Asp Gly Lys Ile
```

```
                    325                 330                 335
His Lys Val Val Val Tyr Glu Asp Gly Val Ile Asn Val Ile Glu Leu
            340                 345                 350

Thr Leu Lys Gln Tyr Pro Ser Pro Val Leu Ala Leu Val Ser Asp Glu
            355                 360                 365

Arg Ser
    370

<210> SEQ ID NO 54
<211> LENGTH: 422
<212> TYPE: PRT
<213> ORGANISM: Caenorhabditis elegans

<400> SEQUENCE: 54

Phe Arg Glu Leu Leu Ile Asp Pro Lys Ala Gly Ala Leu Phe Val Gly
1               5                   10                  15

Ser Glu Gly Ala Ile Phe Arg Leu Trp Ala Tyr Asn Ile Asn Asp Thr
            20                  25                  30

Gly Glu Asn Val Phe Ala Lys Lys Gln Leu Val Leu Ser Glu Ser Glu
        35                  40                  45

Glu Ser Glu Tyr Arg Ser Thr Ala Ser Asp Glu Arg Leu Cys Arg Pro
50                  55                  60

Ser Thr Arg Phe Leu Ala Phe Thr Asn Asn Leu Asp Ser Ile Tyr Val
65                  70                  75                  80

Cys Ser Ser Val Gly Met Arg Pro Glu Ile Arg Val Leu Asp Ser Leu
                85                  90                  95

Ser Leu Arg Asp Gln Gln Glu Pro Arg Thr Glu Ile Gly Ile Cys Val
            100                 105                 110

Val Asp Pro Thr Phe Asn Phe Thr Ala Val Val Asp Ser Asp Ala
        115                 120                 125

Thr Ser Val Tyr Ser Gly Ile Arg Thr Gly Met Gly Gly Glu Asn His
    130                 135                 140

Leu Ile Tyr Arg Pro Pro Leu Thr Lys Asn Gly Lys Gln Leu His Ala
145                 150                 155                 160

Ser Ile Arg Thr Ile Tyr Ser Asp Asn Lys Trp Leu Asn Glu Pro Gln
                165                 170                 175

Phe Val Gly Ser Phe Asp Val Gly Gln His Val Phe Phe Phe Arg
            180                 185                 190

Glu Ile Ala His Asp Asn Ser Phe Gly Glu Arg Ile Val His Ser Arg
        195                 200                 205

Val Ala Arg Val Cys Lys Lys Asp Ile Gly Gly Arg Asn Val Leu Arg
    210                 215                 220

Gln Val Trp Thr Ser Phe Val Lys Ala Arg Leu Asn Cys Ser Val Ser
225                 230                 235                 240

Ala Asn Phe Pro Phe Tyr Phe Asp His Ile Gln Ser Val Lys Arg Val
                245                 250                 255

Asp Lys His Gly Glu Thr Tyr Phe Tyr Ala Thr Phe Ser Thr Ser Glu
            260                 265                 270

Thr Ala Phe Thr Ser Ser Ala Ile Cys Met Phe Gln Leu Ser Ser Ile
        275                 280                 285

Asn His Leu Leu Asp Thr Gly Leu Leu Met Glu Glu Thr Ala Asn Gly
    290                 295                 300

Gln Phe Ser Val Thr Ala Asp Glu Ile Pro Ala His Arg Pro Gly Thr
305                 310                 315                 320
```

```
Cys Ser Gln Asn Ser His Ser Ile Ser Asp Thr Asp Leu His Phe Ala
                325                 330                 335

Lys Thr His Leu Leu Val Ser Asp Ser Ile Ser Gly Gly Thr Pro Ile
            340                 345                 350

Leu Pro Leu Arg Asp His Val Phe Thr His Ile Val Val Asp Gln Leu
        355                 360                 365

Pro Asn Gln Asn Val Ile Phe Ala Phe Asp Ser Ala Asn Arg Arg Val
    370                 375                 380

Trp Lys Ile Ser His Trp Lys Glu Gly Asn Glu Trp Lys Ser Asn Leu
385                 390                 395                 400

Ile Glu Glu Lys Ser Leu Lys Ile Ala Ala Ser Arg Ile Asn Asp Val
                405                 410                 415

Ala Leu Leu Pro Ala Glu
            420

<210> SEQ ID NO 55
<211> LENGTH: 432
<212> TYPE: PRT
<213> ORGANISM: Homo sapiens

<400> SEQUENCE: 55

Leu Asp Ile Gln Met Ile Met Ile Met Asn Gly Thr Leu Tyr Ile Ala
1               5                   10                  15

Ala Arg Asp His Ile Tyr Thr Val Asp Ile Asp Thr Ser His Thr Glu
            20                  25                  30

Glu Ile Tyr Cys Ser Lys Lys Leu Thr Trp Lys Ser Arg Gln Ala Asp
                35                  40                  45

Val Asp Thr Cys Arg Met Lys Gly Lys His Lys Asp Glu Cys His Asn
    50                  55                  60

Phe Ile Lys Val Leu Leu Lys Lys Asn Asp Asp Ala Leu Phe Val Cys
65                  70                  75                  80

Gly Thr Asn Ala Phe Asn Pro Ser Cys Arg Asn Tyr Lys Met Asp Thr
                85                  90                  95

Leu Glu Pro Phe Gly Asp Glu Phe Ser Gly Met Ala Arg Cys Pro Tyr
            100                 105                 110

Asp Ala Lys His Ala Asn Val Ala Leu Phe Ala Asp Gly Lys Leu Tyr
        115                 120                 125

Ser Ala Thr Val Thr Asp Phe Leu Ala Ile Asp Ala Val Ile Tyr Arg
    130                 135                 140

Ser Leu Gly Glu Ser Pro Thr Leu Arg Thr Val Lys His Asp Ser Lys
145                 150                 155                 160

Trp Leu Lys Glu Pro Tyr Phe Val Gln Ala Val Asp Tyr Gly Asp Tyr
                165                 170                 175

Ile Tyr Phe Phe Phe Arg Glu Ile Ala Val Glu Tyr Asn Thr Met Gly
            180                 185                 190

Lys Val Val Phe Pro Arg Val Ala Gln Val Cys Lys Asn Asp Met Gly
        195                 200                 205

Gly Ser Gln Arg Val Leu Glu Lys Gln Trp Thr Ser Phe Leu Lys Ala
    210                 215                 220

Arg Leu Asn Cys Ser Val Pro Gly Asp Ser His Phe Tyr Phe Asn Ile
225                 230                 235                 240

Leu Gln Ala Val Thr Asp Val Ile Arg Ile Asn Gly Arg Asp Val Val
                245                 250                 255

Leu Ala Thr Phe Ser Thr Pro Tyr Asn Ser Ile Pro Gly Ser Ala Val
            260                 265                 270
```

```
Cys Ala Tyr Asp Met Leu Asp Ile Ala Ser Val Phe Thr Gly Arg Phe
            275                 280                 285

Lys Glu Gln Lys Ser Pro Asp Ser Thr Trp Thr Pro Val Pro Asp Glu
        290                 295                 300

Arg Val Pro Lys Pro Arg Pro Gly Cys Cys Ala Gly Ser Ser Ser Leu
305                 310                 315                 320

Glu Arg Tyr Ala Thr Ser Asn Glu Phe Pro Asp Asp Thr Leu Asn Phe
                325                 330                 335

Ile Lys Thr His Pro Leu Met Asp Glu Ala Val Pro Ser Ile Phe Asn
            340                 345                 350

Arg Pro Trp Phe Leu Arg Thr Met Val Arg Tyr Arg Leu Thr Lys Ile
        355                 360                 365

Ala Val Asp Thr Ala Ala Gly Pro Tyr Gln Asn His Thr Val Val Phe
370                 375                 380

Leu Gly Ser Glu Lys Gly Ile Ile Leu Lys Phe Leu Ala Arg Ile Gly
385                 390                 395                 400

Asn Ser Gly Phe Leu Asn Asp Ser Leu Phe Leu Glu Glu Met Ser Val
                405                 410                 415

Tyr Asn Ser Glu Lys Cys Ser Tyr Asp Gly Val Glu Asp Lys Arg Ile
            420                 425                 430

<210> SEQ ID NO 56
<211> LENGTH: 432
<212> TYPE: PRT
<213> ORGANISM: Homo sapiens

<400> SEQUENCE: 56

Leu Asn Ile Gln Arg Val Leu Arg Val Asn Arg Thr Leu Phe Ile Gly
1               5                   10                  15

Asp Arg Asp Asn Leu Tyr Arg Val Glu Leu Glu Pro Pro Thr Ser Thr
            20                  25                  30

Glu Leu Arg Tyr Gln Arg Lys Leu Thr Trp Arg Ser Asn Pro Ser Asp
        35                  40                  45

Ile Asn Val Cys Arg Met Lys Gly Lys Gln Glu Gly Glu Cys Arg Asn
50                  55                  60

Phe Val Lys Val Leu Leu Leu Arg Asp Glu Ser Thr Leu Phe Val Cys
65                  70                  75                  80

Gly Ser Asn Ala Phe Asn Pro Val Cys Ala Asn Tyr Ser Ile Asp Thr
                85                  90                  95

Leu Gln Pro Val Gly Asp Asn Ile Ser Gly Met Ala Arg Cys Pro Tyr
            100                 105                 110

Asp Pro Lys His Ala Asn Val Ala Leu Phe Ser Asp Gly Met Leu Phe
        115                 120                 125

Thr Ala Thr Val Thr Asp Phe Leu Ala Ile Asp Ala Val Ile Tyr Arg
130                 135                 140

Ser Leu Gly Asp Arg Pro Thr Leu Arg Thr Val Lys His Asp Ser Lys
145                 150                 155                 160

Trp Phe Lys Glu Pro Tyr Phe Val His Ala Val Glu Trp Gly Ser His
                165                 170                 175

Val Tyr Phe Phe Phe Arg Glu Ile Ala Met Glu Phe Asn Tyr Leu Glu
            180                 185                 190

Lys Val Val Val Ser Arg Val Ala Arg Val Cys Lys Asn Asp Val Gly
        195                 200                 205

Gly Ser Pro Arg Val Leu Glu Lys Gln Trp Thr Ser Phe Leu Lys Ala
```

-continued

```
                210                 215                 220
Arg Leu Asn Cys Ser Val Pro Gly Asp Ser His Phe Tyr Phe Asn Val
225                 230                 235                 240

Leu Gln Ala Val Thr Gly Val Val Ser Leu Gly Gly Arg Pro Val Val
                245                 250                 255

Leu Ala Val Phe Ser Thr Pro Ser Asn Ser Ile Pro Gly Ser Ala Val
                260                 265                 270

Cys Ala Phe Asp Leu Thr Gln Val Ala Val Phe Glu Gly Arg Phe
                275                 280                 285

Arg Glu Gln Lys Ser Pro Glu Ser Ile Trp Thr Pro Val Pro Glu Asp
290                 295                 300

Gln Val Pro Arg Pro Arg Pro Gly Cys Cys Ala Ala Pro Gly Met Gln
305                 310                 315                 320

Tyr Asn Ala Ser Ser Ala Leu Pro Asp Asp Ile Leu Asn Phe Val Lys
                325                 330                 335

Thr His Pro Leu Met Asp Glu Ala Val Pro Ser Leu Gly His Ala Pro
                340                 345                 350

Trp Ile Leu Arg Thr Leu Met Arg His Gln Leu Thr Arg Val Ala Val
                355                 360                 365

Asp Val Gly Ala Gly Pro Trp Gly Asn Gln Thr Val Val Phe Leu Gly
370                 375                 380

Ser Glu Ala Gly Thr Val Leu Lys Phe Leu Val Arg Pro Asn Ala Ser
385                 390                 395                 400

Thr Ser Gly Thr Ser Gly Leu Ser Val Phe Leu Glu Glu Phe Glu Thr
                405                 410                 415

Tyr Arg Pro Asp Arg Cys Gly Arg Pro Gly Gly Gly Glu Thr Gly Gln
                420                 425                 430

<210> SEQ ID NO 57
<211> LENGTH: 429
<212> TYPE: PRT
<213> ORGANISM: Homo sapiens

<400> SEQUENCE: 57

Leu Asp Phe Gln Arg Phe Leu Thr Leu Asn Arg Thr Leu Leu Val Ala
1               5                   10                  15

Ala Arg Asp His Val Phe Ser Phe Asp Leu Gln Ala Glu Glu Glu Gly
                20                  25                  30

Glu Gly Leu Val Pro Asn Lys Tyr Leu Thr Trp Arg Ser Gln Asp Val
                35                  40                  45

Glu Asn Cys Ala Val Arg Gly Lys Leu Thr Asp Glu Cys Tyr Asn Tyr
50                  55                  60

Ile Arg Val Leu Val Pro Trp Asp Ser Gln Thr Leu Leu Ala Cys Gly
65                  70                  75                  80

Thr Asn Ser Phe Ser Pro Val Cys Arg Ser Tyr Gly Ile Thr Ser Leu
                85                  90                  95

Gln Gln Glu Gly Glu Glu Leu Ser Gly Gln Ala Arg Cys Pro Phe Asp
                100                 105                 110

Ala Thr Gln Ser Asn Val Ala Ile Phe Ala Glu Gly Ser Leu Tyr Ser
                115                 120                 125

Ala Thr Ala Ala Asp Phe Gln Ala Ser Asp Ala Val Val Tyr Arg Ser
                130                 135                 140

Leu Gly Pro Gln Pro Pro Leu Arg Ser Ala Lys Tyr Asp Ser Lys Trp
145                 150                 155                 160
```

```
Leu Arg Glu Pro His Phe Val Gln Ala Leu Glu His Gly Asp His Val
                165                 170                 175

Tyr Phe Phe Arg Glu Val Ser Val Glu Asp Ala Arg Leu Gly Lys
        180                 185                 190

Val Gln Phe Ser Arg Val Ala Arg Val Cys Lys Arg Asp Met Gly Gly
            195                 200                 205

Ser Pro Arg Ala Leu Asp Arg His Trp Thr Ser Phe Leu Lys Leu Arg
210                 215                 220

Leu Asn Cys Ser Val Pro Gly Asp Ser Thr Phe Tyr Phe Asp Val Leu
225                 230                 235                 240

Gln Ala Leu Thr Gly Pro Val Asn Leu His Gly Arg Ser Ala Leu Phe
                245                 250                 255

Gly Val Phe Thr Thr Gln Thr Asn Ser Ile Pro Gly Ser Ala Val Cys
            260                 265                 270

Ala Phe Tyr Leu Asp Glu Ile Glu Arg Gly Phe Glu Gly Lys Phe Lys
        275                 280                 285

Glu Gln Arg Ser Leu Asp Gly Ala Trp Thr Pro Val Ser Glu Asp Arg
    290                 295                 300

Val Pro Ser Pro Arg Pro Gly Ser Cys Ala Gly Val Gly Gly Ala Ala
305                 310                 315                 320

Leu Phe Ser Ser Arg Asp Leu Pro Asp Asp Val Leu Thr Phe Ile
                325                 330                 335

Lys Ala His Pro Leu Leu Asp Pro Ala Val Pro Val Thr His Gln
            340                 345                 350

Pro Leu Leu Thr Leu Thr Ser Arg Ala Leu Leu Thr Gln Val Ala Val
        355                 360                 365

Asp Gly Met Ala Gly Pro His Ser Asn Ile Thr Val Met Phe Leu Gly
370                 375                 380

Ser Asn Asp Gly Thr Val Leu Lys Val Leu Thr Pro Gly Gly Arg Ser
385                 390                 395                 400

Gly Gly Pro Glu Pro Ile Leu Leu Glu Glu Ile Asp Ala Tyr Ser Pro
                405                 410                 415

Ala Arg Cys Ser Gly Lys Arg Thr Ala Gln Thr Ala Arg
            420                 425

<210> SEQ ID NO 58
<211> LENGTH: 435
<212> TYPE: PRT
<213> ORGANISM: Schistocerca gregaria

<400> SEQUENCE: 58

Tyr Arg Thr Phe His Leu Asp Glu Lys Arg Glu Ser Leu Tyr Val Gly
1               5                   10                  15

Ala Leu Asp Lys Val Tyr Lys Leu Asn Leu Thr Asn Ile Ser Leu Ser
                20                  25                  30

Asp Cys Glu Arg Asp Ser Leu Thr Leu Glu Pro Thr Asn Ile Ala Asn
            35                  40                  45

Cys Val Ser Lys Gly Lys Ser Ala Asp Phe Asp Cys Lys Asn His Ile
        50                  55                  60

Arg Val Ile Gln Pro Met Gly Asp Gly Ser Arg Leu Tyr Ile Cys Gly
65                  70                  75                  80

Thr Asn Ala His Ser Pro Lys Asp Trp Val Val Tyr Ser Asn Leu Thr
                85                  90                  95

His Leu Gln Arg His Glu Tyr Val Pro Gly Ile Gly Val Gly Ile Ala
            100                 105                 110
```

-continued

```
Lys Cys Pro Phe Asp Pro Glu Asp Ser Ser Thr Ala Val Trp Val Glu
        115                 120                 125

Asn Asp Leu Pro Gly Leu Tyr Ser Gly Thr Asn Ala Glu Phe Thr Lys
        130                 135                 140

Ala Asp Thr Val Ile Phe Arg Thr Asp Leu Tyr Asn Leu Thr Thr Gly
145                 150                 155                 160

Arg Arg Glu Tyr Ser Phe Lys Arg Thr Leu Lys Tyr Asp Ser Lys Trp
                165                 170                 175

Leu Asp Asn Pro Asn Phe Val Gly Ser Phe Asp Val Gly Glu Tyr Val
            180                 185                 190

Leu Phe Phe Phe Arg Glu Thr Ala Val Glu Tyr Ile Asn Cys Gly Lys
        195                 200                 205

Ser Val Tyr Ser Arg Val Ala Arg Val Cys Lys Lys Asp Val Gly Gly
        210                 215                 220

Lys Asn Ile Leu Ser Gln Asn Trp Ala Thr Phe Leu Lys Ala Arg Leu
225                 230                 235                 240

Asn Cys Ser Ile Pro Gly Glu Phe Pro Phe Tyr Phe Asn Glu Ile Gln
                245                 250                 255

Gly Val Tyr Lys Met Pro Asn Thr Asp Lys Phe Phe Val Phe Ser
            260                 265                 270

Thr Ser Val Thr Gly Leu Thr Gly Ser Ala Ile Cys Ser Phe Thr Leu
        275                 280                 285

Lys Asp Ile Gln Glu Val Phe Ser Gly Lys Phe Lys Glu Gln Ala Thr
        290                 295                 300

Ser Ser Ser Ala Trp Leu Pro Val Leu Pro Ser Arg Val Pro Asp Pro
305                 310                 315                 320

Arg Pro Gly Glu Cys Val Asn Asp Thr Glu Leu Leu Pro Asp Thr Val
                325                 330                 335

Leu Asn Phe Ile Arg Ser His Pro Leu Met Asp Gly Ala Val Ser His
            340                 345                 350

Glu Gly Gly Lys Pro Val Phe Tyr Lys Arg Asp Val Leu Phe Thr Gln
        355                 360                 365

Leu Val Val Asp Lys Leu Lys Val Asn Leu Val Gly Lys Asn Met Glu
        370                 375                 380

Tyr Ile Val Tyr Ala Gly Thr Ser Thr Gly Gln Val Tyr Lys Val
385                 390                 395                 400

Val Gln Trp Tyr Asp Ser Gly Leu Pro Gln Ser Leu Leu Val Asp
                405                 410                 415

Ile Phe Asp Val Thr Pro Pro Glu Pro Val Gln Ala Leu His Leu Ser
            420                 425                 430

Lys Glu Tyr
        435

<210> SEQ ID NO 59
<211> LENGTH: 435
<212> TYPE: PRT
<213> ORGANISM: Drosophila melanogaster

<400> SEQUENCE: 59

Tyr Arg Thr Phe His Met Asn Glu Asp Arg Asp Thr Leu Tyr Val Gly
1               5                   10                  15

Ala Met Asp Arg Val Phe Arg Val Asn Leu Gln Asn Ile Ser Ser Ser
            20                  25                  30

Asn Cys Asn Arg Asp Ala Ile Asn Leu Glu Pro Thr Arg Asp Asp Val
```

```
                35                  40                  45
Val Ser Cys Val Ser Lys Gly Lys Ser Gln Ile Phe Asp Cys Lys Asn
 50                  55                  60

His Val Arg Val Ile Gln Ser Met Asp Gln Gly Asp Arg Leu Tyr Val
 65                  70                  75                  80

Cys Gly Thr Asn Ala His Asn Pro Lys Asp Tyr Val Ile Tyr Ala Asn
                 85                  90                  95

Leu Thr His Leu Pro Arg Ser Glu Tyr Val Ile Gly Val Gly Leu Gly
                100                 105                 110

Ile Ala Lys Cys Pro Tyr Asp Pro Leu Asp Asn Ser Thr Ala Ile Tyr
                115                 120                 125

Val Glu Asn Gly Leu Pro Gly Leu Tyr Ser Gly Thr Asn Ala Glu Phe
                130                 135                 140

Thr Lys Ala Asp Thr Val Ile Phe Arg Thr Asp Leu Tyr Asn Thr Ser
145                 150                 155                 160

Ala Lys Arg Leu Glu Tyr Lys Phe Lys Arg Thr Leu Lys Tyr Asp Ser
                165                 170                 175

Lys Trp Leu Asp Lys Pro Asn Phe Val Gly Ser Phe Asp Ile Gly Glu
                180                 185                 190

Tyr Val Tyr Phe Phe Phe Arg Glu Thr Ala Val Glu Tyr Ile Asn Cys
                195                 200                 205

Gly Lys Ala Val Tyr Ser Arg Ile Ala Arg Val Cys Lys Lys Asp Val
210                 215                 220

Gly Gly Lys Asn Leu Leu Ala His Asn Trp Ala Thr Tyr Leu Lys Ala
225                 230                 235                 240

Arg Leu Asn Cys Ser Ile Ser Gly Glu Phe Pro Tyr Phe Asn Glu
                245                 250                 255

Ile Gln Ser Val Tyr Gln Leu Pro Ser Asp Lys Ser Arg Phe Ala
                260                 265                 270

Thr Phe Thr Thr Ser Thr Asn Gly Leu Ile Gly Ser Ala Val Cys Ser
                275                 280                 285

Phe His Ile Asn Glu Ile Gln Ala Ala Phe Asn Gly Lys Phe Lys Glu
                290                 295                 300

Gln Ser Ser Ser Asn Ser Ala Trp Leu Pro Val Leu Asn Ser Arg Val
305                 310                 315                 320

Pro Glu Pro Arg Pro Gly Thr Cys Val Asn Asp Thr Ser Asn Leu Pro
                325                 330                 335

Asp Thr Val Leu Asn Phe Ile Arg Ser His Pro Leu Met Asp Lys Ala
                340                 345                 350

Val Asn His Glu His Asn Asn Pro Val Tyr Tyr Lys Arg Asp Leu Val
                355                 360                 365

Phe Thr Lys Leu Val Val Asp Lys Ile Arg Ile Asp Ile Leu Asn Gln
                370                 375                 380

Glu Tyr Ile Val Tyr Tyr Val Gly Thr Asn Leu Gly Arg Ile Tyr Lys
385                 390                 395                 400

Ile Val Gln Tyr Tyr Arg Asn Gly Glu Ser Leu Ser Lys Leu Leu Asp
                405                 410                 415

Ile Phe Glu Val Ala Pro Asn Glu Ala Ile Gln Val Met Glu Ile Ser
                420                 425                 430

Gln Thr Arg
            435

<210> SEQ ID NO 60
```

<211> LENGTH: 422
<212> TYPE: PRT
<213> ORGANISM: Schistocerca americana

<400> SEQUENCE: 60

```
His Phe Lys Leu Leu Glu Lys Asp His Asn Ser Leu Leu Val Gly Ala
1               5                   10                  15

Arg Asn Ile Val Tyr Asn Ile Ser Leu Arg Asp Leu Thr Glu Phe Thr
            20                  25                  30

Glu Gln Arg Ile Glu Trp His Ser Gly Ala His Arg Glu Leu Cys
        35                  40                  45

Tyr Leu Lys Gly Lys Ser Glu Asp Asp Cys Gln Asn Tyr Ile Arg Val
    50                  55                  60

Leu Ala Lys Ile Asp Asp Arg Val Leu Ile Cys Gly Thr Asn Ala
65                  70                  75                  80

Tyr Lys Pro Leu Cys Arg His Tyr Ala Leu Lys Asp Gly Asp Tyr Val
                85                  90                  95

Val Glu Lys Glu Tyr Glu Gly Arg Gly Leu Cys Pro Phe Asp Pro Asp
            100                 105                 110

His Asn Ser Thr Ala Ile Tyr Ser Glu Gly Gln Leu Tyr Ser Ala Thr
        115                 120                 125

Val Ala Asp Phe Ser Gly Thr Asp Pro Leu Ile Tyr Arg Gly Pro Leu
    130                 135                 140

Arg Thr Glu Arg Ser Asp Leu Lys Gln Leu Asn Ala Pro Asn Phe Val
145                 150                 155                 160

Asn Thr Met Glu Tyr Asn Asp Phe Ile Phe Phe Phe Arg Glu Thr
                165                 170                 175

Ala Val Glu Tyr Ile Asn Cys Gly Lys Ala Ile Tyr Ser Arg Val Ala
            180                 185                 190

Arg Val Cys Lys His Asp Lys Gly Pro His Gln Phe Gly Asp Arg
        195                 200                 205

Trp Thr Ser Phe Leu Lys Ser Arg Leu Asn Cys Ser Val Pro Gly Asp
    210                 215                 220

Tyr Pro Phe Tyr Phe Asn Glu Ile Gln Ser Thr Ser Asp Ile Ile Glu
225                 230                 235                 240

Gly Asn Tyr Gly Gly Gln Val Glu Lys Leu Ile Tyr Gly Val Phe Thr
                245                 250                 255

Thr Pro Val Asn Ser Ile Gly Gly Ser Ala Val Cys Ala Phe Ser Met
            260                 265                 270

Lys Ser Ile Leu Glu Ser Phe Asp Gly Pro Phe Lys Glu Gln Glu Thr
        275                 280                 285

Met Asn Ser Asn Trp Leu Ala Val Pro Ser Leu Lys Val Pro Glu Pro
    290                 295                 300

Arg Pro Gly Gln Cys Val Asn Asp Ser Arg Thr Leu Pro Asp Val Ser
305                 310                 315                 320

Val Asn Phe Val Lys Ser His Thr Leu Met Asp Glu Ala Val Pro Ala
                325                 330                 335

Phe Phe Thr Arg Pro Ile Leu Ile Arg Ile Ser Leu Gln Tyr Arg Phe
            340                 345                 350

Thr Lys Ile Ala Val Asp Gln Val Arg Thr Pro Asp Gly Lys Ala
        355                 360                 365

Tyr Asp Val Leu Phe Ile Gly Thr Asp Gly Lys Val Ile Lys Ala
    370                 375                 380

Leu Asn Ser Ala Ser Phe Asp Ser Ser Asp Thr Val Asp Ser Val Val
```

```
                385                 390                 395                 400
Ile Glu Glu Leu Gln Val Leu Pro Pro Gly Val Pro Val Lys Asn Leu
                    405                 410                 415

Tyr Val Val Arg Met Asp
                420

<210> SEQ ID NO 61
<211> LENGTH: 420
<212> TYPE: PRT
<213> ORGANISM: Tribolium confusum

<400> SEQUENCE: 61

His Phe Ile Val Leu Asn Gln Asp Glu Thr Ser Ile Leu Val Gly Gly
1               5                   10                  15

Arg Asn Arg Val Tyr Asn Leu Ser Ile Phe Asp Leu Ser Glu Arg Lys
            20                  25                  30

Gly Gly Arg Ile Asp Trp Pro Ser Ser Asp Ala His Gly Gln Leu Cys
        35                  40                  45

Ile Leu Lys Gly Lys Thr Asp Asp Cys Gln Asn Tyr Ile Arg Ile
    50                  55                  60

Leu Tyr Ser Ser Glu Pro Gly Lys Leu Val Ile Cys Gly Thr Asn Ser
65                  70                  75                  80

Tyr Lys Pro Leu Cys Arg Thr Tyr Ala Phe Lys Glu Gly Lys Tyr Leu
                85                  90                  95

Val Glu Lys Glu Val Glu Gly Ile Gly Leu Cys Pro Tyr Asn Pro Glu
            100                 105                 110

His Asn Ser Thr Ser Val Ser Tyr Asn Gly Gln Leu Phe Ser Ala Thr
        115                 120                 125

Val Ala Asp Phe Ser Gly Gly Asp Pro Leu Ile Tyr Arg Glu Pro Gln
    130                 135                 140

Arg Thr Glu Leu Ser Asp Leu Lys Gln Leu Asn Ala Pro Asn Phe Val
145                 150                 155                 160

Asn Ser Val Ala Tyr Gly Asp Tyr Ile Phe Phe Tyr Arg Glu Thr
                165                 170                 175

Ala Val Glu Tyr Met Asn Cys Gly Lys Val Ile Tyr Ser Arg Val Ala
            180                 185                 190

Arg Val Cys Lys Asp Asp Lys Gly Gly Pro His Gln Ser Arg Asp Arg
        195                 200                 205

Trp Thr Ser Phe Leu Lys Ala Arg Leu Asn Cys Ser Ile Pro Gly Glu
    210                 215                 220

Tyr Pro Phe Tyr Phe Asp Glu Ile Gln Ser Thr Ser Asp Ile Val Glu
225                 230                 235                 240

Gly Arg Tyr Asn Ser Asp Asp Ser Lys Lys Ile Ile Tyr Gly Ile Leu
                245                 250                 255

Thr Thr Pro Val Asn Ala Ile Gly Gly Ser Ala Ile Cys Ala Tyr Gln
            260                 265                 270

Met Ala Asp Ile Leu Arg Val Phe Glu Gly Ser Phe Lys His Gln Glu
        275                 280                 285

Thr Ile Asn Ser Asn Trp Leu Pro Val Pro Gln Asn Leu Val Pro Glu
    290                 295                 300

Pro Arg Pro Gly Gln Cys Val Arg Asp Ser Arg Ile Leu Pro Asp Lys
305                 310                 315                 320

Asn Val Asn Phe Ile Lys Thr His Ser Leu Met Glu Asp Val Pro Ala
                325                 330                 335
```

```
Leu Phe Gly Lys Pro Val Leu Val Arg Val Ser Leu Gln Tyr Arg Phe
                340                 345                 350

Thr Ala Ile Thr Val Asp Pro Gln Val Lys Thr Ile Asn Asn Gln Tyr
            355                 360                 365

Leu Asp Val Leu Tyr Ile Gly Thr Asp Gly Lys Val Leu Lys Ala
370                 375                 380

Val Asn Ile Pro Lys Arg His Ala Lys Ala Leu Leu Tyr Arg Lys Tyr
385                 390                 395                 400

Arg Thr Ser Val His Pro His Gly Ala Pro Val Lys Gln Leu Lys Ile
                405                 410                 415

Ala Pro Gly Tyr
            420

<210> SEQ ID NO 62
<211> LENGTH: 420
<212> TYPE: PRT
<213> ORGANISM: Drosophila melanogaster

<400> SEQUENCE: 62

His Phe Lys Leu Val Thr Lys Asp Gly Asn Ser Leu Leu Ile Gly Ala
1               5                   10                  15

Arg Asn Thr Val Phe Asn Leu Ser Ile His Asp Leu Val Glu Gln Gln
                20                  25                  30

Arg Leu Val Trp Thr Ser Pro Glu Asp Thr Lys Met Cys Leu Val
            35                  40                  45

Lys Gly Lys Asp Glu Glu Ala Cys Gln Asn Tyr Ile Arg Ile Met Val
    50                  55                  60

Val Pro Ser Pro Gly Arg Leu Phe Val Cys Gly Thr Asn Ser Phe Arg
65                  70                  75                  80

Pro Met Cys Asn Thr Tyr Ile Ile Ser Asp Ser Asn Tyr Thr Leu Glu
                85                  90                  95

Ala Thr Lys Asn Gly Gln Ala Val Cys Pro Tyr Asp Pro Arg His Asn
            100                 105                 110

Ser Thr Ser Val Leu Ala Asp Asn Glu Leu Tyr Ser Gly Thr Val Ala
        115                 120                 125

Asp Phe Ser Gly Ser Asp Pro Ile Ile Tyr Arg Glu Pro Leu Gln Thr
130                 135                 140

Glu Gln Tyr Asp Ser Leu Ser Leu Asn Ala Pro Asn Phe Val Ser Ser
145                 150                 155                 160

Phe Thr Gln Gly Asp Phe Val Tyr Phe Phe Arg Glu Thr Ala Val
                165                 170                 175

Glu Phe Ile Asn Cys Gly Lys Ala Ile Tyr Ser Arg Val Ala Arg Val
            180                 185                 190

Cys Lys Trp Asp Lys Gly Pro His Arg Phe Arg Asn Arg Trp Thr
        195                 200                 205

Ser Phe Leu Lys Ser Arg Leu Asn Cys Ser Ile Pro Gly Asp Tyr Pro
210                 215                 220

Phe Tyr Phe Asn Glu Ile Gln Ser Ala Ser Asn Leu Val Glu Gly Gln
225                 230                 235                 240

Tyr Gly Ser Met Ser Ser Lys Leu Ile Tyr Gly Val Phe Asn Thr Pro
                245                 250                 255

Ser Asn Ser Ile Pro Gly Ser Ala Val Cys Ala Phe Ala Leu Gln Asp
            260                 265                 270

Ile Ala Asp Thr Phe Glu Gly Gln Phe Lys Glu Gln Thr Gly Ile Asn
        275                 280                 285
```

```
Ser Asn Trp Leu Pro Val Asn Ala Lys Val Pro Asp Pro Arg Pro
    290                 295                 300

Gly Ser Cys His Asn Asp Ser Arg Ala Leu Pro Asp Pro Thr Leu Asn
305                 310                 315                 320

Phe Ile Lys Thr His Ser Leu Met Asp Glu Asn Val Pro Ala Phe Phe
                325                 330                 335

Ser Gln Pro Ile Leu Val Arg Thr Ser Thr Ile Tyr Arg Phe Thr Gln
                340                 345                 350

Ile Ala Val Asp Ala Gln Ile Lys Thr Pro Gly Gly Lys Thr Tyr Asp
            355                 360                 365

Val Ile Phe Val Gly Thr Asp His Gly Lys Ile Ile Lys Ser Val Asn
    370                 375                 380

Ala Glu Ser Ala Asp Ser Ala Asp Lys Val Thr Ser Val Val Ile Glu
385                 390                 395                 400

Glu Ile Asp Val Leu Thr Lys Ser Glu Pro Ile Arg Asn Leu Glu Ile
                405                 410                 415

Val Arg Thr Met
            420

<210> SEQ ID NO 63
<211> LENGTH: 428
<212> TYPE: PRT
<213> ORGANISM: Drosophila melanogaster

<400> SEQUENCE: 63

Phe Lys Ile Leu Asp His Asn Asp Glu Phe Val Leu Val Gly Ala Lys
1               5                   10                  15

Asp Val Ile Tyr Asn Val Ser Leu Asn Gly Leu Lys Glu Ile Ala Arg
            20                  25                  30

Leu Glu Trp His Ser Thr Asp Ala Asp Arg Glu Leu Cys Ala Leu Lys
        35                  40                  45

Gly Lys His Glu Trp Asp Cys His Asn Tyr Leu Arg Val Tyr Ala Leu
    50                  55                  60

Arg Pro Asn Gly Glu Val Leu Leu Cys Gly Thr Asn Ser Tyr Lys Pro
65                  70                  75                  80

Arg Cys Arg His Tyr Thr Ala Val Glu Val Ser Ser Glu Glu Ala Gly
                85                  90                  95

Ser Ala Gly His Ala His Ala Met Arg Tyr Glu Val Ser Arg Asp Val
            100                 105                 110

Glu Ala Gln Gly Leu Cys Pro Tyr Ser Pro Ala His Asn Ser Thr Tyr
        115                 120                 125

Ala Phe Ala Asp Gly His Leu Tyr Ser Ala Thr Val Ala Asp Phe Ser
    130                 135                 140

Gly Gly Asp Pro Leu Ile Tyr Arg Glu Asn Leu Arg Thr Glu Gln Tyr
145                 150                 155                 160

Asp Leu Lys Gln Leu Asn Gln Pro Asp Phe Val Gly Ala Ile Glu Arg
                165                 170                 175

Asn Gly Tyr Val Leu Phe Phe Arg Glu Leu Ser Met Glu Val Met
            180                 185                 190

Asn Phe Gly Lys Ala Val Tyr Ser Arg Val Ala Arg Val Cys Lys Asn
        195                 200                 205

Asp Arg Gly Gly Pro Tyr Ser His Gly Lys Ser Trp Thr Ser Phe Leu
    210                 215                 220

Lys Ala Arg Leu Asn Cys Ser Val Pro Gly Glu Phe Pro Phe Tyr Phe
```

```
                225                 230                 235                 240
Asp Glu Ile Gln Ala Ile Ser Pro Ile Val Glu Ser Gly Ser Lys Ser
                    245                 250                 255

Leu Ile Tyr Ala Val Phe Thr Thr Ser Val Asn Ala Ile Pro Gly Ser
                260                 265                 270

Ala Val Cys Ala Phe Asn Val Asp Ile Leu Ala Ala Phe Asp Gly
            275                 280                 285

Glu Phe Lys Ser Gln Lys Asp Ser Gln Ser His Trp Leu Pro Val Glu
        290                 295                 300

Arg Glu Gln Val Pro Lys Pro Arg Pro Gly Gln Cys Val Glu Asp Ser
305                 310                 315                 320

Arg Thr Leu Thr Ser Ile Ala Val Asn Phe Ile Lys Asn His Pro Leu
                325                 330                 335

Met Glu Glu Ala Val Pro Ala Val His Gly Arg Pro Leu Leu Thr Lys
                340                 345                 350

Val Asn Leu His His Arg Leu Thr Ala Ile Ala Val His Pro Gln Val
            355                 360                 365

Lys Ser Leu Ser Gly Ala Tyr Tyr Asp Val Ile Tyr Ser Gly Thr Asp
        370                 375                 380

Asp Gly Lys Val Thr Lys Phe Ile Asn Ile Leu Ser Thr His Pro Asn
385                 390                 395                 400

Arg Leu Lys Thr Val Ile Ser Glu Met Gln Val Leu Pro Leu Gly
                405                 410                 415

Thr Pro Ile Arg Glu Leu Val Ile Ser Thr Ser Lys
                420                 425

<210> SEQ ID NO 64
<211> LENGTH: 427
<212> TYPE: PRT
<213> ORGANISM: Caenorhabditis elegans

<400> SEQUENCE: 64

His Phe Lys Leu Leu Ala Ala Asp Gly Asp Ser Leu Leu Val Gly Ala
1               5                   10                  15

Arg Asn Ala Val Tyr Asn Leu Ser Leu Ser Thr Leu Ser Val Asn His
                20                  25                  30

Lys Ile Asp Trp Lys Pro Pro Ala Glu His Ile Glu Glu Cys Ile Met
            35                  40                  45

Lys Gly Lys Ser Lys Thr Asp Cys Gln Asn Tyr Ile Arg Val Leu Ala
        50                  55                  60

Arg Lys Ser Ala Gly Val Ser Leu Val Cys Gly Thr His Ala Phe Ser
65                  70                  75                  80

Pro Lys Cys Arg Glu Tyr Thr Val Thr Glu Phe Gly Ile Arg Asn Thr
                85                  90                  95

Arg Gln Phe Asp Gly Gln Gly Ile Ser Pro Tyr Asp Pro Lys His Asn
                100                 105                 110

Ser Ser Ala Leu Tyr Val Pro Gly Thr Asn Gln Leu Phe Val Ala Thr
            115                 120                 125

Val Thr Asp Phe Val Gly Asn Asp Ala Leu Ile Tyr Arg Lys Thr Ile
        130                 135                 140

Asp Glu Thr Pro Ser Ser Lys Ser Ala Ala Asn Ile Arg Thr Gln Ser
145                 150                 155                 160

Tyr Asp Ala Arg Val Leu Asn Ala Pro Asn Phe Val Ala Thr Phe Ala
                165                 170                 175
```

Tyr Lys Glu His Val Tyr Phe Trp Phe Arg Glu Ile Ala Ser Glu Ala
                180                 185                 190

Ile Asp Asn Asn Glu Glu Pro Gln Ile Tyr Ala Arg Val Ala Arg Val
            195                 200                 205

Cys Lys Asn Asp Lys Gly Gly Ala Arg Pro Ala Asn Glu Arg Trp Thr
210                 215                 220

Ser Tyr Leu Lys Ala Arg Leu Asn Cys Ser Leu Pro Ser Gly Ser Ser
225                 230                 235                 240

Pro Phe Tyr Phe Asn Glu Leu Lys Ala Val Ser Asp Pro Ile Asp Ala
                245                 250                 255

Gly Asn Asn Asn His Val Val Tyr Thr Val Phe Ser Thr Pro Asp Ser
            260                 265                 270

Asp Val Arg Met Ser Ala Val Cys Lys Phe Ser Met Lys Lys Ile Arg
        275                 280                 285

Glu Glu Phe Asp Asn Gly Thr Phe Lys His Gln Asn Asn Ala Gln Ser
290                 295                 300

Met Trp Met Ala Phe Asn Arg Asn Glu Val Pro Lys Pro Arg Pro Gly
305                 310                 315                 320

Ser Cys Ser Pro Asp Ser Thr Lys Leu Pro Glu Asn Thr Val Ser Phe
                325                 330                 335

Ile Leu His His Pro Leu Leu His Arg Pro Ile Pro Ser Val Ala Ala
            340                 345                 350

Pro Leu Leu Val Glu Gly Ala Asp Arg Ala Asp Leu Thr Gln Ile Thr
        355                 360                 365

Val Leu Pro Arg Val Arg Ala Val Gly Gly His Asn Tyr Asp Ile Leu
370                 375                 380

Phe Ile Gly Thr Ser Asp Gly Lys Val Leu Lys Val Val Glu Val Asp
385                 390                 395                 400

Gly Asn Ala Thr Val Ile Gln Ser Ala Thr Val Phe Gln Arg Gly Val
                405                 410                 415

Pro Ile Val Asn Leu Leu Thr Thr Lys Glu Ser
            420                 425

<210> SEQ ID NO 65
<211> LENGTH: 412
<212> TYPE: PRT
<213> ORGANISM: Homo sapiens

<400> SEQUENCE: 65

Phe Ser Gln Leu Ala Leu Asp Pro Ser Gly Asn Gln Leu Ile Val Gly
1               5                   10                  15

Ala Arg Asn Tyr Leu Phe Arg Leu Ser Leu Ala Asn Val Ser Leu Leu
                20                  25                  30

Gln Ala Thr Glu Trp Ala Ser Ser Glu Asp Thr Arg Arg Ser Cys Gln
            35                  40                  45

Ser Lys Gly Lys Thr Glu Glu Glu Cys Gln Asn Tyr Val Arg Val Leu
        50                  55                  60

Ile Val Ala Gly Arg Lys Val Phe Met Cys Gly Thr Asn Ala Phe Ser
65                  70                  75                  80

Pro Met Cys Thr Ser Arg Gln Val Gly Asn Leu Ser Arg Thr Thr Glu
                85                  90                  95

Lys Ile Asn Gly Val Ala Arg Cys Pro Tyr Asp Pro Arg His Asn Ser
            100                 105                 110

Thr Ala Val Ile Ser Ser Gln Gly Glu Leu Tyr Ala Ala Thr Val Ile
        115                 120                 125

Asp Phe Ser Gly Arg Asp Pro Ala Ile Tyr Arg Ser Leu Gly Ser Gly
                130                 135                 140

Pro Pro Leu Arg Thr Ala Gln Tyr Asn Ser Lys Trp Leu Asn Glu Pro
145                 150                 155                 160

Asn Phe Val Ala Ala Tyr Asp Ile Gly Leu Phe Ala Tyr Phe Phe Leu
                165                 170                 175

Arg Glu Asn Ala Val Glu His Asp Cys Gly Arg Thr Val Tyr Ser Arg
                180                 185                 190

Val Ala Arg Val Cys Lys Asn Asp Val Gly Gly Arg Phe Leu Leu Glu
                195                 200                 205

Asp Thr Trp Thr Thr Phe Met Lys Ala Arg Leu Asn Cys Ser Arg Pro
                210                 215                 220

Gly Glu Val Pro Phe Tyr Tyr Asn Glu Leu Gln Ser Ala Phe His Leu
225                 230                 235                 240

Pro Glu Gln Asp Leu Ile Tyr Gly Val Phe Thr Thr Asn Val Asn Ser
                245                 250                 255

Ile Ala Ala Ser Ala Val Cys Ala Phe Asn Leu Ser Ala Ile Ser Gln
                260                 265                 270

Ala Phe Asn Gly Pro Phe Arg Tyr Gln Glu Asn Pro Arg Ala Ala Trp
                275                 280                 285

Leu Pro Ile Ala Asn Pro Ile Pro Asn Phe Gln Cys Gly Thr Leu Pro
                290                 295                 300

Glu Thr Gly Pro Asn Glu Asn Leu Thr Glu Arg Ser Leu Gln Asp Ala
305                 310                 315                 320

Gln Arg Leu Phe Leu Met Ser Glu Ala Val Gln Pro Val Thr Pro Glu
                325                 330                 335

Pro Cys Val Thr Gln Asp Ser Val Arg Phe Ser His Leu Val Val Asp
                340                 345                 350

Leu Val Gln Ala Lys Asp Thr Leu Tyr His Val Leu Tyr Ile Gly Thr
                355                 360                 365

Glu Ser Gly Thr Ile Leu Lys Ala Leu Ser Thr Ala Ser Arg Ser Leu
370                 375                 380

His Gly Cys Tyr Leu Glu Glu Leu His Val Leu Pro Pro Gly Arg Arg
385                 390                 395                 400

Glu Pro Leu Arg Ser Leu Arg Ile Leu His Ser Ala
                405                 410

<210> SEQ ID NO 66
<211> LENGTH: 411
<212> TYPE: PRT
<213> ORGANISM: Mus musculus

<400> SEQUENCE: 66

Phe Ser Arg Leu Thr Phe Asp Pro Gly Gln Lys Glu Leu Val Val Gly
1               5                   10                  15

Ala Arg Asn Tyr Leu Phe Arg Leu Glu Leu Gly Asp Leu Ser Leu Ile
                20                  25                  30

Gln Ala Val Glu Trp Glu Cys Asp Glu Ala Thr Lys Lys Ala Cys Tyr
            35                  40                  45

Ser Lys Gly Lys Ser Lys Glu Glu Cys Gln Asn Tyr Ile Arg Val Leu
        50                  55                  60

Leu Val Gly Gly Asp Arg Leu Phe Thr Cys Gly Thr Asn Ala Phe Thr
65                  70                  75                  80

Pro Val Cys Thr Ile Arg Ser Leu Ser Asn Leu Thr Glu Ile His Asp

```
            85                  90                  95
Gln Ile Ser Gly Met Ala Arg Cys Pro Tyr Ser Pro Gln His Asn Ser
        100                 105                 110

Thr Ala Leu Leu Thr Ala Ser Gly Glu Leu Tyr Ala Ala Thr Ala Met
        115                 120                 125

Asp Phe Pro Gly Arg Asp Pro Ala Ile Tyr Arg Ser Leu Gly Thr Leu
    130                 135                 140

Pro Pro Leu Arg Thr Ala Gln Tyr Asn Ser Lys Trp Leu Asn Glu Pro
145                 150                 155                 160

Asn Phe Val Ser Ser Tyr Asp Ile Gly Asn Phe Thr Tyr Phe Phe Phe
                165                 170                 175

Arg Glu Asn Ala Val Glu His Asp Cys Gly Lys Thr Val Phe Ser Arg
            180                 185                 190

Pro Ala Arg Val Cys Lys Asn Asp Ile Gly Gly Arg Phe Leu Leu Glu
            195                 200                 205

Asp Thr Trp Thr Thr Phe Met Lys Ala Arg Leu Asn Cys Ser Arg Pro
    210                 215                 220

Gly Glu Val Pro Phe Tyr Tyr Asn Glu Leu Gln Gly Thr Phe Phe Leu
225                 230                 235                 240

Pro Glu Leu Asp Leu Ile Tyr Gly Ile Phe Thr Thr Asn Val Asn Ser
                245                 250                 255

Ile Ala Ser Ser Ala Val Cys Val Phe Asn Leu Ser Ala Ile Ser Gln
            260                 265                 270

Ala Phe Asn Gly Pro Phe Lys Tyr Gln Glu Asn Ser Arg Ser Ala Trp
            275                 280                 285

Leu Pro Tyr Pro Asn Pro Asn Pro Asn Phe Gln Cys Gly Thr Met Asp
    290                 295                 300

Gln Gly Leu Tyr Val Asn Leu Thr Glu Arg Asn Leu Gln Asp Ala Gln
305                 310                 315                 320

Lys Phe Ile Leu Met His Glu Val Val Gln Pro Val Thr Thr Val Pro
                325                 330                 335

Ser Phe Met Glu Asp Asn Ser Arg Phe Ser His Leu Ala Val Asp Val
            340                 345                 350

Val Gln Gly Arg Glu Thr Leu Val His Ile Ile Tyr Leu Gly Thr Asp
            355                 360                 365

Tyr Gly Thr Ile Lys Lys Val Arg Ala Pro Leu Ser Gln Ser Ser Gly
    370                 375                 380

Ser Cys Leu Leu Glu Glu Ile Glu Leu Phe Pro Glu Arg Arg Ser Glu
385                 390                 395                 400

Pro Ile Arg Ser Leu Gln Ile Leu His Ser Gln
                405                 410

<210> SEQ ID NO 67
<211> LENGTH: 407
<212> TYPE: PRT
<213> ORGANISM: Drosophila melanogaster

<400> SEQUENCE: 67

Tyr Ser Glu Met Leu Phe Asp Val Ala Arg Asn Gln Val Ile Val Gly
1               5                   10                  15

Ala Arg Asp Thr Leu Tyr Arg Met Ser Phe Asp Leu Glu Pro Leu Glu
            20                  25                  30

Arg Ala Ser Trp Gly Ala Thr Pro Ser Glu Ile Ala Met Cys Gln Ala
        35                  40                  45
```

```
Lys Gly Gln Ser Glu Arg Trp Cys Arg Asn Tyr Val Arg Val Leu His
 50                  55                  60

Ser Tyr Gly Glu Asn Gln Leu Tyr Ala Cys Gly Thr Asn Ala Phe Gln
 65                  70                  75                  80

Pro Ser Cys Ser Trp Arg Gln Met Glu Asn Leu Thr Val Thr Gly Val
                 85                  90                  95

Asp Ser Gly Val Val Lys Cys Pro Phe His Pro Gln Ala Asn Ser Thr
             100                 105                 110

Ser Leu Leu Gln Ser Asn Gly Gln Leu Phe Val Gly Thr Ala Thr Asp
         115                 120                 125

Phe Ser Gly Ser Asp Val Ala Ile Leu Arg Thr Gly Val Glu Ser Asn
130                 135                 140

Lys Arg Phe Leu Arg Thr Lys Gln Tyr Asn Asn Asn Trp Leu Ser Gly
145                 150                 155                 160

Ala Gln Phe Val Gly Ser Phe Glu Ala Gly His Phe Val Tyr Phe Leu
                165                 170                 175

Leu Arg Glu Ser Ala Ala Glu His Met Ser Cys Gly Lys Val Ile Tyr
            180                 185                 190

Ser Arg Val Ala Arg Val Cys Lys Asn Asp Val Gly Gly Gly Gly Gln
        195                 200                 205

Leu Leu Arg Asp Asn Trp Thr Ser Phe Leu Lys Ala Arg Leu Asn Cys
210                 215                 220

Ser Leu Pro Gly Glu Tyr Pro Tyr Tyr Phe Asp Glu Ile Gln Gly Met
225                 230                 235                 240

Thr Tyr Ala Glu Ser Glu Ser Ile Leu Tyr Ala Thr Phe Arg Thr Ser
                245                 250                 255

Gly Ser Ser Ile Phe Gly Ser Ala Val Cys Ala Tyr Asn Leu Ser Ser
            260                 265                 270

Ile Asn Ala Ala Phe Asp Gly Pro Phe Lys Gln Gln Glu His Ser Asp
        275                 280                 285

Ala Ala Trp Lys Thr Val Asn Thr Asn Gln Arg Ser Gln Phe Gln Cys
290                 295                 300

Gly Thr Ser Ser Ile Gly His Trp Leu Glu Ser Ser Arg Tyr Gln Leu
305                 310                 315                 320

Met Asp Glu Ala Val Gln Pro Ile Gly Ala Glu Pro Leu Tyr His Ser
                325                 330                 335

Lys Leu Glu Gln Phe Gly Arg Leu Ala Leu Asp Ile Ile Asn Thr Lys
            340                 345                 350

Thr Glu Gln Val His Val Leu Phe Val Ala Ser Ser Gly Asn His Ile
        355                 360                 365

Lys Lys Leu Ser Val Lys Tyr Asp Gly Asp Gly Val Gln Thr Cys Leu
370                 375                 380

Val Glu Leu Trp Gln Ala Asp Asp Thr Gly Thr Ser Ser Leu Leu Asn
385                 390                 395                 400

Met Ala Tyr Leu Lys Val Ser
                405

<210> SEQ ID NO 68
<211> LENGTH: 386
<212> TYPE: PRT
<213> ORGANISM: Mus musculus

<400> SEQUENCE: 68

Ile Gly Ala Ile Ala Ala Ser Arg Ala Asp Gly Val Phe Val Ala Ser
 1               5                  10                  15
```

Gly Ser Cys Leu Asp Gln Leu Asp Tyr Ser Leu Lys Asn Arg Leu Ser
            20                  25                  30

Arg Leu Tyr Arg Asp Gln Ala Gly Asn Cys Thr Glu Pro Val Ser Leu
        35                  40                  45

Ala Pro Pro Ala Arg Pro Arg Pro Gly Ser Ser Phe Ser Lys Leu Leu
    50                  55                  60

Leu Pro Tyr Arg Glu Leu Glu Gly Leu Leu Thr Gly Trp Thr Phe
65                  70                  75                  80

Asp Arg Gly Ala Cys Glu Val Arg Pro Leu Gly Asn Leu Asn Arg Ser
                85                  90                  95

Ser Leu Arg Asn Gly Thr Glu Val Val Ser Cys His Pro Gln Gly Ser
            100                 105                 110

Thr Ala Gly Val Val Tyr Arg Ala Ser Gly Thr Asp Leu Trp Tyr Leu
        115                 120                 125

Ala Val Ala Ala Thr Tyr Val Leu Pro Glu Pro Glu Thr Ala Asn Arg
    130                 135                 140

Cys Asn Pro Ala Ala Ser Asp Arg Asp Thr Ala Ile Ala Leu Lys Asn
145                 150                 155                 160

Thr Glu Gly Arg Ser Leu Ala Thr Gln Glu Leu Gly Arg Leu Lys Leu
            165                 170                 175

Arg Gly Ser Ala Gly Ser Leu His Phe Val Asp Ala Phe Leu Trp Asn
        180                 185                 190

Gly Ser Val Tyr Phe Pro Tyr Tyr Pro Tyr Asn Tyr Thr Ser Gly Ala
    195                 200                 205

Ala Thr Gly Trp Pro Ser Met Ala Arg Ile Ala Gln Ser Thr Glu Val
    210                 215                 220

Leu Phe Gln Gly Gln Ala Ala Leu Asp Cys Asp His Gly His Pro Glu
225                 230                 235                 240

Gly Arg Arg Leu Leu Leu Ser Ser Leu Val Glu Ala Val Asp Ile
            245                 250                 255

Trp Ala Gly Val Phe Ser Ala Ala Thr Gly Glu Gly Gln Glu Arg Arg
        260                 265                 270

Ser Pro Ala Thr Thr Ala Leu Cys Leu Phe Arg Met Ser Glu Ile Gln
    275                 280                 285

Ala His Ala Arg Ser Cys Ser Trp Asp Phe Gln Ala Thr Glu His Asn
    290                 295                 300

Cys Lys Glu Gly Asp Arg Pro Glu Arg Val Gln Pro Ile Ala Ser Ser
305                 310                 315                 320

Thr Leu Ile His Ser Asp Leu Thr Ser Val Tyr Gly Thr Val Val Met
            325                 330                 335

Asn Arg Thr Val Leu Phe Leu Gly Thr Asp Gly Gln Leu Leu Lys
        340                 345                 350

Val Val Leu Gly Glu Asn Leu Thr Ser Asn Cys Pro Glu Val Ile Tyr
    355                 360                 365

Glu Ile Lys Glu Glu Thr Pro Val Phe Tyr Lys Leu Val Pro His Pro
    370                 375                 380

Met Lys
385

<210> SEQ ID NO 69
<211> LENGTH: 54
<212> TYPE: PRT
<213> ORGANISM: Homo sapiens -continued

<400> SEQUENCE: 69

Asn Cys Asn Lys His Lys Ser Cys Ser Glu Cys Leu Thr Ala Thr Asp
1               5                   10                  15

Pro His Cys Gly Trp Cys His Ser Leu Gln Arg Cys Thr Phe Gln Gly
            20                  25                  30

Asp Cys Val His Ser Glu Asn Leu Glu Asn Trp Leu Asp Ile Ser Ser
        35                  40                  45

Gly Ala Lys Lys Cys Pro
    50

<210> SEQ ID NO 70
<211> LENGTH: 53
<212> TYPE: PRT
<213> ORGANISM: Mus musculus

<400> SEQUENCE: 70

Arg Cys Asp Val Tyr Gly Lys Ala Cys Ala Glu Cys Cys Leu Ala Arg
1               5                   10                  15

Asp Pro Tyr Cys Ala Trp Asp Gly Ser Gln Cys Ser Arg Tyr Phe Pro
            20                  25                  30

Thr Ala Lys Arg Arg Thr Arg Arg Gln Asp Ile Arg Asn Gly Asp Pro
        35                  40                  45

Leu Thr Gln Cys Ser
    50

<210> SEQ ID NO 71
<211> LENGTH: 53
<212> TYPE: PRT
<213> ORGANISM: Drosophila melanogaster

<400> SEQUENCE: 71

Asp Cys Ser Asp Tyr Lys Thr Cys Gly Asp Cys Leu Gly Ala Arg Asp
1               5                   10                  15

Pro Tyr Cys Gly Trp Cys Ser Leu Glu Asn Lys Cys Ser Pro Arg Ser
            20                  25                  30

Asn Cys Gln Asp Asp Ala Asn Asp Pro Phe Tyr Trp Val Ser Tyr Lys
        35                  40                  45

Thr Gly Lys Cys Thr
    50

<210> SEQ ID NO 72
<211> LENGTH: 53
<212> TYPE: PRT
<213> ORGANISM: Colius striatus

<400> SEQUENCE: 72

Arg Cys Arg Ile Tyr Gly Thr Ala Cys Ala Asp Cys Cys Leu Ala Arg
1               5                   10                  15

Asp Pro Tyr Cys Ala Trp Asp Gly Asn Ser Cys Ser Arg Phe Tyr Pro
            20                  25                  30

Thr Gly Lys Arg Arg Ser Arg Arg Gln Asp Val Arg His Gly Asn Pro
        35                  40                  45

Leu Thr Gln Cys Arg
    50

<210> SEQ ID NO 73
<211> LENGTH: 52
<212> TYPE: PRT
<213> ORGANISM: Caenorhabditis elegans -continued

<400> SEQUENCE: 73

Asn Cys Ala Gln Gln Thr Ser Cys Ser Lys Cys Val Gln Leu Gln Asp
1               5                   10                  15

Pro His Cys Ala Trp Asp Ser Ser Ile Ala Arg Cys Val His Gly Gly
            20                  25                  30

Ser Trp Thr Gly Asp Gln Phe Ile Gln Asn Met Val Phe Gly Gln Ser
        35                  40                  45

Glu Gln Cys Pro
    50

<210> SEQ ID NO 74
<211> LENGTH: 53
<212> TYPE: PRT
<213> ORGANISM: Homo sapiens

<400> SEQUENCE: 74

Arg Cys Asp Thr Tyr Gly Lys Ala Cys Ala Asp Cys Cys Leu Ala Arg
1               5                   10                  15

Asp Pro Tyr Cys Ala Trp Asp Gly Asn Ala Cys Ser Arg Tyr Ala Pro
            20                  25                  30

Thr Ser Lys Arg Arg Ala Arg Gln Asp Val Lys Tyr Gly Asp Pro
        35                  40                  45

Ile Thr Gln Cys Trp
    50

<210> SEQ ID NO 75
<211> LENGTH: 52
<212> TYPE: PRT
<213> ORGANISM: Mus musculus

<400> SEQUENCE: 75

Asn Cys Gly Arg Leu Gln Ser Cys Ser Glu Cys Ile Leu Ala Gln Asp
1               5                   10                  15

Pro Val Cys Ala Trp Ser Phe Arg Leu Asp Ala Cys Val Ala His Ala
            20                  25                  30

Gly Glu His Arg Gly Met Val Gln Asp Ile Glu Ser Ala Asp Val Ser
        35                  40                  45

Ser Leu Cys Pro
    50

<210> SEQ ID NO 76
<211> LENGTH: 53
<212> TYPE: PRT
<213> ORGANISM: Drosophila melanogaster

<400> SEQUENCE: 76

His Cys Ser Val Tyr Thr Asn Cys Ser Ala Cys Leu Glu Ser Arg Asp
1               5                   10                  15

Pro Phe Cys Gly Trp Cys Ser Leu Glu Lys Arg Cys Thr Val Arg Ser
            20                  25                  30

Thr Cys Gln Arg Asp Thr Ser Ala Ser Arg Trp Leu Ser Leu Gly Ser
        35                  40                  45

Gly Gln Gln Cys Ile
    50

<210> SEQ ID NO 77
<211> LENGTH: 51
<212> TYPE: PRT

```
<213> ORGANISM: Homo sapiens

<400> SEQUENCE: 77

Ser Cys Glu Gln Tyr Thr Thr Cys Gly Glu Cys Leu Ser Ser Gly Asp
1               5                   10                  15

Pro His Cys Gly Trp Cys Ala Leu His Asn Met Cys Ser Arg Arg Asp
            20                  25                  30

Lys Cys Gln Gln Ala Trp Glu Pro Asn Arg Phe Ala Ala Ser Ile Ser
        35                  40                  45

Gln Cys Val
    50

<210> SEQ ID NO 78
<211> LENGTH: 53
<212> TYPE: PRT
<213> ORGANISM: Homo sapiens

<400> SEQUENCE: 78

Phe Cys Gly Lys His Gly Thr Cys Glu Asp Cys Val Leu Ala Arg Asp
1               5                   10                  15

Pro Tyr Cys Ala Trp Ser Pro Pro Thr Ala Thr Cys Val Ala Leu His
            20                  25                  30

Gln Thr Glu Ser Pro Ser Arg Gly Leu Ile Gln Glu Met Ser Gly Asp
        35                  40                  45

Ala Ser Val Cys Pro
    50

<210> SEQ ID NO 79
<211> LENGTH: 53
<212> TYPE: PRT
<213> ORGANISM: Mus musculus

<400> SEQUENCE: 79

Arg Cys Thr Ala Leu Gly Arg Ala Cys Ala Glu Cys Cys Leu Ala Arg
1               5                   10                  15

Asp Pro Tyr Cys Ala Trp Asp Gly Ser Ala Cys Thr Arg Phe Gln Pro
            20                  25                  30

Thr Ala Lys Arg Arg Phe Arg Arg Gln Asp Ile Arg Asn Gly Asp Pro
        35                  40                  45

Ser Thr Leu Cys Ser
    50

<210> SEQ ID NO 80
<211> LENGTH: 53
<212> TYPE: PRT
<213> ORGANISM: Danio rerio

<400> SEQUENCE: 80

Arg Cys Gln Ile Tyr Gly Gln Gly Cys Ala Glu Cys Cys Leu Ala Arg
1               5                   10                  15

Asp Pro Tyr Cys Ala Trp Asp Gly Thr Gln Cys Ser Arg Tyr Ile Pro
            20                  25                  30

Ala Ser Lys Arg Arg Ala Arg Arg Gln Asp Ile Lys His Gly Asp Pro
        35                  40                  45

Ser Ser His Cys Trp
    50

<210> SEQ ID NO 81
<211> LENGTH: 52
```

<212> TYPE: PRT
<213> ORGANISM: Mus musculus

<400> SEQUENCE: 81

Asn Cys Ser Val Tyr Glu Ser Cys Val Asp Cys Val Leu Ala Arg Asp
1               5                   10                  15

Pro His Cys Ala Trp Asp Pro Glu Ser Arg Leu Cys Ser Leu Leu Ser
            20                  25                  30

Gly Ser Thr Lys Pro Trp Lys Gln Asp Met Glu Arg Gly Asn Pro Glu
        35                  40                  45

Trp Val Cys Thr
        50

<210> SEQ ID NO 82
<211> LENGTH: 51
<212> TYPE: PRT
<213> ORGANISM: Homo sapiens

<400> SEQUENCE: 82

Leu Cys Glu Val Tyr Gly Gly Gly Cys His Gly Cys Leu Met Ser Arg
1               5                   10                  15

Asp Pro Tyr Cys Gly Trp Asp Gln Gly Arg Cys Ile Ser Ile Tyr Ser
            20                  25                  30

Ser Glu Arg Ser Val Leu Gln Ser Ile Asn Pro Ala Glu Pro His Lys
        35                  40                  45

Glu Cys Pro
        50

<210> SEQ ID NO 83
<211> LENGTH: 54
<212> TYPE: PRT
<213> ORGANISM: Homo sapiens

<400> SEQUENCE: 83

Ser Cys Ala Gln His Leu Asp Cys Ala Ser Cys Leu Ala His Arg Asp
1               5                   10                  15

Pro Tyr Cys Gly Trp Cys Val Leu Leu Gly Arg Cys Ser Arg Arg Ser
            20                  25                  30

Glu Cys Ser Arg Gly Gln Gly Pro Gly Gln Trp Leu Trp Ser Phe Gln
        35                  40                  45

Pro Glu Leu Gly Cys Leu
        50

<210> SEQ ID NO 84
<211> LENGTH: 53
<212> TYPE: PRT
<213> ORGANISM: Mus musculus

<400> SEQUENCE: 84

Phe Cys Glu Lys His Gly Ser Cys Glu Asp Cys Val Leu Ala Arg Asp
1               5                   10                  15

Pro Tyr Cys Ala Trp Ser Pro Ala Ile Lys Ala Cys Val Thr Leu His
            20                  25                  30

Gln Glu Glu Ala Ser Ser Arg Gly Trp Ile Gln Asp Met Ser Gly Asp
        35                  40                  45

Thr Ser Ser Cys Leu
        50

<210> SEQ ID NO 85

<211> LENGTH: 53
<212> TYPE: PRT
<213> ORGANISM: Homo sapiens

<400> SEQUENCE: 85

Arg Cys Gln Ala Tyr Gly Ala Ala Cys Ala Asp Cys Cys Leu Ala Arg
1               5                   10                  15
Asp Pro Tyr Cys Ala Trp Asp Gly Gln Ala Cys Ser Arg Tyr Thr Ala
            20                  25                  30
Ser Ser Lys Arg Arg Ser Arg Arg Gln Asp Val Arg His Gly Asn Pro
        35                  40                  45
Ile Arg Gln Cys Arg
    50

<210> SEQ ID NO 86
<211> LENGTH: 53
<212> TYPE: PRT
<213> ORGANISM: Tribolium confusum

<400> SEQUENCE: 86

His Cys Ala Ser Lys Thr Arg Cys Lys Asp Cys Val Glu Leu Gln Asp
1               5                   10                  15
Pro His Cys Ala Trp Asp Ala Lys Gln Asn Leu Cys Val Ser Ile Asp
            20                  25                  30
Thr Val Thr Ser Tyr Arg Phe Leu Ile Gln Asp Val Val Arg Gly Asp
        35                  40                  45
Asp Asn Lys Cys Trp
    50

<210> SEQ ID NO 87
<211> LENGTH: 55
<212> TYPE: PRT
<213> ORGANISM: Danio rerio

<400> SEQUENCE: 87

Glu Cys Gly Arg Tyr Gln Thr Cys Leu Asp Cys Val Leu Ala Arg Asp
1               5                   10                  15
Pro His Cys Gly Trp Asp Leu Asp Thr Glu His Cys Ala Thr Ile Asn
            20                  25                  30
Ser Ile His Arg Thr Arg Ser Ser Thr Val Ile Gln Ser Leu Asn Asp
        35                  40                  45
Gly Asp Ala Ser Gln Cys Pro
    50                  55

<210> SEQ ID NO 88
<211> LENGTH: 51
<212> TYPE: PRT
<213> ORGANISM: Homo sapiens

<400> SEQUENCE: 88

Thr Cys Glu Gln Tyr Gln Ser Cys Ala Ala Cys Leu Gly Ser Gly Asp
1               5                   10                  15
Pro His Cys Gly Trp Cys Val Leu Arg His Arg Cys Cys Arg Glu Gly
            20                  25                  30
Ala Cys Leu Gly Ala Ser Ala Pro His Gly Phe Ala Glu Glu Leu Ser
        35                  40                  45
Lys Cys Val
    50

```
<210> SEQ ID NO 89
<211> LENGTH: 52
<212> TYPE: PRT
<213> ORGANISM: Homo sapiens

<400> SEQUENCE: 89

Glu Cys Leu Ser Tyr Pro Thr Cys Thr Gln Cys Arg Asp Ser Gln Asp
1               5                   10                  15

Pro Tyr Cys Gly Trp Cys Val Val Glu Gly Arg Cys Thr Arg Lys Ala
            20                  25                  30

Glu Cys Pro Arg Ala Glu Glu Ala Ser His Trp Leu Trp Ser Arg Ser
        35                  40                  45

Lys Ser Cys Val
    50

<210> SEQ ID NO 90
<211> LENGTH: 48
<212> TYPE: PRT
<213> ORGANISM: Homo sapiens

<400> SEQUENCE: 90

Arg Cys Gln Phe Tyr Arg Thr Arg Ser Thr Cys Ile Gly Ala Gln Asp
1               5                   10                  15

Pro Tyr Cys Gly Trp Asp Val Val Met Lys Lys Cys Thr Ser Leu Glu
            20                  25                  30

Glu Ser Leu Ser Met Thr Gln Trp Glu Gln Ser Ile Ser Ala Cys Pro
        35                  40                  45

<210> SEQ ID NO 91
<211> LENGTH: 51
<212> TYPE: PRT
<213> ORGANISM: Xenopus laevis

<400> SEQUENCE: 91

Ser Cys Glu Gln Tyr Glu Ser Cys Asp Thr Cys Leu Gly Ser Arg Asp
1               5                   10                  15

Pro His Cys Gly Trp Cys Val Leu His Asn Met Cys Ser Arg Lys Asp
            20                  25                  30

Lys Cys Glu Arg Ala Asp Glu Leu His Arg Phe Thr Ser Asp Gln Arg
        35                  40                  45

Gln Cys Val
    50

<210> SEQ ID NO 92
<211> LENGTH: 53
<212> TYPE: PRT
<213> ORGANISM: Danio rerio

<400> SEQUENCE: 92

Gln Cys Asp Leu Tyr Gly Gln Ala Cys Ala Glu Cys Cys Leu Ala Arg
1               5                   10                  15

Asp Pro Tyr Cys Thr Trp Asp Gly His Ser Cys Ser Gln Phe Met Pro
            20                  25                  30

Thr Gly Arg Arg Arg Asn Ile Arg Gln Val Asn Asp Asp Gly Asn Pro
        35                  40                  45

Leu Asn Gln Cys Val
    50

<210> SEQ ID NO 93
<211> LENGTH: 56
```

<212> TYPE: PRT
<213> ORGANISM: Gallus gallus

<400> SEQUENCE: 93

Gln Cys Asp Met Tyr Gly Thr Ala Cys Ala Asp Cys Cys Leu Ala Arg
1               5                   10                  15

Asp Pro Tyr Cys Ala Trp Asp Gly Ile Ser Cys Ser Arg Tyr Tyr Pro
            20                  25                  30

Thr Gly Met Gln Ala Lys Arg Arg Phe Arg Arg Gln Asp Val Arg His
        35                  40                  45

Gly Asn Ala Ala Gln Gln Cys Phe
    50                  55

<210> SEQ ID NO 94
<211> LENGTH: 51
<212> TYPE: PRT
<213> ORGANISM: Mus musculus

<400> SEQUENCE: 94

Ser Cys Val Gln Tyr Thr Ser Cys Glu Leu Cys Leu Gly Ser Arg Asp
1               5                   10                  15

Pro His Cys Gly Trp Cys Val Leu His Ser Ile Cys Ser Arg Gln Asp
            20                  25                  30

Ala Cys Glu Arg Ala Glu Glu Pro Gln Arg Phe Ala Ser Asp Leu Leu
        35                  40                  45

Gln Cys Val
    50

<210> SEQ ID NO 95
<211> LENGTH: 48
<212> TYPE: PRT
<213> ORGANISM: Homo sapiens

<400> SEQUENCE: 95

Asn Cys Ser Val Leu Gln Ser Cys Met Ser Cys Val Gly Ser Pro Tyr
1               5                   10                  15

Pro Cys His Trp Cys Lys Tyr Arg His Thr Cys Thr Ser Arg Pro His
            20                  25                  30

Glu Cys Ser Phe Gln Glu Gly Arg Val His Ser Pro Glu Gly Cys Pro
        35                  40                  45

<210> SEQ ID NO 96
<211> LENGTH: 54
<212> TYPE: PRT
<213> ORGANISM: Homo sapiens

<400> SEQUENCE: 96

Ala Cys Asn Val His Ser Thr Cys Gly Asp Cys Val Gly Ala Ala Asp
1               5                   10                  15

Ala Tyr Cys Gly Trp Cys Ala Leu Glu Thr Arg Cys Thr Leu Gln Gln
            20                  25                  30

Asp Cys Thr Asn Ser Ser Gln Gln His Phe Trp Thr Ser Ala Ser Glu
        35                  40                  45

Gly Pro Ser Arg Cys Pro
    50

<210> SEQ ID NO 97
<211> LENGTH: 57
<212> TYPE: PRT
<213> ORGANISM: Drosophila melanogaster

<400> SEQUENCE: 97

Arg Cys His Asn Asp Lys Ile Thr Ser Cys Ser Glu Cys Val Ala Leu
1               5                   10                  15

Gln Asp Pro Tyr Cys Ala Trp Asp Lys Ile Ala Gly Lys Cys Arg Ser
                20                  25                  30

His Gly Ala Pro Arg Trp Leu Glu Glu Asn Tyr Phe Tyr Gln Asn Val
            35                  40                  45

Ala Thr Gly Gln His Ala Ala Cys Pro
        50                  55

<210> SEQ ID NO 98
<211> LENGTH: 44
<212> TYPE: PRT
<213> ORGANISM: Rattus norvegicus

<400> SEQUENCE: 98

Gly Cys Gly His Phe Gln Ser Cys Ser Gln Cys Leu Ser Ala Pro Tyr
1               5                   10                  15

Phe Ile Gln Cys Gly Trp Cys His Asn Arg Cys Val His Ser Asn Glu
                20                  25                  30

Cys Pro Ser Gly Thr Trp Thr Gln Glu Ile Cys Leu
            35                  40

<210> SEQ ID NO 99
<211> LENGTH: 54
<212> TYPE: PRT
<213> ORGANISM: Xenopus laevis

<400> SEQUENCE: 99

Lys Cys Ser Ala Leu Arg Glu Ser Cys Gly Leu Cys Leu Lys Ser Asp
1               5                   10                  15

Arg Arg Phe Glu Cys Gly Trp Cys Val Ser Glu Lys Lys Cys Thr Leu
                20                  25                  30

Arg Gln Asn Cys Pro Thr Leu Glu Asn Pro Trp Met His Ala Ser Thr
            35                  40                  45

Ala Asn Ser Arg Cys Thr
        50

<210> SEQ ID NO 100
<211> LENGTH: 54
<212> TYPE: PRT
<213> ORGANISM: Homo sapiens

<400> SEQUENCE: 100

Lys Cys Trp Ala Gln Arg Pro Ser Cys Gly Leu Cys Leu Lys Ala Asp
1               5                   10                  15

Pro Arg Phe Asn Cys Gly Trp Cys Ile Ser Glu His Arg Cys Gln Leu
                20                  25                  30

Arg Thr His Cys Pro Ala Pro Lys Thr Asn Trp Met His Leu Ser Gln
            35                  40                  45

Lys Gly Thr Arg Cys Ser
        50

<210> SEQ ID NO 101
<211> LENGTH: 55
<212> TYPE: PRT
<213> ORGANISM: Mus musculus

<400> SEQUENCE: 101

Lys Cys Pro Ala Leu Arg Gln Ser Cys Gly Leu Cys Leu Lys Ala Asp
1               5                   10                  15

Pro Arg Phe Glu Cys Gly Trp Cys Val Ala Glu Arg Arg Cys Ser Leu
            20                  25                  30

Arg His His Cys Pro Ala Asp Ser Pro Ala Ser Trp Met His Ala His
        35                  40                  45

His Gly Ser Ser Arg Cys Thr
    50                  55

<210> SEQ ID NO 102
<211> LENGTH: 51
<212> TYPE: PRT
<213> ORGANISM: Bos taurus

<400> SEQUENCE: 102

Glu Cys Thr Asn Tyr Lys Val Ser Thr Cys Arg Asp Cys Ile Glu Ser
1               5                   10                  15

Gly Pro Gly Cys Ala Trp Cys Gln Lys Leu Asn Phe Thr Gly Gln Gly
            20                  25                  30

Glu Pro Asp Ser Ile Arg Cys Asp Thr Arg Ala Glu Leu Leu Ser Lys
        35                  40                  45

Gly Cys Pro
    50

<210> SEQ ID NO 103
<211> LENGTH: 50
<212> TYPE: PRT
<213> ORGANISM: Oryctolagus cuniculus

<400> SEQUENCE: 103

Arg Cys Ala Ser Ser His Ala Val Ser Cys Ser Glu Cys Leu Ala Leu
1               5                   10                  15

Gly Pro Asp Cys Gly Trp Cys Val His Glu Asp Phe Ile Ser Gly Gly
            20                  25                  30

Pro Arg Ser Glu Arg Cys Asp Ile Val Ser Asn Leu Ile Ser Lys Gly
        35                  40                  45

Cys Pro
    50

<210> SEQ ID NO 104
<211> LENGTH: 44
<212> TYPE: PRT
<213> ORGANISM: Homo sapiens

<400> SEQUENCE: 104

Gly Cys Arg His Phe Gln Ser Cys Ser Gln Cys Leu Ser Ala Pro Pro
1               5                   10                  15

Phe Val Gln Cys Gly Trp Cys His Asp Lys Cys Val Arg Ser Glu Glu
            20                  25                  30

Cys Leu Ser Gly Thr Trp Thr Gln Gln Ile Cys Leu
        35                  40

<210> SEQ ID NO 105
<211> LENGTH: 53
<212> TYPE: PRT
<213> ORGANISM: Mus musculus

<400> SEQUENCE: 105

Asn Cys Ser Leu Tyr Pro Thr Cys Gly Asp Cys Leu Leu Ala Arg Asp

```
                1               5                  10                  15
            Pro Tyr Cys Ala Trp Thr Gly Ser Ala Cys Arg Leu Ala Ser Leu Val
                            20                  25                  30

Lys Glu Leu Cys Lys Asn Ser Ser Tyr Lys Ala Arg Phe Leu Val Pro
                        35                  40                  45

Gly Lys Pro Cys Lys
                    50
```

<210> SEQ ID NO 106
<211> LENGTH: 48
<212> TYPE: PRT
<213> ORGANISM: Xenopus laevis

<400> SEQUENCE: 106

```
            Asn Cys Ser Val His Gln Ser Cys Leu Ser Cys Val Asn Gly Ser Phe
            1               5                  10                  15

Pro Cys His Trp Cys Lys Tyr Arg His Val Cys Thr His Asn Ala Ala
                            20                  25                  30

Asp Cys Ser Phe Gln Glu Gly Arg Val Asn Met Ser Glu Asp Cys Pro
                        35                  40                  45
```

<210> SEQ ID NO 107
<211> LENGTH: 50
<212> TYPE: PRT
<213> ORGANISM: Homo sapiens

<400> SEQUENCE: 107

```
            Asn Cys Ser Gly Leu Arg Thr Cys Gly Gln Cys Leu Glu Gln Pro Gly
            1               5                  10                  15

Cys Gly Trp Cys Asn Asp Arg Gly His Cys Ile Glu Gly Ser Ser Asp
                            20                  25                  30

Thr Asn Leu Cys Pro Lys Glu Lys Asn Tyr Glu Trp Ser Phe Ile Gln
                        35                  40                  45

Cys Pro
                50
```

<210> SEQ ID NO 108
<211> LENGTH: 51
<212> TYPE: PRT
<213> ORGANISM: Homo sapiens

<400> SEQUENCE: 108

```
            Arg Cys Leu Lys Ala Asn Ala Lys Ser Cys Gly Glu Cys Ile Gln Ala
            1               5                  10                  15

Gly Pro Asn Cys Gly Trp Cys Thr Asn Ser Thr Phe Leu Gln Glu Gly
                            20                  25                  30

Met Pro Thr Ser Ala Arg Cys Asp Asp Leu Glu Ala Leu Lys Lys Lys
                        35                  40                  45

Gly Cys Pro
                50
```

<210> SEQ ID NO 109
<211> LENGTH: 44
<212> TYPE: PRT
<213> ORGANISM: Gallus gallus

<400> SEQUENCE: 109

```
            Gly Cys His His Phe Gln Ser Cys Ser Gln Cys Leu Leu Ala Pro Ala
            1               5                  10                  15
```

```
Phe Met Arg Cys Gly Trp Cys Gly Gln Gln Cys Leu Arg Ala Pro Glu
            20                  25                  30

Cys Asn Gly Gly Thr Trp Thr Gln Glu Thr Cys Leu
            35                  40
```

<210> SEQ ID NO 110
<211> LENGTH: 54
<212> TYPE: PRT
<213> ORGANISM: Drosophila melanogaster

<400> SEQUENCE: 110

```
Arg Cys Arg Glu Met Ala Asp Ser Cys Gly Ile Cys Leu Ala Leu Ser
1               5                   10                  15

Glu Lys Tyr Asn Cys Gly Trp Cys Ser Ser Thr Asn Thr Cys Glu Val
            20                  25                  30

Glu Glu Gln Cys Asn Lys Asn Lys Glu Gly Lys Thr Asp Trp Leu Asn
            35                  40                  45

Arg Ser Glu Ile Cys Pro
    50
```

<210> SEQ ID NO 111
<211> LENGTH: 44
<212> TYPE: PRT
<213> ORGANISM: Takifugu rubripes

<400> SEQUENCE: 111

```
Gly Cys Asp His Leu Thr Thr Cys Thr Ser Cys Leu Val Ser Ser Arg
1               5                   10                  15

Val Thr Glu Cys Gly Trp Cys Glu Gly Arg Cys Thr Arg Ala Asn Gln
            20                  25                  30

Cys Pro Pro Ser Val Trp Thr Gln Glu Tyr Cys Thr
            35                  40
```

<210> SEQ ID NO 112
<211> LENGTH: 54
<212> TYPE: PRT
<213> ORGANISM: Mus musculus

<400> SEQUENCE: 112

```
Lys Cys Ala Ala Gln Arg Glu Ser Cys Gly Leu Cys Leu Lys Ala Asp
1               5                   10                  15

His Lys Phe Glu Cys Gly Trp Cys Ser Gly Glu Arg Arg Cys Thr Leu
            20                  25                  30

His Gln His Cys Pro Ser Thr Ser Ser Pro Trp Leu Asp Trp Ser Ser
            35                  40                  45

His Asn Val Lys Cys Ser
    50
```

<210> SEQ ID NO 113
<211> LENGTH: 43
<212> TYPE: PRT
<213> ORGANISM: Caenorhabditis elegans

<400> SEQUENCE: 113

```
Thr Cys Ser His His Ser Ser Cys Thr Glu Cys Leu Val Ser Val Asp
1               5                   10                  15

Pro Leu Cys Gln Trp Cys His Pro Thr Gln Ser Cys Thr Thr Ser Ala
            20                  25                  30

Arg Cys Thr Ser Pro Val Thr Ser Gln Cys Pro
            35                  40
```

<210> SEQ ID NO 114
<211> LENGTH: 43
<212> TYPE: PRT
<213> ORGANISM: Gallus gallus

<400> SEQUENCE: 114

Gly Cys Arg His Phe Ser Thr Cys Asp Arg Cys Leu Arg Ala Glu Arg
1               5                   10                  15

Phe Met Gly Cys Gly Trp Cys Gly Asn Gly Cys Thr Arg His His Glu
            20                  25                  30

Cys Ala Gly Pro Trp Val Gln Asp Ser Cys Pro
        35                  40

<210> SEQ ID NO 115
<211> LENGTH: 43
<212> TYPE: PRT
<213> ORGANISM: Takifugu rubripes

<400> SEQUENCE: 115

Gly Cys Ala His Phe Arg Thr Cys Ser Met Cys Leu Met Ala Pro Arg
1               5                   10                  15

Phe Met Asn Cys Gly Trp Cys Ser Gly Val Cys Ser Arg Gln His Gln
            20                  25                  30

Cys Asp Met Gln Trp Glu Lys Asp Ser Cys Ala
        35                  40

<210> SEQ ID NO 116
<211> LENGTH: 46
<212> TYPE: PRT
<213> ORGANISM: Mus musculus

<400> SEQUENCE: 116

Arg Cys Asp Gln His Thr Asp Cys Tyr Ser Cys Thr Ala Asn Thr Asn
1               5                   10                  15

Asp Cys His Trp Cys Asn Asp His Cys Val Pro Val Asn His Ser Cys
            20                  25                  30

Thr Glu Gly Gln Ile Ser Ile Ala Lys Tyr Glu Ser Cys Pro
        35                  40                  45

<210> SEQ ID NO 117
<211> LENGTH: 48
<212> TYPE: PRT
<213> ORGANISM: Homo sapiens

<400> SEQUENCE: 117

Asn Cys Ser Ala His Gln Leu Cys Leu Ser Cys Val Asn Ser Ala Phe
1               5                   10                  15

Arg Cys His Trp Cys Lys Tyr Arg Asn Leu Cys Thr His Asp Pro Thr
            20                  25                  30

Thr Cys Ser Phe Gln Glu Gly Arg Ile Asn Ile Ser Glu Asp Cys Pro
        35                  40                  45

<210> SEQ ID NO 118
<211> LENGTH: 43
<212> TYPE: PRT
<213> ORGANISM: Homo sapiens

<400> SEQUENCE: 118

Gly Cys Arg His Phe Leu Thr Cys Gly Arg Cys Leu Arg Ala Trp His
1               5                   10                  15

```
Phe Met Gly Cys Gly Trp Cys Gly Asn Met Cys Gly Gln Gln Lys Glu
            20                  25                  30
Cys Pro Gly Ser Trp Gln Gln Asp His Cys Pro
            35                  40
```

<210> SEQ ID NO 119
<211> LENGTH: 50
<212> TYPE: PRT
<213> ORGANISM: Homo sapiens

<400> SEQUENCE: 119

```
Asn Cys Ser Gly Tyr Cys Thr Cys Ser His Cys Leu Glu Gln Pro Gly
1               5                   10                  15
Cys Gly Trp Cys Thr Asp Lys Gly Lys Cys Ile Glu Gly Ser Tyr Asn
            20                  25                  30
Ser Ser Met Cys Leu Glu Asp Ser Arg Tyr Asn Trp Ser Phe Ile His
            35                  40                  45
Cys Pro
    50
```

<210> SEQ ID NO 120
<211> LENGTH: 48
<212> TYPE: PRT
<213> ORGANISM: Drosophila melanogaster

<400> SEQUENCE: 120

```
Asp Cys Ser His His Gly Asn Cys Gln Glu Cys Leu Gln Ser Ser Trp
1               5                   10                  15
Gly Cys Asn Trp Cys Ile Phe Asp Asn Lys Cys Val His Lys Ser Leu
            20                  25                  30
Gln Cys Arg Asn Ile Glu Asn Ala Val Ser Thr Val Gly His Cys Pro
            35                  40                  45
```

<210> SEQ ID NO 121
<211> LENGTH: 45
<212> TYPE: PRT
<213> ORGANISM: Homo sapiens

<400> SEQUENCE: 121

```
Asn Cys Ser Ser Leu Lys Glu Cys Pro Ala Cys Val Glu Thr Gly Cys
1               5                   10                  15
Ala Trp Cys Lys Ser Ala Arg Arg Cys Ile His Pro Phe Thr Ala Cys
            20                  25                  30
Asp Pro Ser Asp Tyr Glu Arg Asn Gln Glu Gln Cys Pro
            35                  40                  45
```

<210> SEQ ID NO 122
<211> LENGTH: 41
<212> TYPE: PRT
<213> ORGANISM: Caenorhabditis elegans

<400> SEQUENCE: 122

```
Asp Cys Ser Gly Tyr Gly Thr Cys Ser Cys Met Ser Ser Glu Tyr
1               5                   10                  15
Asn Cys Ala Trp Cys Ser Gly Leu His Lys Cys Ser Asn Ser Cys Gly
            20                  25                  30
Ala Leu Glu Lys Ser Lys Ala Cys Val
            35                  40
```

<210> SEQ ID NO 123
<211> LENGTH: 58
<212> TYPE: PRT
<213> ORGANISM: Schistocerca americana

<400> SEQUENCE: 123

Arg Cys Gly Ser Asp Lys Ile Thr Asn Cys Arg Glu Cys Val Ser Leu
1               5                   10                  15

Gln Asp Pro Tyr Cys Ala Trp Asp Asn Val Glu Leu Lys Cys Thr Ala
            20                  25                  30

Val Gly Ser Pro Asp Trp Ser Ala Gly Lys Arg Arg Phe Ile Gln Asn
        35                  40                  45

Ile Ser Leu Gly Glu His Lys Ala Cys Gly
    50                  55

<210> SEQ ID NO 124
<211> LENGTH: 47
<212> TYPE: PRT
<213> ORGANISM: Mus musculus

<400> SEQUENCE: 124

Arg Cys Ser Ala Tyr Ser Gln Gly Ala Cys Leu Gly Ala Arg Asp Pro
1               5                   10                  15

Tyr Cys Gly Trp Asp Gly Lys Arg Gln Leu Cys Ser Thr Leu Glu Asp
            20                  25                  30

Ser Ser Asn Met Ser Leu Trp Ile Gln Asn Ile Thr Thr Cys Pro
        35                  40                  45

<210> SEQ ID NO 125
<211> LENGTH: 51
<212> TYPE: PRT
<213> ORGANISM: Gallus gallus

<400> SEQUENCE: 125

Glu Cys Pro Lys Ile Lys Val Gly Thr Cys Lys Asn Cys Ile Gln Ser
1               5                   10                  15

Gly Pro Gly Cys Ala Trp Cys Lys Lys Leu Ser Phe Thr Lys Ala Gly
            20                  25                  30

Glu Pro Asp Ser Asn Arg Cys Asp Thr Ile Glu Gln Leu Gln Gln Arg
        35                  40                  45

Gly Cys Pro
    50

<210> SEQ ID NO 126
<211> LENGTH: 43
<212> TYPE: PRT
<213> ORGANISM: Xenopus laevis

<400> SEQUENCE: 126

Thr Cys Gly His Leu Lys Ser Cys Ser His Cys Leu Ser Ser Pro Ser
1               5                   10                  15

Val Asn Cys Gly Trp Ser Lys Asn His Cys Ser Thr Lys Gln Glu Cys
            20                  25                  30

Leu Asn Glu Glu Trp Ile Gln Glu Thr Cys Pro
        35                  40

<210> SEQ ID NO 127
<211> LENGTH: 49
<212> TYPE: PRT
<213> ORGANISM: Homo sapiens

```
<400> SEQUENCE: 127

Ser Cys Gln Pro Ala Pro Ser Cys Gln Lys Cys Ile Leu Ser His Pro
1               5                   10                  15

Ser Cys Ala Trp Cys Lys Gln Leu Asn Phe Thr Ala Ser Gly Glu Ala
            20                  25                  30

Glu Ala Arg Arg Cys Ala Arg Arg Glu Glu Leu Leu Ala Arg Gly Cys
        35                  40                  45

Pro

<210> SEQ ID NO 128
<211> LENGTH: 48
<212> TYPE: PRT
<213> ORGANISM: Mus musculus

<400> SEQUENCE: 128

Pro Cys Ala Leu Arg Thr Ala Cys Gly Glu Cys Thr Ser Ser Ser Ser
1               5                   10                  15

Glu Cys Met Trp Cys Ser Asn Met Lys Gln Cys Val Asp Ser Asn Ala
            20                  25                  30

Phe Pro Phe Gly Gln Cys Met Glu Trp Tyr Thr Met Ser Ser Cys Pro
        35                  40                  45

<210> SEQ ID NO 129
<211> LENGTH: 50
<212> TYPE: PRT
<213> ORGANISM: Mus musculus

<400> SEQUENCE: 129

Ile Cys Thr Ser Gly Ser Ala Thr Ser Cys Glu Glu Cys Leu Leu Ile
1               5                   10                  15

His Pro Lys Cys Ala Trp Cys Ser Lys Glu Tyr Phe Gly Asn Pro Arg
            20                  25                  30

Ser Ile Thr Ser Arg Cys Asp Leu Lys Ala Asn Leu Ile Arg Asn Gly
        35                  40                  45

Cys Glu
    50

<210> SEQ ID NO 130
<211> LENGTH: 54
<212> TYPE: PRT
<213> ORGANISM: Mus musculus

<400> SEQUENCE: 130

Asp Cys Thr Lys Tyr Arg Phe Cys Val Asp Cys Val Leu Ala Arg Asp
1               5                   10                  15

Pro Tyr Cys Ala Trp Asn Val Asn Thr Ser Arg Cys Val Ala Thr Thr
            20                  25                  30

Ser Gly Arg Ser Gly Ser Phe Leu Val Gln His Val Ala Asn Leu Asp
        35                  40                  45

Thr Ser Lys Met Cys Asn
    50

<210> SEQ ID NO 131
<211> LENGTH: 51
<212> TYPE: PRT
<213> ORGANISM: Pan troglodytes

<400> SEQUENCE: 131

Glu Cys Thr Lys Phe Lys Val Ser Ser Cys Arg Glu Cys Ile Glu Ser
```

```
              1               5                  10                 15
            Gly Pro Gly Cys Thr Trp Cys Gln Lys Leu Asn Phe Thr Gly Pro Gly
                            20                 25                 30

Asp Pro Asp Ser Ile Arg Cys Asp Thr Arg Pro Gln Leu Leu Met Arg
                            35                 40                 45

Gly Cys Ala
                    50

<210> SEQ ID NO 132
<211> LENGTH: 48
<212> TYPE: PRT
<213> ORGANISM: Homo sapiens

<400> SEQUENCE: 132

Gln Cys Asp Ala His Arg Ser Glu Ala Ala Cys Leu Ala Ala Gly Pro
            1               5                  10                 15

Gly Ile Arg Cys Val Trp Asn Thr Gly Ser Ser Gln Cys Ile Ser Trp
                            20                 25                 30

Ala Leu Ala Thr Asp Glu Gln Glu Lys Leu Lys Ser Glu Cys Phe
                            35                 40                 45

<210> SEQ ID NO 133
<211> LENGTH: 48
<212> TYPE: PRT
<213> ORGANISM: Mus musculus

<400> SEQUENCE: 133

Gln Cys Asp Ala His Arg Ser Glu Ala Ala Cys Val Ala Ala Gly Pro
            1               5                  10                 15

Gly Ile Arg Cys Leu Trp Asp Thr Gln Ser Ser Arg Cys Thr Ser Trp
                            20                 25                 30

Glu Leu Ala Thr Glu Glu Gln Ala Glu Lys Leu Lys Ser Glu Cys Phe
                            35                 40                 45

<210> SEQ ID NO 134
<211> LENGTH: 43
<212> TYPE: PRT
<213> ORGANISM: Homo sapiens

<400> SEQUENCE: 134

Asn Cys Ser Phe Gly Arg Ser Asp Cys Ser Leu Cys Arg Ala Ala Asn
            1               5                  10                 15

Pro Asp Tyr Arg Cys Ala Trp Cys Gly Gly Gln Ser Arg Cys Val Tyr
                            20                 25                 30

Glu Ala Leu Cys Asn Thr Thr Ser Glu Cys Pro
                            35                 40

<210> SEQ ID NO 135
<211> LENGTH: 50
<212> TYPE: PRT
<213> ORGANISM: Paramecium tetraurelia

<400> SEQUENCE: 135

Ile Cys Gln Gln Leu Arg Glu Cys Asp Ser Cys Leu Ser Arg Glu Gly
            1               5                  10                 15

Cys Ile Trp Cys Thr Glu Glu Gln Thr Cys Gln Glu Gly Asn Ala Arg
                            20                 25                 30

Asp Gly Ala Phe Phe Asn Ser Cys Asp Ile Trp Val Ser Gly Ser Glu
                            35                 40                 45
```

Cys Pro
    50

<210> SEQ ID NO 136
<211> LENGTH: 48
<212> TYPE: PRT
<213> ORGANISM: Homo sapiens

<400> SEQUENCE: 136

Asp Cys Ser Val Gly His Gly Asp Cys Ser Arg Cys Gln Thr Ala Met
1               5                   10                  15

Pro Gln Tyr Gly Cys Val Trp Cys Glu Gly Glu Arg Pro Arg Cys Val
            20                  25                  30

Thr Arg Glu Ala Cys Gly Glu Ala Glu Ala Val Ala Thr Gln Cys Pro
        35                  40                  45

<210> SEQ ID NO 137
<211> LENGTH: 47
<212> TYPE: PRT
<213> ORGANISM: Caenorhabditis elegans

<400> SEQUENCE: 137

Thr Cys Glu Glu Gln Thr Asp Cys Val Ser Cys Ala Ser Lys Ser Gly
1               5                   10                  15

Cys Gly Trp Cys Ser Ser Gly Glu Gln Cys Leu Pro Asn Glu Gln Glu
            20                  25                  30

Cys Val Asp Gly Pro Gly Met Leu Thr Ser Trp Glu Lys Cys Pro
        35                  40                  45

<210> SEQ ID NO 138
<211> LENGTH: 47
<212> TYPE: PRT
<213> ORGANISM: Strongylocentrotus purpuratus

<400> SEQUENCE: 138

Ala Cys Ser Asp Ala Lys Thr Cys Gly Glu Cys Ile Ser Leu Asp Ser
1               5                   10                  15

Ser Cys Gly Trp Cys Thr Leu Leu Asn Tyr Thr Asp Asp Thr Gly Asn
            20                  25                  30

Pro Gln Cys Asp Leu Ala Ser Ser Leu Ser Gln Arg Gly Cys Ser
        35                  40                  45

<210> SEQ ID NO 139
<211> LENGTH: 53
<212> TYPE: PRT
<213> ORGANISM: Homo sapiens

<400> SEQUENCE: 139

Gly Cys Ala Gln Ala Thr Gln Cys Ala Leu Cys Leu Arg Arg Pro His
1               5                   10                  15

Cys Gly Trp Cys Ala Trp Gly Gly Arg Cys Met Glu Gly Gly Leu Ser
            20                  25                  30

Gly Pro Arg Asp Gly Leu Thr Cys Gly Arg Pro Gly Ala Ser Trp Ala
        35                  40                  45

Phe Leu Ser Cys Pro
            50

<210> SEQ ID NO 140
<211> LENGTH: 50
<212> TYPE: PRT
<213> ORGANISM: Drosophila melanogaster

```
<400> SEQUENCE: 140

Lys Cys Asp Val Leu Gly Pro Asp Cys Ser Leu Cys Val Thr Arg Asp
1               5                   10                  15

Pro Lys Tyr Lys Cys Ala Trp Cys Ser Asn Asn Glu Thr Cys Ile Ala
            20                  25                  30

Asp Lys Asn Ser Ile Ser Ser Gly Ser Lys Ser Ala Ile Glu Asn Glu
        35                  40                  45

Cys Pro
    50

<210> SEQ ID NO 141
<211> LENGTH: 47
<212> TYPE: PRT
<213> ORGANISM: Homo sapiens

<400> SEQUENCE: 141

Pro Cys Ser Leu Arg Thr Ser Cys Ser Asn Cys Thr Ser Asn Gly Met
1               5                   10                  15

Glu Cys Met Trp Cys Ser Ser Thr Lys Arg Cys Val Asp Ser Asn Ala
            20                  25                  30

Phe Pro Tyr Gly Gln Cys Leu Glu Trp Gln Thr Ala Thr Cys Ser
        35                  40                  45

<210> SEQ ID NO 142
<211> LENGTH: 47
<212> TYPE: PRT
<213> ORGANISM: Lytechinus variegatus

<400> SEQUENCE: 142

Ser Cys Leu Gln Ala Arg Thr Cys Gly Asp Cys Ile Ile Thr Asp Pro
1               5                   10                  15

Ser Cys Ala Trp Cys Ala Gln Pro Asp Phe Gln Asp Ala Glu Asn Tyr
            20                  25                  30

Pro Arg Cys Asp Ser Pro Asp Thr Leu Arg Glu Arg Gly Cys Met
        35                  40                  45

<210> SEQ ID NO 143
<211> LENGTH: 50
<212> TYPE: PRT
<213> ORGANISM: Caenorhabditis elegans

<400> SEQUENCE: 143

Val Cys Glu Glu His Lys Thr Cys Gly Glu Cys Gln Arg Asp Pro Gly
1               5                   10                  15

Cys Gly Trp Leu Ala Asp Leu Gly Leu Cys Ile Arg Gly Thr Ser Thr
            20                  25                  30

Gly Pro Leu Glu Pro Lys Pro Glu Asn Ser Thr Trp Tyr Phe Ile Asp
        35                  40                  45

Cys Pro
    50

<210> SEQ ID NO 144
<211> LENGTH: 48
<212> TYPE: PRT
<213> ORGANISM: Homo sapiens

<400> SEQUENCE: 144

Asp Cys Ser Arg Thr Ala Thr Ala Cys Thr Ser Cys Leu Ser Ala Gln
1               5                   10                  15
```

Trp Pro Cys Phe Trp Cys Ser Gln Gln His Ser Cys Val Ser Asn Gln
                20                  25                  30

Ser Arg Cys Glu Ala Ser Pro Asn Pro Thr Ser Pro Gln Asp Cys Pro
            35                  40                  45

<210> SEQ ID NO 145
<211> LENGTH: 47
<212> TYPE: PRT
<213> ORGANISM: Mus musculus

<400> SEQUENCE: 145

Ile Cys Thr Ala Arg Gly Val Asn Ser Cys Gln Gln Cys Leu Ala Val
1               5                   10                  15

Ser Pro Val Cys Ala Trp Cys Ser Asp Glu Thr Leu Ser Gln Gly Ser
                20                  25                  30

Pro Arg Cys Asn Leu Lys Glu Asn Leu Leu Lys Asp Asn Cys Ala
            35                  40                  45

<210> SEQ ID NO 146
<211> LENGTH: 49
<212> TYPE: PRT
<213> ORGANISM: Homo sapiens

<400> SEQUENCE: 146

Leu Cys Leu Gly Gly Ala Glu Thr Cys Glu Asp Cys Leu Leu Ile Gly
1               5                   10                  15

Pro Gln Cys Ala Trp Cys Ala Gln Glu Asn Phe Thr His Pro Ser Gly
                20                  25                  30

Val Gly Glu Arg Cys Asp Thr Pro Ala Asn Leu Leu Ala Lys Gly Cys
            35                  40                  45

Gln

<210> SEQ ID NO 147
<211> LENGTH: 44
<212> TYPE: PRT
<213> ORGANISM: Homo sapiens

<400> SEQUENCE: 147

Arg Cys Tyr Arg Tyr Ala Asp Cys Ala Ser Cys Thr Ala Asn Thr Asn
1               5                   10                  15

Gly Cys Gln Trp Cys Asp Asp Lys Lys Cys Ile Ser Ala Asn Ser Asn
                20                  25                  30

Cys Ser Met Ser Val Lys Asn Tyr Thr Lys Cys His
            35                  40

<210> SEQ ID NO 148
<211> LENGTH: 42
<212> TYPE: PRT
<213> ORGANISM: Caenorhabditis elegans

<400> SEQUENCE: 148

Pro Cys Ala Gln Arg Asn Asn Cys Ser Asp Cys Thr Asp Leu Glu Gln
1               5                   10                  15

Cys Met Trp Cys Pro Ser Thr Asn Arg Cys Ile Asn Leu Glu Ala Tyr
                20                  25                  30

Thr Leu Ser Phe Ala Tyr Gly Gln Cys His
            35                  40

<210> SEQ ID NO 149

```
<211> LENGTH: 50
<212> TYPE: PRT
<213> ORGANISM: Mus musculus

<400> SEQUENCE: 149

Gly Cys Ala Trp Gly Gly Ala Glu Ser Cys Ser Asp Cys Leu Leu Thr
1               5                   10                  15

Gly Pro His Cys Ala Trp Cys Ser Gln Glu Asn Phe Thr His Leu Ser
            20                  25                  30

Gly Ala Gly Glu Arg Cys Asp Thr Pro Ala Asn Leu Leu Ala Lys Gly
        35                  40                  45

Cys Gln
    50

<210> SEQ ID NO 150
<211> LENGTH: 42
<212> TYPE: PRT
<213> ORGANISM: Caenorhabditis elegans

<400> SEQUENCE: 150

Ser Cys Thr Asn Leu Ala Ser Asp Cys Ser Ser Cys Leu Ala Leu Ser
1               5                   10                  15

Pro Ser Leu Ser Cys Gly Trp Cys Asn Arg Gln Cys Ser His Glu Cys
            20                  25                  30

His Glu Ser Lys Ala Thr Ala Val Cys Asp
        35                  40

<210> SEQ ID NO 151
<211> LENGTH: 47
<212> TYPE: PRT
<213> ORGANISM: Xenopus laevis

<400> SEQUENCE: 151

Ile Cys Ala Thr Arg Gly Val Ser Ser Cys Gln Lys Cys Leu Ser Val
1               5                   10                  15

Ser Pro Gln Cys Ala Trp Cys Ser Gln Glu Val Phe Gly Lys Gly Ala
            20                  25                  30

Pro Arg Cys Asp Leu Lys Ser Glu Leu Leu Ser Asn Gly Cys Glu
        35                  40                  45

<210> SEQ ID NO 152
<211> LENGTH: 42
<212> TYPE: PRT
<213> ORGANISM: Acropora millepora

<400> SEQUENCE: 152

Ala Cys Thr Arg Leu Thr Lys Cys Asn Gln Cys Ile Gly Glu Ala Asn
1               5                   10                  15

Cys Ala Trp Cys Ser Asp Lys Asp Phe Gly Ser Ser Arg Cys Asp Ser
            20                  25                  30

Gln Lys Ile Leu Glu Leu Asn Gly Cys Ser
        35                  40

<210> SEQ ID NO 153
<211> LENGTH: 36
<212> TYPE: PRT
<213> ORGANISM: Drosophila melanogaster

<400> SEQUENCE: 153

Asp Cys Ser Thr His Ser Ser Cys Thr Arg Cys Val Ser Ser Glu Phe
1               5                   10                  15
```

-continued

```
Pro Cys Asp Trp Cys Val Glu Ala His Arg Cys Thr His Asp Thr Ala
                20                  25                  30
Glu Asn Cys Arg
        35

<210> SEQ ID NO 154
<211> LENGTH: 50
<212> TYPE: PRT
<213> ORGANISM: Homo sapiens

<400> SEQUENCE: 154

Ala Cys Ser Gln Asn Thr Asn Lys Thr Cys Glu Glu Cys Leu Lys Asn
1               5                   10                  15
Val Ser Cys Leu Trp Cys Asn Thr Asn Lys Ala Cys Leu Asp Tyr Pro
                20                  25                  30
Val Pro Pro Ala Ser Leu Cys Lys Leu Ser Ser Ala Arg Trp Gly Val
            35                  40                  45
Cys Trp
    50

<210> SEQ ID NO 155
<211> LENGTH: 46
<212> TYPE: PRT
<213> ORGANISM: Homo sapiens

<400> SEQUENCE: 155

Ile Cys Asn Lys Leu Thr Ser Cys Lys Ser Cys Ser Leu Asn Leu Asn
1               5                   10                  15
Cys Gln Trp Asp Gln Arg Gln Gln Glu Cys Gln Ala Leu Pro Ala His
                20                  25                  30
Leu Cys Gly Glu Gly Trp Ser His Ile Gly Asp Ala Cys Leu
            35                  40                  45

<210> SEQ ID NO 156
<211> LENGTH: 46
<212> TYPE: PRT
<213> ORGANISM: Caenorhabditis elegans

<400> SEQUENCE: 156

Thr Cys His Leu Ala Ser Asn Cys Ala Glu Cys Leu Ala His Gly Asp
1               5                   10                  15
Pro His Cys Ala Trp Ala Asp Gly Val Asp Cys Ile Asp Ile Arg Thr
                20                  25                  30
Asp Gln Arg Lys Ser Ala Ser Gln Asp Ser Gly Thr Cys Asp
            35                  40                  45

<210> SEQ ID NO 157
<211> LENGTH: 43
<212> TYPE: PRT
<213> ORGANISM: Danio rerio

<400> SEQUENCE: 157

Gly Cys Gln His Phe Leu Thr Cys Ala Val Cys Leu Thr Ala Pro Lys
1               5                   10                  15
Phe Val Gly Cys Gly Trp Cys Ser Gly Val Cys Ser Trp Glu Ser Asp
                20                  25                  30
Cys Asp His His Trp Arg Asn Asp Ser Cys Pro
            35                  40
```

```
<210> SEQ ID NO 158
<211> LENGTH: 53
<212> TYPE: PRT
<213> ORGANISM: Caenorhabditis elegans

<400> SEQUENCE: 158

Tyr Cys Arg Ile Gly Ser Asn Asp Leu Asn Thr Cys Glu Thr Cys Val
1               5                   10                  15

Gly Lys Gly Ser Asn Cys Phe Trp Cys Gly Gly Lys Thr Lys Arg Cys
            20                  25                  30

Met Pro Phe Asp Trp Tyr Tyr Pro Asp Cys Asn Ile Lys His Val Lys
        35                  40                  45

Tyr Asn Val Cys Trp
    50

<210> SEQ ID NO 159
<211> LENGTH: 46
<212> TYPE: PRT
<213> ORGANISM: Homo sapiens

<400> SEQUENCE: 159

Tyr Cys Asn Lys Lys Thr Ser Cys Arg Ser Cys Ala Leu Asp Gln Asn
1               5                   10                  15

Cys Gln Trp Glu Pro Arg Asn Gln Glu Cys Ile Ala Leu Pro Glu Asn
            20                  25                  30

Ile Cys Gly Ile Gly Trp His Leu Val Gly Asn Ser Cys Leu
        35                  40                  45

<210> SEQ ID NO 160
<211> LENGTH: 45
<212> TYPE: PRT
<213> ORGANISM: Homo sapiens

<400> SEQUENCE: 160

Glu Cys Arg Arg Leu Arg Thr Cys Ser Glu Cys Leu Ala Arg His Pro
1               5                   10                  15

Arg Thr Leu Cys Lys Trp Cys Thr Asn Cys Pro Glu Gly Ala Cys Ile
            20                  25                  30

Gly Arg Asn Gly Ser Cys Thr Ser Glu Asn Asp Cys Arg
        35                  40                  45

<210> SEQ ID NO 161
<211> LENGTH: 55
<212> TYPE: PRT
<213> ORGANISM: Homo sapiens

<400> SEQUENCE: 161

Pro Cys His Leu Leu Pro Asn Cys Thr Ser Cys Leu Asp Ser Lys Gly
1               5                   10                  15

Ala Asp Gly Gly Trp Gln His Cys Val Trp Ser Ser Ser Leu Gln Gln
            20                  25                  30

Cys Leu Ser Pro Ser Tyr Cys Met Ala Gly Gly Cys Gly Arg Leu Leu
        35                  40                  45

Arg Gly Pro Glu Ser Cys Ser
    50                  55

<210> SEQ ID NO 162
<211> LENGTH: 41
<212> TYPE: PRT
<213> ORGANISM: Homo sapiens
```

<400> SEQUENCE: 162

Pro Cys Arg Leu Leu Ser Ser Pro Glu Ala Cys Asn Gln Ser Gly Ala
1               5                   10                  15

Cys Thr Trp Cys His Gly Ala Cys Leu Ser Gly Asp Gln Ala His Arg
            20                  25                  30

Leu Gly Cys Gly Gly Ser Pro Cys Ser
        35                  40

<210> SEQ ID NO 163
<211> LENGTH: 46
<212> TYPE: PRT
<213> ORGANISM: Homo sapiens

<400> SEQUENCE: 163

Asp Cys Val Ala Val Thr Ala Gln Cys Gln Ala Cys Val Ser Ser Arg
1               5                   10                  15

Trp Gly Cys Asn Trp Cys Val Trp Gln His Leu Cys Thr His Lys Ala
            20                  25                  30

Ser Cys Asp Ala Gly Pro Met Val Ala Ser His Gln Ser Pro
        35                  40                  45

<210> SEQ ID NO 164
<211> LENGTH: 42
<212> TYPE: PRT
<213> ORGANISM: Homo sapiens

<400> SEQUENCE: 164

Asn Cys Ala Met Gly Ser Pro Asp Cys Ser Gln Cys Leu Gly Arg Glu
1               5                   10                  15

Asp Leu Gly His Leu Cys Met Trp Ser Asp Gly Cys Arg Leu Arg Gly
            20                  25                  30

Pro Leu Gln Pro Met Ala Gly Thr Cys Pro
        35                  40

<210> SEQ ID NO 165
<211> LENGTH: 49
<212> TYPE: PRT
<213> ORGANISM: Homo sapiens

<400> SEQUENCE: 165

Asp Cys Arg Gln Ala Met Leu Pro Cys Ile Ser Cys Val Ser Asn Arg
1               5                   10                  15

Trp Thr Cys Gln Trp Asp Leu Arg Tyr His Glu Cys Arg Glu Ala Ser
            20                  25                  30

Pro Asn Pro Glu Asp Gly Ile Val Arg Ala His Met Glu Asp Ser Cys
        35                  40                  45

Pro

<210> SEQ ID NO 166
<211> LENGTH: 50
<212> TYPE: PRT
<213> ORGANISM: Homo sapiens

<400> SEQUENCE: 166

Glu Cys Arg Arg Leu Arg Thr Cys Ser Glu Cys Leu Ala Arg His Pro
1               5                   10                  15

Arg Thr Leu Gln Pro Gly Asp Gly Glu Ala Ser Ile Pro Arg Cys Lys
            20                  25                  30

Trp Cys Thr Asn Cys Pro Glu Gly Ala Cys Ile Gly Arg Asn Gly Ser

```
                35                  40                  45
Cys Thr
    50

<210> SEQ ID NO 167
<211> LENGTH: 45
<212> TYPE: PRT
<213> ORGANISM: Homo sapiens

<400> SEQUENCE: 167

Arg Cys Lys Lys Ala Pro Val Lys Ser Cys Thr Glu Cys Val Arg Val
1               5                   10                  15

Asp Lys Asp Cys Ala Tyr Cys Thr Asp Glu Met Phe Arg Asp Arg Arg
            20                  25                  30

Cys Asn Thr Gln Ala Glu Leu Leu Ala Ala Gly Cys Gln
            35                  40                  45
```